(12) United States Patent
Dinsmore et al.

(10) Patent No.: US 7,879,839 B2
(45) Date of Patent: Feb. 1, 2011

(54) POTASSIUM CHANNEL INHIBITORS

(75) Inventors: Christopher J. Dinsmore, Newton, MA (US); Jeffrey M. Bergman, Sellersville, PA (US); Douglas C. Beshore, North Wales, PA (US); B. Wesley Trotter, Glenside, PA (US); Kausik K. Nanda, Norristown, PA (US); Richard Isaacs, Harleysville, PA (US); Linda S. Payne, Lansdale, PA (US); Lou Anne Neilson, Sellersville, PA (US); Zhicai Wu, Quakertown, PA (US); Mark T. Bilodeau, Lansdale, PA (US); Peter J. Manley, Harleysville, PA (US); Adrienne E. Balitza, Philadelphia, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 822 days.

(21) Appl. No.: 11/658,114

(22) PCT Filed: Jul. 27, 2005

(86) PCT No.: PCT/US2005/026868

§ 371 (c)(1), (2), (4) Date: Jan. 22, 2007

(87) PCT Pub. No.: WO2006/015159

PCT Pub. Date: Feb. 9, 2006

(65) Prior Publication Data

US 2008/0090794 A1 Apr. 17, 2008

Related U.S. Application Data

(60) Provisional application No. 60/592,177, filed on Jul. 29, 2004.

(51) Int. Cl.
*C07D 401/14* (2006.01)
*A61K 31/438* (2006.01)

(52) U.S. Cl. ............ 514/210.2; 514/228.8; 514/235.5; 514/252.03; 514/255.05; 514/269; 514/278; 514/332; 514/333; 514/339; 514/343; 544/96; 544/124; 544/238; 544/333; 544/405; 546/16; 546/256; 546/261; 546/265; 546/276.4; 546/277.4

(58) Field of Classification Search .................. None
See application file for complete search history.

(56) References Cited

U.S. PATENT DOCUMENTS

| 2,953,562 A | | 9/1960 | Schuler et al. | |
| 5,194,441 A | * | 3/1993 | Zierke et al. | 514/336 |

FOREIGN PATENT DOCUMENTS

| GB | 765853 | 1/1957 |
| WO | WO 00/25770 | 5/2000 |
| WO | WO 02/24655 | 3/2002 |
| WO | WO 03/059873 | 7/2003 |
| WO | WO 2005/030129 | 4/2005 |
| WO | WO 2005/030130 | 4/2005 |
| WO | WO 2005/030217 | 4/2005 |
| WO | WO 2005/030726 | 4/2005 |
| WO | WO 2005/030727 | 4/2005 |
| WO | WO 2005/030729 | 4/2005 |
| WO | WO 2005/030791 | 4/2005 |
| WO | WO 2005/030792 | 4/2005 |
| WO | WO2006/136305 A1 | 12/2006 |

OTHER PUBLICATIONS

Van Heyningen et al, Chemical Abstracts 70:95749, 1969 (Abstract of ZA 6607027).*
Strelets et al, Khimiya Geterotsiklicheskikh Soedinenii (1974), (2), pp. 238-242 with Chemical Abstracts translation.*
Chemical Abstracts 68:77077, Citation of Bieganowska, Maria et al. Acta Poloniae Pharmaceutica (English Translation), (1968), 25(1), 1-6.*
English Language Translation of Strelets et al, Khimiya Geterotsiklicheskikh Soedinenii (1974), (2), pp. 238-242.*
D.M. D'Alessandro, et al., Journal of Chemistry, vol. 56, No. 7, pp. 657-664 (2003).
Linder, et al, "Abkommlinge des Diphenyl-piperidino-propans—eine neue Reihe hustenstillender Mittel", vol. 9, No. 2, pp. 94-99, 1959.
M.R. Kelgelman, et al. "The pinacol Rearrangement in the Heterocyclic Series. III. Numerical Migratory Aptitudes", Journal of the American Chemical Society, vol. 76, pp. 2711-2713 (1954).
P.J. Steel, et al., Dalton Transactions, No. 23, pp. 4505-4515, Database Accession No. 6423228/BRN.
R. Haberi, et al., Monatshefte Fuer Chemie, vol. 88, pp. 47-51 (1957) Database Accession No. 1957:71471.

(Continued)

*Primary Examiner*—Zinna N Davis
(74) *Attorney, Agent, or Firm*—Mark R. Daniel; Richard S. Parr

(57) ABSTRACT

The present invention relates to compounds having the structure useful as potassium channel inhibitors to treat cardiac arrhythmias, and the like.

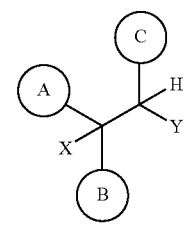

5 Claims, No Drawings

OTHER PUBLICATIONS

W. Czuba, Bulletin DE L'Academie Polonaise Des Sciences, vol. 8, No. 6, pp. 281-284, 1960.
G.N. Walker, Organic Chemistry, vol. 27, pp. 2966-2967, 1962, Database Accession No. 1025723/BRN.
K.K. Chiu, et al., Chemical Society, Section C, Organic Chemistry, vol. 19, pp. 2758-2761, 1969.
K.K. Chiu, et al., Spectrochimica Acta Part A: Molecular and Biomolecular Spectroscopy, vol. 29, No. 11, pp. 1947-1952 (1973).
E.V. Brown, et al., "Pinacol Rearrangement of Quinoline Analogs of Benzopinacol and Evidence for Rearrangement . . . ", Journal of Heterocyclic Chemistry, vol. 6, No. 4, pp. 567-570 (1969).
M.R. Kegelman, et al., The Pinacol Rearrangement in the Heterocyclic Series. I. Pyridine Analogs of Benzopinacol', Journal of the American Chemical Society, vol. 75, pp. 4649-4651 (1953).
M. Abe, et al., Oxidative Ring-Opening Reaction of Cyclopropanone Acetals with Carbonyl Compounds via Photoinduced Electron Transfer., Journal of Organic Chemistry, vol. 60, pp. 3065-3073 (1965).
E.V. Brown, et al., "Photochemical Preparation and Rearrangement of Some Symmetrical Methoxypyridyl Phenyl Glycols (Pinacols)", Journal of Heterocyclic Chemistry, vol. 8, No. 6, pp. 967-973 (1971).
M. L. Black, et al., "2-(2-Pyridyl)-1,2-diarylalkanols as Hypocholesteremic Agents", Journal of Medicinal Chemistry, vol. 10, No. 4, pp. 565-575 (1967).
F.J. Villani, et al., "Hyprocholesteremic Agents. I. Substituted Stilbazoles and Dihydrostilbazoles", Journal of Mecicinal Chemistry, vol. 13, No. 3, pp. 359-366 (1970).
A. Richardson Jr. et al., "triarylpyridylethanols and Triarylpyridylethylenes. Chemistry and Antifertility Effect", Journal of Medicinal Chemistry, vol. 18, No. 7, pp. 689-691 (1975).
Joseph. L Nepole et al. "New Inhibitors of Steroid 11 Beta-Hydroxylas. S.A.R. Studies of Metyrapone Compounds".—J. MED. Chem., vol. 20, No. 6, p. 762-766, XO002504537, 1997.
J.H. Burc Khalter et al.—"2- (2—Pyridyl-) -1, 2-Diaryl Alkanols as Hypocholesteremic Agents" Journal of Medicinal Chemistry, vol. 10, No. 4 p. 565-575, XP002365171, ISSN: 0022-2623, 1967.
Ernst. Anders et al.—"1-Acyl- benzyliden-1, 4 dihydorxypyridine, IV. Reaktionen mit Aldehyden und Ketonen zu 1-Phenyl-1-1(4 pyridyl) -2- alkanolen" SYNTHESIS, vol. 12, p. 899-899, XP002504538, 1978.
Hiroshi Hamana et al.—"Stereo-and Regio-Selective Aldo-Type Reactions of Alkylpyridines with Benzaldehyde." Chem. Lett., vol. 9 p. 1591-1594, XP002504539, 1984.
Supplementary European Search Report; Search by The Hague; Completed Nov. 19, 2008.
"Ion Pair, Reversed Phase Thin Layer Chromatography of Some Basic Drugs and Related Pyridine Derivatives", Maria L Bieganowska et al., Journal of Planar Chromatography, 1992, 5(3), pp. 184-191.
"Ultrasound Accelerated Reductive Coupling of Imine or Iminium Ion Generated in 5M Lithium Perchlorate Solution by Lithium Metal", Mohammad M. Mojtahedi et al., Synthetic Communications, 31 (23), pp. 3587-3592 (2001).
"Quinoline Sulphamido Chalcones, Part II", F.M. Aly et al., J. Serbian Chemical Society, 52 (8) pgs. 469-475 (1987); JSCS-1284.
"New Inhibitors of Steriod 11B-Hydroxylase, Structure-Activity Relationship Studies of Metyrapone-Like Compounds", Joseph Napoi et al., Journal of Medicinal Chemistry, 1977, vol. 20, No. 6, pgs.

* cited by examiner

POTASSIUM CHANNEL INHIBITORS

CROSS REFERENCE TO RELATED APPLICATION

This application is a U.S. National Phase application under 35 U.S.C. §371 of PCT Application Ser. No. PCT/US2005/026868, filed Jul. 27, 2005, which claims priority under 35 U.S.C. §119(e) from U.S. Provisional Application Ser. No. 60/592,177, filed Jul. 29, 2004.

BACKGROUND OF THE INVENTION

The present invention relates broadly to compounds that are useful as potassium channel inhibitors. Compounds in this class may be useful as Kv1.5 antagonists for treating and preventing cardiac arrhythmias, and the like.

Atrial fibrillation (AF) is the most common sustained cardiac arrhythmia in clinical practice and is likely to increase in prevalence with the aging of the population. While AF is rarely fatal, it can impair cardiac function and lead to complications such as the development of congestive heart failure, thromboembolism, or ventricular fibrillation.

Currently available antiarrhythmic agents have been developed for the treatment of ventricular and atrial/supraventricular arrhythmias. Malignant ventricular arrhythmias are immediately life-threatening and require emergency care. Drug therapy for ventricular arrhythmia includes Class Ia (eg. procainamide, quinidine), Class Ic (eg. flecamide, propafenone), and Class III (amiodarone) agents, which pose significant risks of proarrhythmia. These Class I and III drugs have been shown to convert AF to sinus rhythm and to prevent recurrence of AF (Mounsey, J P, DiNarco, J P, *Circulation,* 102:2665-2670), but pose an unacceptable risk of potentially lethal ventricular proarrhythmia and thus may increase mortality (Pratt, C M, Moye, L A, *Am J Cardiol.,* 65:20 B-29B, 1990; Waldo et al, *Lancet,* 348:7-12, 1996; Torp-Pedersen et al, *Expert Opin. Invest. Drugs,* 9:2695-2704, 2000). These observations demonstrate a clear unmet medical need to develop safer and more efficacious drugs for the treatment of atrial arrhythmias. Class III antiarrhythmic agents cause a selective prolongation of the APD without significant depression of cardiac conduction or contractile function. The only selective Class III drug approved for clinical use in atrial fibrillation is dofetilide, which mediates its anti-arrhythmic effects by blocking $I_{Kr}$, the rapidly activating component of $I_K$ found in both atrium and ventricle in humans (Mounsey, J P, DiMarco, J P, *Circulation,* 102:2665-2670). Since $I_{Kr}$ blockers increase APD and refractoriness both in atria and ventricle without affecting conduction per se, theoretically they represent potentially useful agents for the treatment of arrhythmias like AF (Torp-Pedersen, et al, *Expert Opin. Invest. Drugs,* 9:2695-2704, 2000). However, these agents have the major liability of an enhanced risk of proarrhythmia at slow heart rates.

The ultrarapid delayed rectifier K$^+$ current, $I_{Kur}$, has been observed specifically in human atrium and not in ventricle. The molecular correlate of $I_{Kur}$ in the human atrium is the potassium channel designated Kv1.5. $I_{Kur}$ is believed to contribute significantly to repolarization in human atrium. Consequently, a specific blocker of $I_{Kur}$, that is a compound which blocks Kv1.5, would overcome the shortcoming of other compounds by prolonging refractoriness through retardation of the repolarization in the human atrium without causing the delays in ventricular repolarization that underlie arrhythmogenic afterdepolarizations and acquired long QT syndrome observed during treatment with current Class III drugs. Kv1.5 blockers exhibiting these properties have been described (Peukert et al, *J. Med. Chem.,* 46:486-498, 2003; Knobloch et al, *Naunyn-Schmedieberg's Arch. Pharmacol.* 366:482-287, 2002; Merck & Co., Inc. WO0224655, 2002).

The compounds described in this invention represent a novel structural class of Kv1.5 antagonist.

SUMMARY OF THE INVENTION

The invention concerns compounds of formula I which antagonize the Kv1.5 potassium channel:

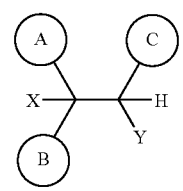

I

The compounds of this invention are useful in the treatment and prevention of cardiac arrhythmias, and the like. Also within the scope of this invention are pharmaceutical formulations comprising a compound of Formula I and a pharmaceutical carrier.

DETAILED DESCRIPTION OF THE DISCLOSURE

The invention includes compounds of formula I:

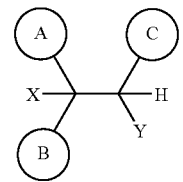

I or a pharmaceutically acceptable salt, wherein:
A is selected from the group consisting of
  1) an aryl ring,
  2) a heteroaryl ring, wherein the point of attachment to the heteroaryl ring is a carbon atom, and the heteroaryl ring is selected from the group consisting of:
     a) a 5-membered unsaturated monocyclic ring with 1, 2, 3, or 4 heteroatom ring atoms selected from the group consisting of N, O or S,
     b) a 6-membered unsaturated monocyclic ring with 1, 2, 3, or 4 heteroatom ring atoms selected from the group consisting of N, O or S, and
     c) an 8-, 9- or 10-membered unsaturated bicyclic ring with 1, 2, 3, or 4 heteroatom ring atoms selected from the group consisting of N, O or S;
  3) $C_1$-$C_{10}$ alkyl, wherein any stable atom is independently unsubstituted or substituted with a group selected from $R^4$,
  4) a $C_3$-$C_{10}$ cycloalkyl ring, wherein any stable ring atom is independently unsubstituted or substituted with a group selected from $R^4$, and
  5) a 4-6 membered saturated heterocyclic ring with 1, 2 or 3 heteroatom ring atoms selected from the group consisting of N, O and S, said aryl, heteroaryl, cycloalkyl, and saturated heterocyclic ring is unsubstituted, mono-substituted with $R^4$, disubstituted with groups independently selected from $R^4$, trisubstituted with groups independently selected from $R^4$, or tetrasubstituted with groups independently selected from $R^4$, and wherein any stable S or N heteroaryl or heterocyclic ring atom is unsubstituted or substituted with oxo;

B is a heteroaryl ring, wherein the point of attachment to the heteroaryl ring is a carbon atom, and wherein the heteroaryl ring is selected from the group consisting of
  a) a 5-membered unsaturated monocyclic ring with 1, 2, 3, or 4 heteroatom ring atoms selected from the group consisting of N, O or S,
  b) a 6-membered unsaturated monocyclic ring with 1, 2, 3, or 4 heteroatom ring atoms selected from the group consisting of N, O or S, and
  c) an 8-, 9- or 10-membered unsaturated bicyclic ring with 1, 2, 3, or 4 heteroatom ring atoms selected from the group consisting of N, O or S;
  said heteroaryl ring is unsubstituted, mono-substituted with $R^4$, disubstituted with groups independently selected from $R^4$, trisubstituted with groups independently selected from $R^4$, or tetrasubstituted with groups independently selected from $R^4$, and wherein any stable S or N heteroaryl ring atom is unsubstituted or substituted with oxo;

C is selected from the group consisting of
  1) an aryl ring, wherein any stable aryl ring atom is independently unsubstituted or substituted with a group selected from $R^4$,
  2) a heteroaryl ring, wherein the point of attachment to the heteroaryl ring is a carbon atom, and the heteroaryl ring is selected from the group consisting of:
    a) a 5-membered unsaturated monocyclic ring with 1, 2, 3, or 4 heteroatom ring atoms selected from the group consisting of N, O or S,
    b) a 6-membered unsaturated monocyclic ring with 1, 2, 3, or 4 heteroatom ring atoms selected from the group consisting of N, O or S, and
    c) an 8-, 9- or 10-membered unsaturated bicyclic ring with 1, 2, 3, or 4 heteroatom ring atoms selected from the group consisting of N, O or S;
  3) a $C_3$-$C_{10}$ cycloalkyl ring, wherein any stable ring atom is independently unsubstituted or substituted with a group selected from $R^4$,
  4) a 4-6 membered saturated heterocyclic ring with 1, 2 or 3 heteroatom ring atoms selected from the group consisting of N, O and S, wherein any stable ring atom is independently unsubstituted or substituted with a group selected from $R^4$,
  5) $C_1$-$C_{10}$ alkyl, wherein any stable atom is independently unsubstituted or substituted with a group selected from $R^4$,
  6) $C(O)R^5$,
  7) $C(O)OR^5$, and
  8) $C(O)N(R^5)_2$, wherein two $R^5$ groups can be linked to form a ring, said aryl, heteroaryl, cycloalkyl, and saturated heterocyclic ring is unsubstituted, mono-substituted with $R^4$, disubstituted with groups independently selected from $R^4$, trisubstituted with groups independently selected from $R^4$, or tetrasubstituted with groups independently selected from $R^4$, and wherein any stable S or N heteroaryl or heterocyclic ring atom is unsubstituted or substituted with oxo;

X is selected from the group consisting of H, $OR^5$, $NR^5R^5$, F, CN, $S(O)_{0-2}R^5$, $C(O)OR^5$, and $C(O)N(R^5)_2$;

Y is selected from the group consisting of

1) $NR^2R^3$,

2) 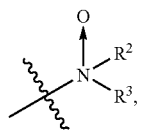

3) $OR^5$,

4) $S(O)_{0-2}R^5$,

5) 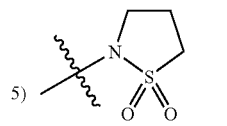

6) 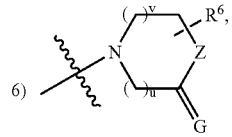

7) 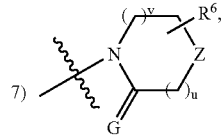

8) 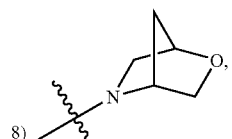

9) 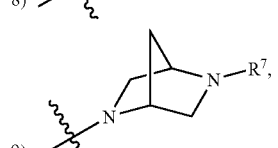

10) 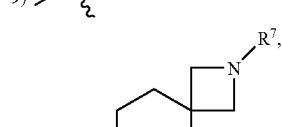

11) 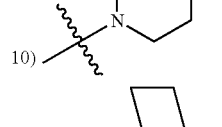

12) 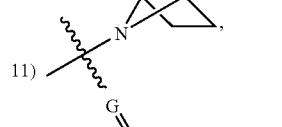 and 13) a nitrogen-containing heteroaryl ring, wherein the point of attachment to the heteroaryl ring is a nitrogen atom, and wherein the heteroaryl ring is selected from the group consisting of:
  a) a 5-membered unsaturated monocyclic ring with 1, 2, 3, or 4 heteroatom ring atoms selected from the group consisting of N, O or S, b) a 6-membered unsaturated monocyclic ring with 1, 2, 3, or 4 heteroatom ring atoms selected from the group consisting of N, O or S, and c) an 8-, 9- or 10-membered unsaturated bicyclic ring with 1, 2, 3, or 4 heteroatom ring atoms selected from the group consisting of N, O or S;

said nitrogen-containing heteroaryl ring is unsubstituted, mono-substituted with $R^4$, disubstituted with groups independently selected from $R^4$, trisubstituted with groups independently selected from $R^4$, or tetrasubstituted with groups independently selected from $R^4$, and wherein any stable S or N heteroaryl or heterocyclic ring atom is unsubstituted or substituted with oxo;

G, each time it occurs, is independently selected from the group consisting of $H_2$ and O;

Z is selected from the group consisting of $C(R^6)_2$, $NR^5$, $NC(O)R^5$, $NC(O)OR^5$, $NC(O)N(R^5)_2$, $NS(O)_{1-2}R^5$, $S(O)_{0-2}$, $—N(R^5)C(O)—$, $—C(R^5)=C(R^6)—$ and O;

$R^a$, in each instance in which it appears, is independently selected from the group consisting of
1) hydrogen,
2) $C_1$-$C_6$ alkyl,
3) halogen,
4) aryl,
5) heterocycle,
6) $C_3$-$C_{10}$ cycloalkyl, and
7) $OR^5$,
said alkyl, aryl, heterocycle and cycloalkyl is unsubstituted or substituted with at least one substituent selected from $R^6$;

$R^2$ and $R^3$ are independently selected from the group consisting of
1) hydrogen,
2) $(CR^a_2)_nOR^5$,
3) $(CR^a_2)_nN(R^5)_2$,
4) $(CR^a_2)_nC(O)R^5$,
5) $(CR^a_2)_nC(O)OR^5$,
6) $(CR^a_2)_nR^5$,
7) $(CR^a_2)_nS(O)_mR^5$,
8) $(CR^a_2)_nS(O)_mN(R^5)_2$,
9) $C(O)R^5$,
10) $C(O)OR^5$,
11) $C(O)N(R^5)_2$,
12) $S(O)_mR^5$,
13) $S(O)_mN(R^5)_2$,
14) $(CR^a_2)_nN(R^5)(CR^a_2)_nC(O)N(R^5)_2$,
15) $(CR^a_2)_nC(O)N(R^5)_2$,
16) $(CR^a_2)_nN(R^5)(CR^a_2)_nC(O)OR^5$, and
17) $(CR^a_2)_nN(R^5)S(O)_mR^5$;

$R^4$, in each instance in which it appears, is independently selected from the group consisting of
1) hydrogen,
2) halogen,
3) $NO_2$,
4) CN,
5) $CR^4=C(R^5)_2$,
6) $C\equiv CR^5$,
7) $(CR^a_2)_nOR^5$,
8) $(CR^a_2)_nN(R^5)_2$,
9) $(CR^a_2)_nC(O)R^5$,
10) $(CR^a_2)_nC(O)OR^5$,
11) $(CR^a_2)_nR^5$,
12) $(CR^a_2)_nS(O)_mR^5$,
13) $(CR^a_2)_nS(O)_mN(R^5)_2$,
14) $OS(O)_mR^5$,
15) $N(R^5)C(O)R^5$,
16) $N(R^5)S(O)_mR^5$,
17) $(CR^a_2)_nN(R^6)R^5$,
18) $(CR^a_2)_nN(R^5)(CR^a_2)_nC(O)N(R^5)_2$,
19) $(CR^a_2)_nN(R^5)(CR^a_2)_nC(O)OR^5$,
20) $N(R^5)(CR^a_2)_nR^5$,
21) $N(R^5)(CR^a_2)_nN(R^5)_2$, and
22) $(CR^a_2)_nC(O)N(R^5)_2$;

$R^5$, in each instance in which it appears, is independently selected from the group consisting of
1) hydrogen,
2) unsubstituted or substituted $C_1$-$C_6$ alkyl,
3) unsubstituted or substituted $C_3$-$C_{10}$ cycloalkyl,
4) unsubstituted or substituted aryl,
5) unsubstituted or substituted heterocycle,
6) $CF_3$,
7) unsubstituted or substituted $C_2$-$C_6$ alkenyl, and
8) unsubstituted or substituted $C_2$-$C_6$ alkynyl,
or in the case where $R^5$ is attached to a nitrogen atom that is disubstituted with $R^5$, each $R^5$ is independently selected from $C_1$-$C_6$ alkyl, and the nitrogen atom together with each $R^5$ form a ring;

$R^6$, in each instance in which it appears, is independently selected from the group consisting of
1) hydrogen,
2) unsubstituted or substituted $C_1$-$C_6$ alkyl,
3) halogen,
4) $OR^5$,
5) $CF_3$,
6) unsubstituted or substituted aryl,
7) unsubstituted or substituted $C_3$-$C_{10}$ cycloalkyl,
8) unsubstituted or substituted heterocycle,
9) $S(O)_mN(R^5)_2$,
10) $C(O)OR^5$,
11) $C(O)R^5$,
12) CN,
13) $C(O)N(R^5)_2$,
14) $N(R^5)C(O)R^5$,
15) $N(R^5)C(O)OR^5$,
16) $N(R^5)C(O)N(R^5)_2$,
17) $OC(O)N(R^5)_2$,
18) $S(O)_mR^5$,
19) $OS(O)_mR^5$,
20) $NO_2$,
21) $N(R^5)_2$;
22) $SC(O)R^5$,
23) $N(R^5)S(O)_mR^5$, $R^7$ is independently selected from the group consisting of
1) $S(O)_mN(R^5)_2$,
2) $C(O)OR^5$,
3) $C(O)R^5$,
4) $C(O)N(R^5)_2$, and
5) $S(O)_mR^5$;

m is independently 0, 1 or 2;
n is independently 0, 1, 2, 3, 4, 5 or 6;
u is 0, 1 or 2; and
v is 0, 1 or 2.

An embodiment of the invention is a compound or a pharmaceutically acceptable salt there of wherein B is a heteroaryl ring, wherein the point of attachment to the heteroaryl ring is a carbon atom, and wherein the heteroaryl ring is selected from the group consisting of pyridine and pyrimidine, wherein the heteroaryl ring is unsubstituted, mono-substituted with $R^4$, disubstituted with groups independently selected from $R^4$, trisubstituted with groups independently selected from $R^4$, or tetrasubstituted with groups independently selected from $R^4$, and wherein the N heteroaryl ring atom is unsubstituted or substituted with oxo; and X is selected from the group consisting of hydrogen, OH, OCH₃ and F.

A preferred embodiment of the invention is a compound or a pharmaceutically acceptable salt thereof wherein A is selected from the group consisting of
1) a phenyl ring,
2) a pyridyl ring, wherein the point of attachment to the pyridyl ring is a carbon atom, and
3) C₁-C₁₀ alkyl, wherein any stable atom is independently unsubstituted or substituted with a group selected from R⁴, wherein the phenyl ring and pyridyl ring are unsubstituted, mono-substituted with R⁴, disubstituted with groups independently selected from R⁴, trisubstituted with groups independently selected from R⁴, or tetrasubstituted with groups independently selected from R⁴, and wherein the N pyridyl ring atom is unsubstituted or substituted with oxo; and C is selected from the group consisting of
1) an aryl ring, wherein any stable aryl ring atom is independently unsubstituted or substituted with a group selected from R⁴,
2) a heteroaryl ring, wherein the point of attachment to the heteroaryl ring is a carbon atom, and the heteroaryl ring is selected from the group consisting of:
   a) a 5-membered unsaturated monocyclic ring with 1, 2, or 3 heteroatom ring atoms selected from the group consisting of N, O or S,
   b) a 6-membered unsaturated monocyclic ring with 1 or 2 N atoms, and
   c) an 8-, 9- or 10-membered unsaturated bicyclic ring with 1 or 2 heteroatom ring atoms selected from the group consisting of N, O or S,
wherein any stable atom is independently unsubstituted or substituted with a group selected from R⁴;
3) a cyclopropyl ring, wherein any stable ring atom is independently unsubstituted or substituted with a group selected from R⁴,
4) a 4-6 membered saturated heterocyclic ring with 1 or 2 heteroatom ring atoms selected from the group consisting of N and O, wherein any stable ring atom is independently unsubstituted or substituted with a group selected from R⁴, and
5) C₁-C₆ alkyl, wherein any stable atom is independently unsubstituted or substituted with a group selected from R⁴.

A more preferred embodiment of the invention is a compound or a pharmaceutically acceptable salt thereof wherein B is a pyridyl ring, wherein the point of attachment to the pyridyl ring is a carbon atom, and wherein the pyridyl ring is unsubstituted, mono-substituted with R⁴, disubstituted with groups independently selected from R⁴, trisubstituted with groups independently selected from R⁴, or tetrasubstituted with groups independently selected from R⁴, and wherein the N atom is unsubstituted or substituted with oxo;

X is selected from the group consisting of hydrogen, OH, OCH₃ and F;

A is selected from the group consisting of
1) a phenyl ring,
2) a pyridyl ring, wherein the point of attachment to the pyridyl ring is a carbon atom, and
3) —C(CH₃)₃, wherein the phenyl ring and pyridyl ring are unsubstituted, mono-substituted with R⁴, disubstituted with groups independently selected from R⁴, trisubstituted with groups independently selected from R⁴, or tetrasubstituted with groups independently selected from R⁴, and wherein the N pyridyl ring atom is unsubstituted or substituted with oxo;

C is selected from the group consisting of

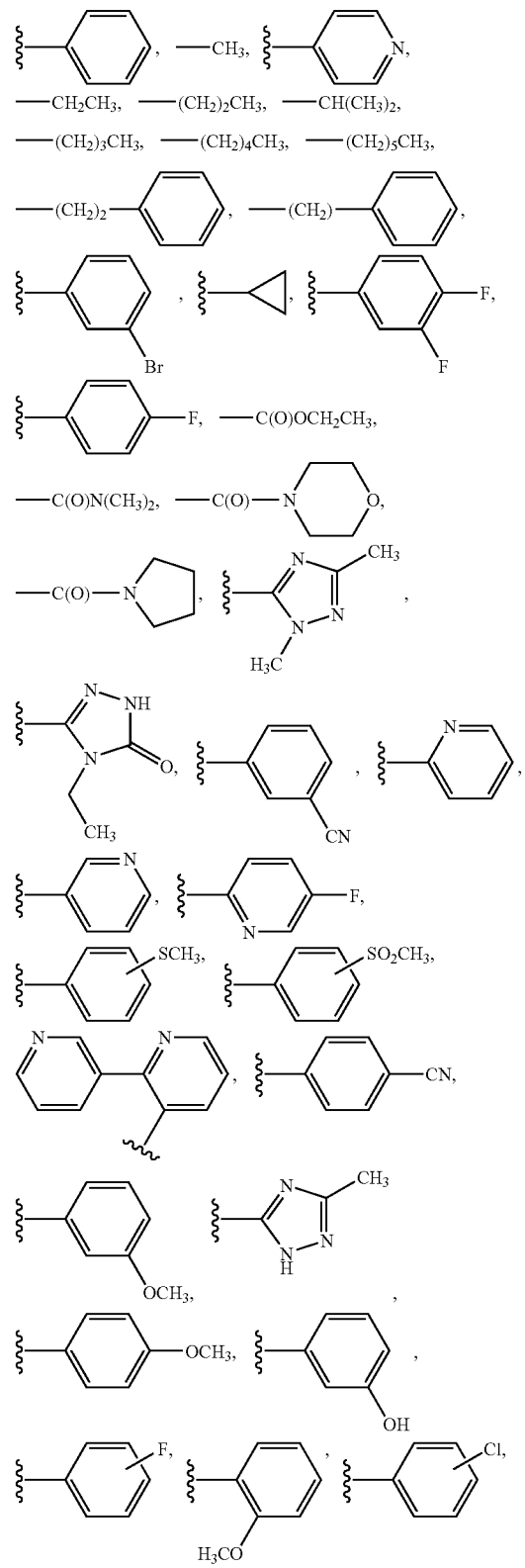

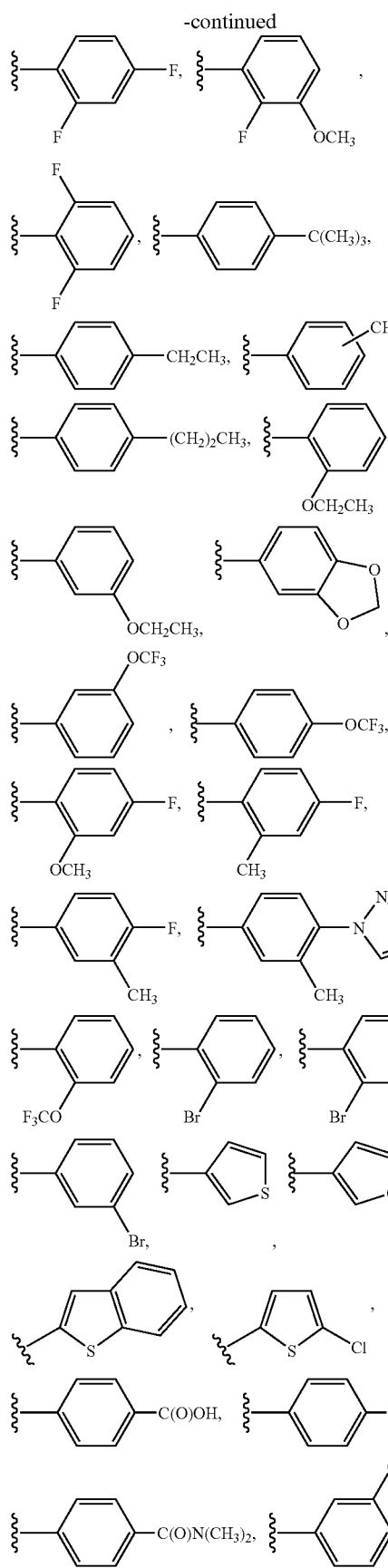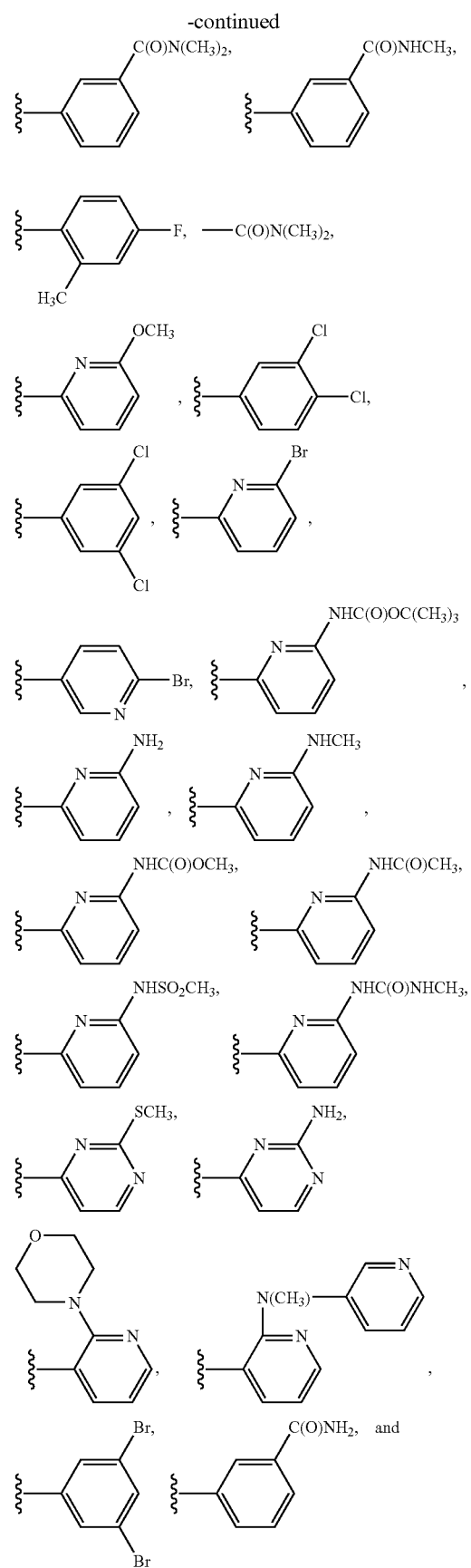

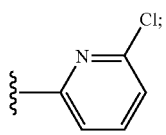
Y is selected from the group consisting of
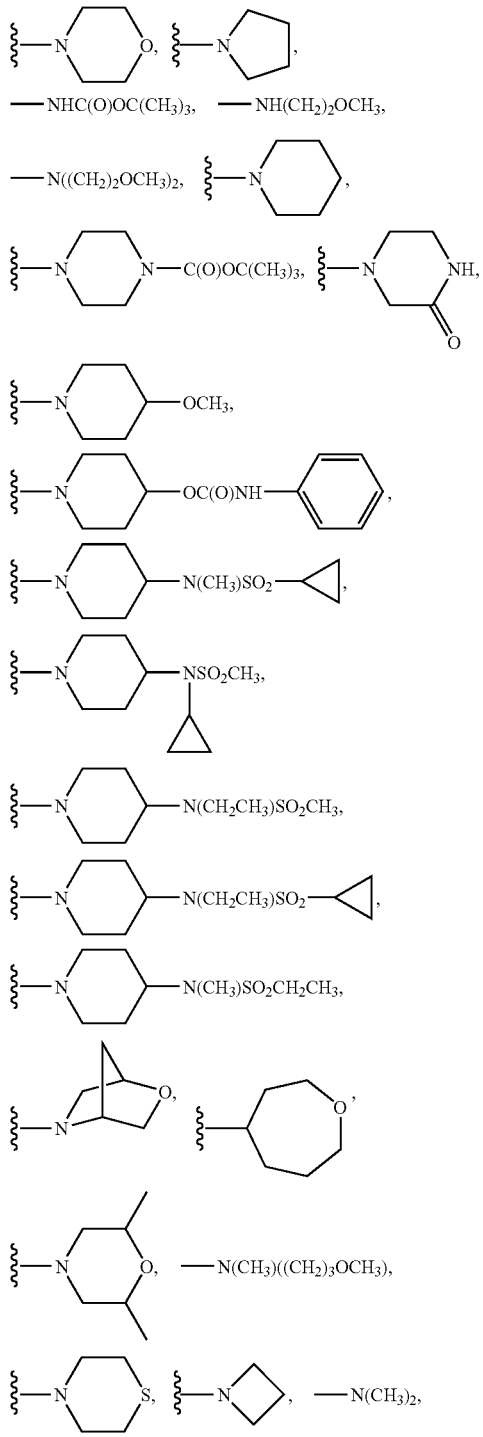
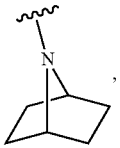
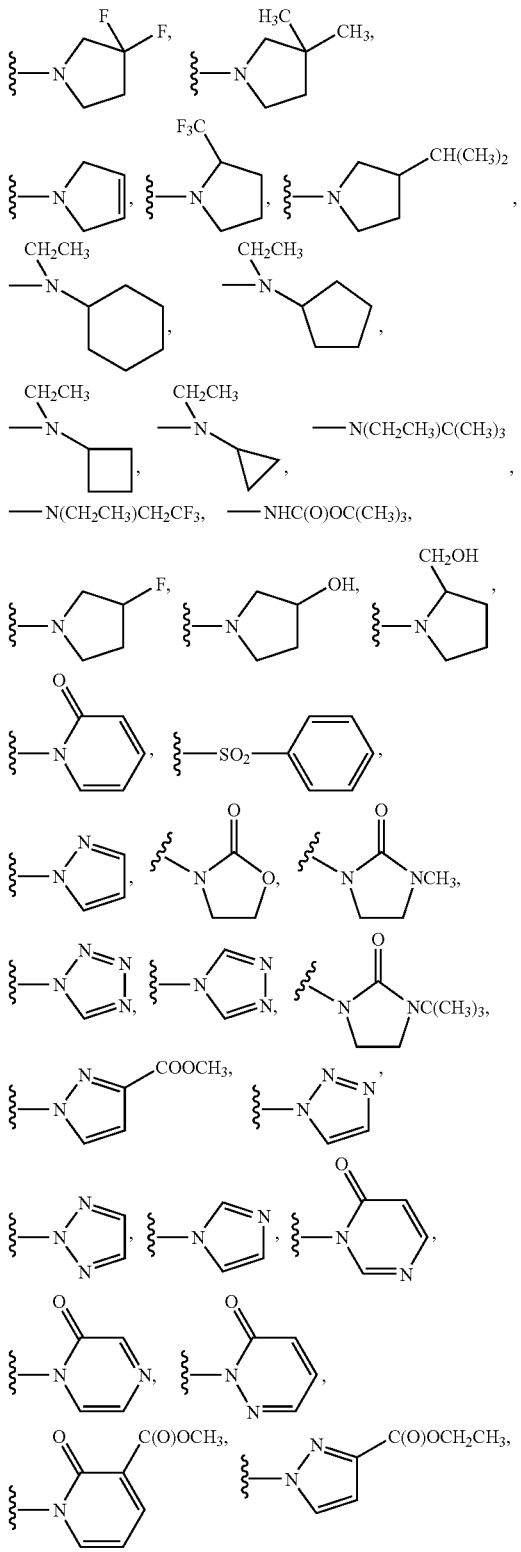

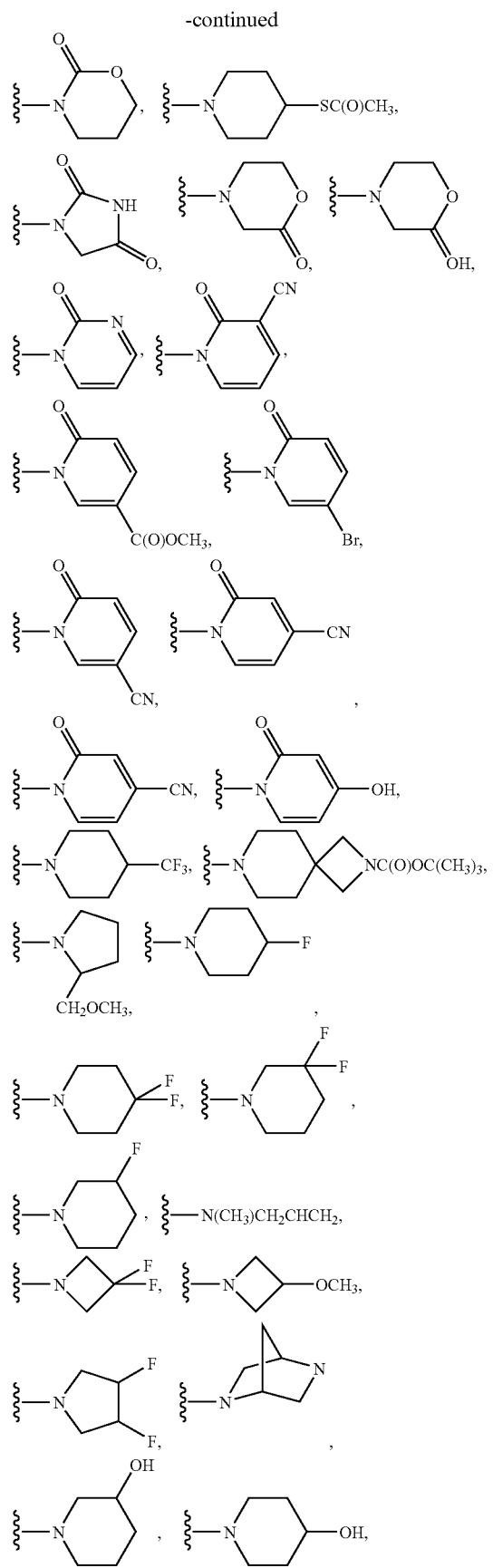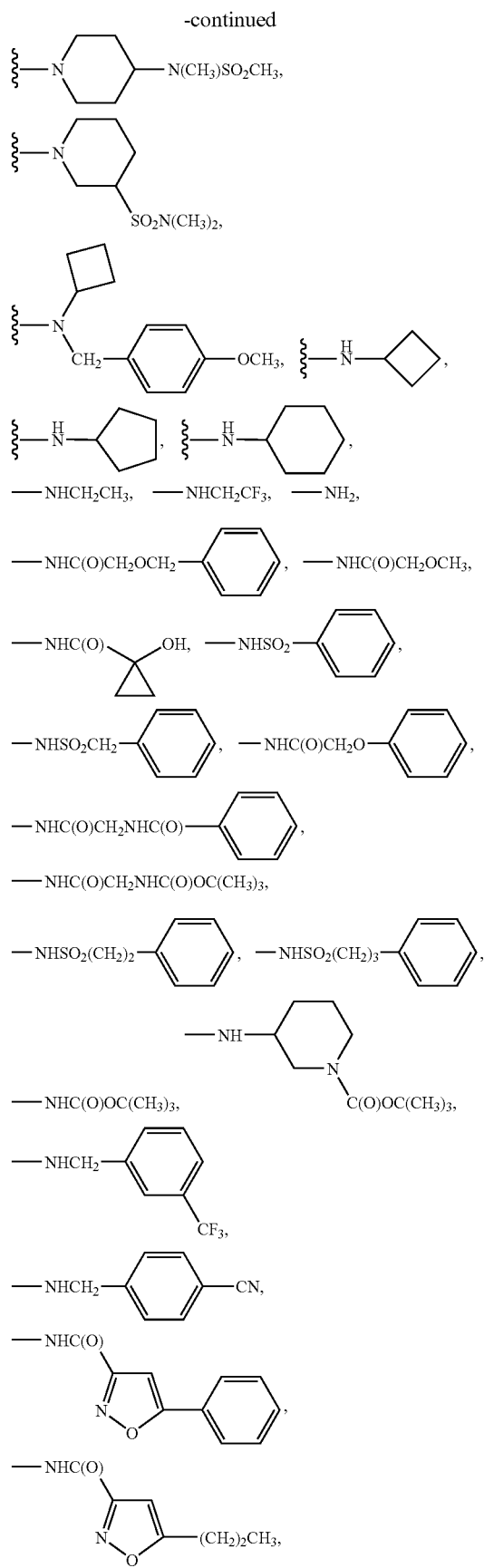

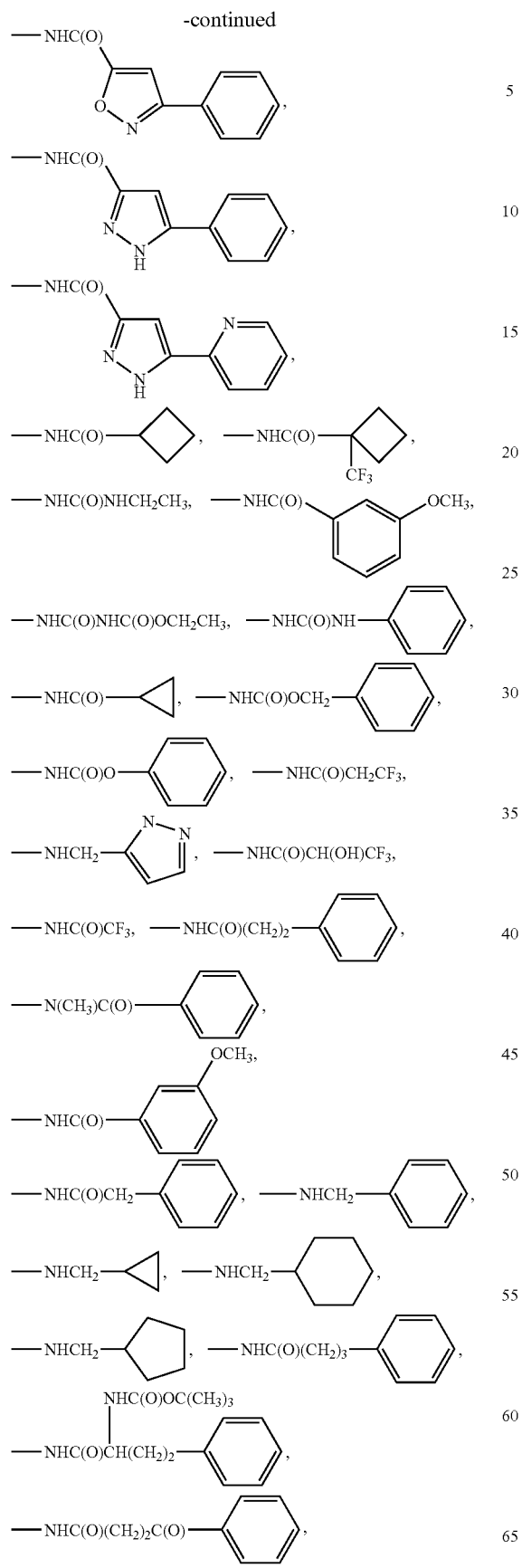

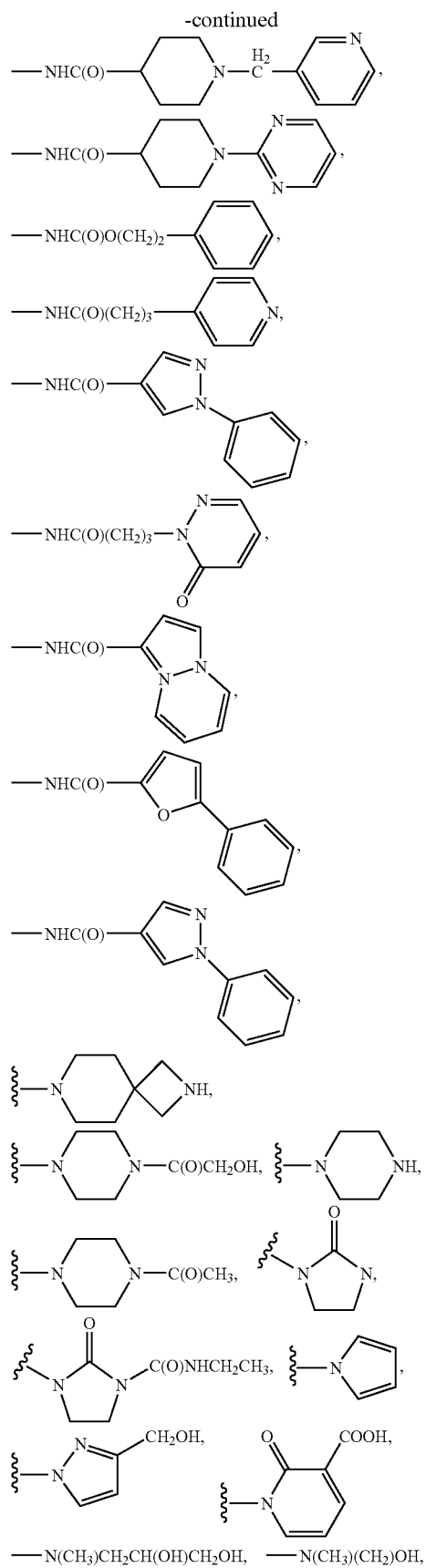
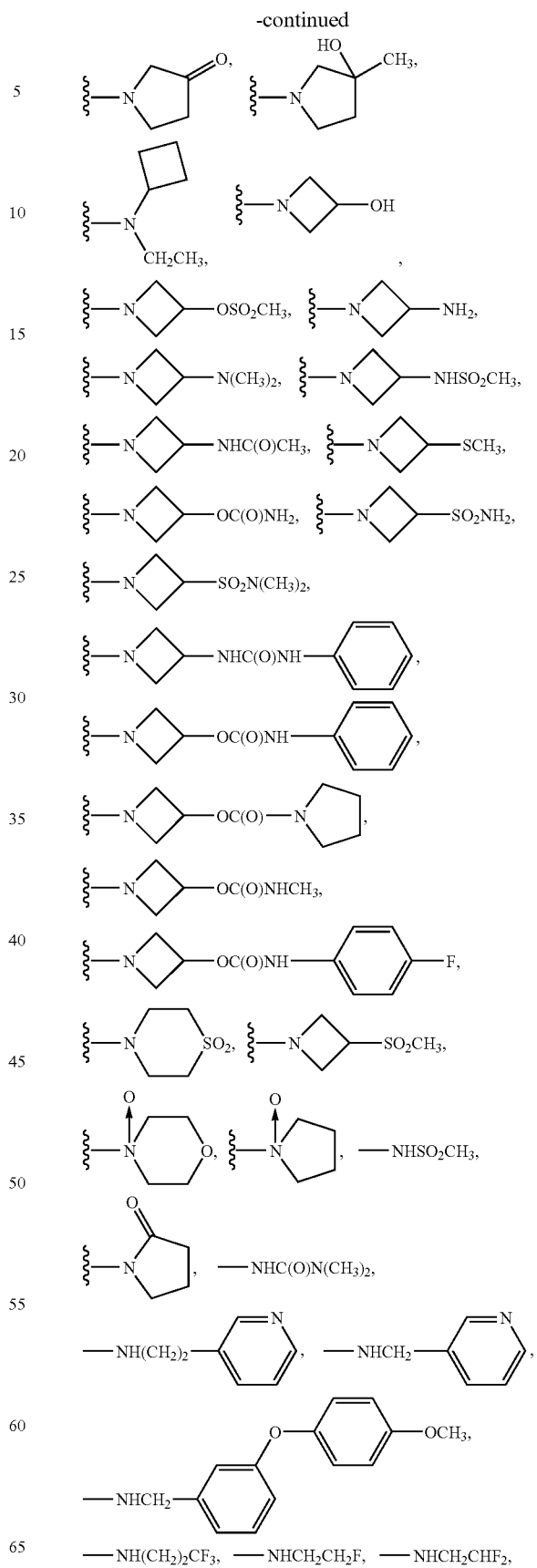

-continued
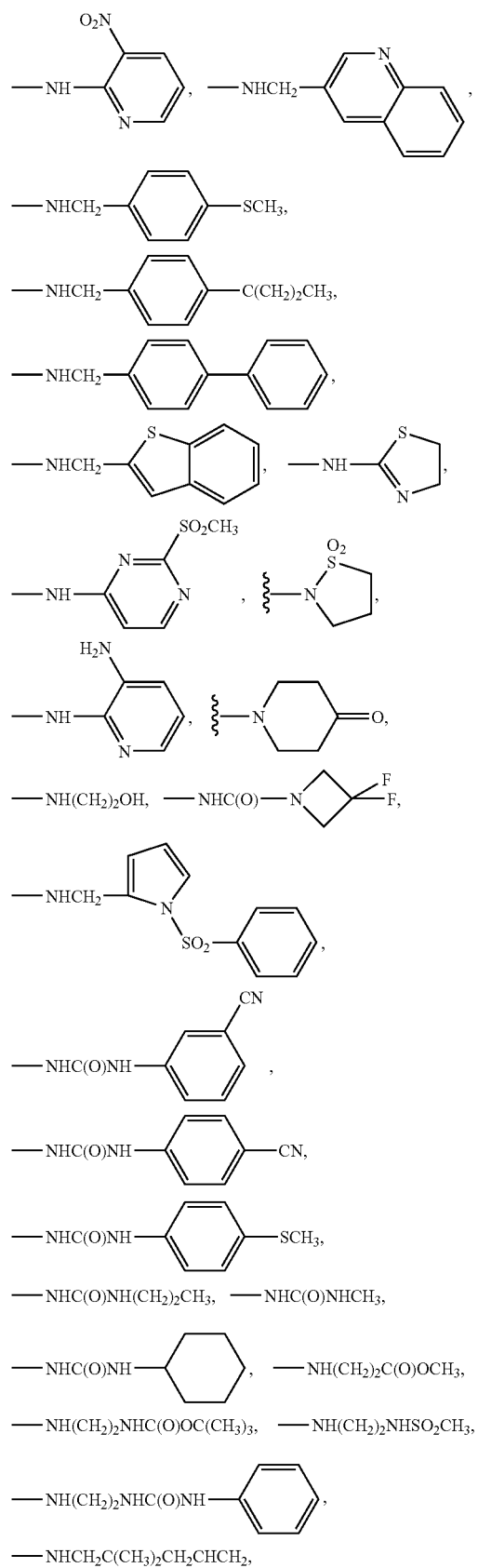
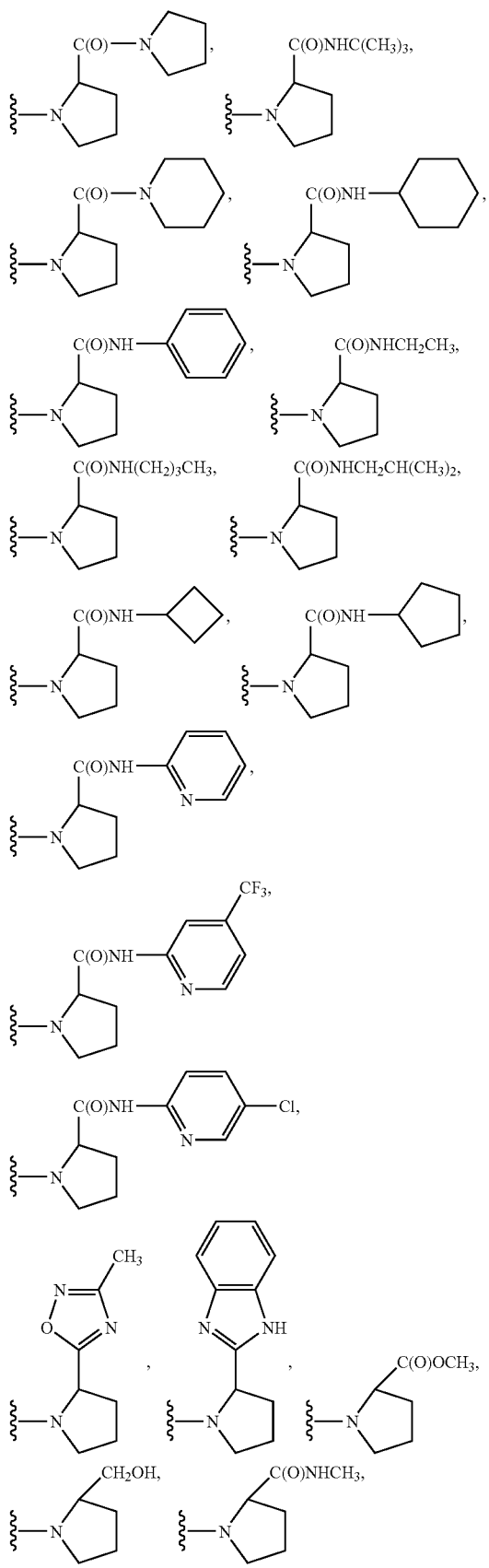

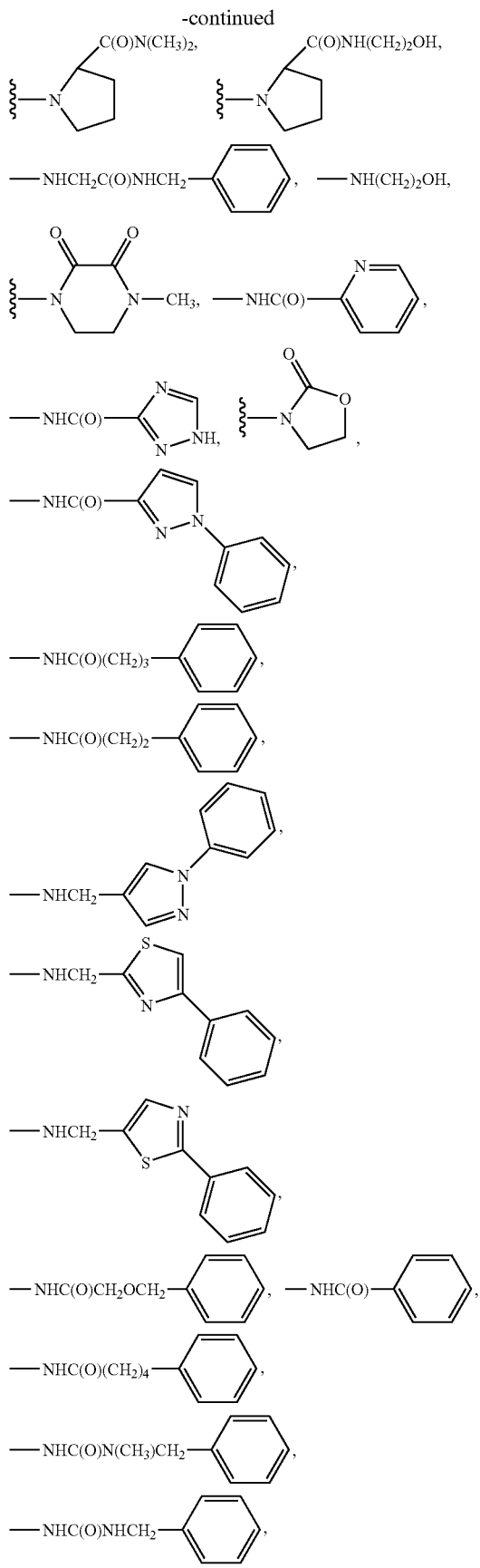

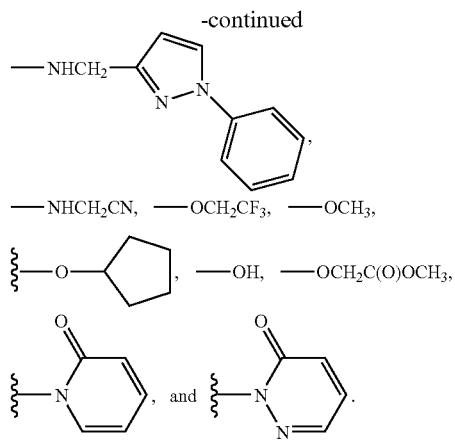

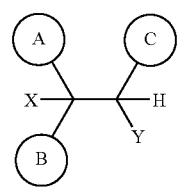

Another embodiment of the invention includes compounds of formula I:

$$\text{(I)}$$

wherein:
A is selected from the group consisting of
1) an aryl ring,
2) a heteroaryl ring, wherein the point of attachment to the heteroaryl ring is a carbon atom, and the heteroaryl ring is selected from the group consisting of:
   a) a 5-membered unsaturated monocyclic ring with 1, 2, 3, or 4 heteroatom ring atoms selected from the group consisting of N, O or S,
   b) a 6-membered unsaturated monocyclic ring with 1, 2, 3, or 4 heteroatom ring atoms selected from the group consisting of N, O or S, and
   c) an 8-, 9- or 10-membered unsaturated bicyclic ring with 1, 2, 3, or 4 heteroatom ring atoms selected from the group consisting of N, O or S;
3) $C_1$-$C_{10}$ alkyl, wherein any stable atom is independently unsubstituted or substituted with a group selected from $R^4$,
4) a $C_3$-$C_{10}$ cycloalkyl ring, wherein any stable ring atom is independently unsubstituted or substituted with a group selected from $R^4$, and
5) a 4-6 membered saturated heterocyclic ring with 1, 2 or 3 heteroatom ring atoms selected from the group consisting of N, O and S,
said aryl, heteroaryl, cycloalkyl, and saturated heterocyclic ring is unsubstituted, mono-substituted with $R^4$, disubstituted with groups independently selected from $R^4$, trisubstituted with groups independently selected from $R^4$, or tetrasubstituted with groups independently selected from $R^4$, and wherein any stable S or N heteroaryl or heterocyclic ring atom is unsubstituted or substituted with oxo;

B is a heteroaryl ring, wherein the point of attachment to the heteroaryl ring is a carbon atom, and wherein the heteroaryl ring is selected from the group consisting of
   a) a 5-membered unsaturated monocyclic ring with 1, 2, 3, or 4 heteroatom ring atoms selected from the group consisting of N, O or S,
   b) a 6-membered unsaturated monocyclic ring with 1, 2, 3, or 4 heteroatom ring atoms selected from the group consisting of N, O or S, and
   c) an 8-, 9- or 10-membered unsaturated bicyclic ring with 1, 2, 3, or 4 heteroatom ring atoms selected from the group consisting of N, O or S;
   said heteroaryl ring is unsubstituted, mono-substituted with $R^4$, disubstituted with groups independently selected from $R^4$, trisubstituted with groups independently selected from $R^4$, or tetrasubstituted with groups independently selected from $R^4$, and wherein any stable S or N heteroaryl ring atom is unsubstituted or substituted with oxo;
C is selected from the group consisting of
   1) an aryl ring, wherein any stable aryl ring atom is independently unsubstituted or substituted with a group selected from $R^4$,
   2) a heteroaryl ring, wherein the point of attachment to the heteroaryl ring is a carbon atom, and the heteroaryl ring is selected from the group consisting of:
      a) a 5-membered unsaturated monocyclic ring with 1, 2, 3, or 4 heteroatom ring atoms selected from the group consisting of N, O or S,
      b) a 6-membered unsaturated monocyclic ring with 1, 2, 3, or 4 heteroatom ring atoms selected from the group consisting of N, O or S, and
      c) an 8-, 9- or 10-membered unsaturated bicyclic ring with 1, 2, 3, or 4 heteroatom ring atoms selected from the group consisting of N, O or S;
   3) a $C_3$-$C_{10}$ cycloalkyl ring, wherein any stable ring atom is independently unsubstituted or substituted with a group selected from $R^4$,
   4) a 4-6 membered saturated heterocyclic ring with 1, 2 or 3 heteroatom ring atoms selected from the group consisting of N, O and S, wherein any stable ring atom is independently unsubstituted or substituted with a group selected from $R^4$,
   5) $C_1$-$C_{10}$ alkyl, wherein any stable atom is independently unsubstituted or substituted with a group selected from $R^4$,
   6) $C(O)R^5$,
   7) $C(O)OR^5$, and
   8) $C(O)N(R^5)_2$, wherein two $R^5$ groups can be linked to form a ring,
   said aryl, heteroaryl, cycloalkyl, and saturated heterocyclic ring is unsubstituted, mono-substituted with $R^4$, disubstituted with groups independently selected from $R^4$, trisubstituted with groups independently selected from $R^4$, or tetrasubstituted with groups independently selected from $R^4$, and wherein any stable S or N heteroaryl or heterocyclic ring atom is unsubstituted or substituted with oxo;
X is selected from the group consisting of H, $OR^5$, $NR^5R^5$, F, CN, $S(O)_{0-2}R^5$, C(O)ORS, and $C(O)N(R^5)_2$;
Y is selected from the group consisting of

1)

$NR^2R^3$,

2)

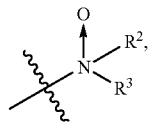

3)

$OR^5$,

4)

$S(O)_{0-2}R^5$,

5)

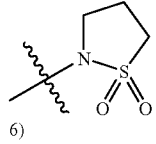

6)

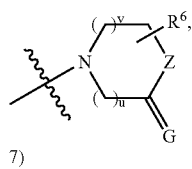

7)

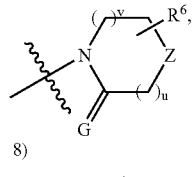

8)

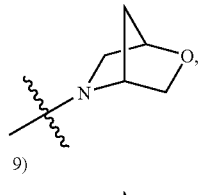

9)

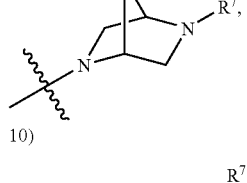

10)

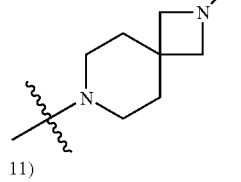

11)

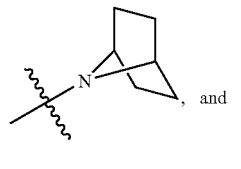, and 12) a nitrogen-containing heteroaryl ring, wherein the point of attachment to the heteroaryl ring is a nitrogen atom, and wherein the heteroaryl ring is selected from the group consisting of:

a) a 5-membered unsaturated monocyclic ring with 1, 2, 3, or 4 heteroatom ring atoms selected from the group consisting of N, O or S,
b) a 6-membered unsaturated monocyclic ring with 1, 2, 3, or 4 heteroatom ring atoms selected from the group consisting of N, O or S, and
c) an 8-, 9- or 10-membered unsaturated bicyclic ring with 1, 2, 3, or 4 heteroatom ring atoms selected from the group consisting of N, O or S;

said nitrogen-containing heteroaryl ring is unsubstituted, mono-substituted with $R^4$, disubstituted with groups independently selected from $R^4$, trisubstituted with groups independently selected from $R^4$, or tetrasubstituted with groups independently selected from $R^4$, and wherein any stable S or N heteroaryl or heterocyclic ring atom is unsubstituted or substituted with oxo;

G is selected from the group consisting of $H_2$ and O;

Z is selected from the group consisting of $C(R^6)_2$, $NR^5$, $NC(O)R^5$, $NC(O)OR^5$, $NC(O)N(R^5)_2$, $NS(O)_{1-2}R^5$, $S(O)_{0-2}$, $-N(R^5)C(O)-$, $-C(R^5)=C(R^6)-$ and O;

$R^a$, in each instance in which it appears, is independently selected from the group consisting of
1) hydrogen,
2) $C_1$-$C_6$ alkyl,
3) halogen,
4) aryl,
5) heterocycle,
6) $C_3$-$C_{10}$ cycloalkyl, and
7) $OR^5$,
said alkyl, aryl, heterocycle and cycloalkyl is unsubstituted or substituted with at least one substituent selected from $R^6$;

$R^2$ and $R^3$ are independently selected from the group consisting of
1) hydrogen,
2) $(CR^a{}_2)_nOR^5$,
3) $(CR^a{}_2)_nN(R^5)_2$,
4) $(CR^a{}_2)_nC(O)R^5$,
5) $(CR^a{}_2)_nC(O)OR^5$,
6) $(CR^a{}_2)_nR^5$,
7) $(CR^a{}_2)_nS(O)_mR^5$,
8) $(CR^a{}_2)_nS(O)_mN(R^5)_2$,
9) $C(O)R^5$,
10) $C(O)OR^5$,
11) $C(O)N(R^5)_2$,
12) $S(O)_mR^5$,
13) $S(O)_mN(R^5)_2$,
14) $(CR^a{}_2)_nN(R^5)(CR^a{}_2)_nC(O)N(R^5)_2$, and
15) $(CR^a{}_2)_nC(O)N(R^5)_2$;

$R^4$, in each instance in which it appears, is independently selected from the group consisting of
1) hydrogen,
2) halogen,
3) $NO_2$,
4) CN,
5) $CR^4=C(R^5)_2$,
6) $C\equiv CR^5$,
7) $(CR^a{}_2)_nOR^5$,
8) $(CR^a{}_2)_nN(R^5)_2$,
9) $(CR^a{}_2)_nC(O)R^5$,
10) $(CR^a{}_2)_nC(O)OR^5$,
11) $(CR^a{}_2)_nR^5$,
12) $(CR^a{}_2)_nS(O)_mR^5$,
13) $(CR^a{}_2)_nS(O)_mN(R^5)_2$,
14) $OS(O)_mR^5$,
15) $N(R^5)C(O)R^5$,
16) $N(R^5)S(O)_mR^5$,
17) $(CR^a{}_2)_nN(R^6)R^5$,
18) $(CR^a{}_2)_nN(R^5)(CR^a{}_2)_nC(O)N(R^5)_2$,
19) $(CR^a{}_2)_nN(R^5)(CR^a{}_2)_nC(O)OR^5$,
20) $N(R^5)(CR^a{}_2)_nR^5$,
21) $N(R^5)(CR^a{}_2)_nN(R^5)_2$, and
22) $(CR^a{}_2)_nC(O)N(R^5)_2$;

$R^5$, in each instance in which it appears, is independently selected from the group consisting of
1) hydrogen,
2) unsubstituted or substituted $C_1$-$C_6$ alkyl,
3) unsubstituted or substituted $C_3$-$C_{10}$ cycloalkyl,
4) unsubstituted or substituted aryl,
5) unsubstituted or substituted heterocycle,
6) $CF_3$,
7) unsubstituted or substituted $C_2$-$C_6$ alkenyl, and
8) unsubstituted or substituted $C_2$-$C_6$ alkynyl,
or in the case where $R^5$ is attached to a nitrogen atom that is disubstituted with $R^5$, each $R^5$ is independently selected from $C_1$-$C_6$ alkyl, and the nitrogen atom together with each $R^5$ form a ring;

$R^6$, in each instance in which it appears, is independently selected from the group consisting of
1) hydrogen,
2) unsubstituted or substituted $C_1$-$C_6$ alkyl,
3) halogen,
4) $OR^5$,
5) $CF_3$,
6) unsubstituted or substituted aryl,
7) unsubstituted or substituted $C_3$-$C_{10}$ cycloalkyl,
8) unsubstituted or substituted heterocycle,
9) $S(O)_mN(R^5)_2$,
10) $C(O)OR^5$,
11) $C(O)R^5$,
12) CN,
13) $C(O)N(R^5)_2$,
14) $N(R^5)C(O)R^5$,
15) $N(R^5)C(O)OR^5$,
16) $N(R^5)C(O)N(R^5)_2$,
17) $OC(O)N(R^5)_2$,
18) $S(O)_mR^5$,
19) $OS(O)_mR^5$,
20) $NO_2$, and
21) $N(R^5)_2$;

$R^7$ is independently selected from the group consisting of
1) $S(O)_mN(R^5)_2$,
2) $C(O)OR^5$,
3) $C(O)R^5$,
4) $C(O)N(R^5)_2$, and
5) $S(O)_mR^5$;

m is independently 0, 1 or 2;
n is independently 0, 1, 2, 3, 4, 5 or 6;
u is 0, 1 or 2; and
v is 0, 1 or 2.

An embodiment of the invention is a compound wherein
B is a heteroaryl ring, wherein the point of attachment to the heteroaryl ring is a carbon atom, and wherein the heteroaryl ring is selected from the group consisting of pyridine and pyrimidine, wherein the heteroaryl ring is unsubstituted, mono-substituted with $R^4$, disubstituted with groups independently selected from $R^4$, trisubstituted with groups independently selected from $R^4$, or tetrasubstituted with groups independently selected from $R^4$, and wherein the N heteroaryl ring atom is unsubstituted or substituted with oxo; and X is selected from the group consisting of hydrogen, OH, $OCH_3$ and F.

A preferred embodiment of the invention is a compound wherein
A is selected from the group consisting of
1) a phenyl ring,
2) a pyridyl ring, wherein the point of attachment to the pyridyl ring is a carbon atom, and
3) $C_1$-$C_{10}$ alkyl, wherein any stable atom is independently unsubstituted or substituted with a group selected from $R^4$,
wherein the phenyl ring and pyridyl ring are unsubstituted, mono-substituted with $R^4$, disubstituted with groups independently selected from $R^4$, trisubstituted with groups independently selected from $R^4$, or tetrasubstituted with groups independently selected from $R^4$, and wherein the N pyridyl ring atom is unsubstituted or substituted with oxo; and C is selected from the group consisting of
1) an aryl ring, wherein any stable aryl ring atom is independently unsubstituted or substituted with a group selected from $R^4$,
2) a heteroaryl ring, wherein the point of attachment to the heteroaryl ring is a carbon atom, and the heteroaryl ring is selected from the group consisting of:
  a) a 5-membered unsaturated monocyclic ring with 1, 2, or 3 heteroatom ring atoms selected from the group consisting of N, O or S,
  b) pyridine, and
  c) an 8-, 9- or 10-membered unsaturated bicyclic ring with 1 or 2 heteroatom ring atoms selected from the group consisting of N, O or S;
3) a cyclopropyl ring, wherein any stable ring atom is independently unsubstituted or substituted with a group selected from $R^4$,
4) a 4-6 membered saturated heterocyclic ring with 1 or 2 heteroatom ring atoms selected from the group consisting of N and O, wherein any stable ring atom is independently unsubstituted or substituted with a group selected from $R^4$, and
5) $C_1$-$C_6$ alkyl, wherein any stable atom is independently unsubstituted or substituted with a group selected from $R^4$.

A more preferred embodiment of the invention is a compound wherein
B is a pyridyl ring, wherein the point of attachment to the pyridyl ring is a carbon atom, and wherein the pyridyl ring is unsubstituted, mono-substituted with $R^4$, disubstituted with groups independently selected from $R^4$, trisubstituted with groups independently selected from $R^4$, or tetrasubstituted with groups independently selected from $R^4$, and wherein the N atom is unsubstituted or substituted with oxo;
X is selected from the group consisting of hydrogen, OH, $OCH_3$ and F;
A is selected from the group consisting of
1) a phenyl ring,
2) a pyridyl ring, wherein the point of attachment to the pyridyl ring is a carbon atom, and
3) —$C(CH_3)_3$,
wherein the phenyl ring and pyridyl ring are unsubstituted, mono-substituted with $R^4$, disubstituted with groups independently selected from $R^4$, trisubstituted with groups independently selected from $R^4$, or tetrasubstituted with groups independently selected from $R^4$, and wherein the N pyridyl ring atom is unsubstituted or substituted with oxo;

C is selected from the group consisting of

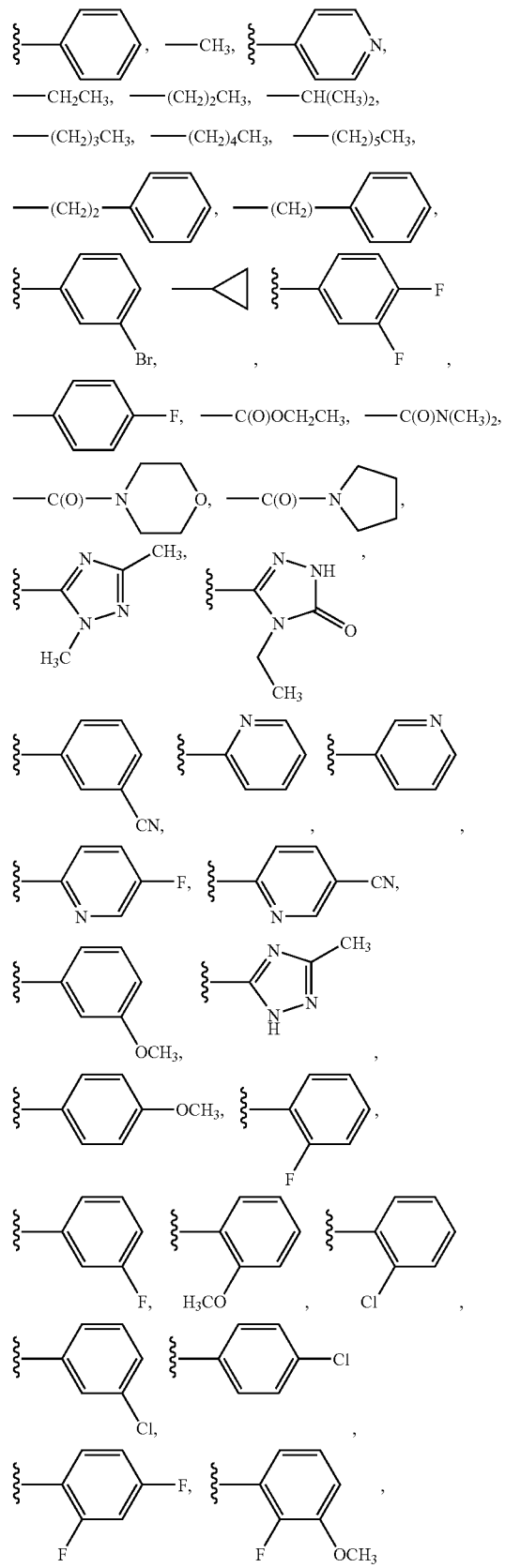

-continued
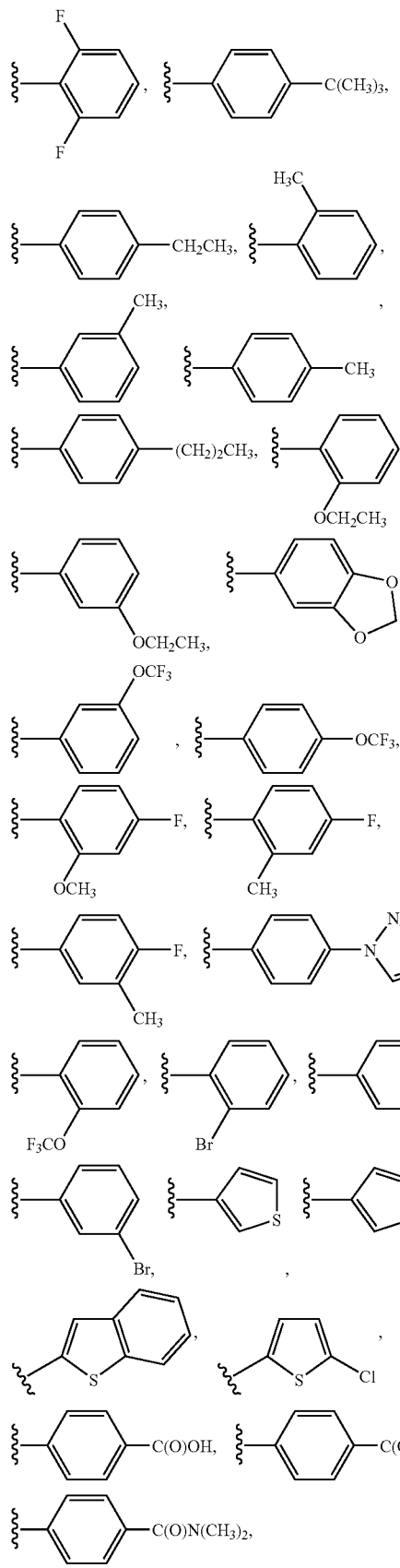
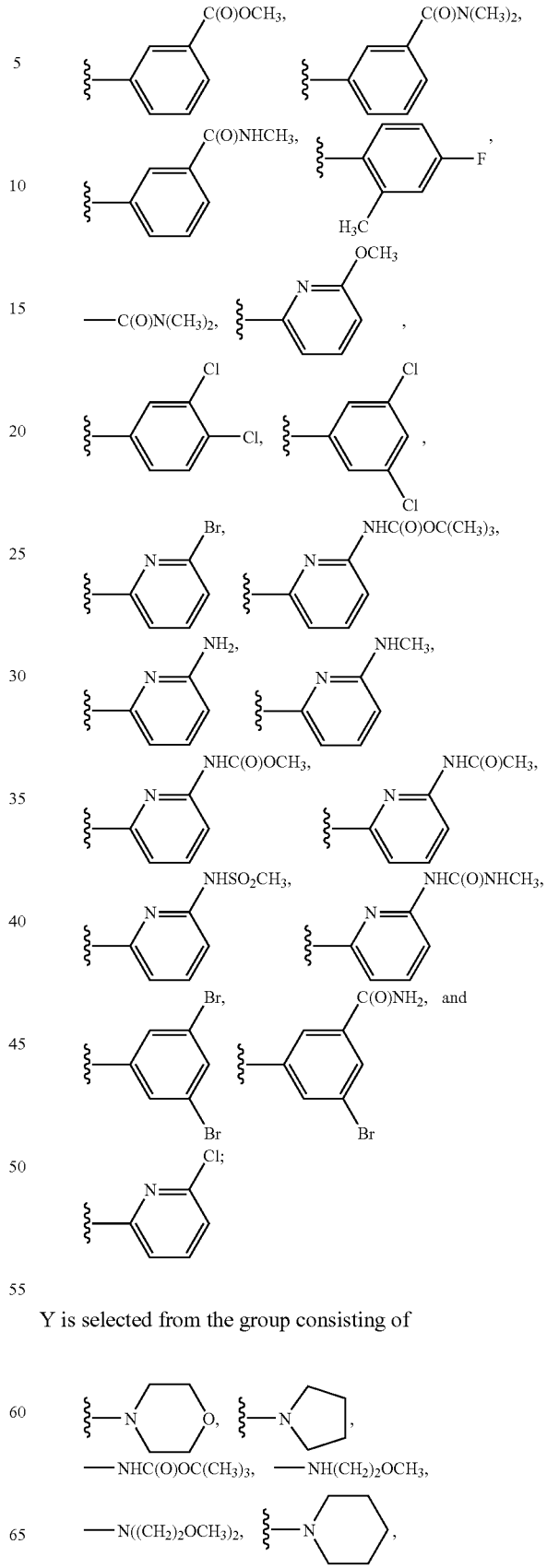
Y is selected from the group consisting of

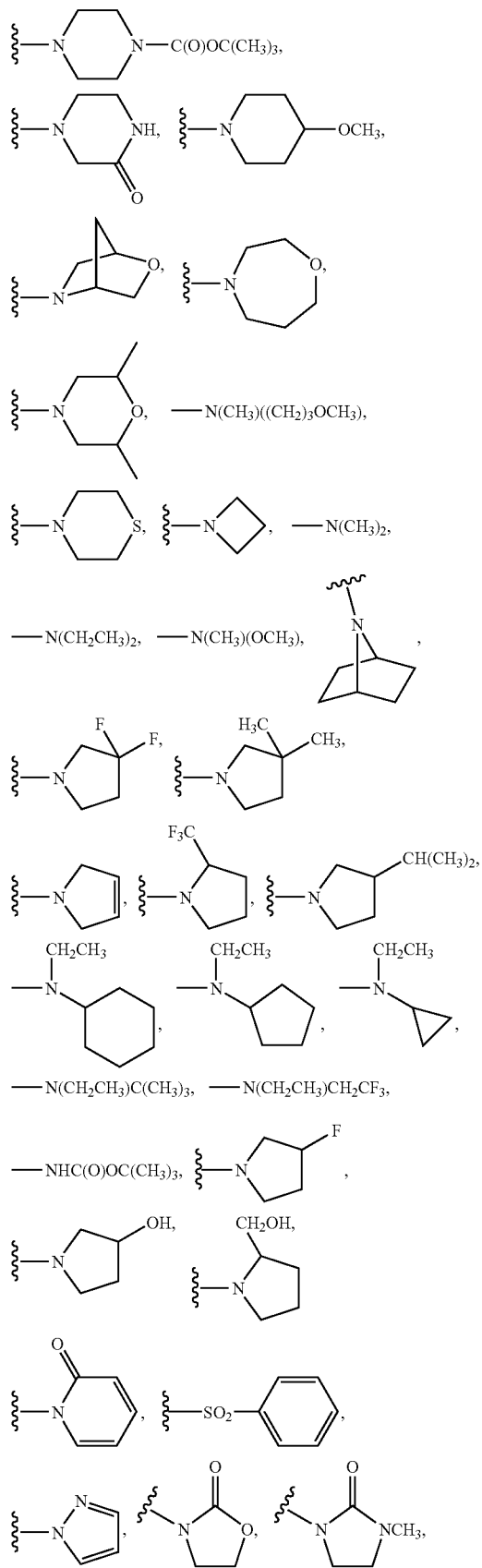
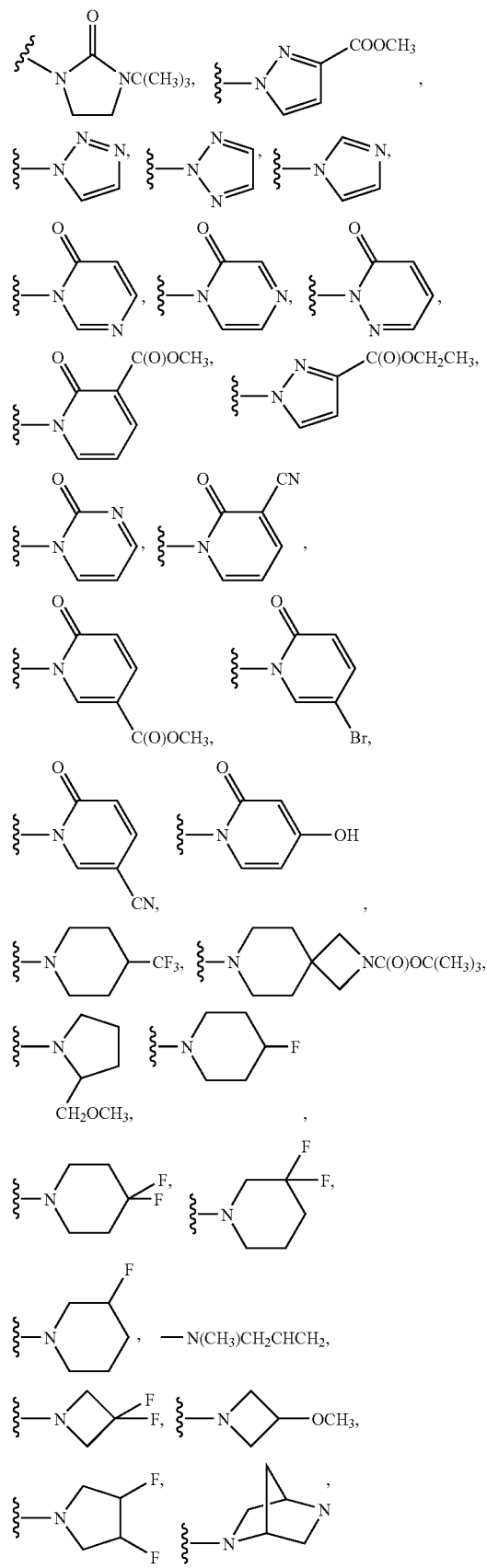

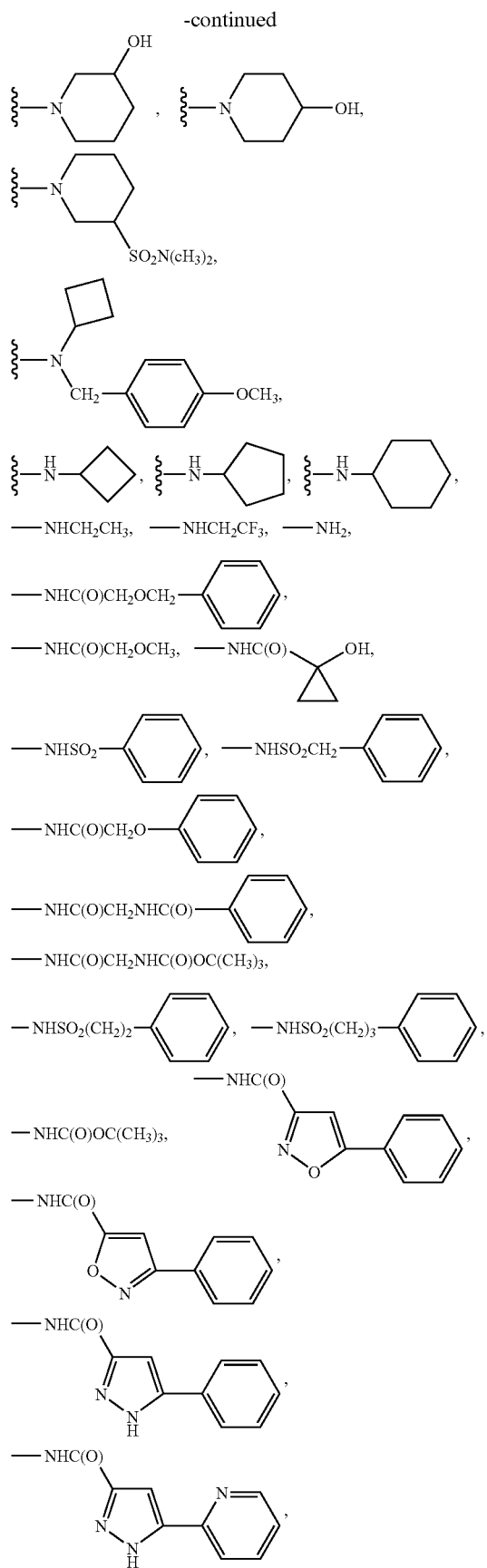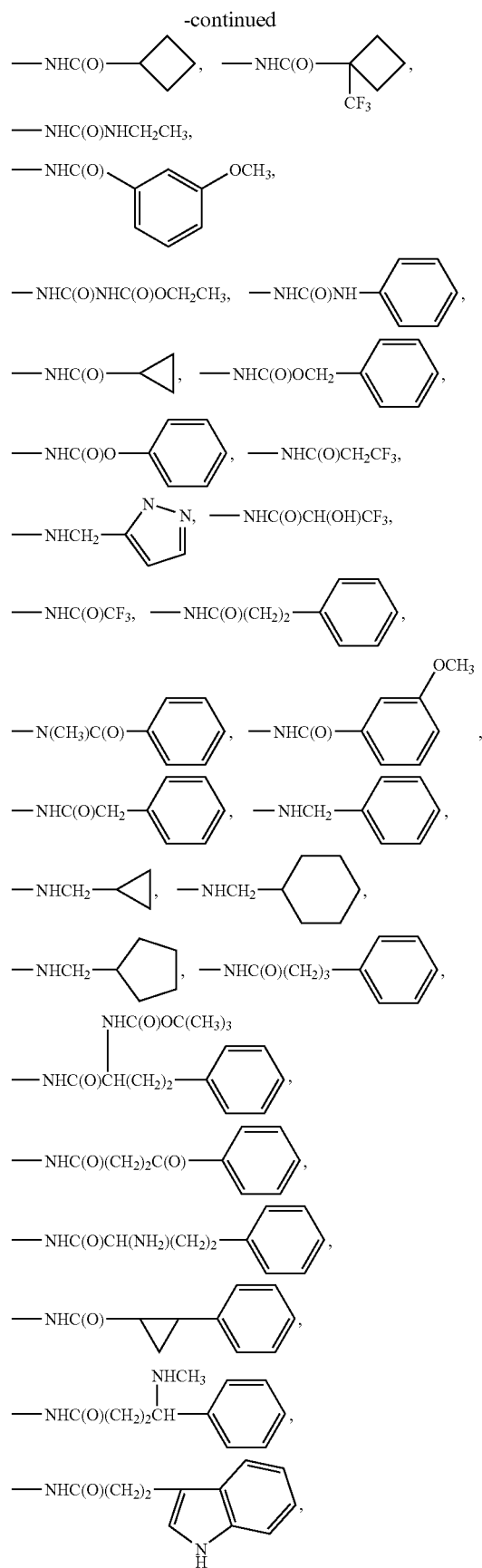

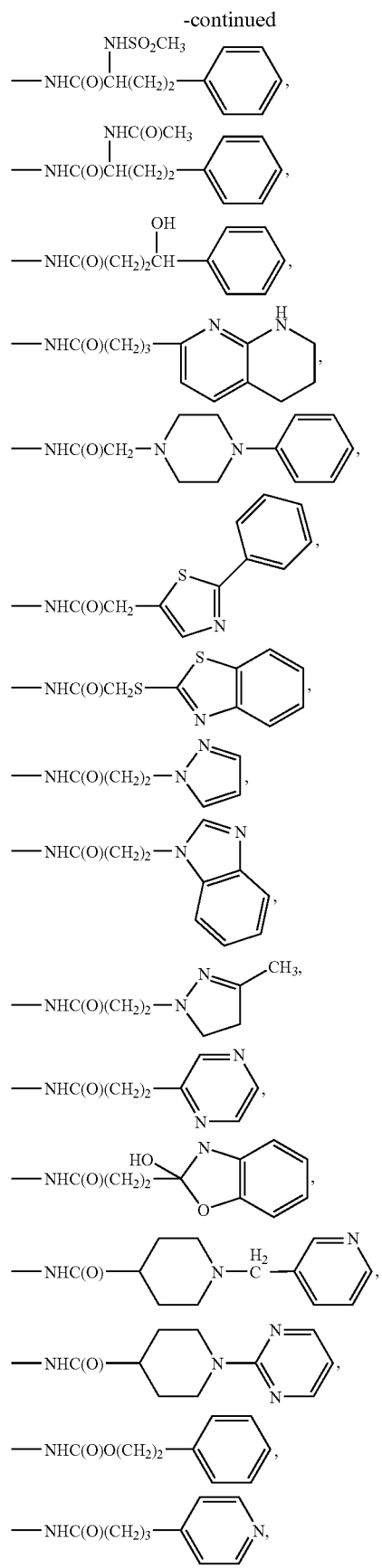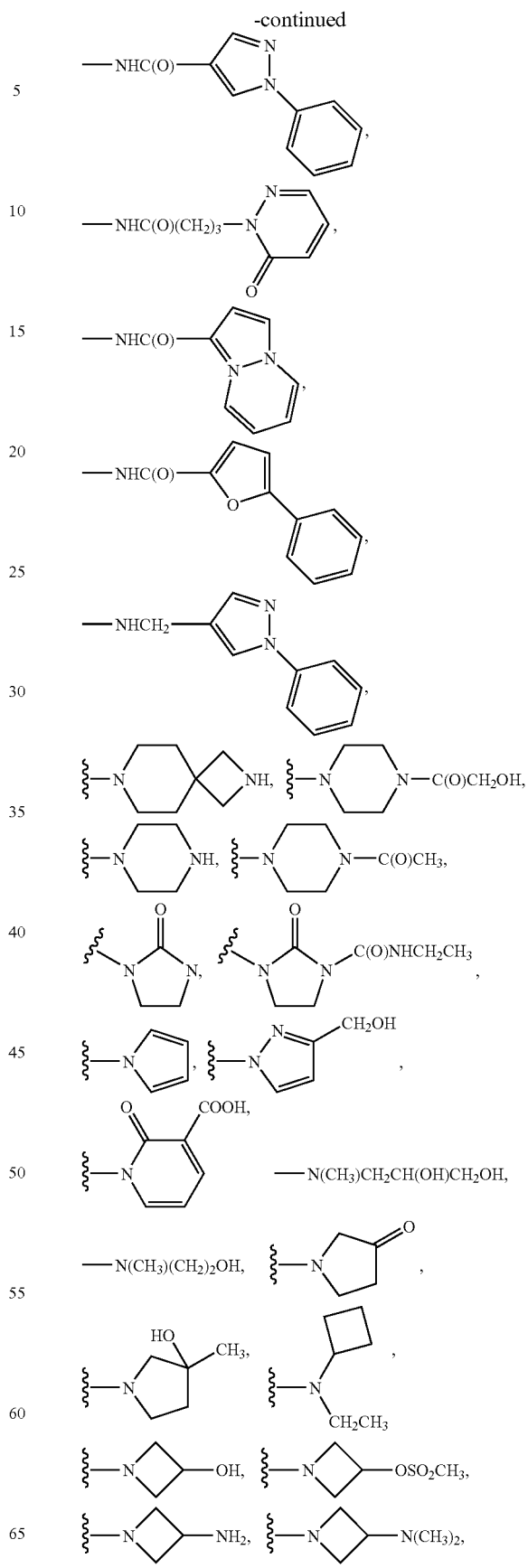

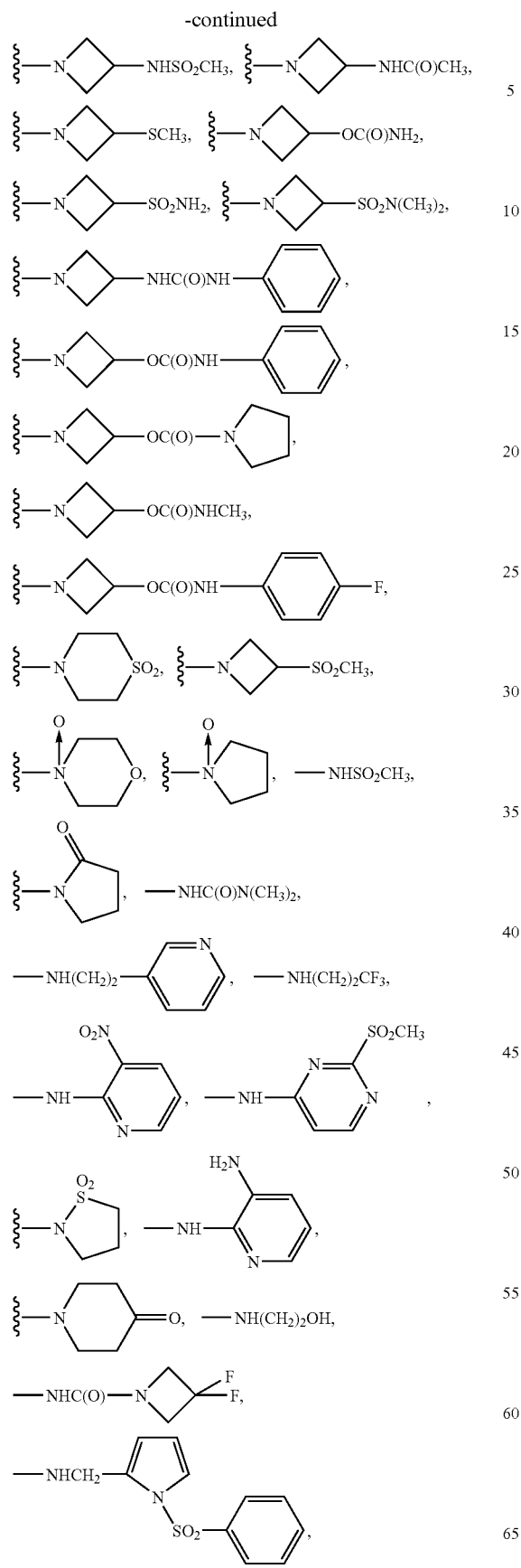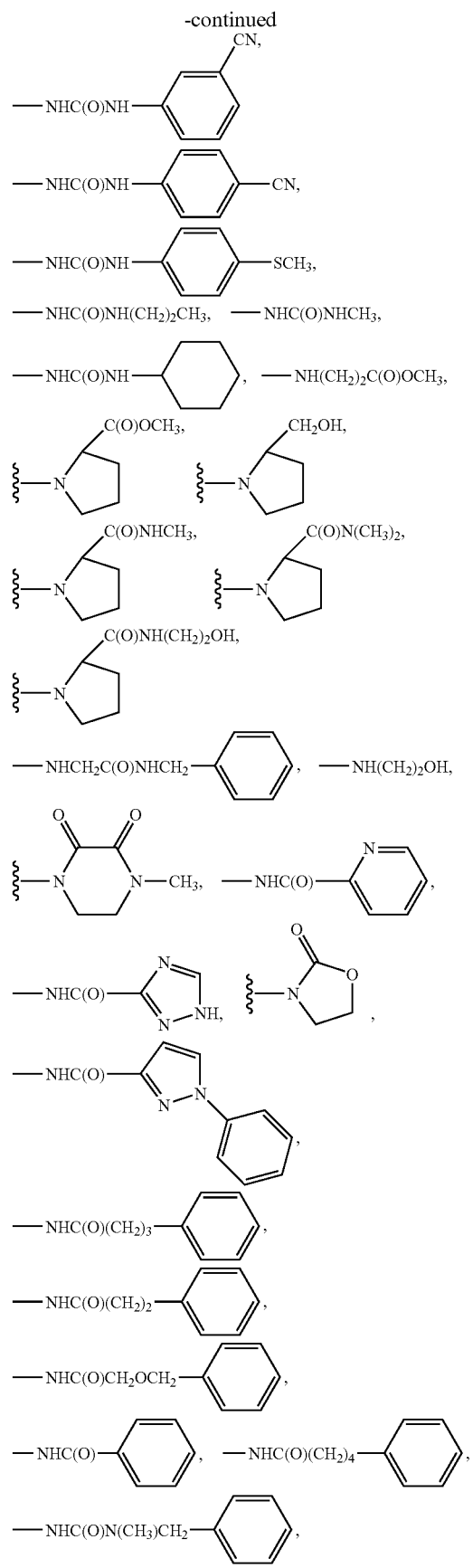

-continued

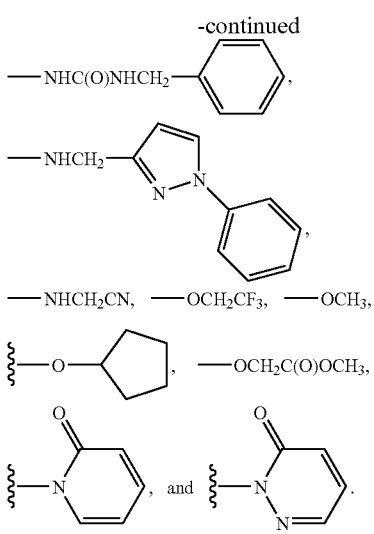

An example of a compound of the invention is a compound selected from the group consisting of
(±)-2-Morpholin-4-yl-2-phenyl-1,1-dipyridin-3-yl-ethanol,
(±)-3-methyl-2-morpholin-4-yl-1,1-dipyridin-3-ylbutan-1-ol,
(±)-2-[(2-methoxyethyl)(methyl)amino]-2-phenyl-1,1-dipyridin-3-ylethanol,
(±)-2-phenyl-2-piperidin-1-yl-1,1-dipyridin-3-ylethanol,
(±)-2-phenyl-1,1-dipyridin-3-yl-2-pyrrolidin-1-ylethanol,
(±)-tert-butyl 4-(2-hydroxy-1-phenyl-2,2-dipyridin-3-ylethyl)piperazine-1-carboxylate,
2-[(1S,4S)-2-oxa-5-azabicyclo[2.2.1]hept-5-yl]-2-phenyl-1,1-dipyridin-3-ylethanol,
(±)-2-(1,4-oxazepan-4-yl)-2-phenyl-1,1-dipyridin-3-ylethanol,
(±)-2-phenyl-1,1-dipyridin-3-yl-2-thiomorpholin-4-ylethanol,
(±)-2-(diethylamino)-2-phenyl-1,1-dipyridin-3-ylethanol,
(±)-2-(7-azabicyclo[2.2.1]hept-7-yl)-2-phenyl-1,1-dipyridin-3-ylethanol,
(±)-2-(3,3-difluoropyrrolidin-1-yl)-2-phenyl-1,1-dipyridin-3-ylethanol,
(±)-2-phenyl-1,1-dipyridin-3-yl-2-[2-(trifluoromethyl)pyrrolidin-1-yl]ethanol,
(±)-2-(2-isopropylpyrrolidin-1-yl)-2-phenyl-1,1-dipyridin-3-ylethanol,
(2R)-2-cyclopropyl-1,1-dipyridin-3-yl-2-pyrrolidin-1-ylethanol,
(±)-2-[cyclobutyl(ethyl)amino]-2-phenyl-1,1-dipyridin-3-ylethanol,
(±)-2-[ethyl(2,2,2-trifluoroethyl)amino]-2-phenyl-1,1-dipyridin-3-ylethanol,
(±)-2-(3-fluoropyrrolidin-1-yl)-2-phenyl-1,1-dipyridin-3-ylethanol,
(±)-2-morpholin-4-yl-1,2-diphenyl-1-pyridin-2-yl-ethanol,
2-morpholin-4-yl-2-phenyl-1-pyridin-2-yl-1-pyridin-3-ylethanol,
(±)-2-phenyl-2-(phenylsulfonyl)-1,1-dipyridin-3-ylethanol,
(±)-2-(1,3-dimethyl-1H-1,2,4-triazol-5-yl)-1,1-dipyridin-3-yl-2-pyrrolidin-1-ylethanol,
(±)-1,2-diphenyl-2-(1H-pyrazol-1-yl)-1-pyridin-4-ylethanol,
(±)-3-(2-hydroxy-1-phenyl-2,2-dipyridin-3-ylethyl)-1,3-oxazolidin-2-one,
(±)-3-[2-hydroxy-1-(2-oxo-1,3-oxazolidin-3-yl)-2,2-dipyridin-3-ylethyl]benzonitrile,
(±)-1-[1-(4-fluorophenyl)-2-hydroxy-2,2-dipyridin-3-ylethyl]-3-methylimidazolidin-2-one,
(±)-1-tert-butyl-3-[1-(4-fluorophenyl)-2-hydroxy-2,2-dipyridin-3-ylethyl]imidazolidin-2-one,
(±)-3-(2-hydroxy-1-pyridin-2-yl-2,2-dipyridin-3-ylethyl)-1,3-oxazolidin-2-one,
(±)-2-(1H-pyrazol-1-yl)-2-pyridin-2-yl-1,1-dipyridin-3-ylethanol,
(±)-2-(1H-pyrazol-1-yl)-1,1,2-tripyridin-3-ylethanol,
(±)-1,1,2-tripyridin-3-yl-2-(1H-1,2,3-triazol-1-yl)ethanol,
(±)-4-[2-hydroxy-2,2-dipyridin-3-yl-1-(2H-1,2,3-triazol-2-yl)ethyl]benzonitrile,
(±)-3-[2-hydroxy-2,2-dipyridin-3-yl-1-(1H-1,2,3-triazol-1-yl)ethyl]benzonitrile,
(±)-(1-benzyl-1H-pyrazol-5-yl)(dipyridin-3-yl)methanol,
(±)-1-[1-(4-fluorophenyl)-2-hydroxy-2,2-dipyridin-3-ylethyl]pyridin-2(1H)-one,
(±)-1-[1-(4-fluorophenyl)-2-hydroxy-2,2-dipyridin-3-ylethyl]pyrazin-2(1H)-one,
(±)-2-[1-(4-fluorophenyl)-2-hydroxy-2,2-dipyridin-3-ylethyl]pyridazin-3(2H)-one,
(R)-1-(2-hydroxy-1-pyridin-2-yl-2,2-dipyridin-3-ylethyl)pyridin-2(1H)-one,
(S)-1-(2-hydroxy-1-pyridin-2-yl-2,2-dipyridin-3-ylethyl)pyridin-2(1H)-one,
(±)-3-(2-hydroxy-2,2-dipyridin-3-yl-1-pyrrolidin-1-ylethyl)benzonitrile,
(±)-2-(4-fluorophenyl)-1,1-dipyridin-3-yl-2-pyrrolidin-1-ylethanol,
(±)-2-(3-methoxyphenyl)-1,1-dipyridin-3-yl-2-pyrrolidin-1-ylethanol,
2-[(2r)-2-(methoxymethyl)pyrrolidin-1-yl]-2-phenyl-1,1-dipyridin-3-ylethanol,
(±)-2-(3-bromophenyl)-1,1-dipyridin-3-yl-2-pyrrolidin-1-ylethanol,
(±)-2-(3,3-difluoroazetidin-1-yl)-2-(4-fluorophenyl)-1,1-dipyridin-3-ylethanol,
(±)-2-(5-chloro-2-thienyl)-1,1-dipyridin-3-yl-2-pyrrolidin-1-ylethanol,
2-[(3R,4R)-3,4-difluoropyrrolidin-1-yl]-2-phenyl-1,1-dipyridin-3-ylethanol,
(±)-1-(2-hydroxy-1-phenyl-2,2-dipyridin-3-ylethyl)piperidin-3-ol,
2-(4-fluorophenyl)-2-[(2S)-2-(hydroxymethyl)pyrrolidin-1-yl]-1,1-dipyridin-3-ylethanol,
(±)-2-(cyclobutylamino)-2-(4-fluorophenyl)-1,1-dipyridin-3-ylethanol,
(±)-2-phenyl-1,1-dipyridin-3-yl-2-[(2,2,2-trifluoroethyl)amino]ethanol,
2-(benzyloxy)-N-[(1R)-2-hydroxy-1-phenyl-2,2-dipyridin-3-ylethyl]acetamide,
N-[(1R)-1-(4-fluorophenyl)-2-hydroxy-2,2-dipyridin-3-ylethyl]-3-pyridin-2-yl-1H-pyrazole-5-carboxamide,
N-[(1R)-1-(4-fluorophenyl)-2-hydroxy-2,2-dipyridin-3-ylethyl]-4-phenylbutanamide, benzyl[(1R)-1-(4-fluorophenyl)-2-hydroxy-2,2-dipyridin-3-ylethyl]carbamate,
N-[(1R)-1-(4-fluorophenyl)-2-hydroxy-2,2-dipyridin-3-ylethyl]-1-phenyl-1H-pyrazole-4-carboxamide,
(±)-2-phenyl-1,1-dipyridin-3-yl-2-(1H-pyrrol-1-yl)ethanol,
(±)-3-(2-hydroxy-1-morpholin-4-yl-2,2-dipyridin-3-ylethyl)benzonitrile,
(±)-3,3'-(1-fluoro-2-phenyl-2-pyrrolidin-1-ylethane-1,1-diyl)dipyridine,
(±)-1-[1-(4-fluorophenyl)-2-hydroxy-2,2-dipyridin-3-ylethyl]azetidin-3-ol, (±)-1-[1-(4-fluorophenyl)-2-hydroxy-2,2-dipyridin-3-yl-ethyl]azetidin-3-yl phenylcarbamate,
(±)-2-(3,3-difluoroazetidin-1-yl)-2-(4-fluorophenyl)-1-(1-oxidopyridin-3-yl)-1-pyridin-3-ylethanol,
(±)-4-[1-(6-methoxypyridin-2-yl)-2,2-dipyridin-3-ylethyl]morpholine,
(±)-N-[1-(4-fluorophenyl)-2-phenyl-2-pyridin-3-ylethyl]-2-methoxyacetamide,
(±)-4-[1-(4-fluorophenyl)-2-phenyl-2-pyridin-3-ylethyl]morpholine,
(±)-1-[1-(4-fluorophenyl)-2,2-dipyridin-3-ylethyl]pyrrolidin-2-one,
(±)-4-[1-(4-fluorophenyl)-2,2-dipyridin-3-ylethyl]morpholine,
(±)-[1-(4-fluorophenyl)-2,2-dipyridin-3-ylethyl](2,2,2-trifluoroethyl)amine,
(±)-4-[1-(3,4-dichlorophenyl)-2,2-dipyridin-3-ylethyl]morpholine,
(±)-4-(1-pyridin-2-yl-2,2-dipyridin-3-ylethyl)morpholine,
(±)-3,3'-[2-(4-fluorophenyl)-2-pyrrolidin-1-ylethane-1,1-diyl]dipyridine,
(±)-4-[1-(4-fluorophenyl)-2-pyridin-2-yl-2-pyridin-3-ylethyl]morpholine,
(±)-4-[1-(3-chlorophenyl)-2,2-dipyridin-3-ylethyl]morpholine,
(±)-4-[1-(3,5-dichlorophenyl)-2,2-dipyridin-3-ylethyl]morpholine,
(±)-[1-(4-fluorophenyl)-2,2-dipyridin-3-ylethyl](3,3,3-trifluoropropyl)amine,
(±)-[1-(3-chlorophenyl)-2,2-dipyridin-3-ylethyl](2,2,2-trifluoroethyl)amine,
(±)-[1-(3,5-dichlorophenyl)-2,2-dipyridin-3-ylethyl](2,2,2-trifluoroethyl)amine,
(±)-[1-(3,4-dichlorophenyl)-2,2-dipyridin-3-ylethyl](2,2,2-trifluoroethyl)amine,
(±)-3,3'-[2-(1,1-dioxidoisothiazolidin-2-yl)-2-(4-fluorophenyl)ethane-1,1-diyl]dipyridine,
(±)-4-[1-(6-methoxypyridin-2-yl)-2-phenyl-2-pyridin-2-ylethyl]morpholine,
(±)-4-[1-(6-bromopyridin-2-yl)-2,2-dipyridin-3-ylethyl]morpholine,
(±)-6-(1-morpholin-4-yl-2,2-dipyridin-3-ylethyl)pyridin-2-amine,
(±)-N-methyl-6-(1-morpholin-4-yl-2,2-dipyridin-3-ylethyl)pyridin-2-amine,
(±)-methyl[6-(1-morpholin-4-yl-2,2-dipyridin-3-ylethyl)pyridin-2-yl]carbamate,
(±)-[1-(3-bromophenyl)-2,2-dipyridin-3-ylethyl]{[1-(phenylsulfonyl)-1H-pyrrol-2-yl]methyl}amine,
(±)-methyl 1-[1-(3-cyanophenyl)-2,2-dipyridin-3-ylethyl]prolinate,
(±)-3-{1-[2-(hydroxymethyl)pyrrolidin-1-yl]-2,2-dipyridin-3-ylethyl}benzonitrile,
(±)-1-[1-(3-cyanophenyl)-2,2-dipyridin-3-ylethyl]-N,N-dimethylprolinamide,
(±)-[1-(3-bromophenyl)-2,2-dipyridin-3-ylethyl]-4-methylpiperazine-2,3-dione,
(±)-3-[1-(6-bromopyridin-2-yl)-2,2-dipyridin-3-ylethyl]-1,3-oxazolidin-2-one,
(±)-3-[1-(2-oxo-1,3-oxazolidin-3-yl)-2,2-dipyridin-3-ylethyl]benzonitrile,
(±)-benzyl (1,2,2-tripyridin-3-ylethyl)carbamate,
(±)-n-[1-(3-cyanophenyl)-2,2-dipyridin-3-ylethyl]-2-phenylcyclopropanecarboxamide,
(±)-3-(1-{[(1-phenyl-1h-pyrazol-4-yl)methyl]amino}-2,2-dipyridin-3-ylethyl)benzonitrile,
(R)-3-(1-morpholin-4-yl-2,2-dipyridin-3-ylethyl)benzonitrile,
(S)-3-(1-morpholin-4-yl-2,2-dipyridin-3-ylethyl)benzonitrile,
(±)-3-[2-(4-fluorophenyl)-1-pyridin-3-yl-2-(2,2,2-trifluoroethoxy)ethyl]pyridine,
(±)-3-[2-(4-fluorophenyl)-2-methoxy-1-pyridin-3-ylethyl]pyridine,
(±)-3-[2-(cyclopentyloxy)-2-(4-fluorophenyl)-1-pyridin-3-ylethyl]pyridine,
(±)-1-[1-(6-chloropyridin-2-yl)-2,2-dipyridin-3-ylethyl]pyridin-2(1H)-one,
(±)-1-(1-pyridin-2-yl-2,2-dipyridin-3-ylethyl)pyridin-2(1H)-one,
(R)-1-(1-pyridin-2-yl-2,2-dipyridin-3-ylethyl)pyridin-2(1H)-one,
(S)-1-(1-pyridin-2-yl-2,2-dipyridin-3-ylethyl)pyridin-2(1)-one,
(±)-2-[1-(1H-pyrazol-1-yl)-2,2-dipyridin-3-ylethyl]pyridine,
(±)-2-[2-(4-fluorophenyl)-1-(1H-pyrazol-1-yl)-2-pyridin-3-ylethyl]pyridine,
(±)-2-[2-(4-fluorophenyl)-1-(1H-pyrazol-1-yl)-2-pyridin-3-ylethyl]pyridine,
(±)-2-[1-(4-fluorophenyl)-2-(1H-imidazol-1-yl)-2-pyridin-3-ylethyl]pyridine,
(±)-1-(1,2,2-tripyridin-3-ylethyl)pyridin-2(1H)-one,
(±)-2-[2,2-dipyridin-3-yl-1-(1H-1,2,3-triazol-1-yl)ethyl]pyridine,
(±)-3-[2,2-dipyridin-3-yl-1-(1H-1,2,3-triazol-1-yl)ethyl]benzonitrile, and
(±)-1-[1(2H)-yl)-2,2-dipyridin-3-ylethyl]pyridin-2(1H)-one.

The above-listed compounds are active in one or more of the assays for Kv1.5 described below.

Another embodiment of the invention is a method of treating or preventing a condition in a mammal, the treatment or prevention of which is effected or facilitated by $K_v1.5$ inhibition, which comprises administering an amount of a compound of Formula I that is effective at inhibiting $K_v1.5$.

A preferred embodiment is a method of treating or preventing cardiac arrhythmias, e.g. atrial fibrillation, atrial flutter, atrial arrhythmia, and supraventricular tachycardia, in a mammal, which comprises administering a therapeutically effective amount of a compound of Formula I.

Another preferred embodiment is a method of preventing thromboembolic events, such as stroke.

Another preferred embodiment is a method of preventing congestive heart failure.

Another preferred embodiment is a method of treating or preventing immunodepression or a disorder involving immunodepression, such as AIDS, cancer, senile dementia, trauma (including wound healing, surgery and shock) chronic bacterial infection, certain central nervous system disorders, and conditions including resistance by transplantation of organs or tissue, graft-versus-host diseases brought about by medulla ossium transplantation. Within this embodiment is a method for treating or preventing immunodepression by administering a compound of the invention with an immunosuppressant compound.

Another preferred embodiment is a method of treating or preventing gliomas including those of lower and higher malignancy, preferably those of higher malignancy.

Another preferred embodiment is a method for inducing in a patient having atrial fibrillation, a condition of normal sinus rhythm, in which the induced rhythm corresponds to the rhythm that would be considered normal for an individual sharing with the patient similar size and age characteristics, which comprises treating the patient with a compound of the invention.

Another preferred embodiment is a method for treating tachycardia, (i.e., rapid heart rate e.g. 100 beats per minute) in a patient which comprises treating the patient with an anti-tachycardia device (e.g. a defibrillator or a pacemaker) in combination with a compound of Claim 1.

The present invention also encompasses a pharmaceutical formulation comprising a pharmaceutically acceptable carrier and the compound of Formula I or a pharmaceutically acceptable crystal form or hydrate thereof. A preferred embodiment is a pharmaceutical composition of the compound of Formula I, comprising, in addition, a second agent.

The compounds of the present invention may have asymmetric centers or asymmetric axes, and this invention includes all of the optical isomers and mixtures thereof. Unless specifically mentioned otherwise, reference to one isomer applies to any of the possible isomers. Whenever the isomeric composition is unspecified, all possible isomers are included.

In addition compounds with carbon-carbon double bonds may occur in Z- and E-forms with all isomeric forms of the compounds being included in the present invention.

| List of abbreviations: | |
|---|---|
| AAS | atomic absorption spectroscopy |
| AIDS | acquired immunodeficiency syndrome |
| AF | atrial fibrillation |
| ACE | angiotensin converting enzyme |
| ACN | acetonitrile |
| APD | action potential duration |
| CHO | Chinese hamster ovary |
| DAST | (diethylamino)sulfur trifluoride |
| DCM | dichloromethane |
| dba | dibenzylidineacetone |
| DMA | dimethylacetamide |
| DMF | dimethylformamide |
| DMSO | dimethylsulfoxide |
| dppf | 1,1'-(diphenylphosphino)ferrocene |
| EDTA | ethylenediaminetetraacetic acid |
| EGTA | ethylenebis(oxyethylenenitrilo)tetraacetic acid |
| ESI | electrospray ionization |
| EtOAc | ethyl acetate |
| Et$_2$O | diethyl ether |
| FAAS | flame atomic absorption spetroscopy |
| FBS | fetal bovine serum |
| HBSS | Hank's balanced salt solution |
| HEPES | N-2-hydroxyethylpiperazine-N'-2-ethanesulphonic acid |
| HPLC | high pressure liquid chromatography |
| HRMS | high resolution mass spectrum |
| i-BuOH | isobutanol |
| i-Pr2Net | N,N-diisopropylethylamine |
| INH | inhibition |
| LDA | lithium diisopropylamide |
| LiHMDS | lithium hexamethyldisilazide |
| LRMS | low resolution mass spectrum |
| LYS | lysate |
| MCPBA | m-chloroperbenzoic acid |
| MeOH | methanol |
| MS | mass spectrum |
| MsCl | methanesulfonyl chloride |
| n-BuLi | n-butyllithium |
| NMO | N-methylmorpholine-N-oxide |
| NMR | nuclear magnetic resonance |
| NSAID | non-steroidal antiinflammatory drug |
| PBS | phosphate-buffered saline |
| RT | room temperature |
| SUP | supernatant |
| TAFI | thrombin-activatable fibrinolysis inhibitor |
| TFA | trifluoroacetic acid |
| THF | tetrahydrofuran |

-continued

| List of abbreviations: | |
|---|---|
| TMSCHN$_2$ | trimethylsilyldiazomethane |
| TPAP | tetrapropylammonium perruthenate |

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or CH$_3$, ethyl may be represented by "Et" or CH$_2$CH$_3$, propyl may be represented by "Pr" or CH$_2$CH$_2$CH$_3$, butyl may be represented by "Bu" or CH$_2$CH$_2$CH$_2$CH$_3$, etc. "C$_{1-6}$ alkyl" (or "C$_1$-C$_6$ alkyl") for example, means linear or branched chain alkyl groups, including all isomers, having the specified number of carbon atoms. C$_{1-6}$ alkyl includes all of the hexyl alkyl and pentyl alkyl isomers as well as n-, iso-, sec- and t-butyl, n- and isopropyl, ethyl and methyl. "C$_{1-4}$ alkyl" means n-, iso-, sec- and t-butyl, n- and isopropyl, ethyl and methyl. The term "alkoxy" represents a linear or branched alkyl group of indicated number of carbon atoms attached through an oxygen bridge.

The term "alkenyl" includes both branched and straight chain unsaturated hydrocarbon groups containing at least two carbon atoms joined by a double bond. The alkene ethylene is represented, for example, by "CH$_2$CH$_2$" or alternatively, by "H$_2$C=CH$_2$". "C$_{2-5}$ alkenyl" (or "C$_2$-C$_5$ alkenyl") for example, means linear or branched chain alkenyl groups having from 2 to 5 carbon atoms and includes all of the pentenyl isomers as well as 1-butenyl, 2-butenyl, 3-butenyl, 1-propenyl, 2-propenyl, and ethenyl (or ethylenyl). Similar terms such as "C$_{2-3}$ alkenyl" have an analogous meaning.

The term "alkynyl" includes both branched and straight chain unsaturated hydrocarbon groups containing at least two carbon atoms joined by a triple bond. The alkyne acetylyene is represented, for example, by "CHCH" or alternatively, by "HC≡CH". "C$_{2-5}$ alkynyl" (or "C$_2$-C$_5$ alkynyl") for example, means linear or branched chain alkynyl groups having from 2 to 5 carbon atoms and includes all of the pentynyl isomers as well as 1-butynyl, 2-butynyl, 3-butynyl, 1-propynyl, 2-propynyl, and ethynyl (or acetylenyl). Similar terms such as "C$_{2-3}$ alkynyl" have an analogous meaning.

Unless otherwise specifically noted as only "unsubstituted" or only "substituted", alkyl, alkenyl and alkynyl groups are unsubstituted or substituted with 1 to 3 substituents on each carbon atom, with halo, C$_1$-C$_{20}$ alkyl, CF$_3$, NH$_2$, N(C$_1$-C$_6$ alkyl)$_2$, NO$_2$, oxo, CN, N3, —OH, —O(C$_1$-C$_6$ alkyl), C$_3$-C$_{10}$ cycloalkyl, C$_2$-C$_6$ alkenyl, C$_2$-C$_6$ alkynyl, (C$_0$-C$_6$ alkyl) S(O)$_{0-2}$—, (C$_0$-C$_6$ alkyl)S(O)$_{0-2}$(C$_0$-C$_6$ alkyl)-, (C$_0$-C$_6$ alkyl)C(O)NH—, H$_2$N—C(NH)—, —O(C$_1$-C$_6$ alkyl) CF$_3$, (C$_0$-C$_6$ alkyl)C(O)—, (C$_0$-C$_6$ alkyl)OC(O)—, (C$_0$-C$_6$ alkyl)O(C$_1$-C$_6$ alkyl)-, (C$_0$-C$_6$ alkyl)C(O)$_{1-2}$(C$_0$-C$_6$ alkyl)-, (C$_0$-C$_6$ alkyl)OC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The term "C$_0$" as employed in expressions such as "C$_{0-6}$ alkyl" means a direct covalent bond. Similarly, when an integer defining the presence of a certain number of atoms in a group is equal to zero, it means that the atoms adjacent thereto are connected directly by a bond. For example, in the structure

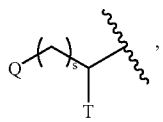

wherein s is an integer equal to zero, 1 or 2, the structure is

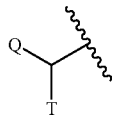

when s is zero.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "$C_{1-6}$ haloalkyl" (which may alternatively be referred to as "$C_1$-$C_6$ haloalkyl" or "halogenated $C_1$-$C_6$ alkyl") means a $C_1$ to $C_6$ linear or branched alkyl group as defined above with one or more halogen substituents. The term "$C_{1-4}$ haloalkyl" has an analogous meaning. The term "$C_{1-6}$ fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

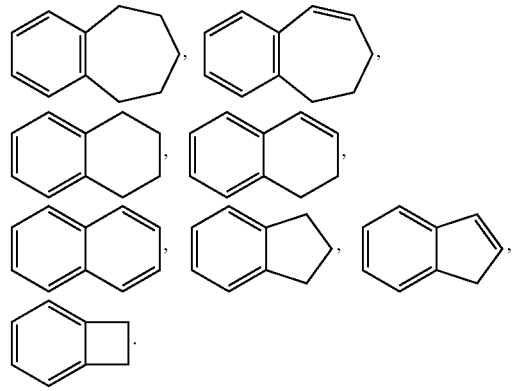

The term "aryl" refers to aromatic mono- and poly-carbocyclic ring systems, wherein the individual carbocyclic rings in the polyring systems are fused or attached to each other via a single bond. Suitable aryl groups include phenyl, naphthyl, and biphenylenyl.

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is independent of, or fused to, the other ring or rings and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. The heterocyclic ring may be attached at any heteroatom or carbon atom, provided that attachment results in the creation of a stable structure. When the heterocyclic ring has substituents, it is understood that the substituents may be attached to any atom in the ring, whether a heteroatom or a carbon atom, provided that a stable chemical structure results.

Unless otherwise specifically noted as only "unsubstituted" or only "substituted", cycloalkyl, aryl and heterocycle groups are unsubstituted or substituted. As used herein, the terms "substituted $C_3$-$C_{10}$ cycloalkyl", "substituted aryl" and "substituted heterocycle" are intended to include the cyclic group containing from 1 to 3 substituents in addition to the point of attachment to the rest of the compound. Preferably, the substituents are selected from the group which includes, but is not limited to, halo, $C_1$-$C_{20}$ alkyl, $CF_3$, $NH_2$, $N(C_1$-$C_6$ alkyl$)_2$, $NO_2$, oxo, CN, N3, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) $S(O)_{0-2}$—, aryl-$S(O)_{0-2}$—, ($C_0$-$C_6$ alkyl)$S(O)_{0-2}$($C_0$-$C_6$ alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. In the case of substituted heteroaryl rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e.,

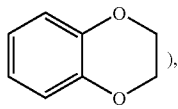), imidazo(2,1-b)(1,3)thiazole, (i.e.,

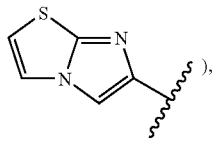), and benzo-1,3-dioxolyl (i.e.,

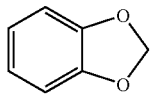),

In certain contexts herein,

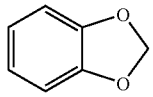

is alternatively referred to as phenyl having as a substituent methylenedioxy attached to two adjacent carbon atoms.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

In compounds of the invention having N-oxide moieties, e.g., pyridyl N-oxide moieties, the N-oxide moiety is structurally depicted using conventional representations. For example, a pyridyl-N-oxide portion is structurally depicted as

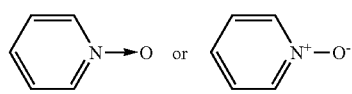

which have equivalent meanings.

For variable definitions containing terms having repeated terms, e.g., $(CR^iR^j)_r$, where r is the integer 2, $R^i$ is a defined variable, and $R^j$ is a defined variable, the value of $R^i$ may differ in each instance in which it occurs, and the value of $R^j$ may differ in each instance in which it occurs. For example, if $R^i$ and $R^j$ are independently selected from the group consisting of methyl, ethyl, propyl and butyl, then $(CR^iR^j)_2$ can be

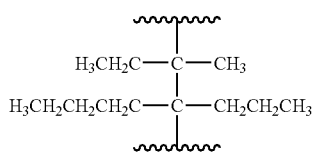

Pharmaceutically acceptable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hydro-scopicity and solubility. As will be understood by those skilled in the art, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are crystal forms, hydrates and solvates of the compounds of Formula I.

Methods for preparing the compounds of this invention are illustrated in the following schemes. Other synthetic protocols will be readily apparent to those skilled in the art. The examples illustrate the preparation of the compounds of Formula I and as such are not to be considered as limiting the invention set forth in the claims appended hereto. Example described hereinafter comprises a further embodiment of the present invention.

SCHEME 1

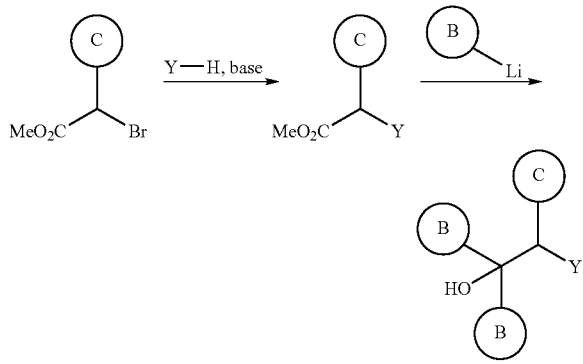

The variables C, B, and Y in the scheme are as defined in "Formula I".

EXAMPLE 1

(±)-2-Morpholin-4-yl-2-phenyl-1,1-dipyridin-3-yl-ethanol

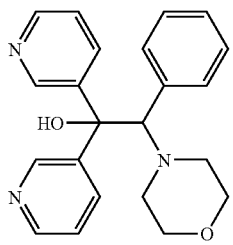

Step A:

Methyl α-bromophenylacetate (3.79 g, 16.5 mmol) was dissolved in 50 mL of dry ACN, to which triethylamine (3.46 mL, 24.8 mmol) and morpholine (1.73 mL, 19.8 mmol) were added and the mixture was stirred for 18 hours. The mixture was poured into water, extracted twice with EtOAc. The combined organic extracts were dried with $Na_2SO_4$, filtered and concentrated in vacuo, providing methyl morpholin-4-yl (phenyl)acetate. ESI+MS: 236.2 $[M+H]^+$.

Step B:

3-Bromopyridine (8.37 mL, 13.9 mmol) was dissolved in 350 mL of dry $Et_2O$ and was cooled to −78° C. n-Butyl lithium (35.1 mL, 2.5M solution in hexanes, 87.8 mmol) was added dropwise via an addition funnel over 30 minutes. After stirring for 15 minutes, a 50 mL (4:1; $Et_2O$/THF) solution of methyl morpholin-4-yl-(phenyl)acetate (6.88 g, 29.3 mmol) was added dropwise over 30 minutes. The reaction was stirred for 1 hour at −78° C. and was warmed to 0° C. and stirred for 30 minutes. The reaction was quenched with $NaHCO_3$(aq sat) and poured into $NaHCO_3$(aq sat), extracted 3× with EtOAc, dried $Na_2SO_4$, filtered and concentrated in vacuo. The residue was purified by silica gel chromatography (100/0/0 to 92/8/0.8 $CH_2Cl_2$/MeOH $NO_4OH$) to provide the titled compound.

$^1$H NMR (500 MHz, $CDCl_3$): δ 9.01 (d, J=1.9 Hz, 1H), 6.53 (dd, J=2.4, 0.7 Hz, 1H), 8.48 (dd, J=4.6, 1.5 Hz, 1H), 8.16 (dd, J=4.8, 1.6 Hz, 1H), 8.02 (dt, J=8.0, 2.3 Hz, 1H), 7.58 (d, J=8.3 Hz, 1H), 7.30-7.22 (m, 3H), 7.16-7.08 (m, 3H), 6.95 (dd, J=8.1, 4.9 Hz, 1H), 5.63 (br s, 1H), 4.55 (s, 1H), 3.59-3.51 (m, 4H), 2.41 (br dt, J=12.0, 4.7 Hz, 2H), 2.18 (br dt, J=11.7, 4.8 Hz, 2H). HRMS [M+H] $C_{22}H_{24}N_3O_2$ calcd 362.1863, found 362.1851.

The following compounds were made according to Scheme 1, where intermediates in the scheme were modified according to literature methods. Example 2 was isolated from a reaction of 2-pyridyllithium (prepared from 2-bromopyridine and t-butyl lithium) with methyl 3-morpholin-4-yl-3-phenylpropanoate. Example 51 was prepared from the corresponding secondary alcohol tert-butyldimethylsilyl ether by standard deprotection. Unless otherwise shown, structures of compounds in Examples 2-51, 58-121, 4-1 to 4-21, 123-201, 202-302, and 5-1 listed in the tables are represented by defining variables

and "Y" of the structure

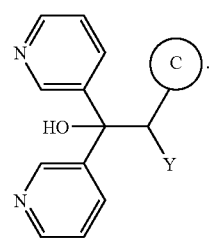

EXAMPLES 2-51

| Example | Compound | Name | MS (M + 1) |
|---|---|---|---|
| 2 | | (±)-3,3-dimethyl-1-morpholin-4-yl-1-phenyl-2-pyridin-2-ylbutan-2-ol (diastereomer A) | 363.2069 (M + Na⁺) |

-continued
| Example | Compound | Name | MS (M + 1) |
|---|---|---|---|
| 3 | 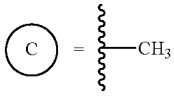 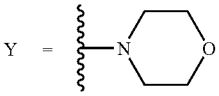 | (±)-2-morpholin-4-yl-1,1-dipyridin-3-ylpropan-1-ol | 300.1701 |
| 4 | 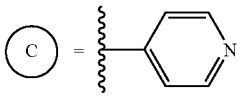 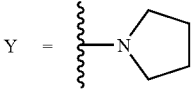 | (±)-1,1-dipyridin-3-yl-2-pyridin-4-yl-2-pyrrolidin-1-ylethanol | 347.1867 |
| 5 | 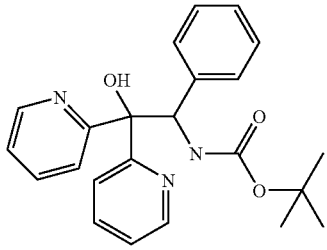 | (±)-tert-butyl(2-hydroxy-1-phenyl-2,2-dipyridin-2-ylethyl)carbamate | 392.1966 |
| 6 | 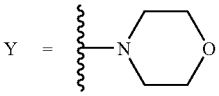  | (±)-2-morpholin-4-yl-1,1-dipyridin-3-ylbutan-1-ol | 314.1864 |
| 7 | 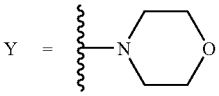 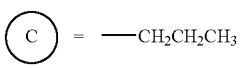 | (±)-2-morpholin-4-yl-1,1-dipyridin-3-ylpentan-1-ol | 328.2019 |
| 8 | 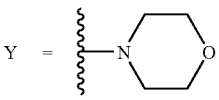 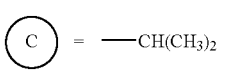 | (±)-3-methyl-2-morpholin-4-yl-1,1-dipyridin-3-ylbutan-1-ol | 328.2019 |
| 9 | 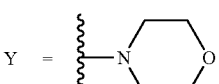 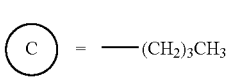 | (±)-2-morpholin-4-yl-1,1-dipyridin-3-ylhexan-1-ol | 342.2173 |

-continued

| Example | Compound | Name | MS (M + 1) |
|---|---|---|---|
| 10 |  C = —(CH₂)₄CH₃<br><br>Y = 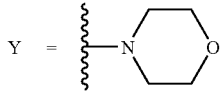 | (±)-2-morpholin-4-yl-1,1-dipyridin-3-ylheptan-1-ol | 356.2330 |
| 11 |  C = —(CH₂)₅CH₃<br><br>Y = 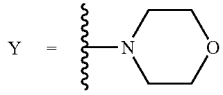 | (±)-2-morpholin-4-yl-1,1-dipyridin-3-yloctan-1-ol | 370.2487 |
| 12 |  C = —CH₂CH₂—<br><br>Y = 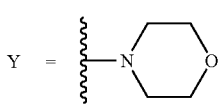 | (±)-2-morpholin-4-yl-4-phenyl-1,1-dipyridin-3-ylbutan-1-ol | 390.2176 |
| 13 |  C = <br><br>Y = —N(CH₃)(CH₂CH₂OCH₃) | (±)-2-[(2-methoxyethyl)(methyl)amino]-2-phenyl-1,1-dipyridin-3-ylethanol | 364.2027 |
| 14 |  C = <br><br>Y = —N(CH₂CH₂OCH₃)₂ | (±)-2-[bis(2-methoxyethyl)amino]-2-phenyl-1,1-dipyridin-3-ylethanol | 408.2279 |
| 15 |  C = <br><br>Y = 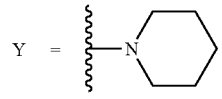 | (±)-2-phenyl-2-piperidin-1-yl-1,1-dipyridin-3-ylethanol | 360.2072 |
| 16 |  C = <br><br>Y = 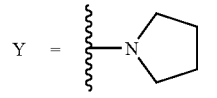 | (±)-2-phenyl-1,1-dipyridin-3-yl-2-pyrrolidin-1-ylethanol | 346.1910 |

-continued

| Example | Compound | Name | MS (M + 1) |
|---|---|---|---|
| 17 | C = 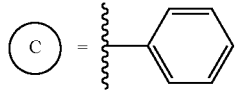<br><br>Y =  | (±)-tert-butyl 4-(2-hydroxy-1-phenyl-2,2-dipyridin-3-ylethyl)piperazine-1-carboxylate | 461.2537 |
| 18 | C = 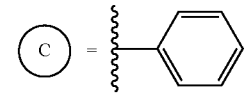<br><br>Y = 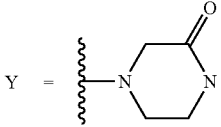 | (±)-4-(2-hydroxy-1-phenyl-2,2-dipyridin-3-ylethyl)piperazin-2-one | 375.1803 |
| 19 | C = 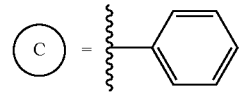<br><br>Y = 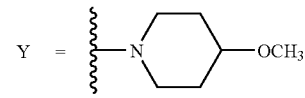 | (±)-2-(4-methoxypiperidin-1-yl)-2-phenyl-1,1-dipyridin-3-ylethanol | 390.2167 |
| 20 | C = 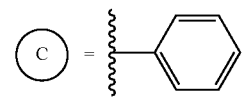<br><br>Y = 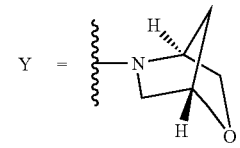 | 2-[(1S,4S)-2-oxa-5-azabicyclo[2.2.1]hept-5-yl]-2-phenyl-1,1-dipyridin-3-ylethanol(1:1 mixture diastereomers) | 374.1846 |
| 21 | C = 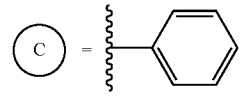<br><br>Y = 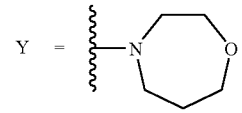 | (±)-2-(1,4-oxazepan-4-yl)-2-phenyl-1,1-dipyridin-3-ylethanol | 376.2001 |
| 22 | C = 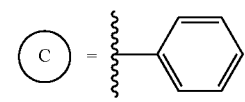<br><br>Y = 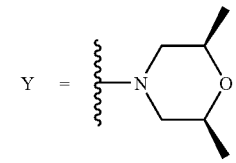 | (±)-2-[(2R,6S)-2,6-dimethylmorpholin-4-yl]-2-phenyl-1,1-dipyridin-3-ylethanol | 390.2168 |

-continued

| Example | Compound | Name | MS (M + 1) |
|---|---|---|---|
| 23 | 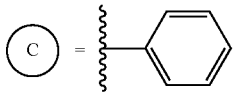 Y = —N(CH₃)((CH₂)₃OCH₃) | (±)-2-[(3-methoxypropyl)(methyl)amino]-2-phenyl-1,1-dipyridin-3-ylethanol | 378.2167 |
| 24 | 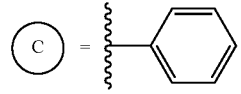 | (±)-2-phenyl-1,1-dipyridin-3-yl-2-thiomorpholin-4-ylethanol | 378.1617 |
| 25 | 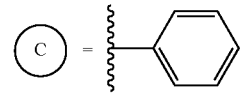 | (±)-2-azetidin-1-yl-2-phenyl-1,1-dipyridin-3-ylethanol | 332.1760 |
| 26 | 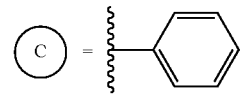 Y = —N(CH₃)₂ | (±)-2-(dimethylamino)-2-phenyl-1,1-dipyridin-3-ylethanol | 320.1752 |
| 27 | 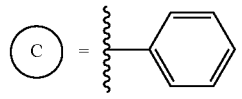 Y = —N(CH₂CH₃)₂ | (±)-2-(diethylamino)-2-phenyl-1,1-dipyridin-3-ylethanol | 348.2064 |
| 28 | 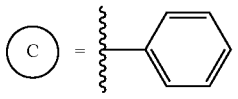 Y = —N(CH₃)OCH₃ | (±)-2-[methoxy(methyl)amino]-2-phenyl-1,1-dipyridin-3-ylethanol | 336.1698 |
| 29 | 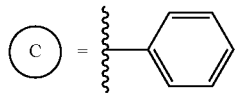 | (±)-2-(7-azabicyclo[2.2.1]hept-7-yl)-2-phenyl-1,1-dipyridin-3-ylethanol | 372.2061 |

-continued

| Example | Compound | Name | MS (M + 1) |
|---|---|---|---|
| 30 | 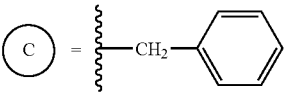 | (±)-2-morpholin-4-yl-3-phenyl-1,1-dipyridin-3-ylpropan-1-ol | 376.2035 |
| 31 | 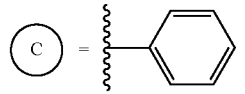 | (±)-2-(3,3-difluoropyrrolidin-1-yl)-2-phenyl-1,1-dypyridin-3-ylethanol | 382.1717 |
| 32 | 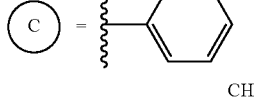 | (±)-2-(3,3-dimethylpyrrolidin-1-yl)-2-phenyl-1,1-dipyridin-3-ylethanol | 374.2210 |
| 33 |  | (±)-2-(2,5-dihydro-1H-pyrrol-1-yl)-2-phenyl-1,1-dipyridin-3-ylethanol | 344.1762 |
| 34 |  | (±)-2-phenyl-1,1-dipyridin-3-yl-2-[2-(trifluoromethyl)pyrrolidin-1-yl]ethanol(diastereomer A) | 414.1798 |
| 35 |  | (±)-2-phenyl-1,1-dipyridin-3-yl-2-[2-(trifluoromethyl)pyrrolidin-1-yl]ethanol(diastereomer B) | 414.1810 |

-continued

| Example | Compound | Name | MS (M + 1) |
|---|---|---|---|
| 36 | 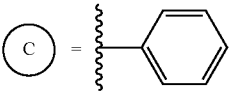 C = phenyl, Y = 2-isopropylpyrrolidin-1-yl | (±)-2-(2-isopropylpyrrolidin-1-yl)-2-phenyl-1,1-dipyridin-3-ylethanol (diastereomer A) | 388.3 |
| 37 | 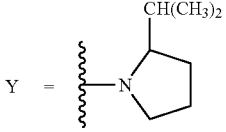 C = phenyl, Y = 2-isopropylpyrrolidin-1-yl | (±)-2-(2-isopropylpyrrolidin-1-yl)-2-phenyl-1,1-dipyridin-3-ylethanol (diastereomer B) | 388.3 |
| 38 | 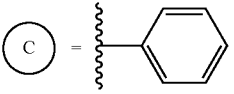 C = 3-bromophenyl, Y = morpholin-4-yl | (±)-2-(3-bromophenyl)-2-morpholin-4-yl-1,1-dipyridin-3-ylethanol | 440.0978 |
| 39 | 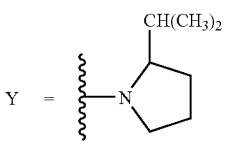 C = cyclopropyl (R), Y = pyrrolidin-1-yl | (2R)-2-cyclopropyl-1,1-dipyridin-3-yl-2-pyrrolidin-1-ylethanol | 310.1915 |
| 40 | 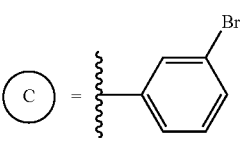 C = cyclopropyl (S), Y = pyrrolidin-1-yl | (2S)-2-cyclopropyl-1,1-dipyridin-3-yl-2-pyrrolidin-1-ylethanol | 310.1913 |
| 41 | 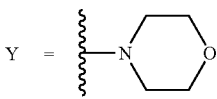 C = phenyl, Y = N(cyclohexyl)(CH$_2$CH$_3$) | (±)-2-[cyclohexyl(ethyl)amino]-2-phenyl-1,1-dipyridin-3-ylethanol | 402.2542 |

-continued

| Example | Compound | Name | MS (M + 1) |
|---|---|---|---|
| 42 | C =   Y = 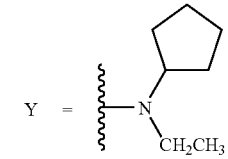 | (±)-2-[cyclopentyl(ethyl)amino]-2-phenyl-1,1-dipyridin-3-ylethanol | 388.2376 |
| 43 | C =   Y = 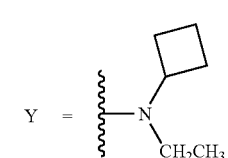 | (±)-2-[cyclobutyl(ethyl)amino]-2-phenyl-1,1-dipyridin-3-ylethanol | 374.2234 |
| 44 | C =   Y = 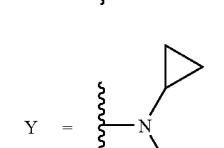 | (±)-2-[cyclopropyl(ethyl)amino]-2-phenyl-1,1-dipyridin-3-ylethanol | 360.2067 |
| 45 | C =   Y = 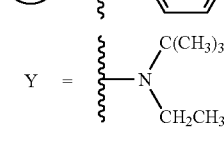 | (±)-2-[tert-butyl(ethyl)amino]-2-phenyl-1,1-dipyridin-3-ylethanol | 376.2378 |
| 46 | C =   Y = 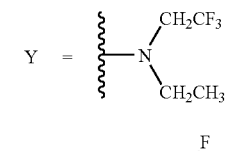 | (±)-2-[ethyl(2,2,2-trifluoroethyl)amino]-2-phenyl-1,1-dipyridin-3-ylethanol | 402.1807 |
| 47 | C = 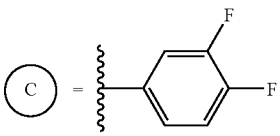  Y = 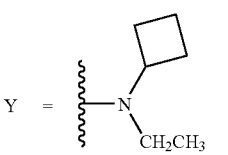 | (±)-2-[cyclobutyl(ethyl)amino]-2-(3,4-difluorophenyl)-1,1-dipyridin-3-ylethanol | 410.2053 |

-continued

| Example | Compound | Name | MS (M + 1) |
|---|---|---|---|
| 48 | C = phenyl; Y = ·····NHC(O)OC(CH₃)₃ | tert-butyl(1S)-2-hydroxy-1-phenyl-2,2-dipyridin-3-ylethylcarbamate | 392.1986 |
| 49 | C = phenyl; Y = ◄NHC(O)OC(CH₃)₃ | tert-butyl(1R)-2-hydroxy-1-phenyl-2,2-dipyridin-3-ylethylcarbamate | 392.1985 |
| 50 | C = phenyl; Y = 3-fluoropyrrolidin-1-yl | (±)-2-(3-fluoropyrrolidin-1-yl)-2-phenyl-1,1-dipyridin-3-ylethanol (1:1 mixture diastereomers) | 364.1813 |
| 51 | C = phenyl; Y = 3-hydroxypyrrolidin-1-yl | (±)-1-(2-hydroxy-1-phenyl-2,2-dipyridin-3-ylethyl)pyrrolidin-3-ol (1:1 mixture diastereomers) | 362.1879 |

The variables C, B, A, and Y in the scheme are as defined in "Formula I".

SCHEME 2

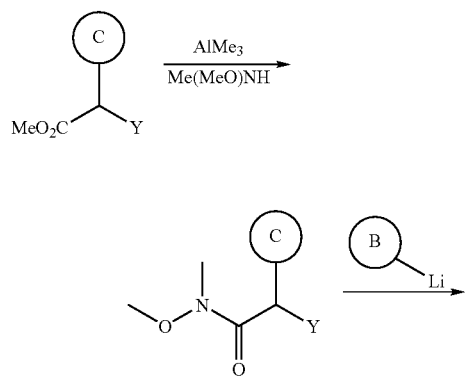

EXAMPLE 52

(±)-2-Morpholin-4-yl-1,2-diphenyl-1-pyridin-2-yl-ethanol (diastereomer A)

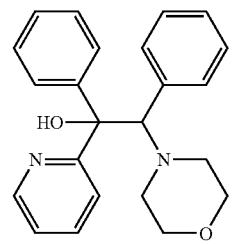

Step A:

N,O-Dimethylhydroxylamine hydrochloride (1.66 g, 17.0 mmol) was suspended in 20 mL of dry TVF and cooled to 0° C. Trimethylaluminum (8.50 mL, 2.0M solution in toluene, 17.0 mmol) was added slowly and stirred for 30 minutes. Methyl morpholin-4-yl-(phenyl)acetate (1.00 g, 4.25 mmol) was added to the cooled mixture in an 8 mL TIFF solution. The reaction was allowed to warm to ambient temperature while for 18 hours. The mixture was poured into 1N HCl(aq)

and stirred for 1 hour. The mixture was then poured into NaHCO$_3$(sat) and extracted 3× with EtOAc. The combined organic layers were washed 1× with brine, dried with Na$_2$SO$_4$, filtered and concentrated in vacuo to provide N-methoxy-N-methyl-2-morpholin-4-yl-2-phenylacetamide. HRMS [M+H] C$_{14}$H$_{21}$N$_2$O$_3$ calc'd 265.1547. found 265.1553.

Step B:

N-Methoxy-N-methyl-2-morpholin-4-yl-2-phenylacetamide (215 mg, 0.813 mmol) was dissolved in 10 mL of dry THF and cooled to −78° C. In a separate flask, 2-bromopyridine (97 μL, 1.0 mmol) was dissolved in 5 mL of dry THF and cooled to −78° C., to which was added tert-Butyl lithium (1.20 mL, 1.7M solution in pentane, 2.0 mmol) dropwise. After stirring for 30 minutes, the mixture transferred to the amide flask dropwise and stirred for approximately one hour. The mixture was quenched with NaHCO$_3$(sat), warmed to ambient temperature and poured into water. The aqueous layer was extracted 3× with EtOAc and the combined organic extracts were dried with Na$_2$SO$_4$, filtered and concentrated in vacuo. The residue was purified by silica gel chromatography (100/0/0 to 9/1/0.1 CH$_2$Cl$_2$/MeOH/NH$_4$OH), providing partially purified titled product. The residue was further purified by preparative reverse phase HPLC. The appropriate fractions were poured into NaHCO$_3$(aq sat) and extracted twice with EtOAc. The combined organic extracts were dried with Na$_2$SO$_4$, filtered and concentrated in vacuo to provide 2-morpholin-4-yl-2-phenyl-1-pyridin-2-ylethanone. ESI+MS: 283.1 [M+H]+.

Step C:

2-Morpholin-4-yl-2-phenyl-1-pyridin-2-yl-ethanone (15 mg, 0.053 mmol) was dissolved in 3 mL of dry THF and cooled to −78° C. Phenylmagnesium bromide (159 μL, 1.0 M solution in TBH, 0.159 mmol) was added dropwise and the mixture was allowed to stir for 15 minutes. The reaction was quenched with 1 mL of aqueous NaHCO$_3$(sat) and warmed to ambient temperature. The mixture was poured into NaHCO$_3$(sat) and extracted 2× with EtOAc. The combined organic extracts were dried with Na$_2$SO$_4$, filtered and concentrated in vacuo. The residue was purified by preparative HPLC. The appropriate fractions were poured into NaHCO$_3$(sat) and extracted 2× with EtOAc. The combined organic extracts were dried with Na$_2$SO$_4$, filtered and concentrated in vacuo to provide the titled compound.

$^1$H NMR (500 MHz, CDCl$_3$): δ 8.19 (d, J=4.6 Hz, 1H), 7.86 (d, J=7.6 Hz, 2H), 7.47-7.41 (m, 2H), 7.36-7.28 (m, 4H), 7.22 (t, J=7.2 Hz, 1H), 7.13-7.05 (m, 2H), 6.86 (ddd, J=6.5, 4.9, 1.4 Hz, 1H), 6.28 br s, 1H), 4.62 (br s, 1H), 3.56-3.39 (br m, 4H), 2.65-2.60 (br m, 2H), 2.42-2.20 (br m, 2H). HRMS [M+H] C$_{23}$H$_{25}$N$_2$O$_2$ calc'd 361.1911, found 361.1914.

The following compounds were made according to Scheme 2, where intermediates in the scheme were modified according to literature methods.

EXAMPLES 53-55

| Example | Compound | Name | MS (M + 1) |
|---|---|---|---|
| 53 | | 2-morpholin-4-yl-2-phenyl-1-pyridin-2-yl-1-pyridin-3-ylethanol(diastereomer A) | 362.1857 |
| 54 | | (±)-3-methyl-2-morpholin-4-yl-1-phenyl-1-pyridin-3-ylbutan-1-ol(diastereomer A) | 327.2079 |
| 55 | | (±)-3-methyl-2-morpholin-4-yl-1-phenyl-1-pyridin-2-ylbutan-1-ol(diastereomer A) | 327.2079 |

SCHEME 3

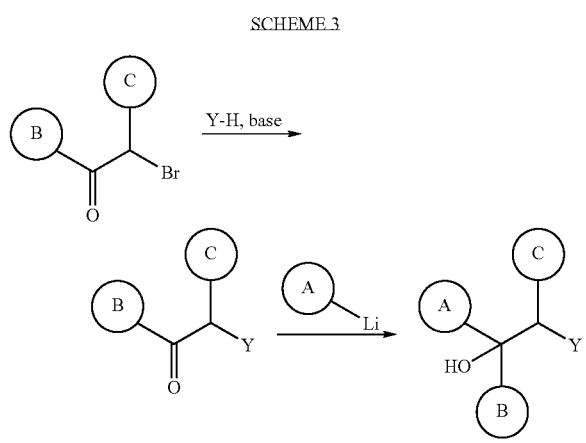

The variables C, B, A, and Y in the scheme are as defined in "Formula I".

The following compound was made according to Scheme 3.

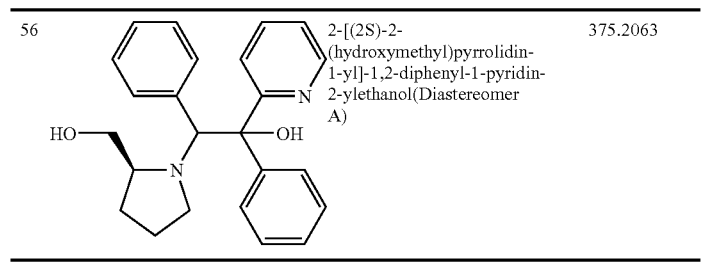

| 56 | | 2-[(2S)-2-(hydroxymethyl)pyrrolidin-1-yl]-1,2-diphenyl-1-pyridin-2-ylethanol(Diastereomer A) | 375.2063 |

SCHEME 4

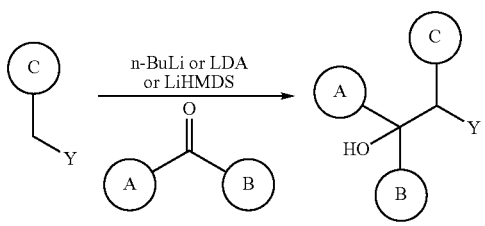

The variables C, B, A, and Y in the scheme are as defined in "Formula I".

EXAMPLE 57

(±)-1-[1-(4-Fluorophenyl)-2-hydroxy-2,2-dipridin-3-ylethyl]pyridin-2(1H)-one

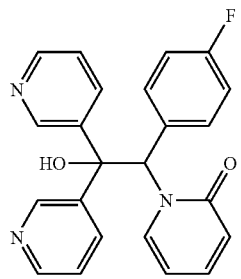

Step A:

n-BuLi (42 mL, 1.6M, 67 mmol) was added to a solution of 3-bromopyridine (5.9 mL, 9.74 g, 62 mmol) in ether (200 mL) at −78 C. The resulting yellow suspension was stirred for 1 h. A solution of nicotinaldehyde (5.3 mL, 6 g, 56 mmol) in ether (25 mL) was then added. After stirring for 0.5 h, the reaction mixture was allowed to warm gradually to 0 C. The reaction mixture was then quenched by addition of half saturated brine (100 mL). The resulting mixture was extracted once with ethyl acetate and once with chloroform. Drying (1:1 $Na_2SO_4$/$K_2CO_3$) and concentration gave dipyridin-3-ylmethanol as a very viscous orange oil which was used without further purification.

$^1$HNMR ($CD_3OD$, 400 MHz) δ 8.58 (d, 2H, J=1.74 Hz); 8.42 (dd, 2H, J=1.28, 4.85 Hz); 7.82 (m, 2H); 7.39 (m, 2H); 5.93 (s, 1H).

Step B:

To a solution of dipyridin-3-ylmethanol (9 g, 48 mmol) in 9:1 methylene chloride/acetonitrile (100 mL) was added powdered 4A molecular sieves (24 g) and NMO (8.5 g, 72 mmol). The resulting mixture was cooled in an ice bath and TPAP (0.85 g, 2.4 mmol) added carefully in 3 portions at 5 min intervals. After stirring for 15 min the ice bath was removed and stirring was continued at RT. After stirring for 3 days, the reaction mixture was filtered through Celite and the cake washed well with methylene chloride and then chloroform. The filtrate was concentrated to approximately ⅓ the original volume then silica gel was added. The remaining solvent was removed leaving the crude material adsorbed onto the silica gel as a dark green powder. This powder was layered on top of an equal volume of silica gel in a Buchner funnel and flushed with ether. These washings were discarded. The silica pad was then flushed repeatedly first with methylene chloride then with chloroform until no further product eluted. The dark red filtrate was concentrated to give a red brown solid. Trituration with ether gave dipyridin-3-ylmethanone as a white powder. The mother liquors were stripped and the residue chromatographed (eluting with 24:1 methylene chloride/methanol). The fractions enriched in product were combined, stripped, and the residue triturated with ether to give a second crop of pure ketone.

$^1$HNMR ($CD_3OD$, 400 MHz) δ 8.92 (m, 2H); 8.79 (m, 2H); 8.22 (m, 2H); 7.61 (m, 2H).

Step C:

NaH (0.61 g, 25 mmol) was added to a solution of 2-hydroxypyridine (2 g, 21 mmol) in DMF (20 mL) at 0 C. After stirring for 15 min, p-fluorobenzyl bromide (4.4 g, 2.9 mmol, 23 mmol) was added and the reaction mixture allowed to warm gradually to RT. The reaction mixture was quenched by addition of ice then poured into ether and extracted several times with ice water. The organic phase was then dried over Na$_2$SO$_4$, concentrated and the resulting yellow oil purified by normal phase Gilson chromatography eluting with 10% DCM, 70% Hexane, 20% EtOAc. 1-(4-Fluorobenzyl)pyridin-2(1H)-one was isolated as a white solid.

$^1$HNMR (CD$_3$OD, 400MHz) δ 7.67 (m, 1H); 7.50 (m, 1H); 7.34 (m, 2H); 7.05 (m, 2H); 6.54 (m, 1H); 6.37 (m, 1H); 5.15 (s, 2H).

Step D:

A solution of dipyridin-3-ylmethanone (1 g, 5.9 mmol) and 1-(4-fluorobenzyl)pyridin-2(1H)-one (1 g, 4.9 mmol) in THF (50 mL) was cooled to −78 C. To the resulting white suspension was added in a dropwise manner, LiHMDS (1M in THF, 6 mL). The resulting cream suspension was stirred for 30 min then allowed to warm up gradually to −30 C over 1 h. The reaction mixture was quenched with saturated NaHCO$_3$ and then it was extracted once with ether and once with ethyl acetate. The combined extracts were dried over Na$_2$SO$_4$ and concentrated. The resulting yellow oil was purified by normal phase Gilson chromatography eluting with 98% DCM, 2% methanol. The product was isolated as a white solid.

$^1$HNMR (CD$_3$OD, 400 MHz) δ 8.63 (s, 1H); 8.49 (br s, 1H); 8.36 (m, 3H); 7.93 (m, 1H); 7.75 (br s, 1H); 7.54 (br s, 2H); 7.34 (m, 3H); 7.15 (br s, 1H); 6.96 (m, 2H); 6.29 (m, 2H).

The following compounds were made according to Scheme 4, where intermediates in the scheme were modified according to literature methods. Examples 58-64 were prepared from 1-benzylpyrrolidine and the requisite ketone using the method of Kessar (*Chem Rev.* 1997, 97, 721). Example 120 was prepared by trifluoroacetic acid deprotection of the corresponding 1-(2,4-dimethoxybenzyl)-3-methyl-1H-pyrazol-1-yl derivative. Example 121 was prepared by hydrogenation of the corresponding pyridinone ring benzyl ether.

EXAMPLES 58-121 AND 4-1 to 4-21

| Example | Compound | Name | MS (M + 1) |
|---|---|---|---|
| 58 | | (±)-1-(1H-indol-4-yl)-2-phenyl-1-pyridin-2-yl-2-pyrrolidin-1-ylethanol (1:1 mixture of diastereomers) | 384.2059 |
| 59 | | (±)-1,2-diphenyl-1-pyridin-2-yl-2-pyrrolidin-1-ylethanol (diastereomer a) | 345.1966 |
| 60 | | (±)-1-(4-methoxypyridin-2-yl)-1,2-diphenyl-2-pyrrolidin-1-ylethanol (diastereomer a) | 375.2063 |
| 61 | | (±)-1-phenyl-2-pyridin-2-yl-1-pyrrolidin-1-ylbutan-2-ol (diastereomer A) | 297.1962 |

| Example | Compound | Name | MS (M + 1) |
|---|---|---|---|
| 62 | | (±)-1-phenyl-2-pyridin-2-yl-1-pyrrolidin-1-ylbutan-2-ol (diastereomer B) | 297.1959 |
| 63 | | (±)-1-phenyl-2-pyridin-2-yl-1-pyrrolidin-1-ylpropan-2-ol | 283.1808 |
| 64 | | (±)-2-phenyl-2-(phenylsulfonyl)-1,1-dipyridin-3-ylethanol | 417.1257 |
| 65 | | (±)-ethyl 3-hydroxy-3-phenyl-3-pyridin-2-yl-2-pyrrolidin-1-ylpropanoate (diastereomer A) | 341.1855 |
| 66 | C = —C(O)N(CH₃)₂ ; Y = —N(pyrrolidine) | (±)-3-hydroxy-N,N-dimethyl-3,3-dipyridin-3-yl-2-pyrrolidin-1-ylpropanamide | 341.2 |
| 67 | C = —C(O)—N(morpholine) ; Y = —N(pyrrolidine) | (±)-3-morpholin-4-yl-3-oxo-1,1-dipyridin-3-yl-2-pyrrolidin-1-ylpropan-1-ol | 383.2070 |

-continued

| Example | Compound | Name | MS (M + 1) |
|---|---|---|---|
| 68 |  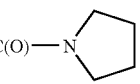 | (±)-3-oxo-1,1-dipyridin-3-yl-2,3-dipyrrolidin-1-ylpropan-1-ol | 367.2124 |
| 69 | 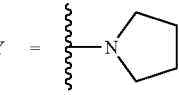  | (±)-2-(1,3-dimethyl-1H-1,2,4-triazol-5-yl)-1,1-dipyridin-3-yl-2-pyrrolidin-1-ylethanol | 365.2090 |
| 70 | 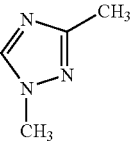 | (±)-1,2-diphenyl-2-(1H-pyrazol-1-yl)-1-pyridin-4-ylethanol (diastereomer A) | 342.1598 |
| 71 | 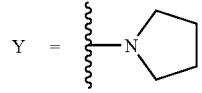 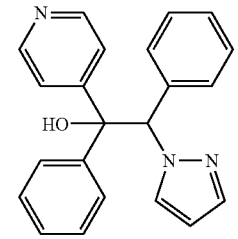 | (±)-2-(1,3-dimethyl-1H-1,2,4-triazol-5-yl)-1,1-dipyridin-3-yl-2-pyrrolidin-1-ylethanol | 365.2090 |
| 72 |  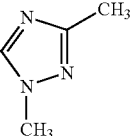 | (±)-4-ethyl-5-(2-hydroxy-2,2-dipyridin-3-yl-1-pyrrolidin-1-ylethyl)-2,4-dihydro-3H-1,2,4-triazol-3-one | 381.2025 |
| 73 | 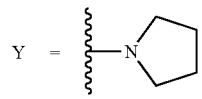  | (±)-3-[1-(4-fluorophenyl)-2-hydroxy-2,2-dipyridin-3-ylethyl]-1,3-oxazolidin-2-one | 380.1444 |

-continued

| Example | Compound | Name | MS (M + 1) |
|---|---|---|---|
| 74 | C = phenyl; Y = 1,3-oxazolidin-2-on-3-yl 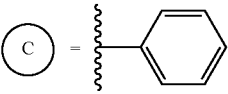 | (±)-3-(2-hydroxy-1-phenyl-2,2-dipyridin-3-ylethyl)-1,3-oxazolidin-2-one | 362.1542 |
| 75 | C = 3-cyanophenyl; Y = 1,3-oxazolidin-2-on-3-yl 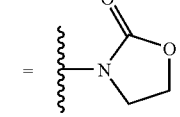 | (±)-3-[2-hydroxy-1-(2-oxo-1,3-oxazolidin-3-yl)-2,2-dipyridin-3-ylethyl]benzonitrile | 387.1464 |
| 76 | C = 4-fluorophenyl; Y = 3-methylimidazolidin-2-on-1-yl 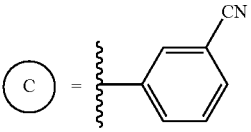 | (±)-1-[1-(4-fluorophenyl)-2-hydroxy-2,2-dipyridin-3-ylethyl]-3-methylimidazolidin-2-one | 393.1767 |
| 77 | C = 4-fluorophenyl; Y = 3-tert-butylimidazolidin-2-on-1-yl 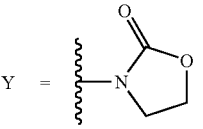 | (±)-1-tert-butyl-3-[1-(4-fluorophenyl)-2-hydroxy-2,2-dipyridin-3-ylethyl]imidazolidin-2-one | 435.2203 |
| 78 | C = pyridin-2-yl; Y = 1,3-oxazolidin-2-on-3-yl 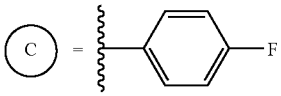 | (±)-3-(2-hydroxy-1-pyridin-2-yl-2,2-dipyridin-3-ylethyl)-1,3-oxazolidin-2-one | 363.1 |
| 79 | C = pyridin-2-yl; Y = 1H-pyrazol-1-yl 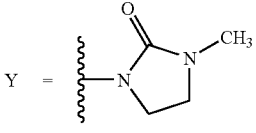 | (±)-2-(1H-pyrazol-1-yl)-2-pyridin-2-yl-1,1-dipyridin-3-ylethanol | 344.1502 |

-continued

| Example | Compound | Name | MS (M + 1) |
|---|---|---|---|
| 80 | 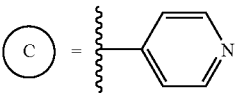 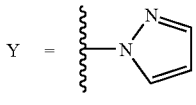 | (±)-2-(1H-pyrazol-1-yl)-1,1-dipyridin-3-yl-2-pyridin-4-ylethanol | 344.1507 |
| 81 | 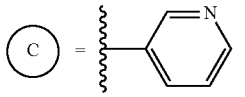 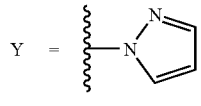 | (±)-2-(1H-pyrazol-1-yl)-1,1,2-tripyridin-3-ylethanol | 344.1504 |
| 82 | 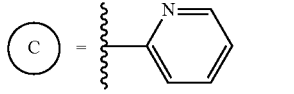 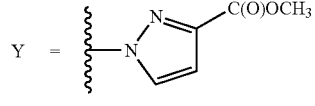 | (±)-methyl 1-(2-hydroxy-1-pyridin-2-yl-2,2-dipyridin-3-ylethyl)-1H-pyrazole-3-carboxylate | 402.1558 |
| 83 | 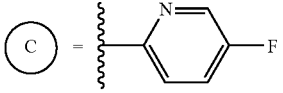 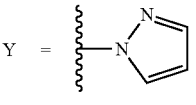 | (±)-2-(5-fluoropyridin-2-yl)-2-(1H-pyrazol-1-yl)-1,1-dipyridin-3-ylethanol | 362.1413 |
| 84 | 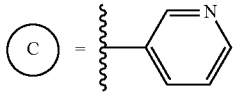 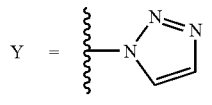 | (±)-1,1,2-tripyridin-3-yl-2-(1H-1,2,3-triazol-1-yl)ethanol | 345.1463 |
| 85 | 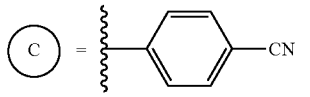 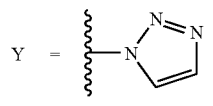 | (±)-4-[2-hydroxy-2,2-dipyridin-3-yl-1-(2H-1,2,3-triazol-2-yl)ethyl]benzonitrile | 369.1456 |
| 86 | 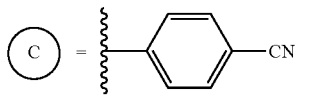 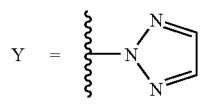 | (±)-4-[2-hydroxy-2,2-dipyridin-3-yl-1-(1H-1,2,3-triazol-1-yl)ethyl]benzonitrile | 369.1457 |

-continued

| Example | Compound | Name | MS (M + 1) |
|---|---|---|---|
| 87 | C = <br>Y = 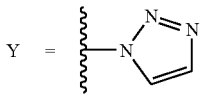 | (±)-3-[2-hydroxy-2,2-dipyridin-3-yl-1-(1H-1,2,3-triazol-1-yl)ethyl]benzonitrile | 369.1459 |
| 88 | C = <br>Y = 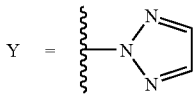 | (±)-3-[2-hydroxy-2,2-dipyridin-3-yl-1-(2H-1,2,3-triazol-2-yl)ethyl]benzonitrile | 369.1454 |
| 89 | C = <br>Y = 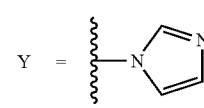 | (±)-2-(1H-imidazol-1-yl)-2-phenyl-1,1-dipyridin-3-ylethanol | 343.1553 |
| 90 | C = <br>Y = 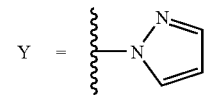 | (±)-(1-benzyl-1H-pyrazol-5-yl)(dipyridin-3-yl)methanol | 343.1554 |
| 91 | C = 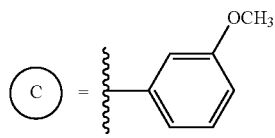<br>Y = 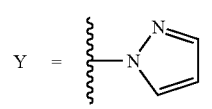 | (±)-2-(3-methoxyphenyl)-2-(1H-pyrazol-1-yl)-1,1-dipyridin-3-ylethanol | 373.1673 |
| 92 | C = 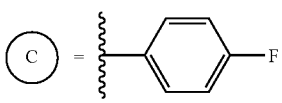<br>Y = 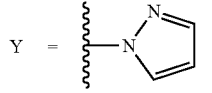 | (±)-2-(4-fluorophenyl)-2-(1H-pyrazol-1-yl)-1,1-dipyridin-3-ylethanol | 361.1466 |

-continued

| Example | Compound | Name | MS (M + 1) |
|---|---|---|---|
| 93 | C = 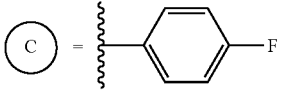<br><br>Y = 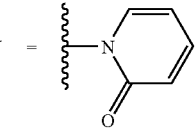 | (±)-1-[1-(4-fluorophenyl)-2-hydroxy-2,2-dipyridin-3-ylethyl]pyridin-2(1H)-one | 388.1461 |
| 94 | C = 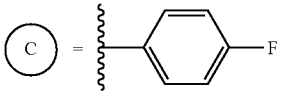<br><br>Y = 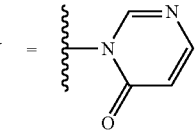 | (±)-3-[1-(4-fluorophenyl)-2-hydroxy-2,2-dipyridin-3-ylethyl]pyrimidin-4(3H)-one | 389.1417 |
| 95 | C = 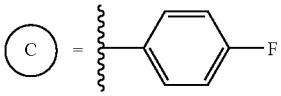<br><br>Y = 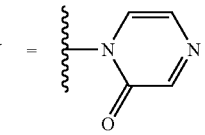 | (±)-1-[1-(4-fluorophenyl)-2-hydroxy-2,2-dipyridin-3-ylethyl]pyrazin-2(1H)-one | 389.1413 |
| 96 | C = 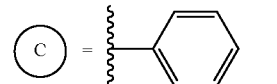<br><br>Y = 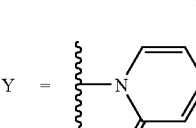 | (±)-3-[2-hydroxy-1-(2-oxopyridin-1(2H)-yl)-2,2-dipyridin-3-ylethyl]benzonitrile | 395.2 |
| 97 | C = 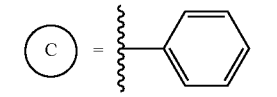<br><br>Y = 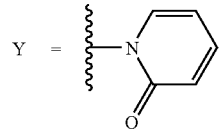 | (±)-1-(2-hydroxy-1-phenyl-2,2-dipyridin-3-ylethyl)pyridin-2(1H)-one | 370.2 |
| 98 | C = 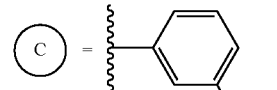<br><br>Y = 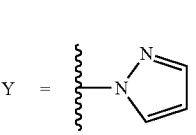 | (±)-3-[2-hydroxy-1-(1H-pyrazol-1-yl)-2,2-dipyridin-3-ylethyl]benzonitrile | 368.1506 |

-continued

| Example | Compound | Name | MS (M + 1) |
|---|---|---|---|
| 99 | 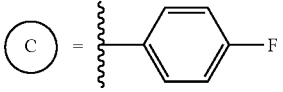 | (±)-2-[1-(4-fluorophenyl)-2-hydroxy-2,2-dipyridin-3-ylethyl]pyridazin-3(2H)-one | 389.1416 |
| 100 | 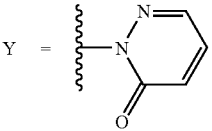 | (±)-4-[2-hydroxy-1-(2-oxopyridin-1(2H)-yl)-2,2-dipyridin-3-ylethyl]benzonitrile | 395.1520 |
| 101 | 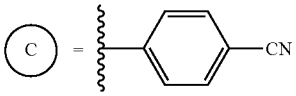 | 1-[1-(4-fluorophenyl)-2-hydroxy-2,2-dipyridin-3-ylethyl]pyridin-2(1H)-one (enantiomer A) | 388.1 |
| 102 | 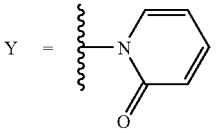 | 1-[1-(4-fluorophenyl)-2-hydroxy-2,2-dipyridin-3-ylethyl]pyridin-2(1H)-one (enantiomer B) | 388.1 |
| 103 | 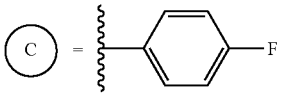 | (±)-methyl 1-[1-(4-fluorophenyl)-2-hydroxy-2,2-dipyridin-3-ylethyl]-2-oxo-1,2-dihydropyridine-3-carboxylate | 446.1512 |
| 104 | 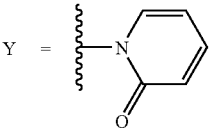 | (±)-ethyl 1-(2-hydroxy-1-phenyl-2,2-dipyridin-3-ylethyl)-1H-pyrazole-4-carboxylate | 415.1786 |

-continued

| Example | Compound | Name | MS (M + 1) |
|---|---|---|---|
| 105 |  C = , Y = | (±)-1-[1-(4-fluorophenyl)-2-hydroxy-2,2-dipyridin-3-ylethyl]pyrimidin-2(1H)-one | 389.2 |
| 106 | 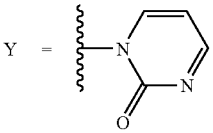 C = , Y = | (±)-1-[1-(4-fluorophenyl)-2-hydroxy-2,2-dipyridin-3-ylethyl]-2-oxo-1,2-dihydropyridine-3-carbonitrile | 413.1 |
| 107 |  C = , Y = | (±)-1-(2-hydroxy-1-pyridin-2-yl-2,2-dipyridin-3-ylethyl)pyridin-2(1H)-one | 371.1520 |
| 108 | 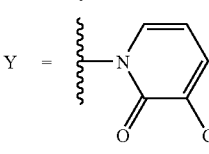 C = , Y = | (±)-2-phenyl-1,1-dipyridin-3-yl-2-(1H-1,2,3-triazol-1-yl)ethanol | 344.1505 |
| 109 | 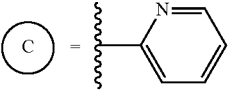 C = , Y = | (±)-1-(2-hydroxy-1-phenyl-2,2-dipyridin-3-ylethyl)pyrazin-2(1H)-one | 371.1516 |
| 110 | 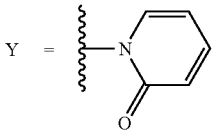 C = , Y = | (±)-2-phenyl-1,1-dipyridin-3-yl-2-(2H-1,2,3-triazol-2-yl)ethanol | 344.1516 |

-continued

| Example | Compound | Name | MS (M + 1) |
|---|---|---|---|
| 111 | C = 4-fluorophenyl; Y = 5-(methoxycarbonyl)-2-oxopyridin-1(2H)-yl  | (±)-methyl 1-[1-(4-fluorophenyl)-2-hydroxy-2,2-dipyridin-3-ylethyl]-6-oxo-1,6-dihydropyridine-3-carboxylate | 446.5 |
| 112 | C = 4-fluorophenyl; Y = 5-bromo-2-oxopyridin-1(2H)-yl 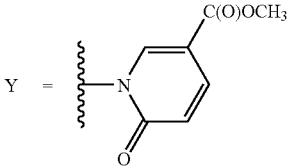 | (±)-5-bromo-1-[1-(4-fluorophenyl)-2-hydroxy-2,2-dipyridin-3-ylethyl]pyridin-2(1H)-one | 468.2 (M + 2) |
| 113 | C = 4-fluorophenyl; Y = 5-cyano-2-oxopyridin-1(2H)-yl  | (±)-1-[1-(4-fluorophenyl)-2-hydroxy-2,2-dipyridin-3-ylethyl]-6-oxo-1,6-dihydropyridine-3-carbonitrile | 413.5 |
| 114 | C = pyridin-3-yl; Y = 2-oxopyridin-1(2H)-yl 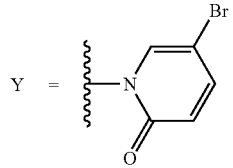 | (±)-1-(2-hydroxy-1,2,2-tripyridin-3-ylethyl)pyridin-2(1H)-one | 371.4 |
| 115 | C = pyridin-2-yl; Y = 3-oxopyridazin-2(3H)-yl  | (±)-2-(2-hydroxy-1-pyridin-2-yl-2,2-dipyridin-3-ylethyl)pyridazin-3(2H)-one | 372.5 |

-continued

| Example | Compound | Name | MS (M + 1) |
|---|---|---|---|
| 116 | C = 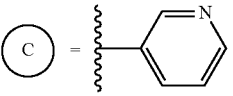  Y = 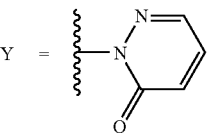 | (±)-2-(2-hydroxy-1,2,2-tripyridin-3-ylethyl)pyridazin-3(2H)-one | 372.2 |
| 117 | C = 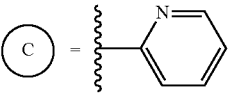  Y = 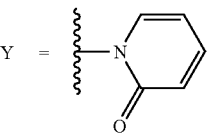 | 1-(2-hydroxy-1-pyridin-2-yl-2,2-dipyridin-3-ylethyl)pyridin-2(1H)-one (enantiomer A) | 371.2 |
| 118 | C = 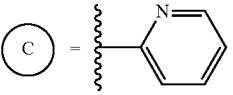  Y = 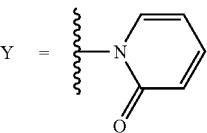 | 1-(2-hydroxy-1-pyridin-2-yl-2,2-dipyridin-3-ylethyl)pyridin-2(1H)-one (enantiomer B) | 371.2 |
| 119 | C = 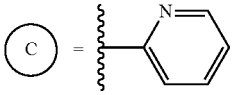  Y = 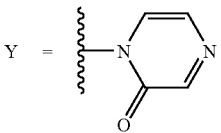 | (±)-1-(2-hydroxy-1-pyridin-2-yl-2,2-dipyridin-3-ylethyl)pyrazin-2(1H)-one | 372.3 |
| 120 | C = 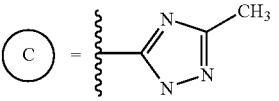  Y = 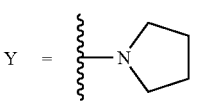 | (±)-2-(3-methyl-1H-1,2,4-triazol-5-yl)-1,1-dipyridin-3-yl-2-pyrrolidin-1-ylethanol | 351.1 |
| 121 | C = 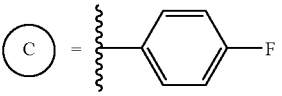  Y = 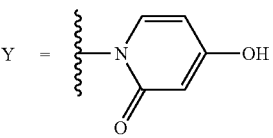 | (±)-1-[1-(4-fluorophenyl)-2-hydroxy-2,2-dipyridin-3-ylethyl]-4-hydroxypyridin-2(1H)-one | 404.5 |

-continued

| Example | Compound | Name | MS (M + 1) |
|---|---|---|---|
| 4-1 | | (±)-1-phenyl-1,2-dipyridin-3-yl-2-(1H-1,2,3-triazol-1-yl)ethanol (Diastereomer A) | 344.1511 |
| 4-2 | | (±)-1-phenyl-1,2-dipyridin-3-yl-2-(1H-1,2,3-triazol-1-yl)ethanol (Diastereomer B) | 344.1512 |
| 4-3 | | (±)-1-phenyl-1-pyridin-2-yl-2-pyridin-3-yl-2-(1H-1,2,3-triazol-1-yl)ethanol (Diastereomer A) | 344.1504 |
| 4-4 | | (±)-1-phenyl-1-pyridin-2-yl-2-pyridin-3-yl-2-(1H-1,2,3-triazol-1-yl)ethanol (Diastereomer B) | 344.1513 |
| 4-5 | C = (4-cyanophenyl); Y = (1H-1,2,3-triazol-1-yl) | (±)-4-[2-hydroxy-2,2-dipyridin-3-yl-1-(1H-1,2,3-triazol-1-yl)ethyl]benzonitrile | 369.1477 |
| 4-6 | | (±)-1-(2-hydroxy-2-phenyl-2-pyridin-2-yl-1-pyridin-3-ylethyl)pyridin-2(1H)-one | 370.3 |

| Example | Name | MS (M + 1) |
|---|---|---|
| 4-7 | (±)-1-(2-hydroxy-2-phenyl-1,2-dipyridin-3-ylethyl)pyridin-2(1H)-one (Diastereomer C) | 370.3 |
| 4-8 | (±)-1-(2-hydroxy-2-phenyl-1,2-dipyridin-3-ylethyl)pyridin-2(1H)-one (Diastereomer D) | 370.3 |
| 4-9 | (±)-1-(2-hydroxy-2-phenyl-2-pyridin-2-yl-1-pyridin-3-ylethyl)pyrazin-2(1H)-one | 371.3 |
| 4-10 | (±)-2-(6-bromopyridin-3-yl)-1,1-dipyridin-3-yl-2-(1H-1,2,3-triazol-1-yl)ethanol | 423.0582 |
| 4-11 | (±)-3-[1-hydroxy-2-(2-oxopyridin-1(2H)-yl)-2-pyridin-2-yl-1-pyridin-3-ylethyl]benzonitrile (Diastereomer X) | 395.2 |
| 4-12 | (±)-3-[1-hydroxy-2-(2-oxopyridin-1(2H)-yl)-2-pyridin-2-yl-1-pyridin-3-ylethyl]benzonitrile (Diastereomer Y) | 395.2 |

-continued

| Example | Compound | Name | MS (M + 1) |
|---|---|---|---|
| 4-13 | 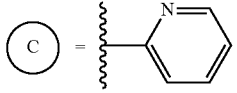 | (±)-3-(2-hydroxy-1-pyridin-2-yl-2,2-dipyridin-3-ylethyl)-1,3-oxazinan-2-one | 377.1607 |
| 4-14 | 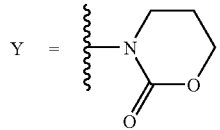 | (±)-3-[2-(6-bromopyridin-3-yl)-1-hydroxy-1-pyridin-3-yl-2-(1H-1,2,3-triazol-1-yl)ethyl]benzonitrile (Diastereomer A) | 447.0558 |
| 4-15 | 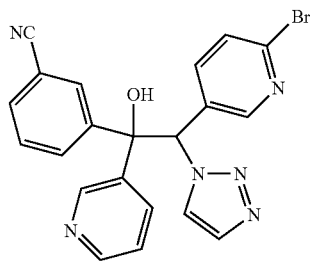 | (±)-3-[2-(6-bromopyridin-3-yl)-1-hydroxy-1-pyridin-3-yl-2-(1H-1,2,3-triazol-1-yl)ethyl]benzonitrile (Diastereomer B) | 447.0559 |
| 4-16 | 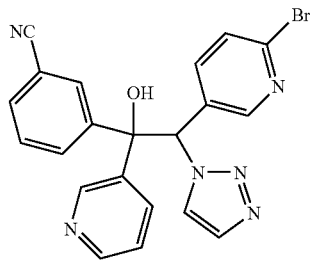 | (±)-3-[1-hydroxy-1,2-dipyridin-3-yl-2-(1H-1,2,3-triazol-1-yl)ethyl]benzonitrile | 369.1457 |
| 4-17 | 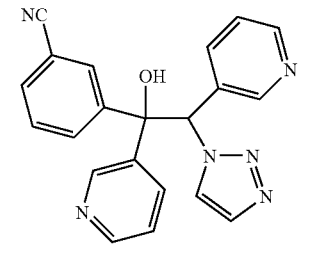 | (±)-3-[1-hydroxy-2-pyridin-2-yl-1-pyridin-3-yl-2-(1H-1,2,3-triazol-1-yl)ethyl]benzonitrile (Diastereomer A) | 369.1464 |

-continued

| Example | Compound | Name | MS (M + 1) |
|---|---|---|---|
| 4-18 | | (±)-3-[1-hydroxy-2-pyridin-2-yl-1-pyridin-3-yl-2-(1H-1,2,3-triazol-1-yl)ethyl]benzonitrile (Diastereomer B) | 369.1464 |
| 4-19 | C = phenyl; Y = 1,3-oxazinan-2-one | (±)-3-(2-hydroxy-1-phenyl-2,2-dipyridin-3-ylethyl)-1,3-oxazinan-2-one | 376.1646 |
| 4-20 | | (±)-3-[1-hydroxy-2-(2-oxo-1,3-oxazinan-3-yl)-2-pyridin-2-yl-1-pyridin-3-ylethyl]benzonitrile | 401.1 |
| 4-21 | C = pyridin-2-yl; Y = 2-oxo-1,2-dihydropyridine-4-CN | (±)-1-(2-hydroxy-1-pyridin-2-yl-2,2-dipyridin-3-ylethyl 2-oxo-1,2-dihydropyridine-carbonitrile | 396.4 |

The variables C, B, and Y in the scheme are as defined in "Formula I".

SCHEME 5

EXAMPLE 122

(±)-3-(2-hydroxy-2,2-dipyridin-3-yl-1-pyrrolidin-1-ylethyl)benzonitrile

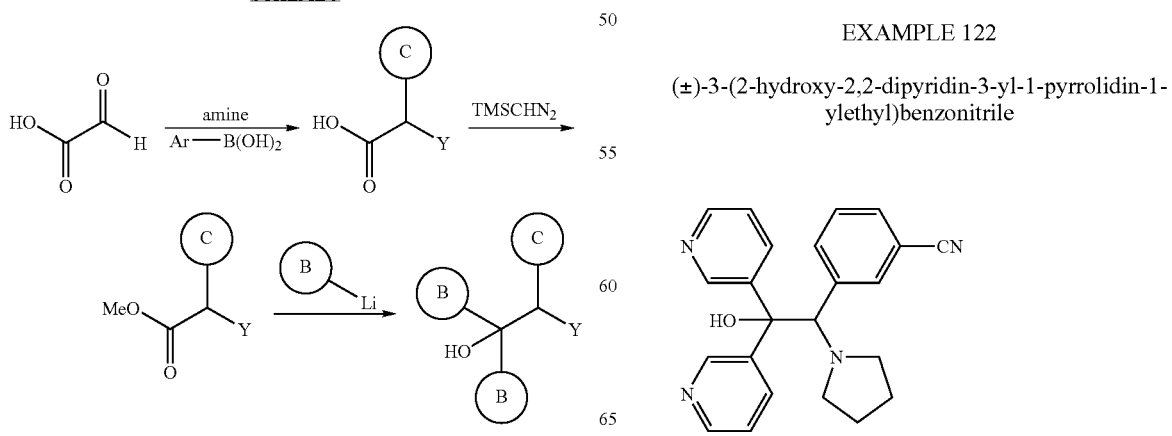

Step A:

To a mixture of glyoxylic acid monohydrate (1.54 g), pyrrolidine (1.19 g), and 220 mL acetonitrile was added 3-bromophenyl boronic acid (3.35 g). The reaction was heated at 80 C for 93 h. After cooling to room temperature, volatiles were removed in vacuo, and the residue was dissolved in 75 mL of benzene and 38 mL of methanol. Trimethylsilyldiazomethane (2M in hexanes, 16.7 mL) was added via syringe, and the reaction was stirred at room temperature for 2.5 h. The volatiles were removed in vacuo, and the residue was purified by flash chromatography to provide 1.53 g of methyl (3-bromophenyl)(pyrrolidin-1-yl)acetate. MS 298, 300 (Br).

Step B:

A solution of 3-bromopyridine (1.62 g) in 40 mL of diethyl ether was cooled to −78 C. n-BuLi (2.87 M in hexanes, 3.6 mL) was added via syringe, and the resulting mixture was stirred for 15 min. A solution of methyl (3-bromophenyl)-(pyrrolidin-1-yl)acetate (1.53 g) in 10 mL of THF was added via cannula. The reaction was stirred for 5 min at −78 C then for 2.5 h at 0 C. After quenching with saturated aqueous $NH_4Cl$, the mixture was partitioned between ethyl acetate and saturated aqueous $NaHCO_3$. The aqueous solution was extracted once with ethyl acetate, and the combined organic solutions were dried ($Na_2SO_4$) and concentrated in vacuo. Flash chromatography provided a solid that was triturated with diethyl ether to give 893 mg of 2-(3-bromophenyl)-1,1-dipyridin-3-yl-2-pyrrolidin-1-ylethanol. HRMS calcd for $C_{22}H_{23}BrN_3O$ $(M+H)^+$: 424.1019; found: 424.1025. $^1H$ NMR ($CDCl_3$, 500 MHz) δ 9.11 (d, J=2.4 Hz, 1H); 8.51-8.48 (m, 2H); 8.14-8.11 (m, 2H); 7.60 (ddd, J=1.6, 2.3, 8.2 Hz, 1H); 7.46 (t, J=3.5 Hz, 1H); 7.29 (dd, J=4.8, 8.1 Hz, 1H); 7.20 (t, J=8.7 Hz, 2H); 6.97-6.92 (m, 2H); 5.94 (s, 1H); 4.44 (s, 1H); 2.26 (m, 4H); 1.63 (m, 4H).

Step C:

2-(3-bromophenyl)-1,1-dipyridin-3-yl-2-pyrrolidin-1-ylethanol (40 mg, 0.094 mmol), $Pd_2(dba)_3$ (3 mg, 0.003 mmol), dppf (4 mg, 0.008 mmol), $Zn(CN)_2$ (22 mg, 0.189 mmol) and zinc powder (1 mg, 0.011 mmol) were combined in a flask, purged with argon, and then 1.5 mL DMA was added. This mixture was heated at 120° C. for 3.5 h then cooled to room temperature. The reaction mixture was then diluted with EtOAc and washed with 2N aqueous $NH_4OH$ (1×). The organic layer was dried over $Na_2SO_4$ and concentrated. The resulting viscous liquid was purified by reverse phase HPLC. Pure fractions were combined and extracted from saturated aqueous $NaHCO_3$ with $CH_2Cl_2$ (3×). The combined organic extracts were dried over $Na_2SO_4$ and concentrated to yield the titled compound as a white solid (22 mg, 63%). HRMS calcd for $C_{23}H_{22}N_4O$ $(M+H)^+$: 371.1853; found: 371.1867. $^1H$ NMR ($CDCl_3$, 500 MHz) δ 9.11 (d, J=2.2 Hz, 1H); 8.51 (dd, J=1.2, 4.6 Hz, 1H); 8.47 (d, J=1.9 Hz, 1H); 8.13 (m, 2H); 7.64 (s, 1H); 7.59 (m, 1H); 7.53 (br d, J=6.6 Hz, 1H); 7.37 (d, J=7.8 Hz, 1H); 7.31 (dd, J=4.6, 7.8 Hz, 1H); 7.21 (t, J=7.8 Hz, 1H); 6.94 (dd, J=4.6, 8.1 Hz, 1H); 5.71 (br, 1H); 5.30 (s, 1H); 2.25 (br d, J=26.9 Hz, 4H); 1.65 (s, 4H).

The following compounds were made according to Scheme 5, where intermediates in the scheme were modified according to literature methods. Example 181 was prepared by acid deprotection of the corresponding tert-butyl carbamate derivative. Examples 182-189 were prepared by fluoride-mediated deprotection of the corresponding primary or secondary tert-butyldimethylsilyl ethers. Example 192 was prepared by trifluoroacetic acid deprotection of Example 191, and Examples 193-201 were prepared in likewise fashion from the corresponding 4-methoxybenzyl amines.

EXAMPLES 123-201

| Example | Compound | Name | MS (M + 1) |
|---|---|---|---|
| 123 | 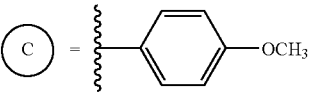 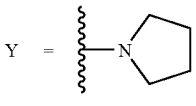 | (±)-2-(4-methoxyphenyl)-1,1-dipyridin-3-yl-2-pyrrolidin-1-ylethanol | 376.2047 |
| 124 | 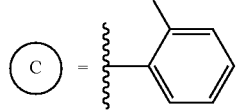 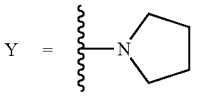 | (±)-2-(2-fluorophenyl)-1,1-dipyridin-3-yl-2-pyrrolidin-1-ylethanol | 364.1817 |

| Example | Compound | Name | MS (M + 1) |
|---|---|---|---|
| 125 | 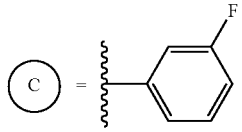 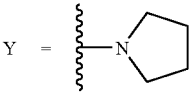 | (±)-2-(3-fluorophenyl)-1,1-dipyridin-3-yl-2-pyrrolidin-1-ylethanol | 364.1816 |
| 126 | 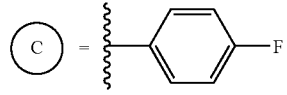 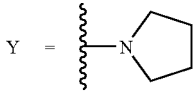 | (±)-2-(4-fluorophenyl)-1,1-dipyridin-3-yl-2-pyrrolidin-1-ylethanol | 364.1817 |
| 127 | 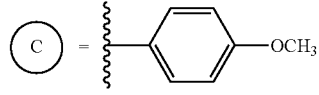 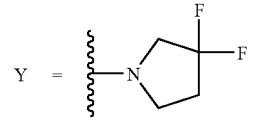 | (±)-2-(3,3-difluoropyrrolidin-1-yl)-2-(4-methoxyphenyl)-1,1-dipyridin-3-ylethanol | 412.1849 |
| 128 | 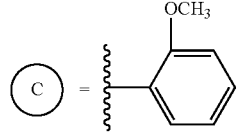 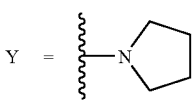 | (±)-2-(2-methoxyphenyl)-1,1-dipyridin-3-yl-2-pyrrolidin-1-ylethanol | 376.2039 |
| 129 | 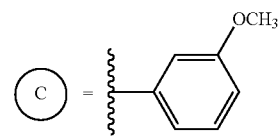 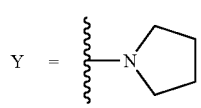 | (±)-2-(3-methoxyphenyl)-1,1-dipyridin-3-yl-2-pyrrolidin-1-ylethanol | 376.2042 |
| 130 | 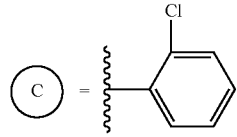 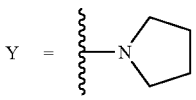 | (±)-2-(2-chlorophenyl)-1,1-dipyridin-3-yl-2-pyrrolidin-1-ylethanol | 380.1536 |

-continued

| Example | Compound | Name | MS (M + 1) |
|---|---|---|---|
| 131 | 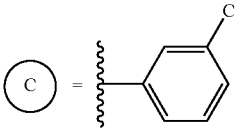 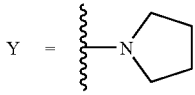 | (±)-2-(3-chlorophenyl)-1,1-dipyridin-3-yl-2-pyrrolidin-1-ylethanol | 380.1525 |
| 132 | 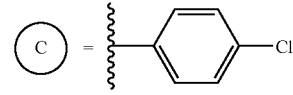 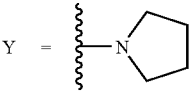 | (±)-2-(4-chlorophenyl)-1,1-dipyridin-3-yl-2-pyrrolidin-1-ylethanol | 380.1546 |
| 133 | 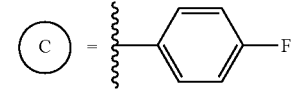 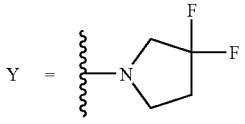 | (±)-2-(3,3-difluoropyrrolidin-1-yl)-2-(4-fluorophenyl)-1,1-dipyridin-3-ylethanol | 400.1646 |
| 134 | 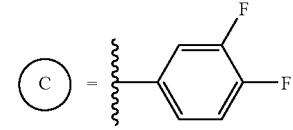 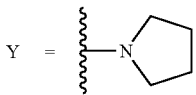 | (±)-2-(3,4-difluorophenyl)-1,1-dipyridin-3-yl-2-pyrrolidin-1-ylethanol | 382.1722 |
| 135 | 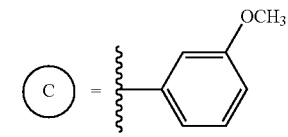 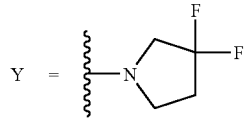 | (±)-2-(3,3-difluoropyrrolidin-1-yl)-2-(3-methoxyphenyl)-1,1-dipyridin-3-ylethanol | 412.1837 |
| 136 | 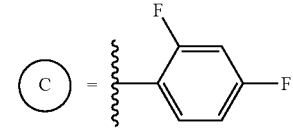 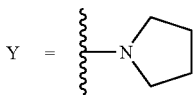 | (±)-2-(2,4-difluorophenyl)-1,1-dipyridin-3-yl-2-pyrrolidin-1-ylethanol | 382.1722 |

-continued

| Example | Compound | Name | MS (M + 1) |
|---|---|---|---|
| 137 | 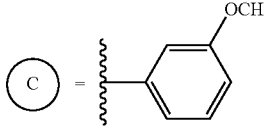 C = 3-methoxyphenyl; Y = piperidin-1-yl | (±)-2-(3-methoxyphenyl)-2-piperidin-1-yl-1,1-dipyridin-3-ylethanol | 390.2173 |
| 138 | 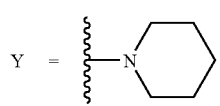 C = 4-fluorophenyl; Y = piperidin-1-yl | (±)-2-(4-fluorophenyl)-2-piperidin-1-yl-1,1-dipyridin-3-ylethanol | 378.1973 |
| 139 | 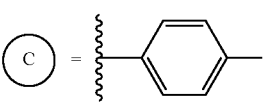 C = 2-fluoro-3-methoxyphenyl; Y = pyrrolidin-1-yl | (±)-2-(2-fluoro-3-methoxyphenyl)-1,1-dipyridin-3-yl-2-pyrrolidin-1-ylethanol | 394.1929 |
| 140 | 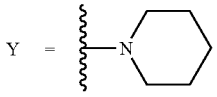 C = 2,6-difluorophenyl; Y = pyrrolidin-1-yl | (±)-2-(2,6-difluorophenyl)-1,1-dipyridin-3-yl-2-pyrrolidin-1-ylethanol | 382.1719 |
| 141 | 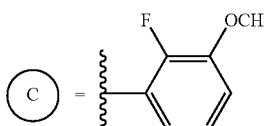 C = 3-methoxyphenyl; Y = 4-(trifluoromethyl)piperidin-1-yl | (±)-2-(3-methoxyphenyl)-1,1-dipyridin-3-yl-2-[4-(trifluoromethyl)piperidin-1-yl]ethanol | 458.2077 |
| 142 | 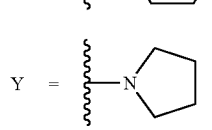 C = 3-methoxyphenyl; Y = piperidinyl-spiro-azetidinyl-NC(O)OC(CH$_3$)$_3$ | (±)-tert-butyl 7-[2-hydroxy-1-(3-methoxyphenyl)-2,2-dipyridin-3-ylethyl]-2,7-diazaspiro[3.5]nonane-2-carboxylate | 531.2993 |

-continued

| Example | Compound | Name | MS (M + 1) |
|---|---|---|---|
| 143 | C = phenyl; Y = (2r)-2-(methoxymethyl)pyrrolidin-1-yl (CH₂OCH₃) | 2-[(2r)-2-(methoxymethyl)pyrrolidin-1-yl]-2-phenyl-1,1-dipyridin-3-ylethanol (1:1 mixture diastereomers) | 390.2175 |
| 144 | C = 4-C(CH₃)₃-phenyl; Y = pyrrolidin-1-yl | (±)-2-(4-tert-butylphenyl)-1,1-dipyridin-3-yl-2-pyrrolidin-1-ylethanol | 402.2554 |
| 145 | C = 4-CH₂CH₃-phenyl; Y = pyrrolidin-1-yl | (±)-2-(4-ethylphenyl)-1,1-dipyridin-3-yl-2-pyrrolidin-1-ylethanol | 374.2264 |
| 146 | C = 2-CH₃-phenyl; Y = pyrrolidin-1-yl | (±)-2-(2-methylphenyl)-1,1-dipyridin-3-yl-2-pyrrolidin-1-ylethanol | 360.2093 |
| 147 | C = 3-CH₃-phenyl; Y = pyrrolidin-1-yl | (±)-2-(3-methylphenyl)-1,1-dipyridin-3-yl-2-pyrrolidin-1-ylethanol | 360.2079 |
| 148 | C = 4-CH₃-phenyl; Y = pyrrolidin-1-yl | (±)-2-(4-methylphenyl)-1,1-dipyridin-3-yl-2-pyrrolidin-1-ylethanol | 360.2078 |

-continued

| Example | Compound | Name | MS (M + 1) |
|---|---|---|---|
| 149 | 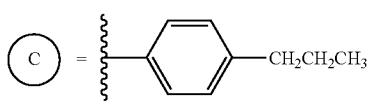 C = (4-propylphenyl), Y = pyrrolidin-1-yl | (±)-2-(4-propylphenyl)-1,1-dipyridin-3-yl-2-pyrrolidin-1-ylethanol | 388.2379 |
| 150 | 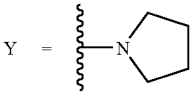 C = (2-ethoxyphenyl), Y = pyrrolidin-1-yl | (±)-2-(2-ethoxyphenyl)-1,1-dipyridin-3-yl-2-pyrrolidin-1-ylethanol | 390.2184 |
| 151 | 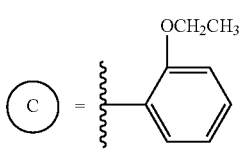 C = (3-ethoxyphenyl), Y = pyrrolidin-1-yl | (±)-2-(3-ethoxyphenyl)-1,1-dipyridin-3-yl-2-pyrrolidin-1-ylethanol | 390.2188 |
| 152 | 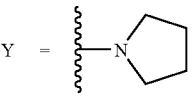 C = (1,3-benzodioxol-5-yl), Y = pyrrolidin-1-yl | (±)-2-(1,3-benzodioxol-5-yl)-1,1-dipyridin-3-yl-2-pyrrolidin-1-ylethanol | 390.1819 |
| 153 | 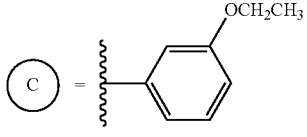 C = [3-(trifluoromethoxy)phenyl], Y = pyrrolidin-1-yl | (±)-1,1-dipyridin-3-yl-2-pyrrolidin-1-yl-2-[3-(trifluoromethoxy)phenyl]ethanol | 430.1738 |

-continued
| Example | Compound | Name | MS (M + 1) |
|---|---|---|---|
| 154 | 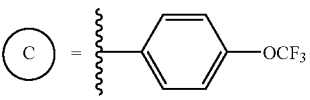 | (±)-1,1-dipyridin-3-yl-2-pyrrolidin-1-yl-2-[4-(trifluoromethoxy)phenyl]ethanol | 430.1736 |
| 155 | 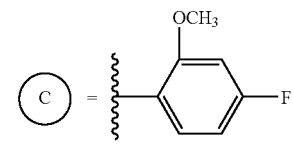 | (±)-2-(4-fluoro-2-methoxyphenyl)-1,1-dipyridin-3-yl-2-pyrrolidin-1-ylethanol | 394.1921 |
| 156 | 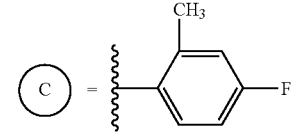 | (±)-2-(4-fluoro-2-methylphenyl)-1,1-dipyridin-3-yl-2-pyrrolidin-1-ylethanol | 378.1975 |
| 157 | 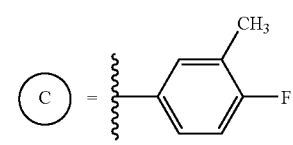 | (±)-2-(4-fluoro-3-methylphenyl)-1,1-dipyridin-3-yl-2-pyrrolidin-1-ylethanol | 378.1970 |
| 158 | 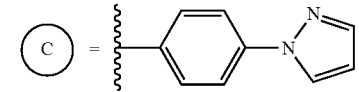 | (±)-2-[4-(1h-pyrazol-1-yl)phenyl]-1,1-dipyridin-3-yl-2-pyrrolidin-1-ylethanol | 412.2120 |

-continued

| Example | Compound | Name | MS (M + 1) |
|---|---|---|---|
| 159 | 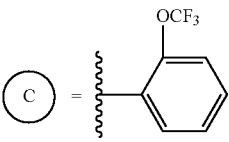 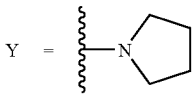 | (±)-1,1-dipyridin-3-yl-2-pyrrolidin-1-yl-2-[2-(trifluoromethoxy)phenyl]ethanol | 430.1743 |
| 160 | 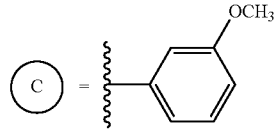 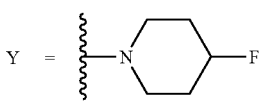 | (±)-2-(4-fluoropiperidin-1-yl)-2-(3-methoxyphenyl)-1,1-dipyridin-3-ylethanol | 408.2091 |
| 161 | 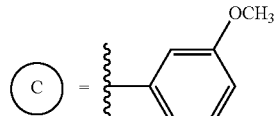 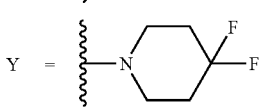 | (±)-2-(4,4-difluoropiperidin-1-yl)-2-(3-methoxyphenyl)-1,1-dipyridin-3-ylethanol | 426.1988 |
| 162 | 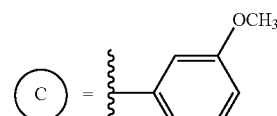 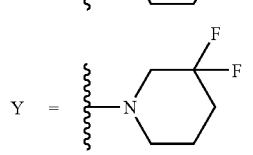 | (±)-2-(3,3-difluoropiperidin-1-yl)-2-(3-methoxyphenyl)-1,1-dipyridin-3-ylethanol | 426.1995 |
| 163 | 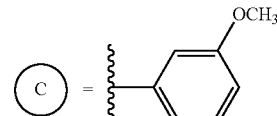 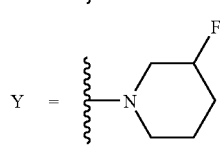 | (±)-2-(3-fluoropiperidin-1-yl)-2-(3-methoxyphenyl)-1,1-dipyridin-3-ylethanol (1:1 mixture diastereomers) | 408.2097 |

-continued
| Example | Compound | Name | MS (M + 1) |
|---|---|---|---|
| 164 | 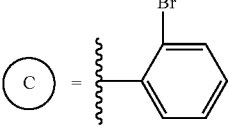 | (±)-2-(2-bromophenyl)-1,1-dipyridin-3-yl-2-pyrrolidin-1-ylethanol | 424.1021 |
| 165 | 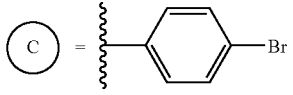 | (±)-2-(4-bromophenyl)-1,1-dipyridin-3-yl-2-pyrrolidin-1-ylethanol | 424.1021 |
| 166 | 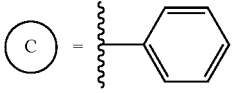 | (±)-2-[allyl(methyl)amino]-2-phenyl-1,1-dipyridin-3-ylethanol | 346.1923 |
| 167 | 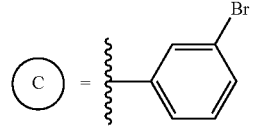 | (±)-2-(3-bromophenyl)-1,1-dipyridin-3-yl-2-pyrrolidin-1-ylethanol | 424.1025 |
| 168 | 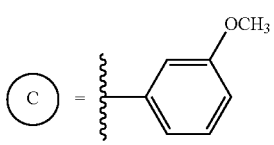 | 2-[(3S)-3-fluoropyrrolidin-1-yl]-2-(3-methoxyphenyl)-1,1-dipyridin-3-ylethanol (diastereomer A) | 394.1931 |

-continued

| Example | Compound | Name | MS (M + 1) |
|---|---|---|---|
| 169 | C = phenyl<br>Y = 3,3-difluoroazetidin-1-yl | (±)-2-(3,3-difluoroazetidin-1-yl)-2-phenyl-1,1-dipyridin-3-ylethanol | 368.1568 |
| 170 | C = 4-fluorophenyl<br>Y = 3,3-difluoroazetidin-1-yl | (±)-2-(3,3-difluoroazetidin-1-yl)-2-(4-fluorophenyl)-1,1-dipyridin-3-ylethanol | 386.1466 |
| 171 | C = 3-thienyl<br>Y = pyrrolidin-1-yl | (±)-1,1-dipyridin-3-yl-2-pyrrolidin-1-yl-2-(3-thienyl)ethanol | 352.1485 |
| 172 | C = 3-furyl<br>Y = pyrrolidin-1-yl | (±)-2-(3-furyl)-1,1-dipyridin-3-yl-2-pyrrolidin-1-ylethanol | 336.1704 |
| 173 | C = 1-benzothien-2-yl<br>Y = pyrrolidin-1-yl | (±)-2-(1-benzothien-2-yl)-1,1-dipyridin-3-yl-2-pyrrolidin-1-ylethanol | 402.1649 |
| 174 | C = 4-fluorophenyl<br>Y = 3-methoxyazetidin-1-yl | (±)-2-(4-fluorophenyl)-2-(3-methoxyazetidin-1-yl)-1,1-dipyridin-3-ylethanol | 380.1765 |

-continued

| Example | Compound | Name | MS (M + 1) |
|---|---|---|---|
| 175 | C = 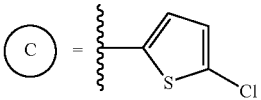<br><br>Y = 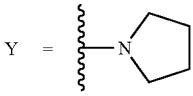 | (±)-2-(5-chloro-2-thienyl)-1,1-dipyridin-3-yl-2-pyrrolidin-1-ylethanol | 386.1110 |
| 176 | C = 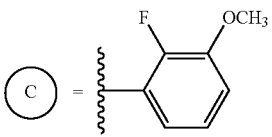<br><br>Y = 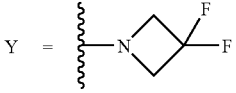 | (±)-2-(3,3-difluoroazetidin-1-yl)-2-(2-fluoro-3-methoxyphenyl)-1,1-dipyridin-3-ylethanol | 416.1573 |
| 177 | C = 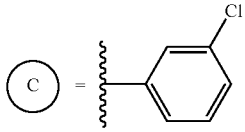<br><br>Y = 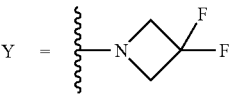 | (±)-2-(3-chlorophenyl)-2-(3,3-difluoroazetidin-1-yl)-1,1-dipyridin-ylethanol | 402.1183 |
| 178 | C = 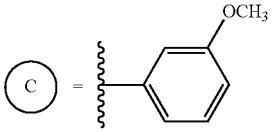<br><br>Y = 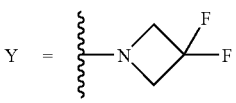 | (±)-2-(3,3-difluoroazetidin-1-yl)-2-(3-methoxyphenyl)-1,1-dipyridin-3-ylethanol | 398.1674 |
| 179 | C = 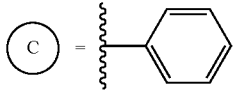<br><br>Y = 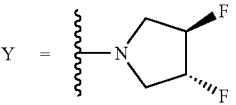 | 2-[(3R,4R)-3,4-difluoropyrrolidin-1-yl]-2-phenyl-1,1-dipyridin-3-ylethanol (diastereomer A) | 382.1744 |

-continued

| Example | Compound | Name | MS (M + 1) |
|---|---|---|---|
| 180 | 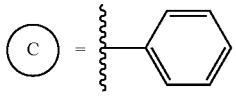 | 2-[(3R,4R)-3,4-difluoropyrrolidin-1-yl]-2-phenyl-1,1-dipyridin-3-ylethanol (diastereomer B) | 382.1740 |
| 181 | 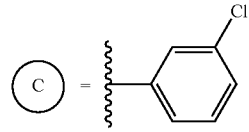 | 2-(3-chlorophenyl)-2-[(1S,4S)-2,5-diazabicyclo[2.2.1]hept-2-yl]-1,1-dipyridin-3-ylethanol (2:1 mixture diastereomers) | 407.1617 |
| 182 | 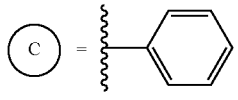 | (±)-1-(2-hydroxy-1-phenyl-2,2-dipyridin-3-ylethyl)piperidin-3-ol (1:1 mixture diastereomers) | 376.2010 |
| 183 | 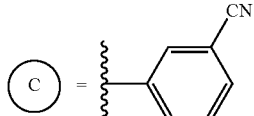 | (±)-3-[2-hydroxy-1-(3-hydroxypiperidin-1-yl)-2,2-dipyridin-3-ylethyl]benzonitrile (2:1 mixture diastereomers) | 401.1947 |
| 184 | 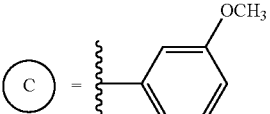 | (±)-1-[2-hydroxy-1-(3-methoxyphenyl)-2,2-dipyridin-3-ylethyl]piperidin-4-ol | 406.2132 |

-continued

| Example | Compound | Name | MS (M + 1) |
|---|---|---|---|
| 185 | C = 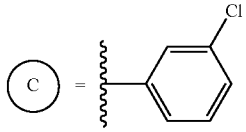<br><br>Y = 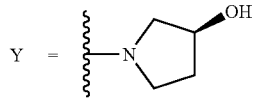 | (3R)-1-[1-(3-chlorophenyl)-2-hydroxy-2,2-dipyridin-3-ylethyl]pyrrolidin-3-ol (1:1 mixture diastereomers) | 396.1490 |
| 186 | C = 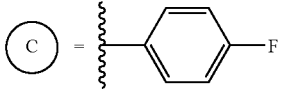<br><br>Y = 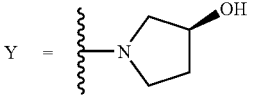 | (3R)-1-[1-(4-fluorophenyl)-2-hydroxy-2,2-dipyridin-3-ylethyl]pyrrolidin-3-ol (1:1 mixture diastereomers) | 380.1770 |
| 187 | C = 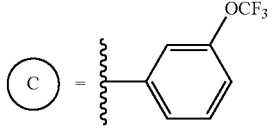<br><br>Y = 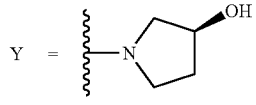 | (3R)-1-{2-hydroxy-2,2-dipyridin-3-yl-1-[3-(trifluoromethoxy)phenyl]ethyl}pyrrolidin-3-ol (1:1 mixture diastereomers) | 446.1694 |
| 188 | C = 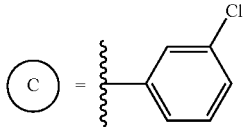<br><br>Y = 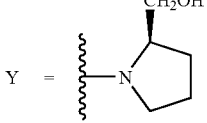 | 2-(3-chlorophenyl)-2-[(2S)-2-(hydroxymethyl)pyrrolidin-1-yl]-1,1-dipyridin-3-ylethanol (diastereomer A) | 410.1642 |
| 189 | C = 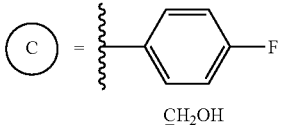<br><br>Y = 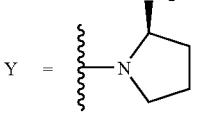 | 2-(4-fluorophenyl)-2-[(2S)-2-(hydroxymethyl)pyrrolidin-1-yl]-1,1-dipyridin-3-ylethanol (diastereomer A) | 394.1943 |

-continued

| Example | Compound | Name | MS (M + 1) |
|---|---|---|---|
| 190 | 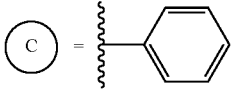 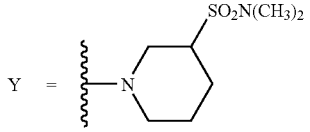 | (±)-1-(2-hydroxy-1-phenyl-2,2-dipyridin-3-ylethyl)-n,n-dimethylpiperidine-3-sulfonamide (diastereomer A) | 467.2109 |
| 191 | 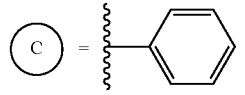 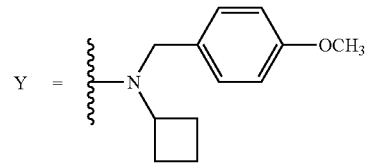 | (±)-2-[cyclobutyl(4-methoxybenzyl)amino]-2-(4-fluorophenyl)-1,1-dipyridin-3-ylethanol | 484.2425 |
| 192 | 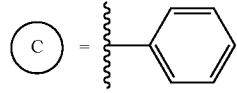 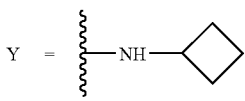 | (±)-2-(cyclobutylamino)-2-phenyl-1,1-dipyridin-3-ylethanol | 346.1918 |
| 193 | 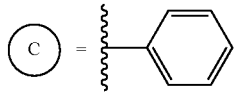 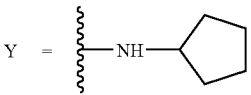 | (±)-2-(cyclopentylamino)-2-phenyl-1,1-dipyridin-3-ylethanol | 360.2075 |
| 194 | 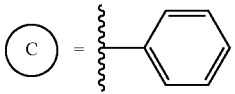 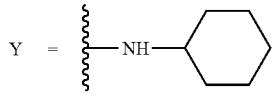 | (±)-2-(cyclohexylamino)-2-phenyl-1,1-dipyridin-3-ylethanol | 374.2230 |
| 195 | 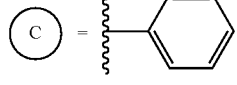 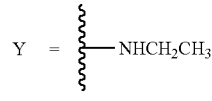 | (±)-2-(ethylamino)-2-phenyl-1,1-dipyridin-3-ylethanol | 320.1769 |

-continued

| Example | Compound | Name | MS (M + 1) |
|---|---|---|---|
| 196 | 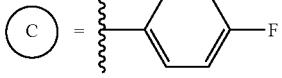 | (±)-2-(cyclobutylamino)-2-(4-fluorophenyl)-1,1-dipyridin-3-ylethanol | 364.1818 |
| 197 | 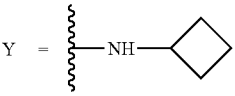 | (±)-2-phenyl-1,1-dipyridin-3-yl-2-[(2,2,2-trifluoroethyl)amino]ethanol | 374.1471 |
| 198 | 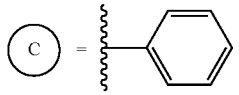 | (±)-2-phenyl-1,1-dipyridin-3-yl-2-[(2,2,2-trifluoroethyl)amino]ethanol | 376.2016 |
| 199 | 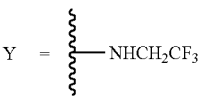 | (±)-2-(3-chlorophenyl)-2-(cyclobutylamino)-1,1-dipyridin-3-ylethanol | 380.1521 |
| 200 | 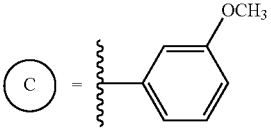 | (±)-2-(4-fluorophenyl)-1,1-dipyridin-3-yl-2-[(2,2,2-trifluoroethyl)amino]ethanol | 392.1378 |
| 201 | 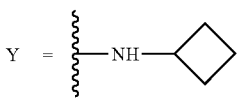 | (±)-2-(3-chlorophenyl)-1,1-dipyridin-3-yl-2-[(2,2,2-trifluoroethyl)amino]ethanol | 408.1100 |

The following compounds were made from compounds in Examples 1-201, using methods known to those skilled in the art. Examples 202, 203, 281 and 284 were prepared by acid deprotection of Examples 48, 49, 142 and 17, respectively. Example 217 was prepared by acid deprotection of the corresponding tert-butyl carbamate. Examples 204-280, 282 and 285, were prepared from Examples 202, 203, 217 or 284 by acylations or reductive aminations or combinations of both.

Example 283 was prepared by O-alkylation of Example 1. Example 286 was prepared by trifluoroacetic acid treatment of Example 77, and Example 287 was prepared from Example 286. Example 288 was prepared by MnO$_2$ oxidation for Example 33. Examples 289 and 290 were prepared by reduction of Examples 82 and 104, respectively. The acid 291 was prepared from bromide 165 by palladium mediated carbonylation, and was converted to amides 292 and 293 by standard amide coupling. Amides 295 and 296 were prepared in likewise fashion from the carboxylic acid derived from carbonylation of bromide 167, and ester 294 was prepared from the same acid using trimethylsilyldiazomethane. Example 297 was prepared by hydrolysis of Example 103. Example 298 was prepared by palladium mediated cyanation of bromide 38. Example 299 was prepared from example 166 by olefin dihydroxylation, and Example 300 was prepared from example 299 by NaIO$_4$ oxidative cleavage followed by sodium borohydride reduction. Example 301 prepared by oxidation of example 51, and 301 was converted to 302 using excess methyl Grignard.

EXAMPLES 202-302 AND 5-1

| Example | Compound | Name | MS (M + 1) |
|---|---|---|---|
| 202 | 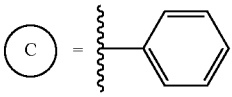 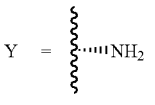 | (2S)-2-amino-2-phenyl-1,1-dipyridin-3-ylethanol | 292.1454 |
| 203 | 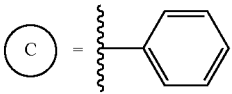 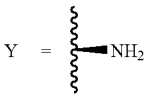 | (2R)-2-amino-2-phenyl-1,1-dipyridin-3-ylethanol | 292.1455 |
| 204 | 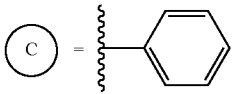 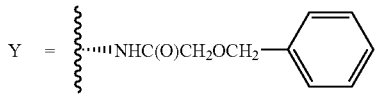 | 2-(benzyloxy)-N-[(1S)-2-hydroxy-1-phenyl-2,2-dipyridin-3-ylethyl]acetamide | 440.1970 |
| 205 | 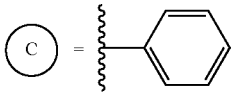 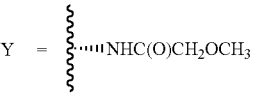 | N-[(1S)-2-hydroxy-1-phenyl-2,2-dipyridin-3-ylethyl]-2-methoxyacetamide | 364.1657 |
| 206 | 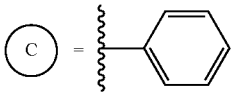 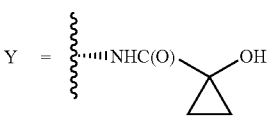 | 1-hydroxy-N-[(1S)-2-hydroxy-1-phenyl-2,2-dipyridin-3-ylethyl]cyclopropane-carboxamide | 376.1664 |

-continued

| Example | Compound | Name | MS (M + 1) |
|---|---|---|---|
| 207 | 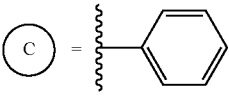 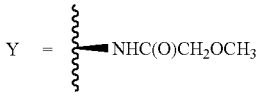 | N-[(1R)-2-hydroxy-1-phenyl-2,2-dipyridin-3-ylethyl]-2-methoxyacetamide | 364.2 |
| 208 | 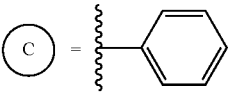 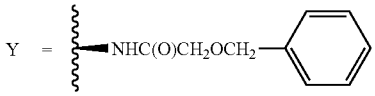 | 2-(benzyloxy)-N-[(1R)-2-hydroxy-1-phenyl-2,2-dipyridin-3-ylethyl]-acetamide | 440.1974 |
| 209 | 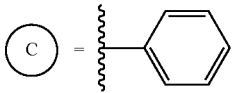 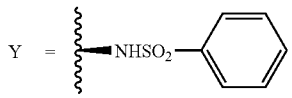 | N-[(1R)-2-hydroxy-1-phenyl-2,2-dipyridin-3-ylethyl]benzenesulfonamide | 432.2 |
| 210 | 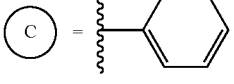 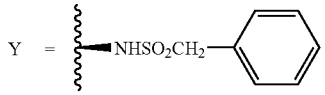 | N-[(1R)-2-hydroxy-1-phenyl-2,2-dipyridin-3-ylethyl]-1-phenylmethanesulfonamide | 446.3 |
| 211 | 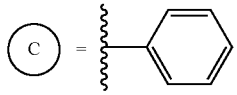 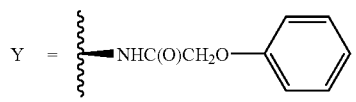 | N-[(1R)-2-hydroxy-1-phenyl-2,2-dipyridin-3-ylethyl]-2-phenoxyacetamide | 426.4 |
| 212 | 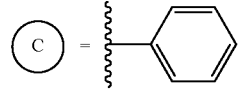 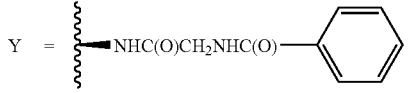 | (1R)-$N^2$-benzoyl-$N^1$-(2-hydroxy-1-phenyl-2,2-dipyridin-3-ylethyl)glycinamide | 453.2 |
| 213 | 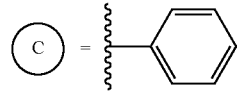 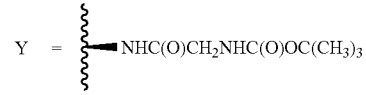 | (1R)-$N^2$-Boc-$N^1$-(2-hydroxy-1-phenyl-2,2-dipyridin-3-ylethyl)glycinamide | 449.5 |

-continued

| Example | Compound | Name | MS (M + 1) |
|---|---|---|---|
| 214 | 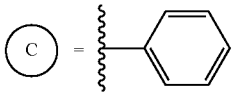 C = phenyl; Y = NHSO₂(CH₂)₂-phenyl | N-[(1R)-2-hydroxy-1-phenyl-2,2-dipyridin-3-ylethyl]-2-phenylethanesulfonamide | 460.0 |
| 215 | 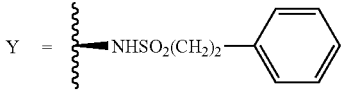 C = phenyl; Y = NHSO₂(CH₂)₃-phenyl | N-[(1R)-2-hydroxy-1-phenyl-2,2-dipyridin-3-ylethyl]-3-phenylpropane-1-sulfonamide | 474.2 |
| 216 | 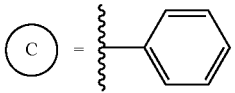 C = 4-fluorophenyl; Y = NHC(O)OC(CH₃)₃ | tert-butyl (1R)-1-(4-fluorophenyl)-2-hydroxy-2,2-dipyridin-3-ylethylcarbamate | 410.1879 |
| 217 | 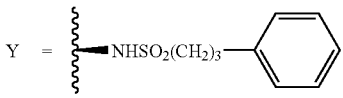 C = 4-fluorophenyl; Y = NH₂ | (2R)-2-amino-2-(4-fluorophenyl)-1,1-dipyridin-3-ylethanol | 310.2 |
| 218 | 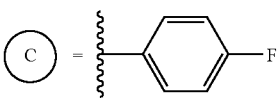 C = 4-fluorophenyl; Y = NHC(O)-5-phenylisoxazol-3-yl | N-[(1R)-1-(4-fluorophenyl)-2-hydroxy-2,2-dipyridin-3-ylethyl]-5-phenylisoxazole-3-carboxamide | 481.3 |
| 219 |  C = 4-fluorophenyl; Y = NHC(O)-3-phenylisoxazol-5-yl | N-[(1R)-1-(4-fluorophenyl)-2-hydroxy-2,2-dipyridin-3-ylethyl]-3-phenylisoxazole-5-carboxamide | 481.3 |

-continued

| Example | Compound | Name | MS (M + 1) |
|---|---|---|---|
| 220 | 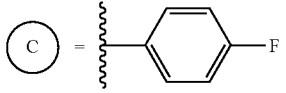 | N-[(1R)-1-(4-fluorophenyl)-2-hydroxy-2,2-dipyridin-3-ylethyl]-3-phenyl-1H-pyrazole-5-carboxamide | 480.6 |
| 221 | 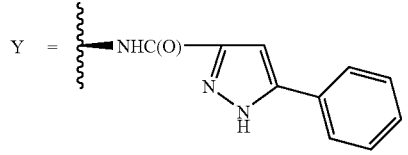 | N-[(1R)-1-(4-fluorophenyl)-2-hydroxy-2,2-dipyridin-3-ylethyl]-3-pyrdin-2-yl-1H-pyrazole-5-carboxamide | 481.3 |
| 222 | 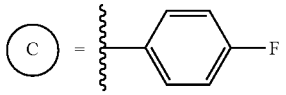 | N-[(1S)-2-hydroxy-1-phenyl-2,2-dipyridin-3-ylethyl]cyclobutanecarboxamide | 374.1886 |
| 223 | 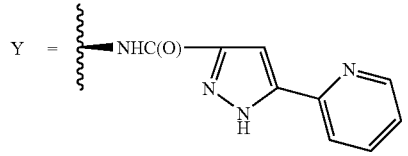 | N-[(1S)-2-hydroxy-1-phenyl-2,2-dipyridin-3-ylethyl]-1-(trifluoromethyl)cyclobutane carboxamide | 442.1736 |
| 224 | 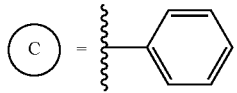 | N-ethyl-N'-[(1S)-2-hydroxy-1-phenyl-2,2-dipyridin-3-ylethyl]urea | 363.1816 |
| 225 | 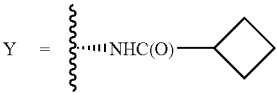 | N-[(1R)-2-hydroxy-1-phenyl-2,2-dipyridin-3-ylethyl]-3-methoxybenzamide | 426.1801 |

-continued

| Example | Compound | Name | MS (M + 1) |
|---|---|---|---|
| 226 | C = phenyl; Y = ⋯NHC(O)NHC(O)OCH₂CH₃ | (1R)-ethyl {[(2-hydroxy-1-phenyl-2,2-dipyridin-3-ylethyl)amino]carbonyl} carbamate | 407.1717 |
| 227 | C = phenyl; Y = NHC(O)NHCH₂CH₃ | (1R)-N-ethyl-N'-(2-hydroxy-1-phenyl-2,2-dipyridin-3-ylethyl)urea | 363.1815 |
| 228 | C = phenyl; Y = NHC(O)NH—phenyl | (1R)-N-(2-hydroxy-1-phenyl-2,2-dipyridin-3-ylethyl)-N-phenylurea | 411.1816 |
| 229 | C = phenyl; Y = NHC(O)—cyclopropyl | N-[(1R)-2-hydroxy-1-phenyl-2,2-dipyridin-3-ylethyl]cyclopropane-carboxamide | 360.1 |
| 230 | C = phenyl; Y = NHC(O)—cyclobutyl | (1R)-N-(2-hydroxy-1-phenyl-2,2-dipyridin-3-ylethyl)cyclobutane-carboxamide | 374.1855 |
| 231 | C = phenyl; Y = NHC(O)—cyclobutyl(CF₃) | (1R)-N-(2-hydroxy-1-phenyl-2,2-dipyridin-3-ylethyl)-1-(trifluoromethyl)cyclobutane carboxamide | 442.1714 |
| 232 | C = phenyl; Y = NHC(O)OCH₂—phenyl | benzyl[(1R)-2-hydroxy-1-phenyl-2,2-dipyridin-3-ylethyl]carbamate | 426.1799 |

-continued

| Example | Compound | Name | MS (M + 1) |
|---|---|---|---|
| 233 | C = phenyl<br><br>Y = NHC(O)O—phenyl | phenyl[(1R)-2-hydroxy-1-phenyl-2,2-dipyridin-3-ylethyl]carbamate | 412.1655 |
| 234 | C = phenyl<br><br>Y = NHC(O)CH$_2$CF$_3$ | (1R)-3,3,3-trifluoro-n-(2-hydroxy-1-phenyl-2,2-dipyridin-3-ylethyl)propanamide | 402.1405 |
| 235 | C = phenyl<br><br>Y = NHCH$_2$-(1H-pyrazol-5-yl) | (2R)-2-phenyl-2-[(1H-pyrazol-5-ylmethyl)amino]-1,1-dipyridin-3-ylethanol | 372.1825 |
| 236 | C = phenyl<br><br>Y = NHC(O)CH(CF$_3$)(OH) | (1R)-3,3,3-trifluoro-2-hydroxy-N--(2-hydroxy-1-phenyl-2,2-dipyridin-3-ylethyl)propanamide | 418.1369 |
| 237 | C = phenyl<br><br>Y = NHC(O)CF$_3$ | (1R)-2,2,2-trifluoro-N-(2-hydroxy-1-phenyl-2,2-dipyridin-3-ylethyl)acetamide | 388.1283 |
| 238 | C = phenyl<br><br>Y = NHC(O)(CH$_2$)$_2$—phenyl | (1R)-N-(2-hydroxy-1-phenyl-2,2-dipyridin-3-ylethyl)-3-phenylpropanamide | 424.2017 |
| 239 | C = phenyl<br><br>Y = N(CH$_3$)C(O)—phenyl | (1R)-N-[(1R)-2-hydroxy-1-phenyl-2,2-dipyridin-3-ylethyl]-N-methylbenzamide | 410.1860 |

-continued

| Example | Compound | Name | MS (M + 1) |
|---|---|---|---|
| 240 | 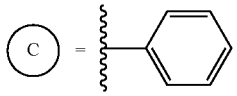 | (1R)-N-2-hydroxy-1-phenyl-(2,2-dipyridin-3-ylethyl)-2-methoxybenzamide | 426.4 |
| 241 | 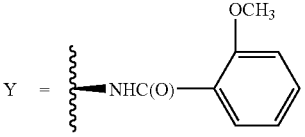 | (1R)-N-(2-hydroxy-1-phenyl-2,2-dipyridin-3-ylethyl)-2-phenylacetamide | 410.1860 |
| 242 | 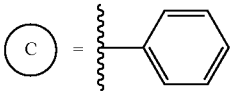 | (1R)-2-(benzylamino)-2-phenyl-1,1-dipyridin-3-ylethanol | 382.1912 |
| 243 |  | (1R)-2-[(cyclopropylmethyl)amino]-2-phenyl-1,1-dipyridin-3-ylethanol | 346.1913 |
| 244 | 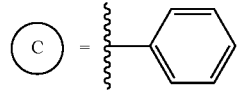 | (1R)-2-[(cyclohexylmethyl)amino]-2-phenyl-1,1-dipyridin-3-ylethanol | 388.2381 |
| 245 | 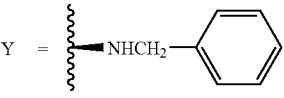 | (2R)-2-[(cyclopentylmethyl)amino]-2-phenyl-1,1-dipyridin-3-ylethanol | 374.2218 |

-continued

| Example | Compound | Name | MS (M + 1) |
|---|---|---|---|
| 246 | 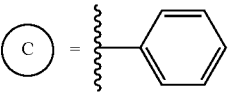 | (1R)-N--(2-hydroxy-1-phenyl-2,2-dipyridin-3-ylethyl)-4-phenylbutanamide | 438.2174 |
| 247 | 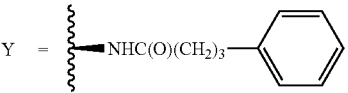 | tert-butyl[(1S)-1-({[(1R)-2-hydroxy-1-phenyl-2,2-dipyridin-3-ylethyl]amino}carbonyl)-3-phenylpropyl]carbamate | 553.2786 |
| 248 | 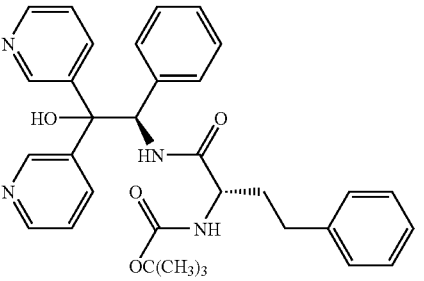 | tert-butyl[(1R)-1-({[(1R)-2-hydroxy-1-phenyl-2,2-dipyridin-3-ylethyl]amino}carbonyl)-3-phenylpropyl]carbamate | 553.2787 |
| 249 | 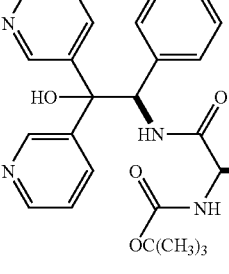 | N-[(1R)-2-hydroxy-1-phenyl-2,2-dipyridin-3-ylethyl]-4-oxo-4-phenylbutanamide | 452.1950 |
| 250 | 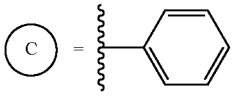 | (2S)-2-amino-N-[(1R)-2-hydroxy-1-phenyl-2,2-dipyridin-3-ylethyl]-4-phenylbutanamide | 453.2269 |

-continued

| Example | Compound | Name | MS (M + 1) |
|---|---|---|---|
| 251 | | (2R)-2-amino-N-[(1R)-2-hydroxy-1-phenyl-2,2-dipyridin-3-ylethyl]-4-phenylbutanamide | 453.2268 |
| 252 | C = phenyl; Y = NHC(O)-cyclopropyl-phenyl | trans-N-[(1R)-2-hydroxy-1-phenyl-2,2-dipyridin-3-ylethyl]-2-phenylcyclopropanecarboxamide | 436.2015 |
| 253 | C = phenyl; Y = NHC(O)(CH$_2$)$_2$CH(NHCH$_3$)-phenyl | N-[(1R)-2-hydroxy-1-phenyl-2,2-dipyridin-3-ylethyl]-4-(methylamino)-4-phenylbutanamide | 467.2435 |
| 254 | C = phenyl; Y = NHC(O)(CH$_2$)$_2$-(1H-indol-3-yl) | N-[(1R)-2-hydroxy-1-phenyl-2,2-dipyridin-3-ylethyl]-3-(1H-indol-3-yl)propanamide | 463.2127 |
| 255 | | (2S)-[(1R)-2-hydroxy-1-phenyl-2,2-dipyridin-3-ylethyl]-2-[(methylsulfonyl)amino]-4-phenylbutanamide | 531.2051 |

-continued

| Example | Compound | Name | MS (M + 1) |
|---|---|---|---|
| 256 | | (2S)-[(1R)-2-hydroxy-1-phenyl-2,2-dipyridin-3-ylethyl]-2-[(methylsulfonyl)amino]-4-phenylbutanamide | 531.2054 |
| 257 | | (2S)-2-(acetylamino)-N-[(1R)-2-hydroxy-1-phenyl-2,2-dipyridin-3-ylethyl]-4-phenylbutanamide | 495.2394 |
| 258 | | (2R)-2-(acetylamino)-N-[(1R)-2-hydroxy-1-phenyl-2,2-dipyridin-3-ylethyl]-4-phenylbutanamide | 495.2395 |
| 259 | C = phenyl; Y = NHC(O)(CH$_2$)$_2$CH(OH)-phenyl | 4-hydroxy-N-[(1R)-2-hydroxy-1-phenyl-2,2-dipyridin-3-ylethyl]-4-phenylbutanamide | 454.2137 |
| 260 | C = phenyl; Y = NHC(O)(CH$_2$)$_3$-(5,6,7,8-tetrahydro-1,8-naphthyridin-2-yl) | N-[(1R)-2-hydroxy-1-phenyl-2,2-dipyridin-3-ylethyl]-4-(5,6,7,8-tetrahydro-1,8-napthyridin-2-yl)butanamide | 494.2547 |
| 261 | C = phenyl; Y = NHC(O)CH$_2$-N(4-phenylpiperazin-1-yl) | N-[(1R)-2-hydroxy-1-phenyl-2,2-dipyridin-3-ylethyl]-2-(4-phenylpiperazin-1-yl)acetamide | 494.2552 |

-continued

| Example | Compound | Name | MS (M + 1) |
|---|---|---|---|
| 262 | 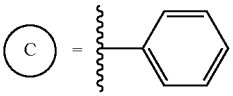 | N-[(1R)-2-hydroxy-1-phenyl-2,2-dipyridin-3-ylethyl]-2-(2-phenyl-1,3-thiazol-5-yl)acetamide | 493.1699 |
| 263 | 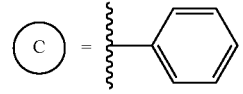 | 2-(1,3-benzothiazol-2-ylthio)--N-[(1R)-2-hydroxy-1-phenyl-2,2-dipyridin-3-ylethyl]acetamide | 499.1249 |
| 264 | 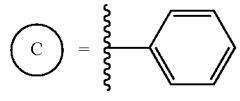 | 3-(1-H-benzimidazol-1-yl)-N-[(1R)-2-hydroxy-1-phenyl-2,2-dipyridin-3-ylethyl]propanamide | 464.2077 |
| 265 | 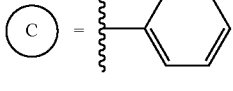 | N-[(1R)-2-hydroxy-1-phenyl-2,2-dipyridin-3-ylethyl]-3-(1-H-pyrazol-1-yl)propanamide | 414.1927 |
| 266 | 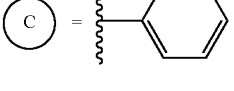 | N-[(1R)-2-hydroxy-1-phenyl-2,2-dipyridin-3-ylethyl]-3-(3-methyl-1-h-pyrazol-1-yl)propanamide | 428.2076 |
| 267 | 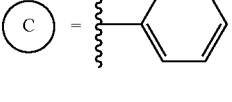 | N-[(1R)-2-hydroxy-1-phenyl-2,2-dipyridin-3-ylethyl]-3-pyrazin-2-ylpropanamide | 426.1920 |

-continued

| Example | Compound | Name | MS (M + 1) |
|---|---|---|---|
| 268 | C = phenyl; Y = NHC(O)(CH₂)₂-[2-hydroxy-2,3-dihydro-1,3-benzoxazol-2-yl] | 3-(2-hydroxy-2,3-dihydro-1,3-benzoxazol-2-yl)-N-[(1R)-2-hydroxy-1-phenyl-2,2-dipyridin-3-ylethyl]propanamide | 483.2040 |
| 269 | C = phenyl; Y = NHC(O)-piperidin-4-yl-1-(pyridin-3-ylmethyl) | N-[(1R)-2-hydroxy-1-phenyl-2,2-dipyridin-3-ylethyl]-1-(pyridin-3-ylmethyl)piperidine-4-carboxamide | 494.2562 |
| 270 | C = phenyl; Y = NHC(O)-piperidin-4-yl-1-(pyrimidin-2-yl) | N-[(1R)-2-hydroxy-1-phenyl-2,2-dipyridin-3-ylethyl]-1-pyrimidin-2-ylpiperidine-4-carboxamide | 481.2350 |
| 271 | C = 4-fluorophenyl; Y = NHC(O)(CH₂)₃-phenyl | N-[(1R)-1-(4-fluorophenyl)-2-hydroxy-2,2-dipyridin-3-ylethyl]-4-phenylbutanamide | 456.2089 |
| 272 | C = 4-fluorophenyl; Y = NHC(O)CH₂OCH₂-phenyl | 2-(benzyloxy)-N-[(1R)-1-(4-fluorophenyl)-2-hydroxy-2,2-dipyridin-3-ylethyl]acetamide | 458.1885 |
| 273 | C = 4-fluorophenyl; Y = NHC(O)OCH₂-phenyl | benzyl [(1R)-1-(4-fluorophenyl)-2-hydroxy-2,2-dipyridin-3-ylethyl]carbamate | 444.1725 |

| Example | Compound | Name | MS (M + 1) |
|---|---|---|---|
| 274 | C = phenyl; Y = NHC(O)O(CH₂)₂-phenyl | 2-phenylethyl [(1R)-2-hydroxy-1-phenyl-2,2-dipyridin-3-ylethyl]carbamate | 440.1907 |
| 275 | C = phenyl; Y = NHC(O)(CH₂)₃-(pyridin-4-yl) | N-[(1R)-2-hydroxy-1-phenyl-2,2-dipyridin-3-ylethyl]-4-pyridin-4-ylbutanamide | 439.2129 |
| 276 | C = 4-fluorophenyl; Y = NHC(O)-(1-phenyl-1H-pyrazol-4-yl) | N-[(1R)-1-(4-fluorophenyl)-2-hydroxy-2,2-dipyridin-3-ylethyl]-1-phenyl-1H-pyrazole-4-carboxamide | 480.1830 |
| 277 | C = 4-fluorophenyl; Y = NHC(O)(CH₂)₃-(6-oxopyridazin-1(6H)-yl) | N-[(1R)-1-(4-fluorophenyl)-2-hydroxy-2,2-dipyridin-3-ylethyl]-4-(6-oxopyridazin-1(6H)-yl)butanamide | 474.1928 |
| 278 | C = 4-fluorophenyl; Y = NHC(O)-pyrazolo[1,5-a]pyridin-2-yl | N-[(1R)-1-(4-fluorophenyl)-2-hydroxy-2,2-dipyridin-3-ylethyl]pyrazolo[1,5-a]pyridine-2-carboxamide | 454.1688 |
| 279 | C = 4-fluorophenyl; Y = NHC(O)-(5-phenyl-2-furyl) | N-[(1R)-2-hydroxy-1-phenyl-2,2-dipyridin-3-ylethyl]-5-phenyl-2-furamide | 462.1818 |

-continued

| Example | Compound | Name | MS (M + 1) |
|---|---|---|---|
| 280 | C = (4-fluorophenyl); Y = NHCH₂-(1-phenyl-pyrazol-4-yl) | (2R)-2-phenyl-2-{[(1-phenyl-1h-pyrazol-4-yl)methyl]amino}-1,1-dipyridin-3-ylethanol | 448.2136 |
| 280a | C = (4-fluorophenyl); Y = NHC(O)-(5-propylisoxazol-3-yl) | (±)-N-[1-(4-fluorophenyl)-2-hydroxy-2,2-dipyridin-3-ylethyl]-5-propylisoxazole-3-carboxamide | 447.1849 |
| 281 | C = (3-methoxyphenyl); Y = 2,7-diazaspiro[3.5]non-7-yl | (±)-2-(2,7-diazaspiro[3.5]non-7-yl)-2-(3-methoxyphenyl)-1,1-dipyridin-3-ylethanol | 461.2435 |
| 282 | C = phenyl; Y = 4-(hydroxyacetyl)piperazin-1-yl | (±)-2-phenyl-2-(N-hydroxyacetyl)-piperazin-1-yl-1,1-dipyridin-3-ylethanol | 419.2097 |
| 283 | 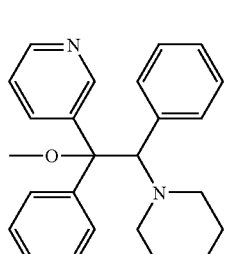 | (±)-4-(2-methoxy-1-phenyl-2,2-dipyridin-3-ylethyl)morpholine | 376.2023 |

-continued

| Example | Compound | Name | MS (M + 1) |
|---|---|---|---|
| 284 | C = 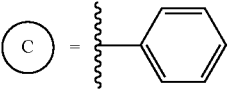<br><br>Y = 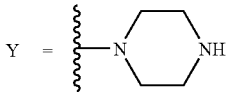 | (±)-2-phenyl-2-piperazin-1-yl-1,1-dipyridin-3-ylethanol | 361.2020 |
| 285 | C = 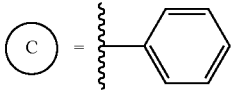<br><br>Y = 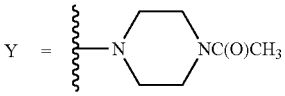 | (±)-2-(4-acetylpiperazin-1-yl)-2-phenyl-1,1-dipyridin-3-ylethanol | 403.2126 |
| 286 | C = 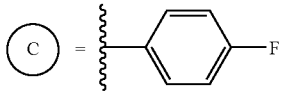<br><br>Y = 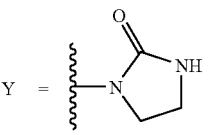 | (±)-1-[1-(4-fluorophenyl)-2-hydroxy-2,2-dipyridin-3-ylethyl]imidaazolidin-2-one | 379.1575 |
| 287 | C = 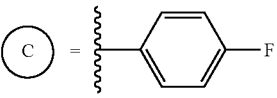<br><br>Y = 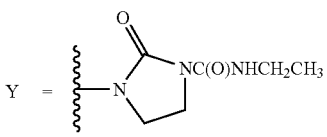 | (±)-N-ethyl-3-[1-(4-fluorophenyl)-2-hydroxy-2,2-dipyridin-3-ylethyl]-2-oxoimidazolidine-1-carboxamide | 450.1 |
| 288 | C = 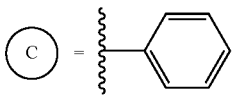<br><br>Y = 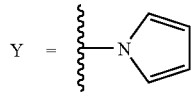 | (±)-2-phenyl-1,1-dipyridin-3-yl-2-(1H-pyrrol-1-yl)ethanol | 342.1607 |

-continued

| Example | Compound | Name | MS (M + 1) |
|---|---|---|---|
| 289 | C = 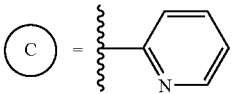<br>Y = 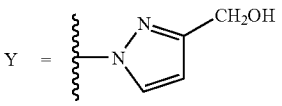 | (±)-2-[3-(hydroxymethyl)-1H-pyrazol-1-yl]-2-pyridin-2-yl-1,1-dipyridin-3-ylethanol | 374.1624 |
| 290 | C = 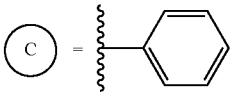<br>Y = 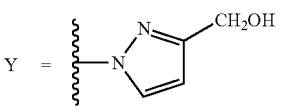 | (±)-2-[4-(hydroxymethyl)-1H-pyrazol-1-yl]-2-phenyl-1,1-dipyridin-3-ylethanol | 373.2 |
| 291 | C = 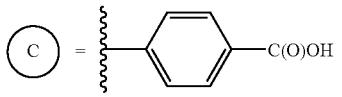<br>Y = 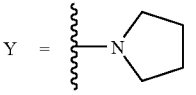 | (±)-4-(2-hydroxy-2,2-dipyridin-3-yl-1-pyrrolidin-1-ylethyl)benzoic acid | 390.1795 |
| 292 | C = <br>Y = 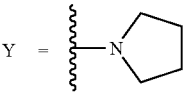 | (±)-4-(2-hydroxy-2,2-dipyridin-3-yl-1-pyrrolidin-1-ylethyl)-N-methylbenzamide | 403.2108 |
| 293 | C = <br>Y = 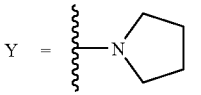 | (±)-4-(2-hydroxy-2,2-dipyridin-3-yl-1-pyrrolidin-1-ylethyl)-N,N-dimethylbenzamide | 417.2287 |

-continued

| Example | Compound | Name | MS (M + 1) |
|---|---|---|---|
| 294 | C = 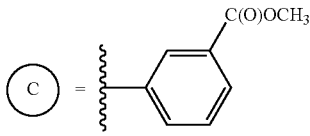 C(O)OCH₃<br><br>Y = pyrrolidine | (±)-methyl 3-(2-hydroxy-2,2-dipyridin-3-yl-1-pyrrolidin-1-ylethyl)benzoate | 404.1956 |
| 295 | C = 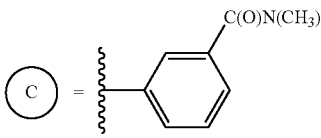 C(O)N(CH₃)₂<br><br>Y = pyrrolidine | (±)-3-(2-hydroxy-2,2-dipyridin-3-yl-1-pyrrolidin-1-ylethyl)-N,N-dimethylbenzamide | 417.2301 |
| 296 | C = 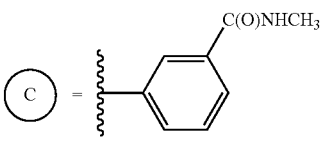 C(O)NHCH₃<br><br>Y = pyrrolidine | (±)-3-(2-hydroxy-2,2-dipyridin-3-yl-1-pyrrolidin-1-ylethyl)-N-methylbenzamide | 403.2147 |
| 297 | C = 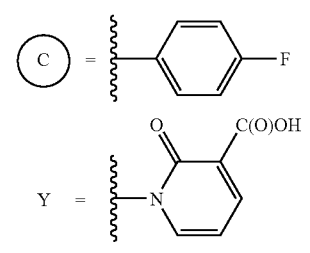 F<br><br>Y = 2-oxo-pyridine-3-C(O)OH | (±)-1-[1-(4-fluorophenyl)-2-hydroxy-2,2-dipyridin-3-ylethyl]-2-oxo-1,2-dihydropyridine-3-carboxylic acid | 432.1354 |
| 298 | C = 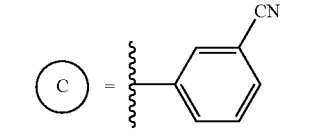 CN<br><br>Y = morpholine | (±)-3-(2-hydroxy-1-morpholin-4-yl-2,2-dipyridin-3-ylethyl)benzonitrile | 387.1817 |

-continued

| Example | Compound | Name | MS (M + 1) |
|---|---|---|---|
| 299 | C = <br><br>Y =  N(CH₃)CH₂CH(OH)CH₂OH | (±)-3-[(2-hydroxy-1-phenyl-2,2-dipyridin-3-ylethyl)(methyl)amino]propane-1,2-diol (1:1 mixture diastereomers) | 380.1959 |
| 300 | C = <br><br>Y = 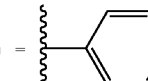 N(CH₃)CH₂CH₂OH | (±)-2-[hydroxyethyl(methyl)amino]-2-phenyl-1,1-dipyridin-3-ylethanol | 350.1851 |
| 301 | C = <br><br>Y = 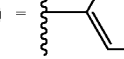 | (±)-1-(2-hydroxy-1-phenyl-2,2-dipyridin-3-ylethyl)pyrrolidin-3-one | 360.1709 |
| 302 | C = <br><br>Y = 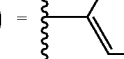 | (±)-1-(2-hydroxy-1-phenyl-2,2-dipyridin-3-ylethyl)-3-methylpyrrolidin-3-ol (5:1 mixture diastereomers) | 376.2009 |
| 5-1 | C = <br><br>Y = 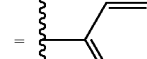 | (±)-N-[1-(4-fluorophenyl)-2-hydroxy-2,2-dipyridin-3-ylethyl]-5-propylisoxazole-3-carboxamide | 447.1849 |

The following fluorinated compounds were made by treatment of Examples 1-201 compounds with DAST, in accordance with literature methods. Structures of compounds 303-319 are represented by defining variables and "Ⓒ" of the structure

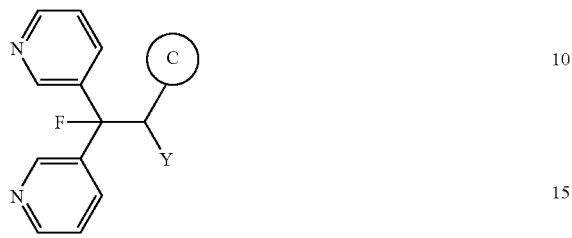

EXAMPLES 303-319

| Example | Compound | Name | MS (M + 1) |
|---|---|---|---|
| 303 | Ⓒ = —phenyl; Y = —N(2,5-dihydropyrrol-1-yl) | (±)-3,3'-[2-(2,5-dihydro-1H-pyrrol-1-yl)-1-fluoro-2-phenylethane-1,1-diyl]dipyridine | 346.1719 |
| 304 | Ⓒ = —(3-chlorophenyl); Y = —N(3,3-difluoroazetidin-1-yl) | (±)-3,3'-[2-(3-chlorophenyl)-2-(3,3-difluoroazetidin-1-yl)-1-fluoroethane-1,1-diyl]dipyridine | 404.2 |
| 305 | Ⓒ = —(3-methoxyphenyl); Y = —N(3-hydroxypyrrolidin-1-yl) | (3R)-1-[2-fluoro-1-(3-methoxyphenyl)-2,2-dipyridin-3-ylethyl]pyrrolidin-3-ol | 394.1921 |
| 306 | Ⓒ = —(3-thienyl); Y = —N(pyrrolidin-1-yl) | (±)-3,3'-[1-fluoro-2-pyrrolidin-1-yl-2-(3-thienyl)ethane-1,1-diyl]dipyridine | 354.1448 |

-continued

| Example | Compound | Name | MS (M + 1) |
|---|---|---|---|
| 307 | 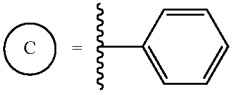 C = 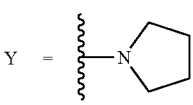<br><br>Y = 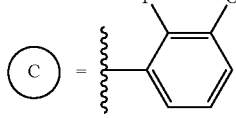 | (±)-3,3'-(1-fluoro-2-phenyl-2-pyrrolidin-1-ylethane-1,1-diyl]dipyridine | 348.1871 |
| 308 | C = 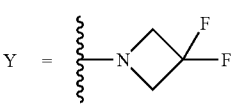<br><br>Y = 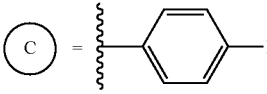 | (±)-3,3-difluoro-1-[2-fluoro-1-(2-fluoro-3-methoxyphenyl)-2,2-dipyridin-3-ylethyl]azetidine | 418.3 |
| 309 | C = 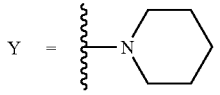<br><br>Y = 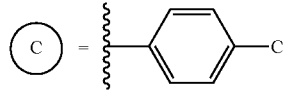 | (±)-3,3'-[1-fluoro-2-(4-fluorophenyl)-2-piperidin-1-ylethane-1,1-diyl]dipyridine | 380.1938 |
| 310 | C = 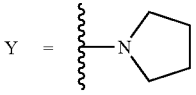<br><br>Y = 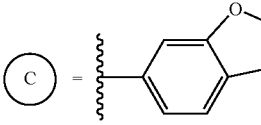 | (±)-3,3'-[1-fluoro-2-(4-methylphenyl)-2-pyrrolidin-1-ylethane-1,1-diyl]dipyridine | 362.2031 |
| 311 | C = 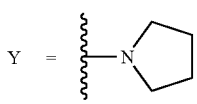<br><br>Y = 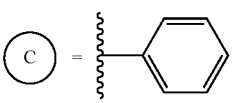 | (±)-3,3'-[2-(1,3-benzodioxol-5-yl)-1-fluoro-2-pyrrolidin-1-ylethane-1,1-diyl]dipyridine | 392.1822 |
| 312 | C = 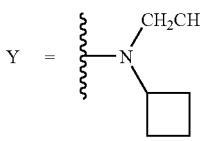<br><br>Y =  | (±)-N-ethyl-N-(2-fluoro-1-phenyl-2,2-dipyridin-3-ylethyl)cyclobutanamine | 376.2190 |

-continued

| Example | Compound | Name | MS (M + 1) |
|---------|----------|------|------------|
| 313 | C = 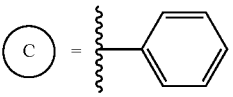<br><br>Y = 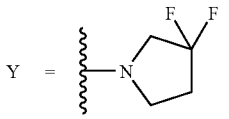 | (±)-3,3'-[2-(3,3-difluoropyrrolidin-1-yl)-1-fluoro-2-phenylethane-1,1-diyl]dipyridine | 384.1681 |
| 314 | C = 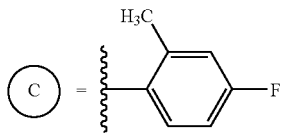<br><br>Y = 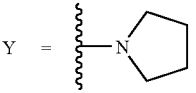 | (±)-3,3'-[1-fluoro-2-(4-fluoro-2-methylphenyl)-2-pyrrolidin-1-ylethane-1,1-diyl]dipyridine | 380.1943 |
| 315 | C = 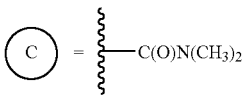<br><br>Y = 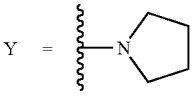 | (±)-3-fluoro-N,N-dimethyl-3,3-dipyridin-3-yl-2-pyrrolidin-1-ylpropanamide | 343.1932 |
| 316 | C = 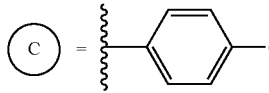<br><br>Y = 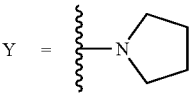 | (±)-3,3'-{1-fluoro-2-pyrrolidin-1-yl-2-[4-(trifluoromethoxy)phenyl]ethane-1,1-diyl}dipyridine | 432.1736 |
| 317 | C = 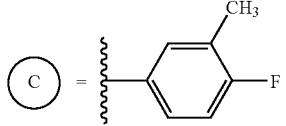<br><br>Y = 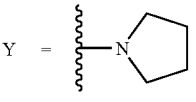 | (±)-3,3'-[1-fluoro-2-(4-fluoro-3-methylphenyl)-2-pyrrolidin-1-ylethane-1,1-diyl]dipyridine | 380.1957 |
| 318 | C = 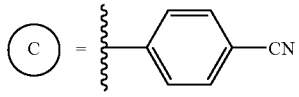<br><br>Y = 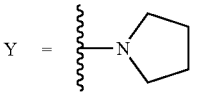 | (±)-4-(2-fluoro-2,2-dipyridin-3-yl-1-pyrrolidin-1-ylethyl)benzonitrile | 373.1834 |

-continued

| Example | Compound | Name | MS (M + 1) |
|---|---|---|---|
| 319 | C = (3-cyanophenyl); Y = pyrrolidin-1-yl | (±)-3-(2-fluoro-2,2-dipyridin-3-yl-1-pyrrolidin-1-ylethyl)benzonitrile | 373.1828 |

The following compounds were made from 2-(3-{[tert-butyl(dimethyl)silyl]oxy}azetidin-1-yl)-2-(4-fluorophenyl)-1,1-dipyridin-3-ylethanol, which was prepared in accordance with scheme 5, using methods known to those skilled in the art. Unless otherwise shown, structures of compounds 320-334 and 335-342 are represented by defining variables "C" and "Y" of the structure

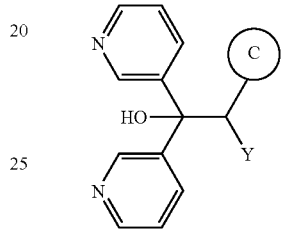

EXAMPLES 320-334

| Example | Compound | Name | MS (M + 1) |
|---|---|---|---|
| 320 | C = (4-fluorophenyl); Y = 3-hydroxyazetidin-1-yl | (±)-1-[1-(4-fluorophenyl)-2-hydroxy-2,2-dipyridin-3-ylethyl]azetidin-3-ol | 366.1595 |
| 321 | C = (4-fluorophenyl); Y = 3-(methanesulfonyloxy)azetidin-1-yl | (±)-1-[1-(4-fluorophenyl)-2-hydroxy-2,2-dipyridin-3-ylethyl]azetidin-3-yl methanesulfonate | 444.1374 |
| 322 | C = (4-fluorophenyl); Y = 3-aminoazetidin-1-yl | (±)-2-(3-aminoazetidin-1-yl)-2-(4-fluorophenyl)-1,1-dipyridin-3-ylethanol | 365.1763 |

-continued

| Example | Compound | Name | MS (M + 1) |
|---|---|---|---|
| 323 |  Y = 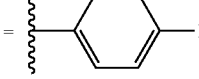 | (±)-2-[3-(dimethylamino)azetidin-1-yl]-2-(4-fluorophenyl)-1,1-dipyridin-3-ylethanol | 393.2064 |
| 324 |  Y = 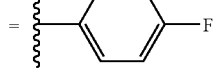 | (±)-N-{1-[1-(4-fluorophenyl)-2-hydroxy-2,2-dipyridin-3-ylethyl]azetidin-3-yl}methanesulfonamide | 443.1534 |
| 325 |  Y = 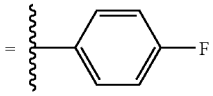 | (±)-N-{1-[1-(4-fluorophenyl)-2-hydroxy-2,2-dipyridin-3-ylethyl]azetidin-3-yl}acetamide | 407.1857 |
| 326 |  Y = 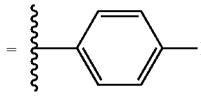 | (±)-2-(4-fluorophenyl)-2-[3-(methylthio)azetidin-1-yl]-1,1-dipyridin-3-ylethanol | 396.1554 |
| 327 |  Y = 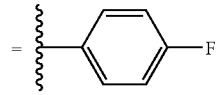 | (±)-1-[1-(4-fluorophenyl)-2-hydroxy-2,2-dipyridin-3-ylethyl]azetidin-3-yl carbamate | 409.1667 |
| 328 |  Y = 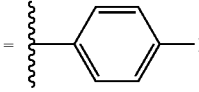 | (±)-1-[1-(4-fluorophenyl)-2-hydroxy-2,2-dipyridin-3-ylethyl]azetidin-3-sulfonamide | 429.1357 |

-continued

| Example | Compound | Name | MS (M + 1) |
|---|---|---|---|
| 329 | 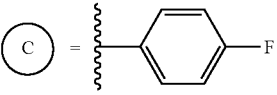 | (±)-1-[1-(4-fluorophenyl)-2-hydroxy-2,2-dipyridin-3-ylethyl]-N,N-dimethylazetidin-3-sulfonamide | 457.1700 |
| 330 | 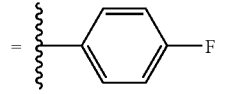 | (±)-N-{1-[1-(4-fluorophenyl)-2-hydroxy-2,2-dipyridin-3-ylethyl]azetidin-3-yl}-N'-phenylurea | 484.2135 |
| 331 | 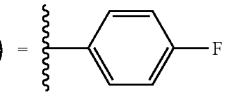 | (±)-1-[1-(4-fluorophenyl)-2-hydroxy-2,2-dipyridin-3-ylethyl]azetidin-3-yl phenylcarbamate | 485.1966 |
| 332 | 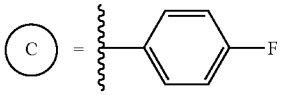 | (±)-1-[1-(4-fluorophenyl)-2-hydroxy-2,2-dipyridin-3-ylethyl]azetidin-3-yl pyrrolidine-1-carboxylate | 463.2154 |
| 333 | 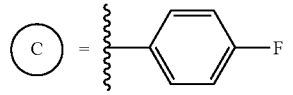 | (±)-1-[1-(4-fluorophenyl)-2-hydroxy-2,2-dipyridin-3-ylethyl]azetidin-3-yl methylcarbamate | 423.1845 |
| 334 | 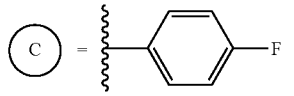 | (±)-1-[1-(4-fluorophenyl)-2-hydroxy-2,2-dipyridin-3-ylethyl]azetidin-3-yl(4-fluorophenyl)carbamate | 503.1897 |

The following compounds were made from compounds in Examples 1-201, using oxidation methods known to those skilled in the art. MCPBA oxidation was used to convert example 24 to 335, example 316 to 336 and 337, example 1 to 338, and example 16 to 339. Methyltrioxorhenium was used to convert example 1 to 340 and 341, and example 170 to 342

EXAMPLES 335-342

| Example | Compound | Name | MS (M + 1) |
|---|---|---|---|
| 335 | 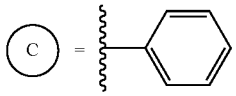 | (±)-2-(1,1-dioxidothiomorpholin-4-yl)-2-phenyl-1,1-dipyridin-3-ylethanol | 410.1513 |
| 336 | 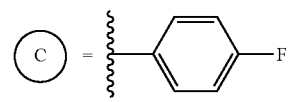 | (±)-2-(4-fluorophenyl)-2-[3-(methylsulfonyl)azetidin-1-yl]-1,1-dipyridin-3-ylethanol | 428.1457 |
| 337 | 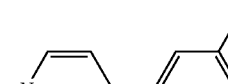 | (±)-2-(4-fluorophenyl)-2-[3-(methylsulfonyl)azetidin-1-yl]-1-(1-oxidopyridin-3-yl)-1-pyridin-3-ylethanol (1:1 mixture diastereomers) | 444.1391 |
| 338 | 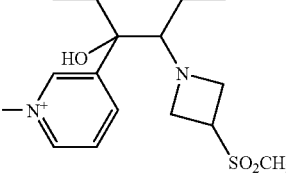 | (±)-2-(4-oxidomorpholin-4-yl)-2-phenyl-1,1-dipyridin-3-ylethanol | 378.1799 |
| 339 | 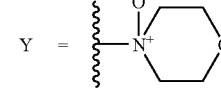 | (±)-2-(1-oxidopyrrolidin-1-yl)-2-phenyl-1,1-dipyridin-3-ylethanol | 362.1859 |
| 340 | 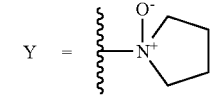 | (±)-2-(4-oxidomorpholin-4-yl)-1,1-bis(1-oxidopyridin-3-yl)-2-phenylethanol | 410.1711 |

-continued

| Example | Compound | Name | MS (M + 1) |
|---|---|---|---|
| 341 | | (±)-2-morpholin-4-yl-1,1-bis(1-oxidopyridin-3-yl)-2-phenylethanol | 394.1762 |
| 342 | | (±)-2-(3,3-difluoroazetidin-1-yl)-2-(4-fluorophenyl)-1-(1-oxidopyridin-3-yl)-1-pyridin-3-ylethanol(1:1 mixture diastereomers) | 402.1447 |

SCHEME 6

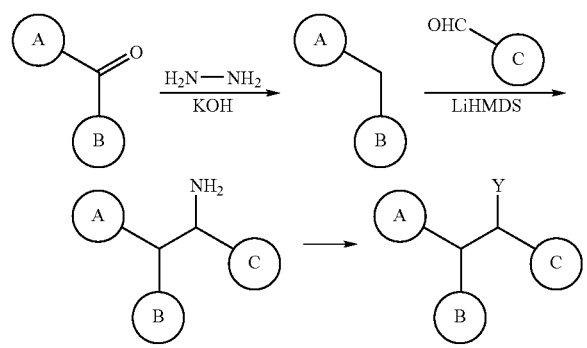

The variables C, B, A, and Y in the scheme are as defined in "Formula I".

EXAMPLE 343

(±)-4-[1-(6-methoxypyridin-2-yl)-2,2-dipyridin-3-ylethyl]morpholine

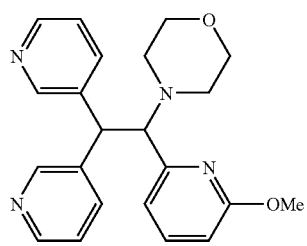

Step A:

Dipyridin-3-ylmethanone (1-1, 2.630 g, 14.28 mmol) was suspended in ethylene glycol (28 mL). KOH (1.682 g, 29.98 mmol) was added and the reaction was stirred at RT for 1 hr until most of the solids were dissolved. Hydrazine monohydrate (1.596 mL, 32.84 mmol) was added and the mixture was heated to 185° C. After 1 hr 45 min, the reaction was cooled to RT, diluted with $H_2O$ (150 mL), and extracted with $CH_2Cl_2$ (4×100 mL). The combined organics were washed with water, washed with brine (2×), dried over $Na_2SO_4$, filtered, and concentrated in vacuo to afford 3-(pyridin-3-ylmethyl)pyridine as a light yellow solid. $^1H$ NMR ($CDCl_3$) δ 8.52-8.49 (m, 4H), 7.47-7.45 (m, 2H), 7.25-7.22 (m, 2H), 3.99 (s, 2H). [M+H]+=171.2.

Step B:

LiHMDS (2.45 mL, 1.2 M in THF, 2.94 mmole) was added to a flame-dried round bottom flask. The mixture was cooled to 0° C. then 6-methoxypyridine-2-carbaldehyde (Comins, Daniel L.; Killpack, Michael O. J. Org. Chem. 1990, 55, 69-73, 161 mg, 1.18 mmole) was added. After 30 minutes di-3-pyridylmethane (200 mg, 1.18 mmole) in dry THF (2.0 mL) was added. After 2 hr the mixture was warmed to RT, quenched with saturated $NH_4Cl$, and extracted with $CH_2Cl_2$ (3×) and iBuOH (2×). The combined organic layers were dried ($MgSO_4$), filtered, and concentrated. The residue was taken up in MeOH (5 mL) and $H_2NOH$ (0.4 mL, 50% in $H_2O$) was added. After 18 hr the mixture was concentrated. Flash column (gradient, 0-10% MeOH/$CH_2Cl_2$) gave 1-(6-methoxypyridin-2-yl)-2,2-dipyridin-3-ylethanamine as a pale yellow oil (168 mg, 47%): $^1H$-NMR (500 MHz, $CDCl_3$) δ 8.64 (d, J=1.95 Hz, 1H), 8.51 (dd, J=1.46 and 3.17 Hz, 1H), 8.36 (d, J=1.95 Hz, 1H), 8.32 (dd, J=1.46 and 3.18 Hz, 1H), 7.76 (d, J=7.82 Hz, 1H), 7.49 (d, J=8.06 Hz, 1H), 7.37-7.27 (m, 2H), 7.09 (m, 1H), 6.56 (d, J=7.08 Hz, 1H), 6.52 (d, J=7.81 Hz, 1H), 4.59 (d, J=9.28 Hz, 1H), 4.42 (d, J=9.28 Hz, 1H), 3.91 (s, 3H).

Step C:

To a solution of 1-(6-methoxypyridin-2-yl)-2,2-dipyridin-3-ylethanamine (75 mg, 0.25 mmole) in $CH_3CN$ (1 mL) was added a solution of 2,2'-oxydiacetaldehyde in H$_2$O (1.47 mL, 0.5 M, 0.73 mmole). After 10 minutes NaBH$_3$CN (92 mg, 1.47 mmole) was added. After 2 hr 1N HCl (2 mL) was added. After 1 hr the pH was adjusted to 8 and the mixture extracted with CH$_2$Cl$_2$ (3×) and iBuOH (1×). The combined organic layers were dried (MgSO$_4$), filtered, and concentrated. Flash column (gradient, 0-10% MeOH/CH$_2$Cl$_2$) gave mixed fractions. Fractions containing the product were pooled and concentrated. The mixture was purified by reverse phase HPLC (5-100% CH$_3$CN/H$_2$O+0.1% TFA). Fractions containing the product were pooled, made basic with saturated NaHCO$_3$, and extracted with CH$_2$Cl$_2$ (3×). The combined organic layers were dried (MgSO$_4$), filtered, and concentrated to give the title compound (15 mg, 16%) as a white solid: $^1$H-NMR (500 MHz, CDCl$_3$) δ 8.70 (bs, 1H), 8.48 (bs, 1H), 8.39 (bs, 1H), 8.26 (bd, J=3.9 Hz, 1H), 7.71 (d, J=7.82 Hz, 1H), 7.44-7.36 (m, 2H), 7.28 (m, 1H), 7.03 (m, 1H), 6.52 (m, 2H), 5.01 (d, J=11.72 Hz, 1H), 4.27 (d, J=11.72 Hz, 1H), 3.96 (s, 3H), 3.49 (m, 2H), 3.35 (m, 2H), 2.63 (m, 2H), 2.42 (m, 2H); HRMS, calc'd for C$_{22}$H$_{25}$N$_4$O$_2$ (M+1), 377.1972; found 377.1944.

The following compounds were made according to Scheme 6, where intermediates in the Scheme were modified according to literature methods. Example 347 was prepared by reaction of the corresponding (1-aryl-2,2-dipyridin-3-yl-ethyl)amine with 4-chlorobutyryl chloride followed by ring closure under basic conditions. Example 368 was prepared by reaction of the amine with 3-chloropropanesulfonyl chloride followed by ring closure under basic conditions. Examples 372, 375-378 were prepared by palladium catalyzed amination of 371 with the corresponding carbamate, amide, sulfonamide or urea. Example 373 was prepared by deprotection of 372. Example 379 was prepared by methylation of 372 and deprotection. Examples 380 and 381 were prepared from the corresponding (1-aryl-2,2-dipyridin-3-ylethyl)amine using the method of Tschaen et al. (*J. Org. Chem.* 1995, 60, 4324). Example 394 was prepared by treatment of the corresponding primary amine with methyl-4-bromo-2-oxopentanoate under reductive amination conditions. Ester reduction of the compound in example 394 provided example 395. Ester hydrolysis of the compound in example 394 provided the corresponding carboxylic acid, which was subjected to standard peptide coupling conditions to provide the amides in examples 396, 397, and 398. Example 401 was prepared by reductive amination of [1-(3-bromophenyl)-2,2-dipyridin-3-ylethyl]amine with methyl[methyl(2-oxoethyl)amino](oxo)acetate, according to a published procedure (*Tetrahedron Lett.* 2000, 41, 8735). Examples 405 and 406 were prepared by reaction of the corresponding (1-aryl-2,2-dipyridin-3-ylethyl)amine with 2-chloroethyl chloroformate followed by ring closure under basic conditions. Unless otherwise shown, structures of compounds 344-420 and 6-1 to 6-87 are represented by defining variables

and "Y" of the structure

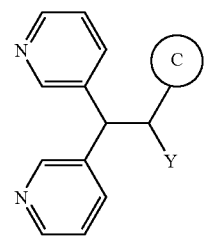

EXAMPLES 344-420 AND 6-1 TO 6-87

| Example | Compound | Name | MS (M + 1) |
|---|---|---|---|
| 344 | | (±)-N-[1-(4-fluorophenyl)-2-phenyl-2-pyridin-3-ylethyl]methanesulfonamide | 371.3 |
| 345 | | (±)-N-[1-(4-fluorophenyl)-2-phenyl-2-pyridin-3-ylethyl]-2-methoxyacetamide | 365.1642 |

-continued

| Example | Compound | Name | MS (M + 1) |
|---|---|---|---|
| 346 | | (±)-4-[1-(4-fluorophenyl)-2-phenyl-2-pyridin-3-ylethyl]morpholine | 363.1862 |
| 347 | C = 4-fluorophenyl; Y = pyrrolidin-2-on-1-yl | (±)-1-[1-(4-fluorophenyl)-2,2-dipyridin-3-ylethyl]pyrrolidin-2-one | 362.1663 |
| 348 | C = 4-fluorophenyl; Y = morpholino | (±)-4-[1-(4-fluorophenyl)-2,2-dipyridin-3-ylethyl]morpholine | 364.1 |
| 349 | C = 4-fluorophenyl; Y = —NHCH$_2$CF$_3$ | (±)-[1-(4-fluorophenyl)-2,2-dipyridin-3-ylethyl](2,2,2-trifluoroethyl)amine | 376.2 |
| 350 | C = 3,4-dichlorophenyl; Y = morpholino | (±)-4-[1-(3,4-dichlorophenyl)-2,2-dipyridin-3-ylethyl]morpholine | 414.1111 |
| 351 | C = pyridin-2-yl; Y = morpholino | (±)-4-(1-pyridin-2-yl-2,2-dipyridin-3-ylethyl)morpholine | 347.1893 |

-continued
| Example | Compound | Name | MS (M + 1) |
|---|---|---|---|
| 352 | 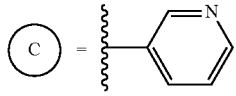 | (±)-4-(1,2,2-tripyridin-3-ylethyl)morpholine | 347.1896 |
| 353 | 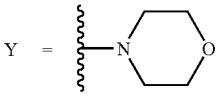 | (±)-N'-[1-(4-fluorophenyl)-2,2-dipyridin-3-ylethyl]-N,N-dimethylurea | 365.1763 |
| 354 | 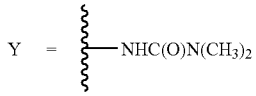 | (±)-3,3'-[2-(4-fluorophenyl)-2-pyrrolidin-1-ylethane-1,1-diyl]dipyridine | 348.1879 |
| 355 | 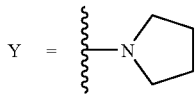 | (±)-4-[1-(4-fluorophenyl)-2-pyridin-2-yl-2-pyridin-3-ylethyl]morpholine | 364.1834 |
| 356 | 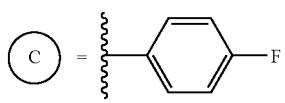 | (±)-[1-(4-fluorophenyl)-2,2-dipyridin-3-ylethyl](2-pyridin-3-ylethyl)amine | 399.2 |
| 357 | 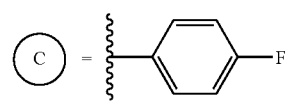 | (±)-N-[1-(4-fluorophenyl)-2,2-dipyridin-3-ylethyl]cyclobutanamine | 347.9 |

-continued
| Example | Compound | Name | MS (M + 1) |
|---|---|---|---|
| 358 | 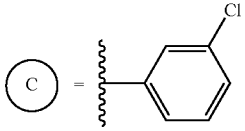 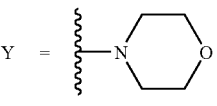 | (±)-4-[1-(3-chlorophenyl)-2,2-dipyridin-3-ylethyl]morpholine | 380.1504 |
| 359 | 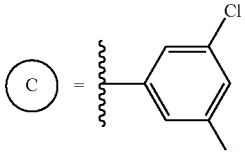 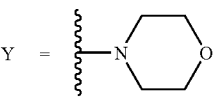 | (±)-4-[1-(3,5-dichlorophenyl)-2,2-dipyridin-3-ylethyl]morpholine | 414.1114 |
| 360 | 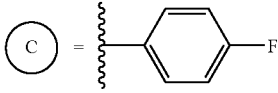 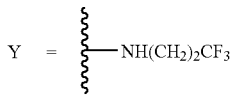 | (±)-[1-(4-fluorophenyl)-2,2-dipyridin-3-ylethyl](3,3,3-trifluoropropyl)amine | 390.1 |
| 361 | 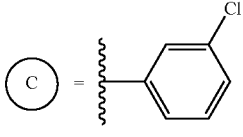 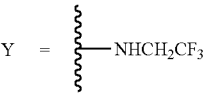 | (±)-[1-(3-chlorophenyl)-2,2-dipyridin-3-ylethyl](2,2,2-trifluoroethyl)amine | 392.1 |
| 362 | 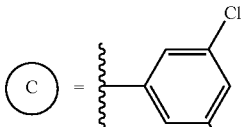 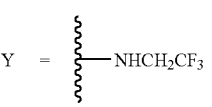 | (±)-[1-(3,5-dichlorophenyl)-2,2-dipyridin-3-ylethyl](2,2,2-trifluoroethyl)amine | 426.0 |

-continued
| Example | Compound | Name | MS (M + 1) |
|---|---|---|---|
| 363 | 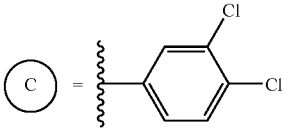 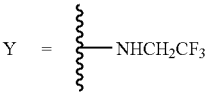 | (±)-[1-(3,4-dichlorophenyl)-2,2-dipyridin-3-ylethyl](2,2,2-trifluoroethyl)amine | 427.8 |
| 364 | 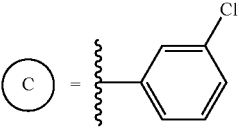 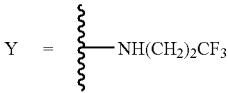 | (±)-N-[1-(3-chlorophenyl)-2,2-dipyridin-3-ylethyl]-3,3,3-trifluoropropan-1-amine | 406.0 |
| 365 | 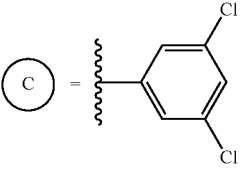 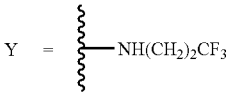 | (±)-N-[1-(3,5-dichlorophenyl)-2,2-dipyridin-3-ylethyl]-3,3,3-trifluoropropan-1-amine | 441.8 |
| 366 | 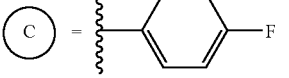 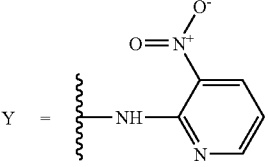 | (±)-N-[1-(4-fluorophenyl)-2,2-dipyridin-3-ylethyl]-3-nitropyridin-2-amine | 416.1 |
| 367 | 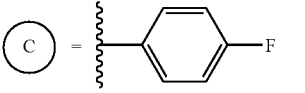 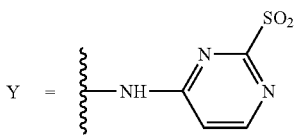 | (±)-N-[1-(4-fluorophenyl)-2,2-dipyridin-3-ylethyl]-2-(methylsulfonyl)pyrimidin-4-amine | 450.1 |

-continued

| Example | Compound | Name | MS (M + 1) |
|---|---|---|---|
| 368 | C = 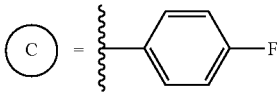 <br> Y = 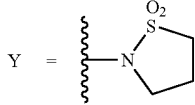 | (±)-3,3'-[2-(1,1-dioxidoisothoazolidin-2-yl)-2-(4-fluorophenyl)ethane-1,1-diyl]dipyridine | 398.1 |
| 369 | 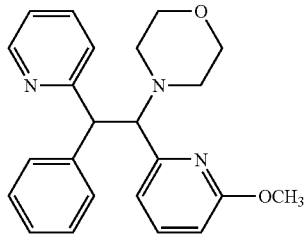 | (±)-4-[1-(6-methoxypyridin-2-yl)-2-phenyl-2-pyridin-2-ylethyl]morpholine | 398.1830 (M + Na+) |
| 370 | C = 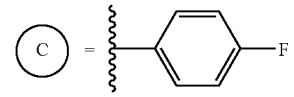 <br> Y = 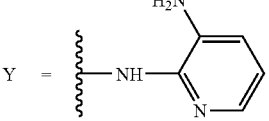 | (±)-N~2~-[1-(4-fluorophenyl)-2,2-dipyridin-3-ylethyl]pyridine-2,3-diamine | 386.1 |
| 371 | C = 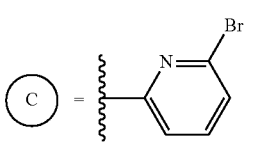 <br> Y = 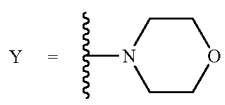 | (±)-4-[1-(6-bromopyridin-2-yl)-2,2-dipyridin-3-ylethyl]morpholine | 425.1005 |
| 372 | C = 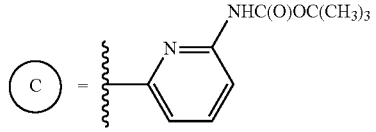 <br> Y = 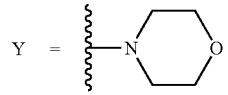 | (±)-tert-butyl [6-(1-morpholin-4-yl-2,2-dipyridin-3-ylethyl)pyridin-2-yl]carbamate | 462.2547 |
| 373 | C = 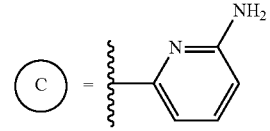 <br> Y = 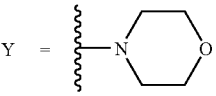 | (±)-6-(1-morpholin-4-yl-2,2-dipyridin-3-ylethyl)pyridin-2-amine | 362.1957 |

-continued

| Example | Compound | Name | MS (M + 1) |
|---|---|---|---|
| 374 | C = (pyridine with NHCH₃)<br>Y = morpholine | (±)-N-methyl-6-(1-morpholin-4-yl-2,2-dipyridin-3-ylethyl)pyridin-2-amine | 376.2126 |
| 375 | C = (pyridine with NHC(O)OCH₃)<br>Y = morpholine | (±)-methyl [6-(1-morpholin-4-yl-2,2-dipyridin-3-ylethyl)pyridin-2-yl]carbamate | 420.2017 |
| 376 | C = (pyridine with NHC(O)OCH₃)<br>Y = morpholine | (±)-N-[6-(1-morpholin-4-yl-2,2-dipyridin-3-ylethyl)pyridin-2-yl]acetamide | 404.2068 |
| 377 | C = (pyridine with NHSO₂CH₃)<br>Y = morpholine | (±)-N-[6-(1-morpholin-4-yl-2,2-dipyridin-3-ylethyl)pyridin-2-yl]methanesulfonamide | 440.1734 |
| 378 | C = (pyridine with NHC(O)NHCH₃)<br>Y = morpholine | (±)-N-methyl-N'-[6-(1-morpholin-4-yl-2,2-dipyridin-3-ylethyl)pyridin-2-yl]urea | 419.2182 |
| 379 | C = (4-fluorophenyl)<br>Y = NHSO₂(CH₂)₃-phenyl | (±)-N-[1-(4-fluorophenyl)-2,2-dipyridin-3-ylethyl]-3-phenylpropane-1-sulfonamide | 476.1794 |

-continued

| Example | Compound | Name | MS (M + 1) |
|---|---|---|---|
| 380 | C = 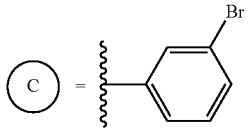<br>Y = 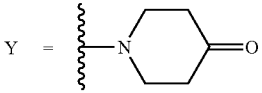 | (±)-1-[1-(3-bromophenyl)-2,2-dipyridin-3-ylethyl]piperidin-4-one | 436.1023 |
| 381 | C = 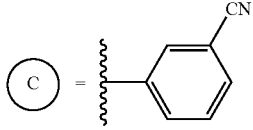<br>Y = 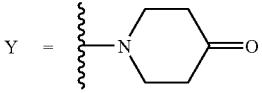 | (±)-3-[1-(4-oxopiperidin-1-yl)-2,2-dipyridin-3-ylethyl]benzonitrile | 383.1859 |
| 382 | C = 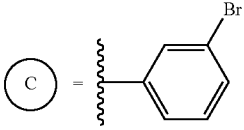<br>Y = 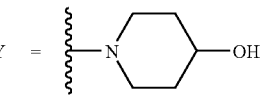 | (±)-1-[1-(3-bromophenyl)-2,2-dipyridin-3-ylethyl]piperidin-4-ol | 438.1181 |
| 383 | C = 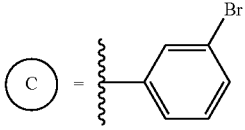<br>Y = —NH(CH$_2$)$_2$OH | (±)-2-{[1-(3-bromophenyl)-2,2-dipyridin-3-ylethyl]amino}ethanol | 398.0875 |
| 384 | C = 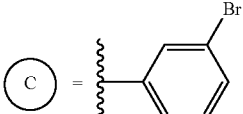<br>Y = —NHC(O)—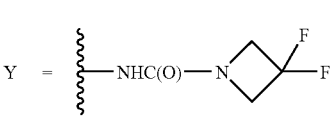 | (±)-N-[1-(3-bromophenyl)-2,2-dipyridin-3-ylethyl]-3,3-difluoroazetidine-1-carboxamide | 473.0779 |

-continued
| Example | Compound | Name | MS (M + 1) |
|---|---|---|---|
| 385 | 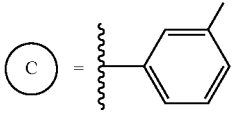 | (±)-[1-(3-bromophenyl)-2,2-dipyridin-3-ylethyl]{[1-(phenylsulfonyl)-1H-pyrrol-2-yl]methyl}amine | 573.0959 |
| 386 | 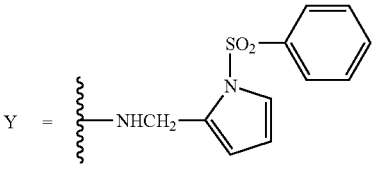 | (±)-N-[1-(3-bromophenyl)-2,2-dipyridin-3-ylethyl]-N'-(3-cyanophenyl)urea | 498.0930 |
| 387 | 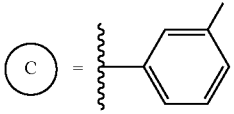 | (±)-N-[1-(3-bromophenyl)-2,2-dipyridin-3-ylethyl]-N'-(4-cyanophenyl)urea | 498.0930 |
| 388 | 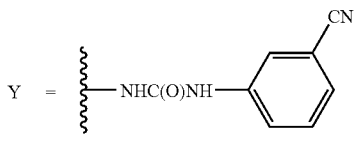 | (±)-N-[1-(3-bromophenyl)-2,2-dipyridin-3-ylethyl]-N'-[4-(methylthio)phenyl]urea | 519.0850 |
| 389 | 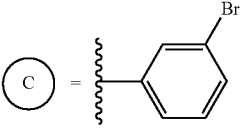 | (±)-N-[1-(3-bromophenyl)-2,2-dipyridin-3-ylethyl]-N'-phenylurea | 473.0966 |

-continued
| Example | Compound | Name | MS (M + 1) |
|---|---|---|---|
| 390 | 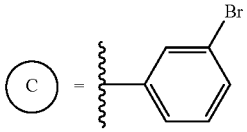  | (±)-N-[1-(3-bromophenyl)-2,2-dipyridin-3-ylethyl]-N'-propylurea | 439.1134 |
| 391 | 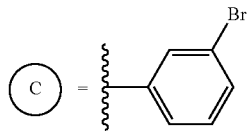 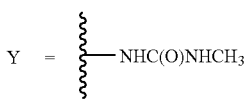 | (±)-N-[1-(3-bromophenyl)-2,2-dipyridin-3-ylethyl]-N'-methylurea | 411.0821 |
| 392 | 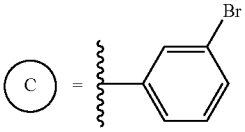  | (±)-N-[1-(3-bromophenyl)-2,2-dipyridin-3-ylethyl]-N'-cyclohexylurea | 479.1448 |
| 393 | 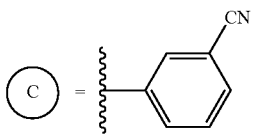 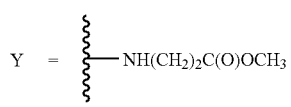 | (±)-methyl N-[1-(3-cyanophenyl)-2,2-dipyridin-3-ylethyl]-beta-alaninate | 387.1815 |
| 394 | 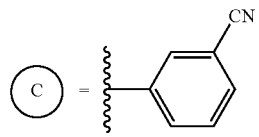 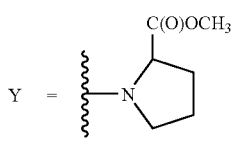 | (±)-methyl 1-[1-(3-cyanophenyl)-2,2-dipyridin-3-ylethyl]prolinate(diastereomer A) | 413.1978 |

-continued

| Example | Compound | Name | MS (M + 1) |
|---|---|---|---|
| 395 | 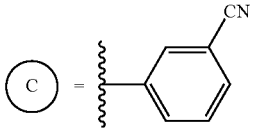 C = (3-cyanophenyl); Y = (2-hydroxymethyl)pyrrolidin-1-yl | (±)-3-{1-[2-(hydroxymethyl)pyrrolidin-1-yl]-2,2-dipyridin-3-ylethyl}benzonitrile (diastereomer A) | 385.2020 |
| 396 | 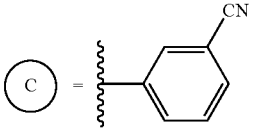 C = (3-cyanophenyl); Y = 2-(N-methylcarbamoyl)pyrrolidin-1-yl | (±)-1-[1-(3-cyanophenyl)-2,2-dipyridin-3-ylethyl]-N-methylprolinamide (diastereomer A) | 412.2137 |
| 397 | 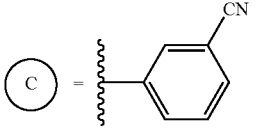 C = (3-cyanophenyl); Y = 2-(N,N-dimethylcarbamoyl)pyrrolidin-1-yl | (±)-1-[1-(3-cyanophenyl)-2,2-dipyridin-3-ylethyl]-N,N-dimethylprolinamide (diastereomer A) | 446.2291 |
| 398 | 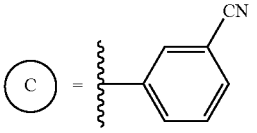 C = (3-cyanophenyl); Y = 2-[N-(2-hydroxyethyl)carbamoyl]pyrrolidin-1-yl | (±)-1-[1-(3-cyanophenyl)-2,2-dipyridin-3-ylethyl]-N-(2-hydroxyethyl)prolinamide (diastereomer A) | 442.2235 |
| 399 | 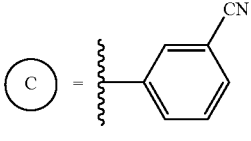 C = (3-cyanophenyl); Y = —NHCH$_2$C(O)NHCH$_2$—phenyl | (±)-N$^1$-benzyl-N$^2$-[1-(3-cyanophenyl)-2,2-dipyridin-3-ylethyl]glycinamide | 448.2143 |

-continued
| Example | Compound | Name | MS (M + 1) |
|---|---|---|---|
| 400 | 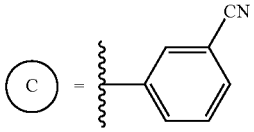 | (±)-3-{1-[(2-hydroxyethyl)amino]-2,2-dipyridin-3-ylethyl}benzonitrile | 345.1 |
| 401 | 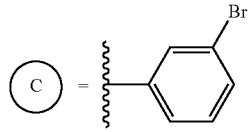 | (±)-1-[1-(3-bromophenyl)-2,2-dipyridin-3-ylethyl]-4-methylpiperazine-2,3-dione | 465.0928 |
| 402 | 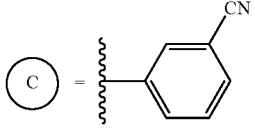 | (±)-N-[1-(3-cyanophenyl)-2,2-dipyridin-3-ylethyl]pyridine-2-carboxamide | 406.1652 |
| 403 | 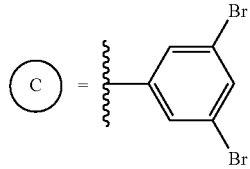 | (±)-4-[1-(3,5-dibromophenyl)-2,2-dipyridin-3-ylethyl]morpholine | 502.0123 |
| 404 | 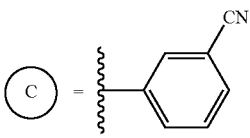 | (±)-N-[1-(3-cyanophenyl)-2,2-dipyridin-3-ylethyl]-1H-1,2,4-triazole-3-carboxamide | 396.1578 |

-continued

| Example | Compound | Name | MS (M + 1) |
|---|---|---|---|
| 405 | C = 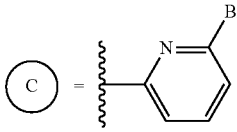<br>Y = 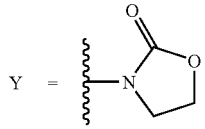 | (±)-3-[1-(6-bromopyridin-2-yl)-2,2-dipyridin-3-ylethyl]-1,3-oxazolidin-2-one | 425.0603 |
| 406 | C = 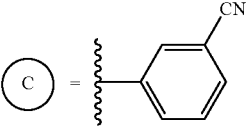<br>Y = 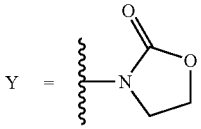 | (±)-3-[1-(2-oxo-1,3-oxazolidin-3-yl)-2,2-dipyridin-3-ylethyl]benzonitrile | 371.1473 |
| 407 | C = 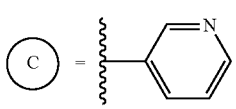<br>Y = 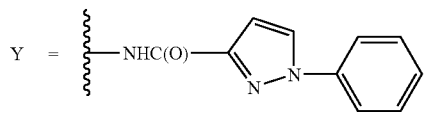 | (±)-1-phenyl-N-(1,2,2-tripyridin-3-ylethyl)-1H-pyrazole-4-carboxamide | 447.1928 |
| 408 | C = 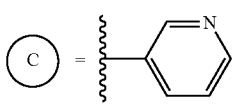<br>Y = 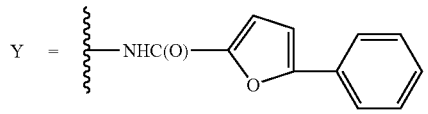 | (±)-5-phenyl-N-(1,2,2-tripyridin-3-ylethyl)-2-furamide | 447.1814 |
| 409 | C = 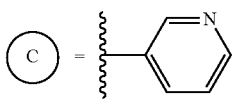<br>Y = 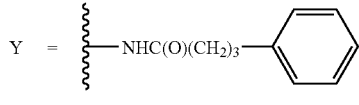 | (±)-4-phenyl-N-(1,2,2-tripyridin-3-ylethyl)butanamide | 423.2181 |
| 410 | C = 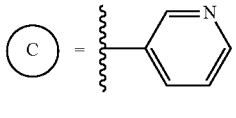<br>Y = 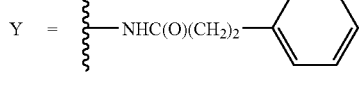 | (±)-3-phenyl-N-(1,2,2-tripyridin-3-ylethyl)propanamide | 409.2021 |

-continued

| Example | Compound | Name | MS (M + 1) |
|---|---|---|---|
| 411 | C = (3-pyridyl); Y = NHC(O)OCH₂-phenyl | (±)-benzyl(1,2,2-tripyridin-3-ylethyl)carbamate | 411.1805 |
| 412 | C = (3-pyridyl); Y = NHC(O)CH₂OCH₂-phenyl | (±)-2-(benzyloxy)-N-(1,2,2-tripyridin-3-ylethyl)acetamide | 425.1955 |
| 413 | C = (3-pyridyl); Y = NHC(O)CH₂-phenyl | (±)-2-phenyl-N-(1,2,2-tripyridin-3-ylethyl)acetamide | 395.1867 |
| 414 | C = (3-pyridyl); Y = NHC(O)-phenyl | (±)-N-(1,2,2-tripyridin-3-ylethyl)benzamide | 381.1671 |
| 415 | C = (3-pyridyl); Y = NHC(O)(CH₂)₄-phenyl | (±)-5-phenyl-N-(1,2,2-tripyridin-3-ylethyl)pentanamide | 437.6 |
| 416 | C = (3-cyanophenyl); Y = NHC(O)-(2-phenylcyclopropyl) | (±)-N-[1-(3-cyanophenyl)-2,2-dipyridin-3-ylethyl]-2-phenyl-cyclopropanecarboxamide | 445.1980 |

-continued
| Example | Compound | Name | MS (M + 1) |
|---|---|---|---|
| 417 | 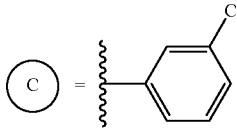 | (±)-N-[1-(3-cyanophenyl)-2,2-dipyridin-3-ylethyl]-5-phenyl-2-furamide | 471.1780 |
| 418 | 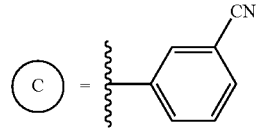 | (±)-N-benzyl-N'-[1-(3-cyanophenyl)-2,2-dipyridin-3-ylethyl]-N-methylurea | 448.2105 |
| 419 | 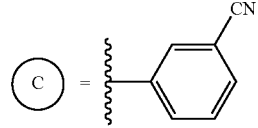 | (±)-N-benzyl-N'-[1-(3-cyanophenyl)-2,2-dipyridin-3-ylethyl]urea | 434.1936 |
| 420 | 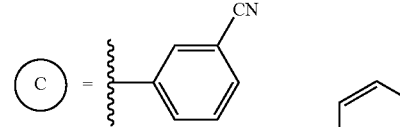 | (±)-3-(1-{[(1-phenyl-1H-pyrazol-4-yl)methyl]amino}-2,2-dipyridin-3-ylethyl)benzonitrile | 457.7 |
| 6-1 | 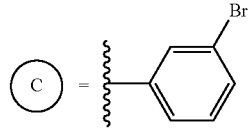 | (S)-{1-[1-(3-bromophenyl)-2,2-dipyridin-3-ylethyl]piperidin-4-yl}ethanethioate | 496.1062 |

-continued
| Example | Compound | Name | MS (M + 1) |
|---|---|---|---|
| 6-2 | 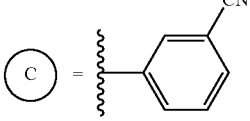 | (±)-3-[1-(2,4-dioxoimidazolidin-1-yl)-2,2-dipyridin-3-ylethyl]benzonitrile | 384.1 |
| 6-3 | 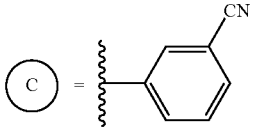 | (±)-3-[1-(2-oxomorpholin-4-yl)-2,2-dipyridin-3-ylethyl)benzonitrile | 385.1655 |
| 6-4 | 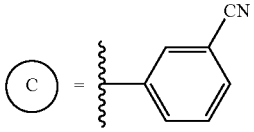 | (±)-3-[1-(2-hydroxymorpholin-4-yl)-2,2-dipyridin-3-ylethyl]benzonitrile | 387.1815 |
| 6-5 | 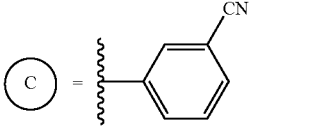 | (±)-1-[1-(3-cyanophenyl)-2,2-dipyridin-3-ylethyl]-N,N-bis(1-{1-[1-(3-cyanophenyl)-2,2-dipyridin-3-ylethyl]prolyl}-pyrrolidin-2-yl)prolinamide | 452.2435 |
| 6-6 | 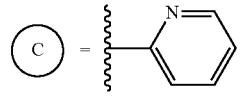 | (±)-3-(1-pyridin-2-yl-2,2-dipyridin-3-ylethyl)-1,3-oxazolidin-2-one | 347.1487 |

-continued
| Example | Compound | Name | MS (M + 1) |
|---|---|---|---|
| 6-7 | 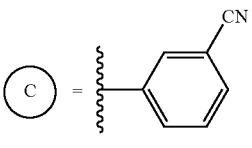 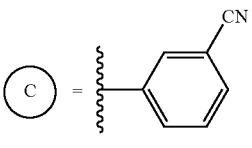 | (±)-tert-butyl 2-{[1-(3-cyanophenyl)-2,2-dipyridin-3-ylethyl]amino}ethylcarbamate | 444.2414 |
| 6-8 | 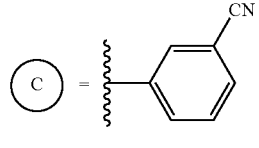 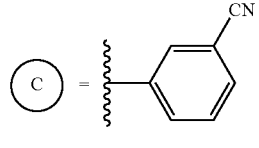 | (±)-3-[1-(2-oxo-1,3-oxazinan-3-yl)-2,2-dipyridin-3-ylethyl]benzonitrile | 384.1655 |
| 6-9 | 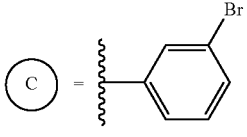 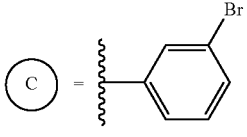 | (±)-N-(2-{[1-(3-bromophenyl)-2,2-dipyridin-3-ylethyl]amino}ethyl)-methanesulfonamide | 475.08 |
| 6-10 | 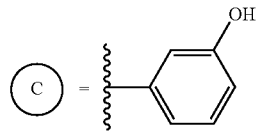 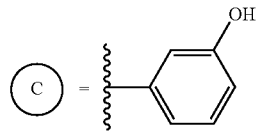 | (±)-3-(1-morpholin-4-yl-2,2-dipyridin-3-ylethyl)phenol | 362.1864 |
| 6-11 | 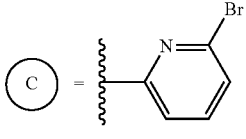 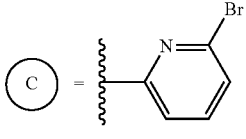 | (±)-3-[1-(6-bromopyridin-2-yl)-2,2-dipyridin-3-ylethyl]-1,3-oxazinan-2-one | 439.0767 |

-continued
| Example | Compound | Name | MS (M + 1) |
|---|---|---|---|
| 6-12 | 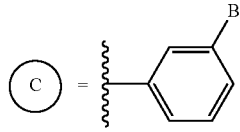 | (±)-N-(2-{[1-(3-bromophenyl)-2,2-dipyridin-3-ylethyl]amino}-ethyl)-n'-phenylurea | 516.1428 |
| 6-13 | 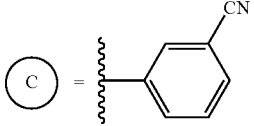 | (±)-N-(tert-butyl)-1-[1-(3-cyanophenyl)-2,2-dipyridin-3-ylethyl]prolinamide | 454.261 |
| 6-14 | 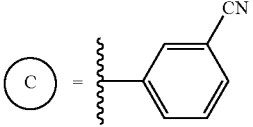 | (±)-1-[1-(3-cyanophenyl)-2,2-dipyridin-3-ylethyl]-piperidinylprolinamide | 466.2577 |
| 6-15 | 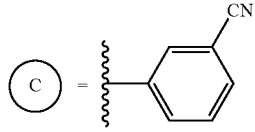 | (±)-1-[1-(3-cyanophenyl)-2,2-dipyridin-3-ylethyl]-N-cyclohexylprolinamide | 480.1538 |
| 6-16 | 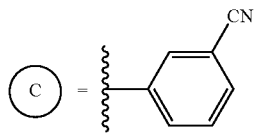 | (±)-1-[1-(3-cyanophenyl)-2,2-dipyridin-3-ylethyl]-N-phenylprolinamide | 474.2268 |

-continued
| Example | Compound | Name | MS (M + 1) |
|---|---|---|---|
| 6-17 | 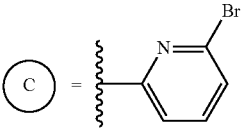 | (±)-methyl 1-[1-(6-bromopyridin-2-yl)-2,2-dipyridin-3-ylethyl]prolinate | 467.1065 |
| 6-18 | 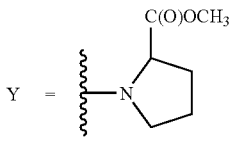 | (±)-3-(1-{[(1-phenyl-1H-pyrazol-4-yl)methyl]amino}-2,2-dipyridin-3-ylethyl)benzonitrile | 404.2073 |
| 6-19 | 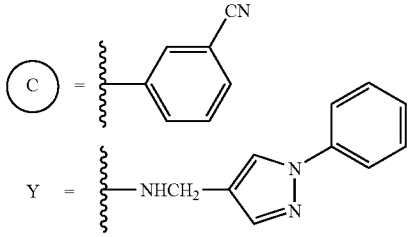 | (±)-methyl 1-[1-(4-fluorophenyl)-2,2-dipyridin-3-ylethyl]prolinate | 406.192 |
| 6-20 | 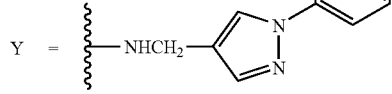 | (±)-methyl 1-[1-(6-aminopyridin-2-yl)-2,2-dipyridin-3-ylethyl]prolinate | 404.2073 |
| 6-21 | 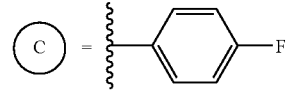 | (±)-N-{1-[1-(3-cyanophenyl)-2,2-dipyridin-3-ylethyl]piperidin-4-yl}-N-methylmethanesulfonamide | 476.2107 |

-continued

| Example | Compound | Name | MS (M + 1) |
|---|---|---|---|
| 6-22 | 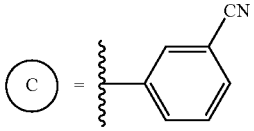 C = (3-cyanophenyl group); Y = (2-oxopyrrolidin-1-yl) | (±)-3-[1-(2-oxopyrrolidin-1-yl)-2,2-dipyridin-3-ylethyl]benzonitrile | 369.172 |
| 6-23 | 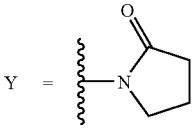 C = (3-cyanophenyl); Y = piperidin-4-yl OC(O)NH-phenyl | (±)-1-[1-(3-cyanophenyl)-2,2-dipyridin-3-ylethyl]piperidin-4-yl phenylcarbamate | 504.2386 |
| 6-24 | 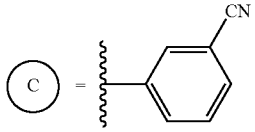 C = (4-fluorophenyl); Y = pyrrolidine-2-C(O)NHCH₃ | (±)-1-[1-(4-fluorophenyl)-2,2-dipyridin-3-ylethyl]-N-methylprolinamide | 405.2085 |
| 6-25 | 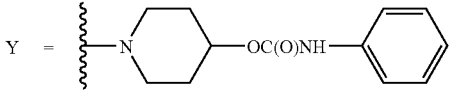 C = (4-fluorophenyl); Y = pyrrolidine-2-C(O)NHCH₂CH₃ | (±)-N-ethyl-1-[1-(4-fluorophenyl)-2,2-dipyridin-3-ylethyl]prolinamide | 419.2228 |
| 6-26 | 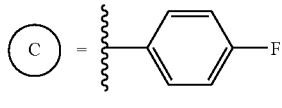 C = (3-cyanophenyl); Y = piperidin-4-yl-N(CH₃)SO₂-cyclopropyl | (±)-N-{1-[1-(3-cyanophenyl)-2,2-dipyridin-3-ylethyl]piperidin-4-yl}-N-methylcyclopropanesulfonamide | 502.2268 |

-continued
| Example | Compound | Name | MS (M + 1) |
|---|---|---|---|
| 6-27 | 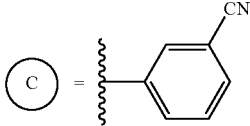 | (±)-3-[1-(1,1-dioxidoisothiazolidin-2-yl)-2,2-dipyridin-3-ylethyl]benzonitrile | 405.1381 |
| 6-28 | 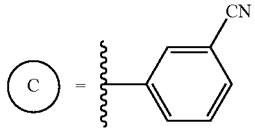 | (±)-3-[1-(4,5-dihydro-1,3-thiazol-2-ylamino)-2,2-dipyridin-3-ylethyl]benzonitrile | 471.1398 |
| 6-29 | 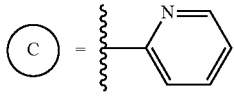 | (±)-methyl 1-(1-pyridin-2-yl-2,2-dipyridin-3-ylethyl)prolinate | 389.1964 |
| 6-30 | 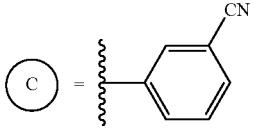 | (±)-N-butyl-1-[1-(3-cyanophenyl)-2,2-dipyridin-3-ylethyl]prolinamide | 454.2573 |
| 6-31 | 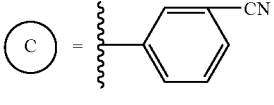 | (±)-1-[1-(3-cyanophenyl)-2,2-dipyridin-3-ylethyl]-N-isobutylprolinamide | 454.2603 |

-continued

| Example | Compound | Name | MS (M + 1) |
|---|---|---|---|
| 6-32 | 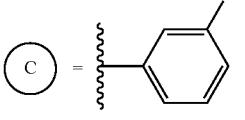 | (±)-1-[1-(3-cyanophenyl)-2,2-dipyridin-3-ylethyl]-N-cyclobutylprolinamide | 452.2435 |
| 6-33 | 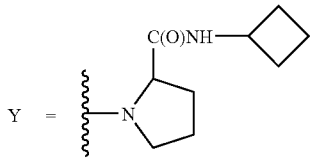 | (±)-1-[1-(3-cyanophenyl)-2,2-dipyridin-3-ylethyl]-N-cyclopentylprolinamide | 466.2597 |
| 6-34 | 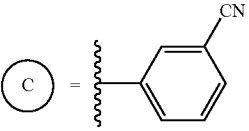 | (±)-1-[1-(4-fluorophenyl)-2,2-dipyridin-3-ylethyl]-N-pyridin-2-ylprolinamide | 468.2193 |
| 6-35 | 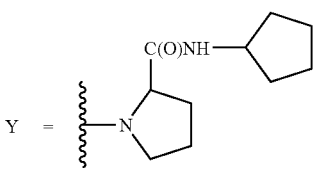 | (±)-1-[1-(3-cyanophenyl)-2,2-dipyridin-3-ylethyl]-N-[4-(trifluoromethyl)pyridin-2-yl]prolinamide | 543.2113 |
| 6-36 | 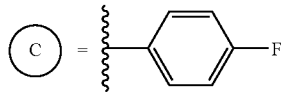 | (±)-N-(5-chloropyridin-2-yl)-1-[1-(3-cyanophenyl)-2,2-dipyridin-3-ylethyl]prolinamide | 509.1885 |

-continued

| Example | Compound | Name | MS (M + 1) |
|---|---|---|---|
| 6-37 | C = 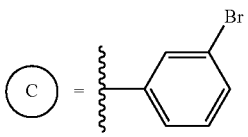<br>Y = 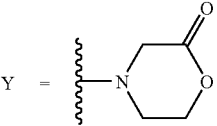 | (±)-4-[1-(3-bromophenyl)-2,2-dipyridin-3-ylethyl]morpholin-2-one | 438.0836 |
| 6-38 | C = 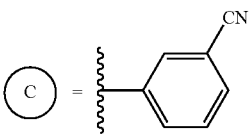<br>Y = 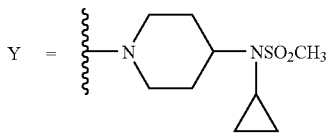 | (±)-N-{1-[1-(3-cyanophenyl)-2,2-dipyridin-3-ylethyl]piperidin-4-yl}-N-cyclopropylmethanesulfonamide | 502.2274 |
| 6-39 | C = 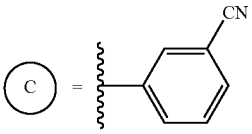<br>Y = 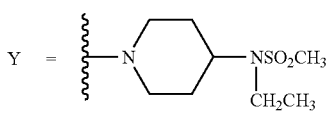 | (±)-N-{1-[1-(3-cyanophenyl)-2,2-dipyridin-3-ylethyl]piperidin-4-yl}-N-ethylmethanesulfonamide | 490.2277 |
| 6-40 | C = 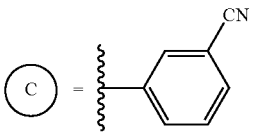<br>Y = 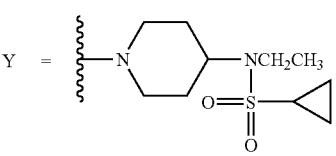 | (±)-N-{1-[1-(3-cyanophenyl)-2,2-dipyridin-3-ylethyl]piperidin-4-yl}-N-ethylcyclopropanesulfonamide | 516.4 |
| 6-41 | C = 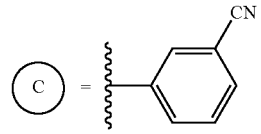<br>Y = 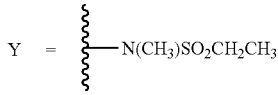 | (±)-N-{1-[1-(3-cyanophenyl)-2,2-dipyridin-3-ylethyl]piperidin-4-yl}-N-methylethanesulfonamide | 490.2301 |

-continued

| Example | Name | MS (M + 1) |
|---|---|---|
| 6-42 | (±)-methyl 1-[1-(3-cyanophenyl)-2-pyrazin-2-yl-2-pyridin-3-ylethyl]prolinate | 414.1946 |
| 6-43 | (±)-2-{1-[1-(4-fluorophenyl)-2,2-dipyridin-3-ylethyl]pyrrolidin-2-yl}-1H-benzimidazole | 464.2278 |
| 6-44 | (±)-methyl 1-[1-(6-methoxypyridin-2-yl)-2,2-dipyridin-3-ylethyl]prolinate | 419.2099 |
| 6-45 | (±)-3-{1-[2-(1H-benzimidazol-2-yl)pyrrolidin-1-yl]-2,2-dipyridin-3-ylethyl}benzonitrile | 471.2305 |

-continued

| Example | Compound | Name | MS (M + 1) |
|---|---|---|---|
| 6-46 | C = (6-methoxypyridin-2-yl); Y = 2-(C(O)NHC(CH₃)₃)-pyrrolidin-1-yl | (±)-N-(tert-butyl)-1-[1-(6-methoxypyridin-2-yl)-2,2-dipyridin-3-ylethyl]prolinamide | 460.2725 |
| 6-47 | C = (6-methoxypyridin-2-yl); Y = 2-(1H-benzimidazol-2-yl)pyrrolidin-1-yl | (±)-2-{1-[1-(6-methoxypyridin-2-yl)-2,2-dipyridin-3-ylethyl]pyrrolidin-2-yl}-1H-benzimidazole | 477.2426 |
| 6-48 | C = (3-cyanophenyl); Y = —NH—(1-Boc-piperidin-3-yl) | (±)-tert-butyl 3-{[1-(3-cyanophenyl)-2,2-dipyridin-3-ylethyl]amino}piperidine-1-carboxylate | 484.5 |
| 6-49 | C = (6-aminopyridin-2-yl); Y = 2-(CH₂OH)-pyrrolidin-1-yl | (±)-{1-[2-(6-aminopyridin-2-yl)-1,2-dipyridin-3-ylethyl]-pyrrolidin-2-yl}methanol | 376.2137 |
| 6-50 | C = (3-cyanophenyl); Y = —NHCH₂—(4-phenyl-1,3-thiazol-2-yl) | (±)-3-(1-{[(4-phenyl-1,3-thiazol-2-yl)methyl]amino}-2,2-dipyridin-3-ylethyl)benzonitrile | 474.1764 |

-continued
| Example | Compound | Name | MS (M + 1) |
|---|---|---|---|
| 6-51 | 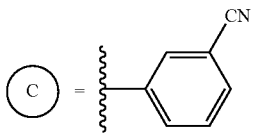 | (±)-3-(1-{[(2-phenyl-1,3-thiazol-5-yl)methyl]amino}-2,2-dipyridin-3-ylethyl)benzonitrile | 474.1772 |
| 6-52 | 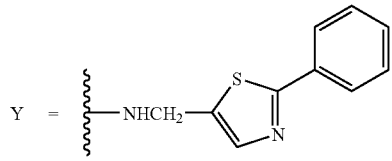 | (±)-3-{2,2-dipyridin-3-yl-1-[(pyridin-2-ylmethyl)amino]ethyl}benzonitrile | 392.1875 |
| 6-53 | 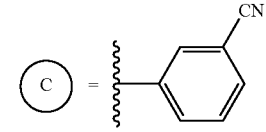 | (±)-3-(1-{[3-(4-methoxy-phenoxy)benzyl]amino}-2,2-dipyridin-3-ylethyl)benzonitrile | 513.2304 |
| 6-54 | 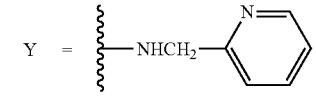 | (±)-3-{2,2-dipyridin-3-yl-1-[(quinolin-3-ylmethyl)amino]-ethyl}benzonitrile | 442.2035 |
| 6-55 | 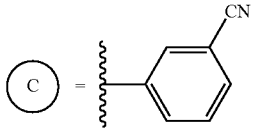 | (±)-3-(1-{[4-(methylthio)benzyl]amino}-2,2-dipyridin-3-ylethyl)benzonitrile | 437.1817 |

-continued

| Example | Compound | Name | MS (M + 1) |
|---|---|---|---|
| 6-56 | 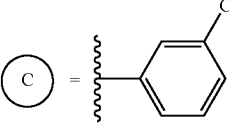 C = <br> Y = NHCH$_2$C(CH$_3$)$_2$(CH$_2$CHCH$_2$) | (±)-3-{1-[(2,2-dimethylpent-4-en-1-yl)amino]-2,2-dipyridin-3-ylethyl}benzonitrile | 397.2395 |
| 6-57 | 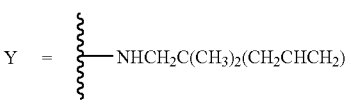 C = <br> Y = —NHCH$_2$— —O(CH$_2$)$_2$CH$_3$ | (±)-3-{1-[(4-propoxybenzyl)amino]-2,2-dipyridin-3-ylethyl}benzonitrile | 449.2351 |
| 6-58 | 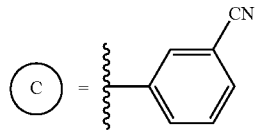 C = <br> Y = —NHCH$_2$— biphenyl | (±)-3-{1-[(biphenyl-4-ylmethyl)amino]-2,2-dipyridin-3-ylethyl}benzonitrile | 467.2251 |
| 6-59 | 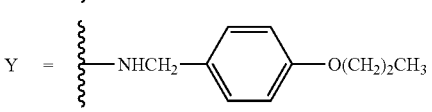 C = <br> Y = —NHCH$_2$— benzothienyl | (±)-3-{1-[(1-benzothien-2-ylmethyl)amino]-2,2-dipyridin-3-ylethyl}benzonitrile | 447.1645 |
| 6-60 | 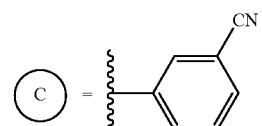 C = <br> Y = —NHCH$_2$— CF$_3$ | (±)-3-(2,2-dipyridin-3-yl-1-{[3-(trifluoromethyl)benzyl]amino}ethyl)benzonitrile | 459.1804 |
| 6-61 | 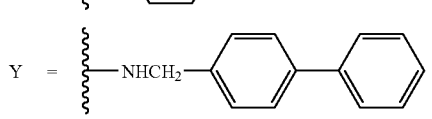 C = <br> Y = —NHCH$_2$— —CN | (±)-3-{1-[(4-cyanobenzyl)amino]-2,2-dipyridin-3-ylethyl}benzonitrile | 416.1876 |

| Example | Compound | Name | MS (M + 1) |
|---|---|---|---|
| 6-62 | 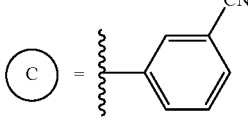 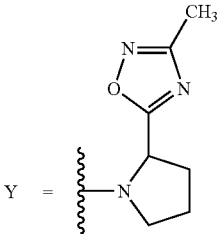 | (±)-3-{1-[2-(3-methyl-1,2,4-oxadiazol-5-yl)pyrrolidin-1-yl]-2,2-dipyridin-3-ylethyl}benzonitrile | 437.2085 |
| 6-63 | 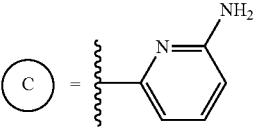 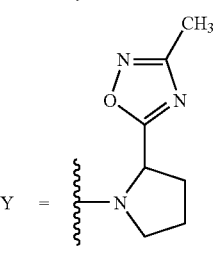 | (±)-6-{1-[2-(3-methyl-1,2,4-oxadiazol-5-yl)pyrrolidin-1-yl]-2,2-dipyridin-3-ylethyl}pyridin-2-amine | 428.2174 |
| 6-64 | 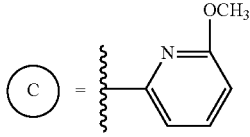 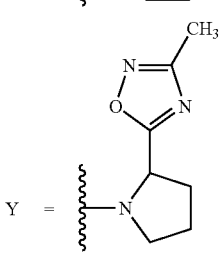 | (±)-2-methoxy-6-{1-[2-(3-methyl-1,2,4-oxadiazol-5-yl)pyrrolidin-1-yl]-2,2-dipyridin-3-ylethyl}pyridine | 443.2168 |
| 6-65 | 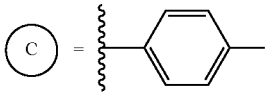 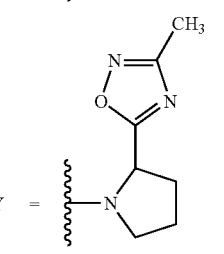 | (±)-3-{2-(4-fluorophenyl)-2-[(3-methyl-1,2,4-oxadiazol-5-yl)pyrrolidin-1-yl]-1-pyridin-3-ylethyl}pyridine | 430.2014 |

-continued

| Example | Compound | Name | MS (M + 1) |
|---|---|---|---|
| 6-66 | | (±)-3-{1-[2-(3-methyl-1,2,4-oxadiazol-5-yl)pyrrolidin-1-yl]-2-pyrazin-2-yl-2-pyridin-3-ylethyl}benzonitrile | 438.2012 |
| 6-67 | | (±)-3-{1-[2-(3-methyl-1,2,4-oxadiazol-5-yl)pyrrolidin-1-yl]-2-pyrazin-2-yl-2-pyridin-3-ylethyl}benzonitrile | 438.2013 |
| 6-68 | C = , Y = | (±)-3-[1-(3-hydroxypiperidin-1-yl)-2,2-dipyridin-3-ylethyl]-benzonitrile (Diastereomer A) | 385.2012 |
| 6-69 | C = , Y = | (±)-3-[1-(3-hydroxypiperidin-1-yl)-2,2-dipyridin-3-ylethyl]-benzonitrile (Diastereomer B) | 385.2012 |
| 6-70 | | (±)-4-[2-(6-aminopyridin-2-yl)-2-(3-hydroxypiperidin-1-yl)-1-pyridin-3-ylethyl]benzonitrile | 400.2129 |

-continued

| Example | Compound | Name | MS (M + 1) |
|---|---|---|---|
| 6-71 | 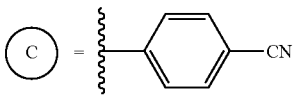 C = (4-cyanophenyl); Y = NHCH₂CF₃ | (±)-4-{2,2-dipyridin-3-yl-1-[(2,2,2-trifluoroethyl)amino]-ethyl}benzonitrile | 383.145 |
| 6-72 | 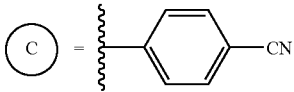 C = (4-cyanophenyl); Y = NHCH₂CH₂F | (±)-4-{1-[(2-fluoroethyl)amino]-2,2-dipyridin-3-ylethyl}benzonitrile | 347.167 |
| 6-73 | 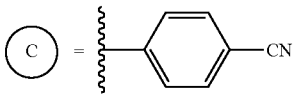 C = (4-cyanophenyl); Y = NHCH₂CHF₂ | (±)-4-{1-[(2-difluoroethyl)amino]-2,2-dipyridin-3-ylethyl}benzonitrile | 365.1576 |
| 6-74 | 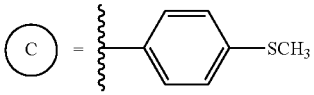 C = (4-methylthiophenyl); Y = NHCH₂CF₃ | (±)-N-{1-[4-(methylthio)-phenyl]-2,2-dipyridin-3-ylethyl}-N-(2,2,2-trifluoroethyl)amine | 404.1407 |
| 6-75 | 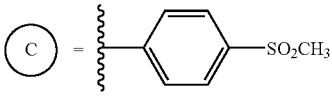 C = (4-methylsulfonylphenyl); Y = NHCH₂CF₃ | (±)-N-{1-[4-(methylsulfonyl)-phenyl]-2,2-dipyridin-3-ylethyl}-N-(2,2,2-trifluoroethyl)amine | 436.1305 |
| 6-76 | 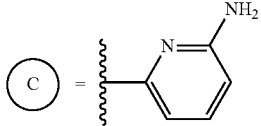 C = (6-aminopyridin-2-yl); Y = NHCH₂CF₃ | (±)-6-{2,2-dipyridin-3-yl-1-[(2,2,2-trifluoroethyl)amino]ethyl}pyridin-2-amine | 374.1596 |

-continued

| Example | Compound | Name | MS (M + 1) |
| --- | --- | --- | --- |
| 6-77 | C = 2-SCH₃-phenyl<br>Y = NHCH₂CF₃ | (±)-N-{1-[2-(methylthio)phenyl]-2,2-dipyridin-3-ylethyl}-N-(2,2,2-trifluoroethyl)amine | 404.1411 |
| 6-78 | C = 2-SO₂CH₃-phenyl<br>Y = NHCH₂CF₃ | (±)-N-{1-[2-(methylsulfonyl)phenyl]-2,2-dipyridin-3-ylethyl}-N-(2,2,2-trifluoroethyl)amine | 436.1301 |
| 6-79 | C = 3-SCH₃-phenyl<br>Y = NHCH₂CF₃ | (±)-N-{1-[3-(methylthio)phenyl]-2,2-dipyridin-3-ylethyl}-N-(2,2,2-trifluoroethyl)amine | 404.1404 |
| 6-80 | C = 3-SO₂CH₃-phenyl<br>Y = NHCH₂CF₃ | (±)-N-{1-[3-(methylsulfonyl)phenyl]-2,2-dipyridin-3-ylethyl}-N-(2,2,2-trifluoroethyl)amine | 436.1305 |
| 6-81 | C = 2,3′-bipyridin-3-yl<br>Y = NH₂ | (±)-1-(2,3′-bipyridin-3-yl)-2,2-dipyridin-3-ylethanamine | 354 |

-continued

| Example | Compound | Name | MS (M + 1) |
|---|---|---|---|
| 6-82 | C = (2,3'-bipyridin-3-yl); Y = —NHCH₂CF₃ | (±)-1-(2,3'-bipyridin-3-yl)-2,2-dipyridin-3-yl-N-(2,2,2-trifluoroethyl)ethanamine | 436.1 |
| 6-83 | C = 4-fluorophenyl; Y = 1,3-oxazolidin-2-on-3-yl | (±)-3-[1-(4-fluorophenyl)-2,2-dipyridin-3-ylethyl]-1,3-oxazolidin-2-one | 364.0 |
| 6-84 | C = 4-chlorophenyl; Y = 1,3-oxazolidin-2-on-3-yl | (±)-3-[1-(4-chlorophenyl)-2,2-dipyridin-3-ylethyl]-1,3-oxazolidin-2-one | 371.1 |
| 6-85 | C = 4-chlorophenyl; Y = —NHC(O)OCH₂—phenyl | benzyl (±)-1-(4-chlorophenyl)-2,2-dipyridin-3-ylethylcarbamate | 444.0 |
| 6-86 | C = 4-cyanophenyl; Y = 1,3-oxazolidin-2-on-3-yl | (±)-4-[1-(2-oxo-1,3-oxazolidin-3-yl)-2,2-dipyridin-3-ylethyl]benzonitrile | 317.15 |

-continued

| Example | Compound | Name | MS (M + 1) |
|---|---|---|---|
| 6-87 | C = ⟨4-chlorophenyl⟩-Cl | (±)-neopentyl 1-(4-chlorophenyl)-2,2-dipyridin-3-ylethylcarbamate | 424 |
| | Y = —NHC(O)OCH₂C(CH₃)₃ | | |

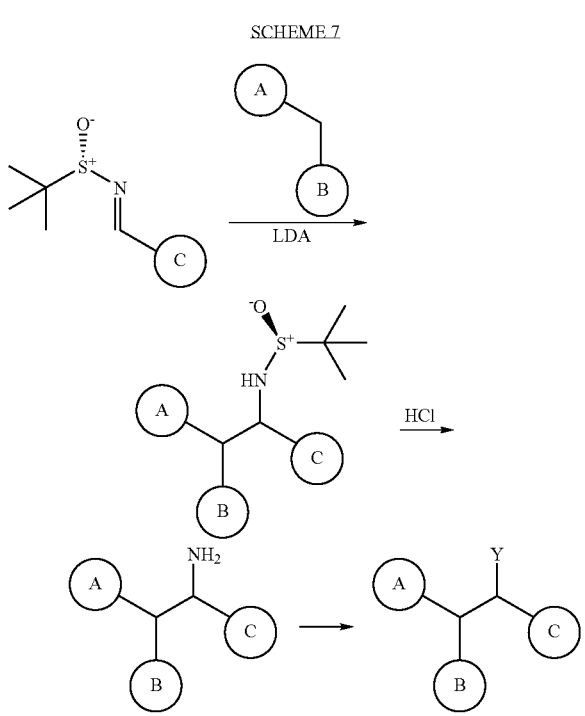

SCHEME 7

The variables C, B, A, and Y in the scheme are as defined in "Formula I".

EXAMPLE 421

3-(1-morpholin-4-yl-2,2-dipyridin-3-ylethyl)benzonitrile (enantiomer B)

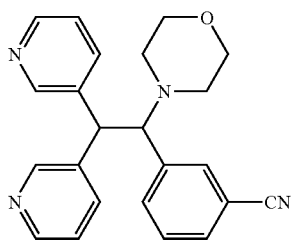

Step A:

In a flame dried flask under $N_2$, 3-cyanobenzaldehyde (7.050 g, 53.76 mmol) was dissolved in anhydrous dioxane (100 mL). Ti(IV) ethoxide (28.183 mL, 134.40 mmol) was added followed by (S)-(−)-2-methyl-2-propanesulfinamide (7.167 g, 59.14 mmol). The rxn was heated to 110° C. After 2.5 hr the reaction was cooled to RT and brine (150 mL) was added. A precipitate formed and the reaction was rapidly stirred for 1 hr. The suspension was filtered through celite and the filter cake was washed with brine and ethyl acetate. The layers of the filtrate were separated. The aqueous layer was extracted with ethyl acetate (1×). The combined organics were dried over $Na_2SO_4$, filtered, and concentrated in vacuo to afford (S)—N-[(3-cyanophenyl)methylidene]-2-methylpropane-2-sulfinamide as a light orange solid. $^1H$ NMR ($CD_3OD$) (8.61 (s, 1H), 8.26 (s, 1H), 8.22-8.20 (m, 1H), 7.94-7.92 (m, 1H), 7.72 (t, 1H, J=7.81 Hz), 1.28 (s, 9H).

Step B:

In a flame dried flask under $N_2$, diisopropylamine (1.647 mL, 11.75 mmol) was dissolved in anhydrous THF (5 mL) and the solution was cooled to 0° C. nBuLi (2.5 M solution in hexanes, 4.406 mL, 11.02 mmol) was added and the reaction was stirred at 0° C. for 15 min. A solution of 3-(pyridin-3-ylmethyl)pyridine (1.250 g, 7.34 mmol) in anhydrous THF (15 mL) was slowly added and the reaction became dark red. After 15 min, a solution of (S)—N-[(3-cyanophenyl)methylidene]-2-methylpropane-2-sulfinamide (1.893 g, 8.08 mmol) in anhydrous THF (10 mL) was added. The reaction was stirred at 0° C. for 2.5 h and was quenched with saturated aqueous $NH_4Cl$ (150 mL). The product was extracted with ethyl acetate (4×100 mL). The combined organics were dried over $Na_2SO_4$, filtered, concentrated in vacuo and purified by reverse phase HPLC (DeltaPak C18, 47 mm×300 mm, 15 □, 0% $CH_3OH$/100% $H_2O$ to 100% $CH_3OH$/0% $H_2O$). The fractions containing each diastereomer were separately combined and concentrated in vacuo to afford N-[1-(3-cyanophenyl)-2,2-dipyridin-3-ylethyl]-2-methylpropane-2-sulfinamide as two diastereomers;

diastereomer A as a foamy white solid and diastereomer B as a white solid.

Diastereomer A: $^1H$ NMR ($CDCl_3$) δ 8.67 (s, 1H), 8.62 (d, 1H, J=4.64 Hz), 8.37 (d, 1H, J=4.64 Hz), 8.17 (d, 1H, J=1.95 Hz), 7.94-7.93 (m, 1H), 7.57 (s, 1H), 7.53-7.51 (m, 1H), 7.43 (dd, 1H, J=4.88 Hz), 7.39-7.37 (m, 2H), 7.32 (t, 1H, J=7.57 Hz), 7.13 (dd, 1H, J=4.64 Hz), 5.15 (d, 1H, J=10.75 Hz), 4.22 (d, 1H, J=10.98 Hz), 1.06 (s, 9H). [M+H]+=405.1.

Diastereomer B: $^1H$ NMR ($CDCl_3$) δ 8.66 (s, 1H), 8.54 (d, 1H, J=3.91 Hz), 8.37 (s, 2H), 7.73-7.71 (m, 1H), 7.55-7.50 (m, 3H), 7.47-7.45 (m, 1H), 7.39 (t, 1H, J=7.57 Hz), 7.43 (dd, 1H, J=4.88 Hz), 7.14 (dd, 1H, J=4.88 Hz), 5.16 (dd, 1H, J=7.57 Hz), 4.44 (d, 1×, J=10.74 Hz), 3.52 (d, 1H, J=7.81 Hz), 0.96 (s, 9H). [M+H]+=404.9.

Step C:

N-[1-(3-cyanophenyl)-2,2-dipyridin-3-ylethyl]-2-methyl-propane-2-sulfinamide (Diastereomer B, 1.567 g, 3.87 mmol) was dissolved in CH₃OH (15 mL) and the solution was cooled to 0° C. HCl (4 M solution in dioxane, 2.905 mL, 11.62 mmol) was added drop-wise. The reaction was allowed to warm to RT and was stirred for 7 hr. The reaction was diluted with H₂O and the pH was adjusted to pH=7 using saturated aqueous NaHCO₃. The product was extracted with ethyl acetate (3×75 mL) followed by isobutanol (6×50 mL). The combined organics were dried over Na₂SO₄, filtered and concentrated in vacuo to afford 3-(1-amino-2,2-dipyridin-3-ylethyl)benzonitrile as a foamy light yellow solid.

Enantiomer B: ¹H NMR (CD₃OD) δ 8.78 (d, 1H, J=1.53 Hz), 8.51 (d, 1H, J=3.66 Hz), 8.35 (d, 1H, J=1.53 Hz), 8.25-8.24 (m, 1H), 8.18-8.14 (m, 1H), 7.84-7.79 (m, 2H), 7.72-7.70 (m, 1H), 7.60-7.43 (m, 3H), 7.26 (dd, 1H, J=4.88 Hz), 5.13 (d, 1H, J=10.99 Hz), 4.53 (d, 1H, J=11.29 Hz). [M+H]+=301.1.

Step D:

According to the procedure in Example 343, Step C, 3-(1-Amino-2,2-dipyridin-3-ylethyl)benzonitrile (Enantiomer B, 0.503 g, 1.68 mmol) was converted to the title compound. The product was purified by reverse phase HPLC (5-95% CH₃CN/H₂O+0.05% NH₄OH) followed by flash column chromatography (0-9% CH₃OH/CH₂Cl₂). The fractions were combined and concentrated in vacuo to afford the title compound as a foamy white solid. Enantiomer B: ¹H NMR (CDCl₃) δ 8.67 (d, 1H, J=1.95 Hz), 8.51 (dd, 1H, J=1.22 Hz), 8.37 (d, 1H, J=2.20 Hz), 8.30 (dd, 1H, J=1.22 Hz), 7.69-7.67 (m, 1H), 7.52-7.50 (m, 1H), 7.43-7.37 (m, 4H), 7.29 (dd, 1H, J=4.88 Hz), 7.07 (dd, 1H, J=4.88 Hz), 4.62 (d, 1H, J=11.96 Hz), 4.37 (d, 1H, J=12.21 Hz), 3.53-3.50 (m, 2H), 3.49-3.37 (m, 2H), 2.50-2.47 (m, 2H), 2.29-2.26 (m, 2H). [M+H]+=371.1870.

The following compounds were made according to Scheme 7, where intermediates in the scheme were modified according to literature methods. Examples 7-3 and 7-4 were synthesized using the tert-butyl sulfonimine rather than the tert-butyl sulfinimine using literature procedures.

EXAMPLES 422-423 AND 7-1 TO 7-4

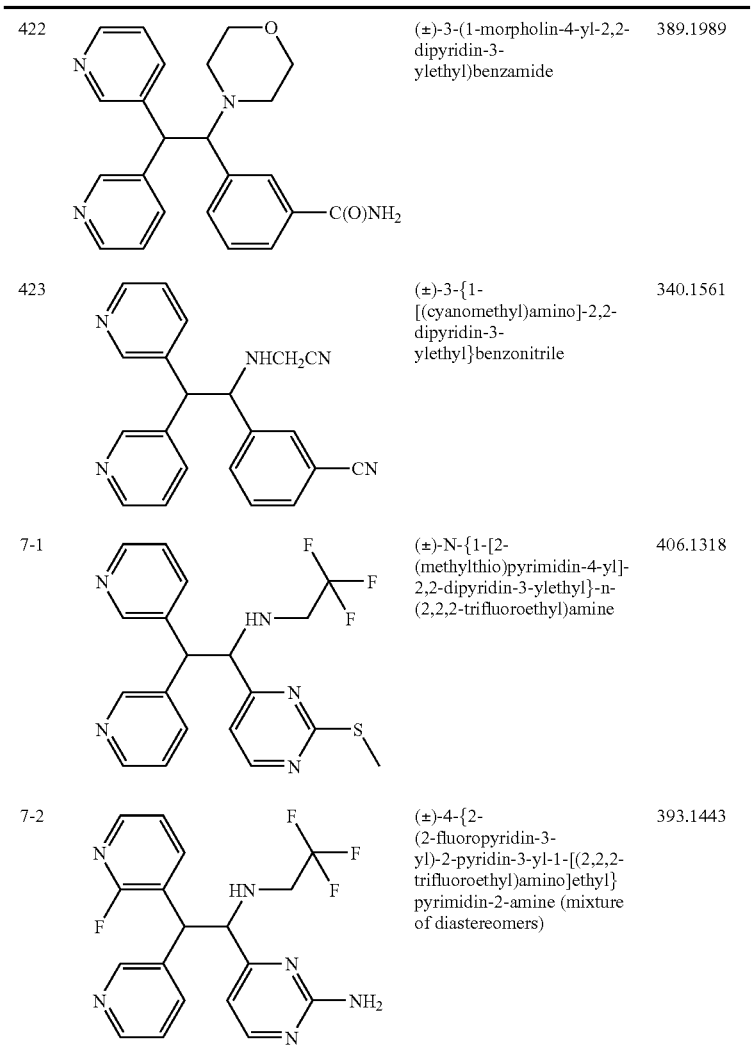

| 422 | (±)-3-(1-morpholin-4-yl-2,2-dipyridin-3-ylethyl)benzamide | 389.1989 |
| 423 | (±)-3-{1-[(cyanomethyl)amino]-2,2-dipyridin-3-ylethyl}benzonitrile | 340.1561 |
| 7-1 | (±)-N-{1-[2-(methylthio)pyrimidin-4-yl]-2,2-dipyridin-3-ylethyl}-n-(2,2,2-trifluoroethyl)amine | 406.1318 |
| 7-2 | (±)-4-{2-(2-fluoropyridin-3-yl)-2-pyridin-3-yl-1-[(2,2,2-trifluoroethyl)amino]ethyl}pyrimidin-2-amine (mixture of diastereomers) | 393.1443 |

| | | | |
|---|---|---|---|
| 7-3 | 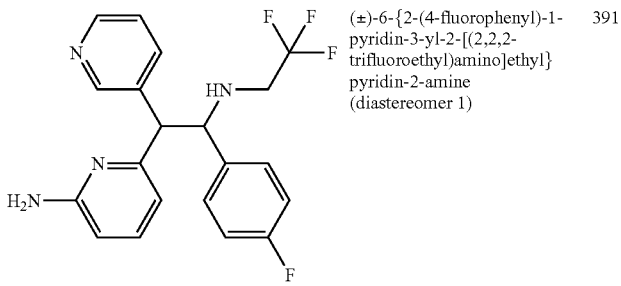 | (±)-6-{2-(4-fluorophenyl)-1-pyridin-3-yl-2-[(2,2,2-trifluoroethyl)amino]ethyl}pyridin-2-amine (diastereomer 1) | 391 |
| 7-4 | 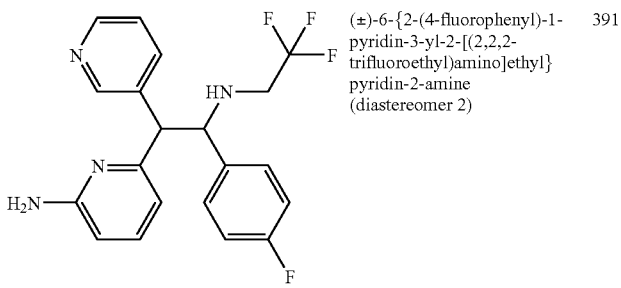 | (±)-6-{2-(4-fluorophenyl)-1-pyridin-3-yl-2-[(2,2,2-trifluoroethyl)amino]ethyl}pyridin-2-amine (diastereomer 2) | 391 |

SCHEME 8

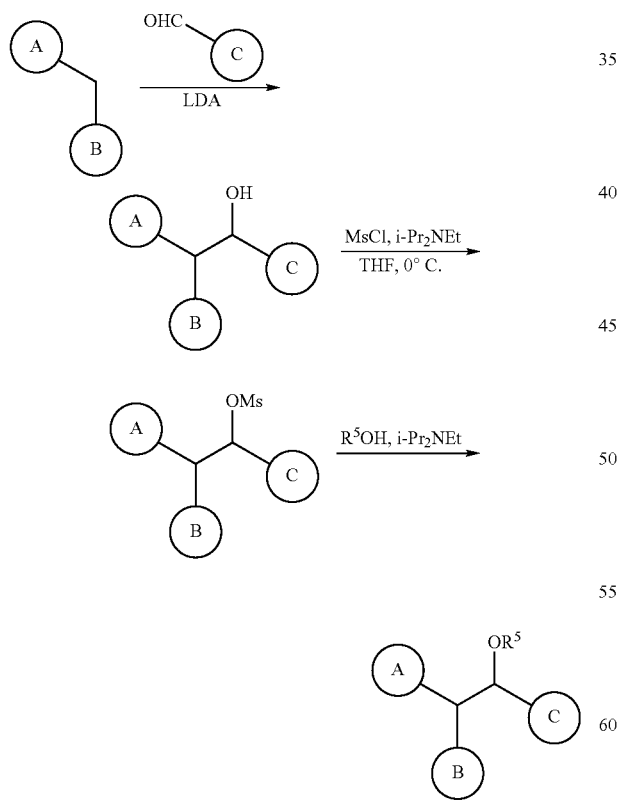

The variables C, B, A, and $R^5$ in the scheme are as defined in "Formula I".

EXAMPLE 424

(±)-3-[2-(4-fluorophenyl)-1-pyridin-3-yl-2-(2,2,2-trifluoroethoxy)ethyl]pyridine

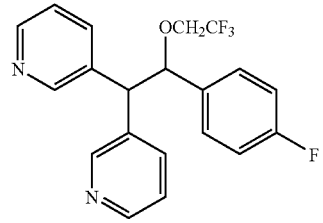

Step A:

To the solution of 3-(pyridin-3-ylmethyl)pyridine (0.195 g, 1.15 mmol) in THF (5 mL) at −78° C. was added LDA (0.7 mL, 1.8 M) and stirred for 1 h. 4-Fluorobenzaldehyde (0.171 g, 1.37 mmol) in THF (1 mL) was added. The mixture was stirred at −78° C. for 10 min and at −45° C. for 0.5 h. The reaction was quenched with ice and extracted with $CH_2Cl_2$. The combined organic layer was dried, filtered, and concentrated to give a solid. The solid was triturated with $CH_2Cl_2$ to give 1-(4-fluorophenyl)-2,2-dipyridin-3-ylethanol. $^1$H-NMR (500 MHz, $CDCl_3$) δ 8.60 (d, 1H, J=1.7), 8.45 (d, 1H, J=1.9), 8.38 (dd, 1H, J=4.7, 1.2), 8.27 (dd, 1H, J=4.6, 1.2), 7.91 (d, 1H, J=7.8), 7.76 (d, 1H, J=8.0), 7.34-7.29 (m, 3H), 7.19 (dd, 1H, J=7.8, 4.9), 7.02 (t, 2H, J=8.8), 5.68 (d, 1H, J=4.9), 5.45 (dd, 1H, J=8.5, 4.8), 4.34 (d, 1H, J=8.8). LRMS m/z (M+H) Calcd: 295.3. found: 295.1.

Step B:

To the solution of 1-(4-fluorophenyl)-2,2-dipyridin-3-ylethanol (0.2 g, 0.68 mmol) in THF (4 mL) was added i-$Pr_2$NEt (0.4 mL, 2.3 mmol) at 0° C. followed by methanesulfonyl chloride (0.1 mL, 1.3 mmol). The reaction mixture was stirred for 10 h. Diluted with saturated NaHCO$_3$ and extracted with CH$_2$Cl$_2$. The combined organic layer was dried, filtered, and concentrated to give 1-(4-fluorophenyl)-2,2-dipyridin-3-ylethyl methanesulfonate. LRMS m/z (M+H) Calcd: 373.4. found: 373.0.

Step C:

The mixture of 1-(4-fluorophenyl)-2,2-dipyridin-3-ylethyl methanesulfonate (0.1 g, 0.27 mmol) and i-Pr$_2$NEt (0.1 mL) in CF$_3$CH$_2$OH (1 mL) was heated to reflux for 10 h. Diluted with aqueous Na$_2$CO$_3$ (2M) and extracted with CH$_2$Cl$_2$. The combined organic layer was dried, filtered, and concentrated. The residue was purified by reverse phase HPLC (5-100% CH$_3$CN/H$_2$O+0.1% TFA) to give the trifluoroacetate salt of (±)-3-[2-(4-fluorophenyl)-1-pyridin-3-yl-2-(2,2,2-trifluoroethoxy)ethyl]pyridine. $^1$H-NMR (500 MHz, CDCl$_3$) δ 11.38 (broad, 2H), 8.68 (d, 2H, J=32.7), 8.55 (d, 2H, J=14.9), 8.0 (d, 1H, J=8.0), 7.75 (d, 1H, J=8.0), 7.58-7.60 (m, 1H), 7.40-7.42 (m, 1H), 7.08-7.11 (m, 2H), 6.99-7.02 (t, 2H, J=8.3), 5.16 (d, 1H, J=7.3), 4.40 (d, 1H, J=7.3), 3.63-3.76 (m, 2H). (LRMS m/z (M+H) Calcd: 377.3. found: 377.2.

The following compounds were made according to Scheme 8, where intermediates in the Scheme were modified according to literature methods.

EXAMPLES 425-427 AND 8-1 TO 8-2

| Example | Compound | Name | MS (M + 1) |
|---|---|---|---|
| 425 | | (±)-3-[2-(4-fluorophenyl)-2-methoxy-1-pyridin-3-ylethyl]pyridine | 309.3 |
| 426 | | (±)-3-[2-(cyclopentyloxy)-2-(4-fluorophenyl)-1-pyridin-3-ylethyl]pyridine | 363.2 |
| 427 | | (±)-methyl [1-(4-fluorophenyl)-2,2-dipyridin-3-ylethoxy]acetate | 367.1 |
| 8-1 | | (±)-1-(2-morpholin-4-ylpyridin-3-yl)-2,2-dipyridin-3-ylethanol | 363.182 |

-continued

| Example | Compound | Name | MS (M + 1) |
|---|---|---|---|
| 8-2 | | (±)-1-{2-[methyl(pyridin-3-yl)amino]pyridin-3-yl}-2,2-dipyridin-3-ylethanol | 384.1798 |

SCHEME 9

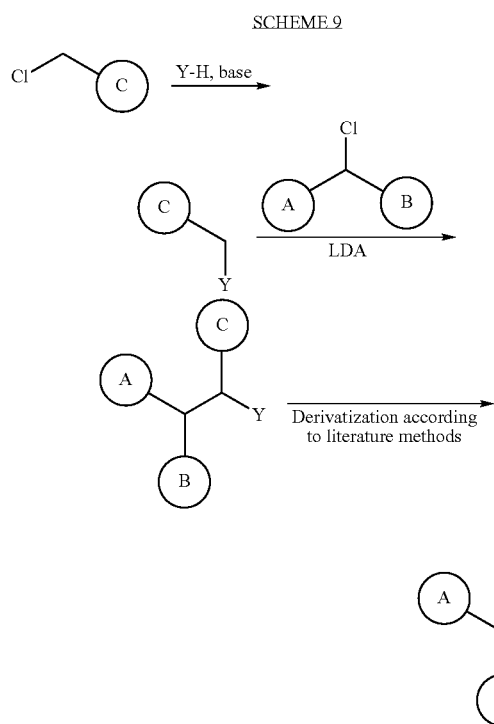

The variables C, B, A, and Y in the scheme are as defined in "Formula I".

EXAMPLE 428

(±)-1-[1-(6-chloropyridin-2-yl)-2,2-dipyridin-3-yl-ethyl]pyridin-2(1H)-one

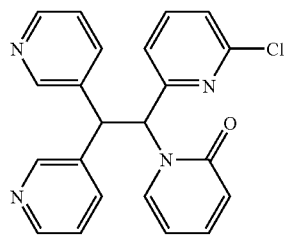

Step A:

To the solution of 2-chloro-6-chloromethylpyridine (1.62 g, 10 mmol) in DMF (10 mL) was added 2-hydroxypyridine (0.95 g, 10 mmol) and $Cs_2CO_3$ (6.52 g, 20 mmol). The mixture was stirred overnight, then diluted with water and extracted with $CH_2Cl_2$. The combined organic layer was dried, filtered, and concentrated to give a solid. The solid was purified by silica gel chromatography (2-4% MeOH in $CH_2Cl_2$) to give 1-[(6-chloropyridin-2-yl)methyl]pyridin-2(1H)-one. $^1$H-NMR (500 MHz, $CDCl_3$) δ 7.62 (t, 1H, J=7.8), 7.51 (dd, 1H, J=6.8, 2.0), 7.31-7.37 (m, 2H), 7.25 (d, 1H, 3=8.3), 6.59 (d, 1H, J=9.2), 6.21 (td, 1H, J=6.6, 1.3), 5.19 (s, 2H). LRMS m/z (M+H) Calcd: 221.7. found: 221.0.

Step B:

To the solution of 1-[(6-chloropyridin-2-yl)methyl]pyridin-2(1H)-one (0.3 g, 1.36 mmol) in THF (6 mL) at −78° C. was added LDA(0.83 mL, 1.8 M) and stirred at −78° C. for 1 h. The solution of 3-[chloro(pyridin-3-yl)methyl]pyridine (0.278 g, 1.36 mmol) in THF (3 mL) was added and the mixture was warmed to 0° C. and stirred at 0° C. for 1 h. The reaction was quenched with water and extracted with $CH_2Cl_2$. The combined organic layer was dried, filtered, and concentrated. The residue was purified by silica gel chromatography (3% MeOH in $CH_2Cl_2$) to give (±)-1-[1-(6-chloropyridin-2-yl)-2,2-dipyridin-3-ylethyl]pyridin-2(1H)-one. $^1$H-NMR (500 MHz, $CDCl_3$) δ 8.58 (d, 1H, J=2.2), 8.53 (d, 1H, J=2.0), 8.42 (dd, 1H, J=4.6, 1.2), 8.35 (dd, 1H, J=4.6, 1.2), 7.92 (d, 1H, 3=6.6), 7.84 (d, 1H, J=8.0), 7.64 (d, 1H, J=8.0), 7.48 (t, 1H, J=7.7), 7.25-7.09 (m, 6H), 6.41 (d, 1H, J=9.0), 6.09 (t, 1H, J=6.7), 5.30 (d, 1H, J=12.2). LRMS m/z (M+H) Calcd: 389.8. found: 389.0.

The following compounds were made according to Scheme 9 where intermediates in the Scheme were modified according to literature methods. Unless otherwise shown, structures of compounds 429-437, 9-1 to 9-5 and 444-446 are represented by defining variables

and "Y" of the structure

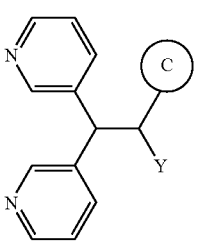

EXAMPLES 429-437 and 9-1 to 9-5
| Example | Compound | Name | MS (M + 1) |
|---|---|---|---|
| 429 | 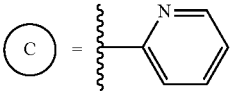 | (±)-1-(1-pyridin-2-yl-2,2-dipyridin-3-ylethyl]pyridin-2(1H)-one | 355.0 |
| 430 | 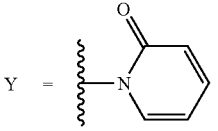 | (±)-2-[1-(1H-pyrazol-1-yl)-2,2-dipyridin-3-ylethyl]pyridine | 328.0 |
| 431 | 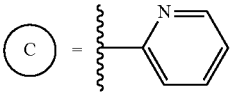 | (±)-1-[2-(4-fluorophenyl)-1-pyridin-2-yl-2-pyridin-3-ylethyl]pyridin-2(1H)-one (Diastereomer A) | 372.1499 |
| 432 | 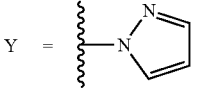 | (±)-1-[2-(4-fluorophenyl)-1-pyridin-2-yl-2-pyridin-3-ylethyl]pyridin-2(1H)-one (Diastereomer B) | 372.1499 |
| 433 | 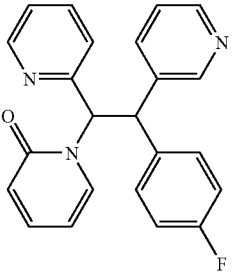 | (±)-1-[2-(4-fluorophenyl)-1,2-dipyridin-3-ylethyl]pyridin-2(1H)-one (Diastereomer A) | 372.1500 |

| Example | Compound | Name | MS (M + 1) |
|---|---|---|---|
| 434 | | (±)-1-[2-(4-fluorophenyl)-1,2-dipyridin-3-ylethyl]pyridin-2(1H)-one (Diastereomer B) | 372.1505 |
| 435 | | (±)-2-[2-(4-fluorophenyl)-1-(1H-pyrazol-1-yl)-2-pyridin-3-ylethyl]pyridine (Diastereomer A) | 345.1503 |
| 436 | | (±)-2-[2-(4-fluorophenyl)-1-(1H-pyrazol-1-yl)-2-pyridin-3-ylethyl]pyridine (Diastereomer B) | 345.1502 |
| 437 | | (±)-2-[1-(4-fluorophenyl)-2-(1H-imidazol-1-yl)-2-pyridin-3-ylethyl]pyridine (mixture of idiastereomers) | 345.1503 |
| 438 | C = pyridin-3-yl, Y = pyridin-2(1H)-on-1-yl | (±)-1-(1,2,2-tripyridin-3-ylethyl)pyridin-2(1H)-one | 355.5 |

-continued
| Example | Compound | Name | MS (M + 1) |
|---|---|---|---|
| 439 | 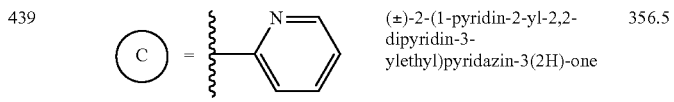 | (±)-2-(1-pyridin-2-yl-2,2-dipyridin-3-ylethyl)pyridazin-3(2H)-one | 356.5 |
| 440 | 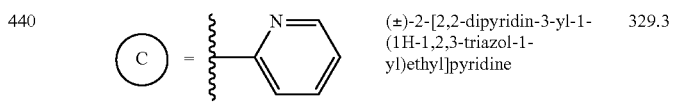 | (±)-2-[2,2-dipyridin-3-yl-1-(1H-1,2,3-triazol-1-yl)ethyl]pyridine | 329.3 |
| 441 | 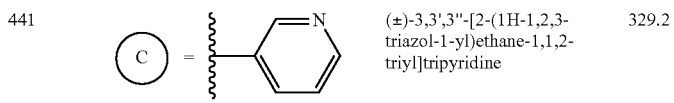 | (±)-3,3',3''-[2-(1H-1,2,3-triazol-1-yl)ethane-1,1,2-triyl]tripyridine | 329.2 |
| 442 | 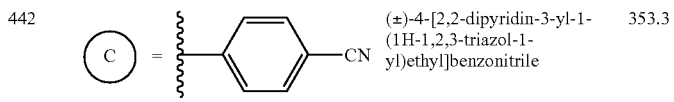 | (±)-4-[2,2-dipyridin-3-yl-1-(1H-1,2,3-triazol-1-yl)ethyl]benzonitrile | 353.3 |
| 443 | 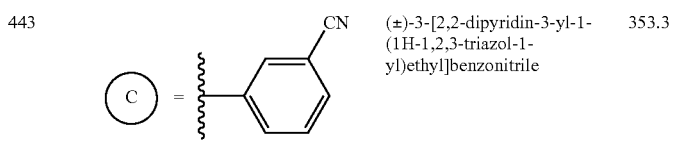 | (±)-3-[2,2-dipyridin-3-yl-1-(1H-1,2,3-triazol-1-yl)ethyl]benzonitrile | 353.3 |

-continued
| Example | Compound | Name | MS (M + 1) |
|---|---|---|---|
| 9-1 |  | (±)-3,3',3''-[2-(1H-tetrazol-1-yl)ethane-1,1,2-triyl]tripyridine | 330.1464 |
| 9-2 | 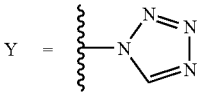 | (±)-3-[2-pyridin-2-yl-1-pyridin-3-yl-2-(1H-1,2,3-triazol-1-yl)ethyl]benzonitrile | 353.4 |
| 9-3 | 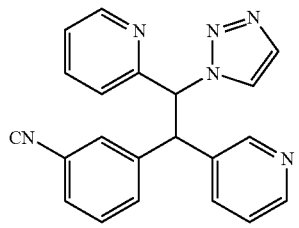 | (±)-2-[2,2-dipyridin-3-yl-1-(4H-1,2,4-triazol-4-yl)ethyl]pyridine | 329.1525 |
| 9-4 | 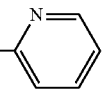 | (±)-4-{2-(4-chlorophenyl)-1-[2-(methylthio)pyrimidin-4-yl]-2-pyridin-3-ylethyl}morpholine | 427.1 |
| 9-5 | 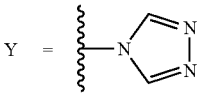 | (±)-4-[2-(4-chlorophenyl)-1-morpholin-4-yl-2-pyridin-3-ylethyl]pyrimidin-2-amine | 396 |

The following compounds were made from Example 428 using methods known to those skilled in the art.

EXAMPLES 444-446

| Example | Compound | Name | MS (M + 1) |
|---|---|---|---|
| 444 | 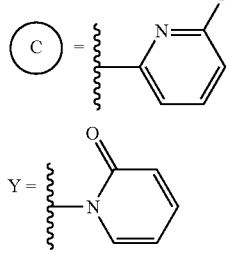 | (±)-1-(1-{6-[(2-hydroxyethyl)amino]pyridin-2-yl}-2,2-dipyridin-3-ylethyl)pyridin-2(1H)-one | 448.1 |
| 445 | 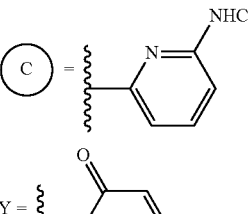 | (±)-N-{6-[1-(2-oxopyridin-1(2H)-yl)-2,2-dipyridin-3-ylethyl]pyridin-2-ylcarbamate | 470.0 |
| 446 | 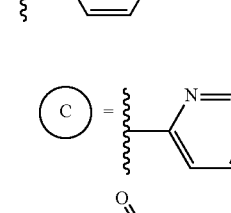 | (±)-1-[1(2H)-yl)-2,2-dipyridin-3-ylethyl]pyridin-2(1H)-one | 370.1 |

SCHEME 10

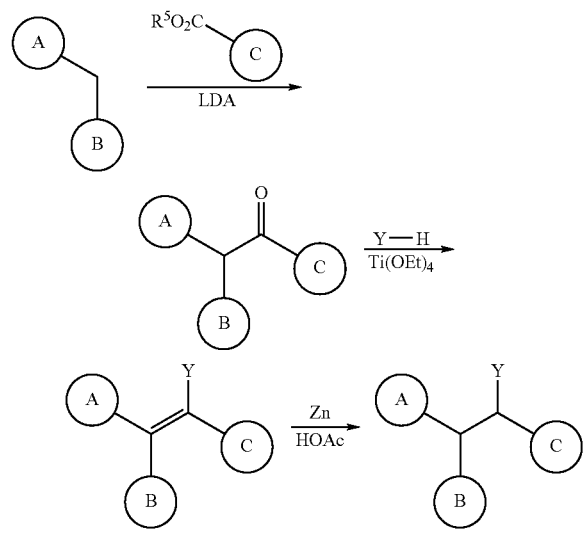

The variables A, B, C, Y, and $R^5$ in the scheme are as defined in "Formula I".

EXAMPLE 447

(±)-6-[1-(3,3-difluoropyrrolidin-1-yl)-2,2-dipyridin-3-ylethyl]pyridin-2-amine

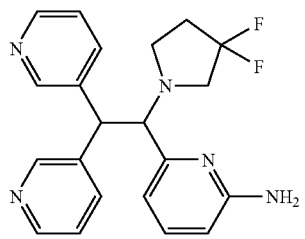

Step A:
To a solution of di-3-pyridylmethane (250 mg, 1.47 mmol) in dry TIE (5 mL) was added LDA (2.1 mL, 3.16 mmol)

slowly at −78° C. After 30 min a solution of methyl 2-bromopyridine-6-carboxylate (349 mg, 1.62 mmol) in dry THF (3 mL) was added slowly. After 30 min the cooling bath was removed and the mixture allowed to warm to RT. After 4 hr the mixture was diluted with saturated NH$_4$Cl and extracted with EtOAc (3×). The combined organic layers were dried (MgSO$_4$), filtered, and concentrated. Flash column (100% EtOAc) gave 1-(6-bromopyridin-2-yl)-2,2-dipyridin-3-ylethanone as a yellow oil. $^1$H-NMR (500 MHz, CDCl$_3$) δ 8.66 (m, 2 H), 8.53 (m, 2 H), 8.06 (dd, J=0.98 and 6.35 Hz, 1 H), 7.80 (m, 4 H), 7.28 (m, 2 H), 6.79 (s, 1 H).

Step B:

To a solution of 1-(6-bromopyridin-2-yl)-2,2-dipyridin-3-ylethanone (154 mg, 0.44 mmol) in dry 1,4-dioxane (2 mL) was added 3,3-difluoropyrrolidine hydrochloride (75 mg, 0.52 mmol), TEA (0.079 mL, 0.57 mmol), and Ti(OEt)$_4$ (0.18 mL, 0.87 mmol). The mixture was heated to reflux. After 2 hr the mixture was cooled to RT, diluted with brine, and filtered through a pad of Celite. The pad was washed with EtOAc. The filtrate layers were separated and the aqueous layer extracted with EtOAc (3×). The combined organic layers were dried (MgSO$_4$), filtered, and concentrated to a brown foam which was used in the next step without purification.

Step C:

To a solution of crude imine (134 mg, 0.3 mmol) in HOAc (3 mL) was added Zn dust (198 mg, 3.02 mmol) at RT. After 16 hr the mixture was filtered through a pad of Celite and concentrated. The residue was taken up in 1M NaOH and extracted with CH$_2$Cl$_2$ (3×). The combined organic layers were dried (MgSO$_4$), filtered, and concentrated. Flash column (gradient, 0-10% MeOH/CH$_2$Cl$_2$) gave 2-bromo-6-[1-(3,3-difluoropyrrolidin-1-yl)-2,2-dipyridin-3-ylethyl]pyridine as a yellow solid. $^1$H-NMR (500 MHz, CDCl$_3$) δ 8.72 (s, 1 H), 8.49 (d, J=4.89 Hz, 1 H), 8.37 (s, 1 H), 8.27 (d, J=4.88 Hz, 1 H), 7.75 (d, J=7.57 Hz, 1 H), 7.43 (d, J=7.57 Hz, 1 H), 7.37 (t, J=7.32 Hz, 1 H), 7.30 (m, 2H), 7.04 (dd, J=4.89 and 2.93 Hz, 1 H), 6.88 (d, J=7.33 Hz, 1 H), 4.88 (d, J=11.71 Hz, 1 H), 4.53 (d, J=11.48 Hz, 1H), 3.10 (m, 1 H), 2.88 (m, 2 H), 2.70 (m, 1 H), 2.0 (m, 2 H).

Step D:

The 2-bromo-6-[1-(3,3-difluoropyrrolidin-1-yl)-2,2-dipyridin-3-ylethyl]pyridine (73 mg, 0.16 mmol), tert-butyl carbamate (23 mg, 0.2 mmol), Cs$_2$CO$_3$ (75 mg, 0.23 mmol), Pd$_2$(dba)$_3$ (3 mg, 0.003 mmol), and xantphos (6 mg, 0.01 mmol) were combined in dry 1,4-dioxane (1.5 mL). The mixture was degassed (3× pump/N2) then heated to 100° C. After 5 hr the mixture was cooled to RT, diluted with EtOAc, filtered through a pad of Celite, and concentrated. The residue was taken up in 1 mL CH$_2$Cl$_2$ to which was added 1 mL TFA at RT. After 90 min the mixture was concentrated. The residue was taken up in saturated NaHCO$_3$ and extracted with CH$_2$Cl$_2$ (3×). The combined organic layers were dried (MgSO$_4$), filtered, and concentrated. Flash column (gradient, 0-10% MeOH/CH$_2$Cl$_2$) gave the title compound as a yellow foam. $^1$H-NMR (500 MHz, CDCl$_3$) δ 8.68 (d, J=2.20 Hz, 1 H), 8.47 (d, J=4.15 Hz, 1 H), 8.37 (d, J=2.19 Hz, 1 H), 8.25 (d, J=3.90 Hz, 1 H), 7.74 (d, J=8.06 Hz, 1 H), 7.41 (d, J=7.81 Hz, 1 H), 7.25 (m, 2 H), 7.02 (m 1 H), 6.27 (m, 2 H), 4.85 (d, J=11.47 Hz, 1 H), 4.39 (s, 2 H), 4.35 (d, J=11.72 Hz, 1 H), 3.10 (m, 1 H), 2.86 (m, 2 H), 2.67 (m, 1 H), 2.0 (m, 2 H); MS (M+H)$^+$ 382.0.

Using the methodologies described below, representative compounds of the invention were evaluated and found to exhibit activity in the Kv1.5 assays, thereby demonstrating and confirming the utility of the compounds of this invention as Kv1.5 inhibitors and antiarrhythmics. Compounds of this type may exhibit forward rate-dependence, blocking the outward K$^+$ currents to a greater extent or preferentially at faster rates of depolarization or heart rates. Such a compound could be identified in electrophysiological studies as described below. For example, during a train of depolarizations delivered at frequencies of 1 Hz and 3 Hz, the block is "rate-dependent" if the amount of block observed during a 10 second train at 3 Hz is greater than that at 1 Hz. A Kv1.5 blocker may also display use-dependence, during which the block of the outward K$^+$ currents increases with use, or during repetitive depolarization of a cardiac cell. Use dependence of block occurs to a greater extent with each successive depolarization in a train or sequence of pulses or depolarizations at a given rate or frequency. For example, during a train of 10 depolarizations at a frequency of 1 Hz, the block is "use-dependent" if the amount of block is greater for the 10$^{th}$ pulse than for the 1$^{st}$ pulse of the train. A Kv1.5 blocker may exhibit both use-dependence and rate-dependence.

A Kv1.5 blocker may also be identified through electrophysiological studies of native I$_{Kur}$ using cardiac myocytes or other tissue from various species including, but not limited to, human, rat, mouse, dog, monkey, ferret, rabbit, guinea pig, or goat. In native tissues Kv1.5 may exist as a homo-oligomer, or as a hetero-oligomer with other Kv family members, or may exist in a complex with a β-subunit. Compounds of this invention may block Kv1.5 homo- or hetero-oligomers or Kv1.5 in complexes with β-subunits.

Kv1.5 Assays

The high throughput Kv1.5 planar patch clamp assay is a systematic primary screen. It confirms activity and provides a functional measure of the potency of agents that specifically affect Kv1.5 potassium channels. Kiss et al. (Assay and Drug Dev. Tech., 1(1-2):127-135, 2003) and Schroeder et al. (J. of Biomol. Screen., 8(1); 50-64, 2003) describe the use of this instrument for Kv1.5 as well as other voltage gated ion channels.

Chinese hamster ovary cells (CHO) stably expressing the human Kv1.5 potassium channel alpha subunit, cloned from human heart, are grown to 90-100% confluence in Ham's F12 medium supplemented with 10% FBS, 100 U/ml penicillin, 100 µg/ml streptomycin, 1000 µg/ml G-418 sulfate. Cells are subcultured by treatment with Versene, then suspended in phosphate-buffered saline (PBS) and centrifuged The cell pellet is resuspended in PBS and the resulting suspension placed in the cell reservoir of the IonWorks™ HT instrument.

Electrophysiological recordings are performed with intracellular solution containing (mM): K-gluconate 100, KCl 40, MgCl$_2$ 3.2, EGTA 3, N-2-hydroxylethylpiperazine-N'-2-ethanesulphonic acid (HEPES)5, adjusted to pH 7.3. Amphotericin (Sigma) is prepared as 30 mg/ml stock solution and diluted to a final working concentration of 0.1 mg/ml in internal buffer solution. The external solution is Dulbecco's PBS (Invitrogen) and contains (mM): CaCl$_2$ 0.90, KCl 2.67, K$_3$PO$_4$ 1.47, MgCl$_2$ 0.50, NaCl 138, Na$_3$PO$_4$ 8.10 and has a pH of 7.4. All compounds are prepared as 10 mM stock solutions in DMSO. Compounds are diluted into external buffer, then transferred from the drug plate to the Patchplate during the experiment (final DMSO concentration <0.66% vol.).

Kv1.5 ionic currents are recorded at room temperature. Membrane currents are amplified (RMS~10 pA) and sampled at 10 kHz. Leak subtraction was performed in all experiments by applying a 160 ms hyperpolarizing (10 mV) pre-pulses 200 ms before the test pulses to measure leak conductance. The patch clamp stimulus protocol is as follows:

1. Patchplate wells are loaded with 3.5 μL of external buffer.
2. Planar micropipette hole resistances (Rp) is determined by applying a 10 mV, 160 ms potential difference across each hole (Hole test).
3. Cells are pipetted into the Patchplate and form high resistance seals with the 1-2 μm holes at the bottom of each Patchplate well. A seal test scan is performed to determine how many of the Patchplate wells have cells that have formed seals.
4. In order to gain electrical access to the cells, intracellular solution containing amphotericin is circulated for 4 minutes on the bottom side of the Patchplate.
5. Pre-compound addition test pulse is applied to each well on the Patchplate. Protocol: Cells are voltage clamped at a membrane holding potential of −80 mV for 15 seconds. This is followed by application of a 5 Hz stimulus train (27×150 ms depolarizations to +40 mV). The membrane potential steps to +40 mV evoke outward (positive) ionic currents.
6. Compound is added to each well of the Patchplate. Compounds are allowed to incubate for 5 minutes.
7. Post-compound addition test pulse protocol is applied. Protocol: Cells are voltage clamped at a membrane holding potential of −80 mV for 15 seconds. This is followed by application of a 5 Hz stimulus train (27×150 ms depolarizations to +40 mV).

Data analysis is conducted off-line. Paired comparisons between pre-drug and post-drug additions are used to determine the inhibitory effect of each compound. % inhibition of the peak control current during the $27^{th}$ depolarization to +40 mV (in the 5 Hz train) is plotted as a function of antagonist concentration. The concentrations of drug required to inhibit current by 50% ($IC_{50}$) are determined by fitting of the Hill equation to the concentration response data: % of Control=$100\times(1+([Drug]/IC_{50})^p)^{-1}$ For each cell four arithmetic metrics are obtained:
1) seal resistance
2) baseline metric (the mean current at −70 mV from 5 to 45 ms before the first depolarization to +40 mV)
3) current run up metric (pre-compound mean current amplitude during the $1^{st}$ depolarization to +40 mV minus the pre-compound mean current amplitude during the $27^{th}$ depolarization to +40 mV)
4) peak current (maximum current amplitude during the $27^{th}$ depolarization to +40 mV during the 5 Hz train).

All metrics are obtained during both the pre- and post-compound addition traces. Cells are eliminated from further analysis if:
1) seal resistance is <50 MΩ
2) baseline metric is >±100 pA during the pre-compound
3) current run up metric is ≧−0.2 nA
4) pre-read peak metric is <400 pA.

The above-listed compounds provide ≧20% inhibition at a concentration of 33 μM or less in the high throughput Kv1.5 planar patch clamp assay described above.

Atomic Absorption Spectroscopy Protocol:

This assay identifies agents that specifically block the human Kv1.5 K$^+$ channel heterologously expressed in CHO cells as measured by Rb$^+$ efflux using Flame Atomic Absorption Spectroscopy (FAAS). The application of FAAS for measuring ion channel activity was adapted from Terstappen et al, *Anal. Biochem.*, 272:149-155, 1999.

CHO cells expressing human Kv1.5 are cultured as described above, then harvested with trypsin-EDTA and washed with medium.

1. 40,000 cells per well are seeded in a 96-well cell culture plate (assay plate) and the cells are allowed to grow for 48 hours at 37° C.
2. The medium is removed and 200 μl of Rb Load Buffer (Aurora Biomed, Vancouver, BC) is added for 3 hours at 37° C. under 5% $CO_2$.
3. The cells are washed 5 times with 200 μl Hank's Balanced Salt Solution (HBSS) followed by the addition of 100 μl HBSS containing test compound or 0.5% DMSO.
4. After 10 min, 100 μl of HEPES-buffered saline containing 140 mM KCl is added and plate is incubated at RT for 5 min. with gentle shaking.
5. Immediately thereafter, 150 μl of supernatant is transferred to a fresh 96 well plate and the remaining supernatant aspirated.
6. 120 μl of Cell Lysis Buffer (Aurora Biomed, Vancouver, BC) is added to the assay plate and shaken for 10 min. prior to analysis.
7. Rb content is measured in samples of supernatant (SUP) and lysate (LYS) using an ICR-8000 automated AAS instrument (Aurora Biomed, Vancouver, BC).

% FLUX=100%*(SUP/(LYS+SUP)). % INH=100%*(1−(A−B)/(C−B)), where A is % FLUX in the presence of tested compound, B is % FLUX in the presence of 10 mM (6-methoxy-2-methyl-1-oxo-4-phenyl-1,2-dihydroisoquinolin-3-yl)-N,N-dimethylmethanaminium chloride, C is % FLUX in the presence of 0.25% DMSO.

The above-listed compounds provide ≧25% inhibition at a concentration of 25 μM or less in the AAS assay described above.

The compounds of this invention can be administered for the treatment or prevention of afflictions, diseases and illnesses according to the invention by any means that effects contact of the active ingredient compound with the site of action in the body of a warm-blooded animal. For example, administration, can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1-500 milligrams per day. Ordinarily, from 10 to 100 milligrams per day in one or more applications is effective to obtain desired results. These dosages are the effective amounts for the treatment and prevention of afflictions, diseases and illnesses described above, e.g., cardiac arrhythmias such as atrial fibrillation, atrial flutter, atrial arrhythmia, and supraventricular tachycardia, thromboembolic events such as stroke and congestive heart failure, and immunodepression.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

Compounds of the invention can be administered as the sole active ingredient or in combination with a second active ingredient, including other antiarrhythmic agents having Kv1.5 blocking activities such as quinidine, propafenone, ambasilide, amiodarone, flecamide, sotalol, bretylium, dofetilide, almokalant, bepridil, clofilium, other compounds having Kv1.5 blocking activities such as clotrimazole, ketoconazole, bupivacaine, erythromycin, verapamil, nifedipine, zatebradine, bisindolylmaleimide, or other cardiovascular agents such as, but not limited to, ACE inhibitors such as benazepril, captopril, enalapril, fosinopril, lisinopril, moexipril, perindopril erbumine, quinapril, ramipril, and trandolapril, angiotensin II antagonists such as candesartan, eprosartan, irbesartan, losartan, olmesartan, telmisartan, and valsartan, cardiac glycosides such as digoxin, L-type calcium channel blockers, T-type calcium channel blockers, selective and nonselective beta blockers, an immunosuppresant compound, endothelin antagonists, thrombin inhibitors, aspirin, nonselective NSAIDs other than aspirin such as naproxen, warfarin, factor Xa inhibitors, low molecular weight heparin, unfractionated heparin, clopidogrel, ticlopidine, IIb/IIIa receptor antagonists such as tirofiban, 5HT receptor antagonists, integrin receptor antagonists, thromboxane receptor antagonists, TAFI inhibitors and P2T receptor antagonists. Compounds of the invention can also be administered as the sole active ingredient or in combination with a pacemaker or defibrillator device.

What is claimed is:

1. A compound of the formula

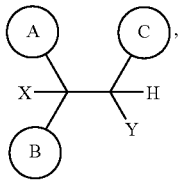

or a pharmaceutically acceptable salt thereof, wherein

A is selected from the group consisting of
1) a phenyl ring, and
2) a pyridyl ring, wherein the point of attachment to the pyridyl ring is a carbon atom, wherein the phenyl ring and pyridyl ring are unsubstituted, mono-substituted with $R^4$, disubstituted with groups independently selected from $R^4$, trisubstituted with groups independently selected from $R^4$, or tetrasubstituted with groups independently selected from $R^4$, and wherein the N pyridyl ring atom is unsubstituted or substituted with oxo; and C is selected from the group consisting of
1) an aryl ring, wherein any stable aryl ring atom is independently unsubstituted or substituted with a group selected from $R^4$, and
2) $C_1$—$C_6$ alkyl, wherein any stable atom is independently unsubstituted or substituted with a group selected from $R^4$;

B is a heteroaryl ring, wherein the point of attachment to the heteroaryl ring is a carbon atom, and wherein the heteroaryl ring is selected from the group consisting of pyridine and pyrimidine, wherein the heteroaryl ring is unsubstituted, mono-substituted with $R^4$, disubstituted with groups independently selected from $R^4$, trisubstituted with groups independently selected from $R^4$, or tetrasubstituted with groups independently selected from $R^4$, and wherein the N heteroaryl ring atom is unsubstituted or substituted with oxo;

X is OH;

Y is selected from the group consisting of

1) OH,

2) 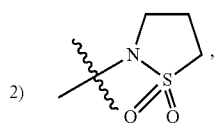

3) 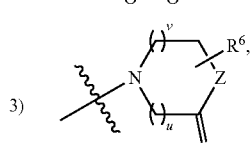

4) 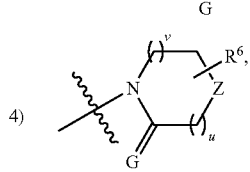

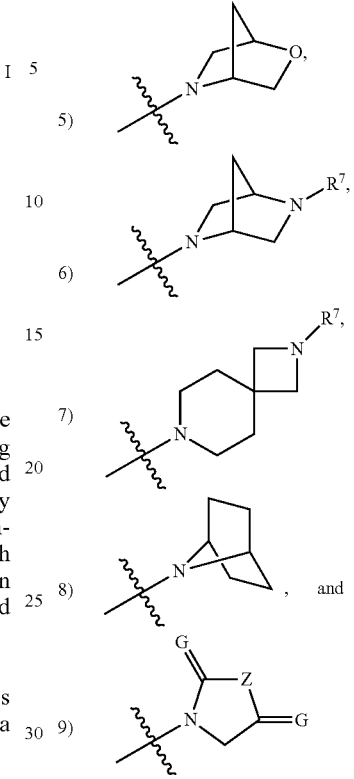

G, each time it occurs, is independently selected from the group consisting of $H_2$ and O;

Z is selected from the group consisting of $C(R^6)_2$, $NR^5$, $NC(O)R^5$, $NC(O)OR^5$, $NC(O)N(R^5)_2$, $NS(O)_{1-2}R^5$, $S(O)_{0-2}$, —$N(R^5)C(O)$—, —$C(R^5)$=$C(R^6)$— and O;

$R^a$, in each instance in which it appears, is independently selected from the group consisting of
1) hydrogen,
2) $C_1$—$C_6$ alkyl,
3) halogen,
4) aryl,
5) heterocycle,
6) $C_3$—$C_{10}$ cycloalkyl, and
7) $OR^5$,
said alkyl, aryl, heterocycle and cycloalkyl is unsubstituted or substituted with at least one substituent selected from $R^6$;

$R^4$, in each instance in which it appears, is independently selected from the group consisting of
1) hydrogen,
2) halogen,
3) $NO_2$,
4) CN,
5) $CR^4$=$C(R^5)_2$,
6) C≡$CR^5$,
7) $(CR^a{}_2)_nOR^5$,
8) $(CR^a{}_2)_nN(R^5)_2$,
9) $(CR^a{}_2)_nC(O)R^5$,
10) $(CR^a{}_2)_nC(O)OR^5$,
11) $(CR^a{}_2)_nR^5$,
12) $(CR^a{}_2)_nS(O)_mR^5$,
13) $(CR^a{}_2)_nS(O)_mN(R^5)_2$,
14) $OS(O)_mR^5$,
15) $N(R^5)C(O)R^5$, 16) $N(R^5)S(O)_m R^5$,
17) $(CR^a{}_2)_n N(R^6)R^5$,
18) $(CR^a{}_2)_n N(R^5)(CR^a{}_2)_n C(O)N(R^5)_2$,
19) $(CR^a{}_2)_n N(R^5)(CR^a{}_2)_n C(O)OR^5$,
20) $N(R^5)(CR^a{}_2)_n R^5$,
21) $N(R^5)(CR^a{}_2)_n N(R^5)_2$, and
22) $(CR^a{}_2)_n C(O)N(R^5)_2$;

$R^5$, in each instance in which it appears, is independently selected from the group consisting of
1) hydrogen,
2) unsubstituted or substituted $C_1$—$C_6$ alkyl,
3) unsubstituted or substituted $C_3$—$C_{10}$ cycloalkyl,
4) unsubstituted or substituted aryl,
5) unsubstituted or substituted heterocycle,
6) $CF_3$,
7) unsubstituted or substituted $C_2$—$C_6$ alkenyl, and
8) unsubstituted or substituted $C_2$—$C_6$ alkynyl, or in the case where $R^5$ is attached to a nitrogen atom that is disubstituted with $R^5$, each R5 is independently selected from $C_1$—$C_6$ alkyl, and the nitrogen atom together with each $R^5$ form a ring;

$R^6$, in each instance in which it appears, is independently selected from the group consisting of
1) hydrogen,
2) unsubstituted or substituted $C_1$—$C_6$ alkyl,
3) halogen,
4) $OR^5$,
5) $CF_3$,
6) unsubstituted or substituted aryl,
7) unsubstituted or substituted $C_3$—$C_{10}$ cycloalkyl,
8) unsubstituted or substituted heterocycle,
9) $S(O)_m(R^5)_2$,
10) $C(O)OR^5$,
11) $C(O)R^5$,
12) $CN$,
13) $C(O)N(R^5)_2$,
14) $N(R^5)C(O)R^5$,
15) $N(R^5)C(O)OR^5$,
16) $N(R^5)C(O)N(R^5)_2$,
17) $OC(O)N(R^5)_2$,
18) $S(O)_m R^5$,
19) $OS(O)_m R^5$,
20) $NO_2$,
21) $N(R^5)_2$,
22) $SC(O)R^5$,
23) $N(R^5)S(O)_m R^5$, $R^7$ is independently selected from the group consisting of
1) $S(O)_m N(R^5)_2$,
2) $C(O)OR^5$,
3) $C(O)R^5$,
4) $C(O)N(R^5)_2$, and
5) $S(O)_m R^5$;

m is independently 0, 1 or 2;
n is independently 0, 1, 2, 3, 4, 5 or 6;
u is 0, 1 or 2; and
v is 0, 1 or 2 provided the compound is not

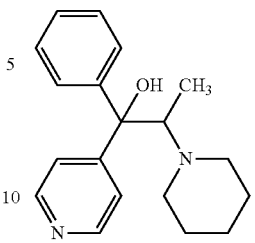

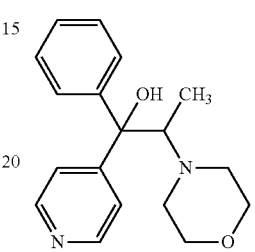

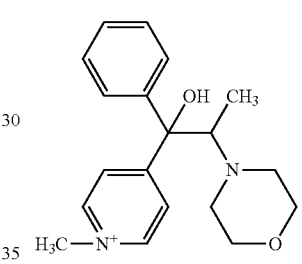

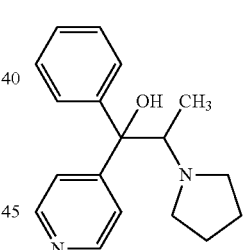

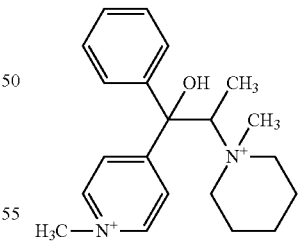

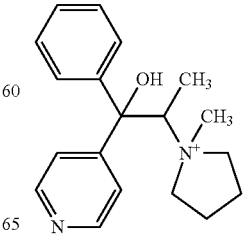

-continued

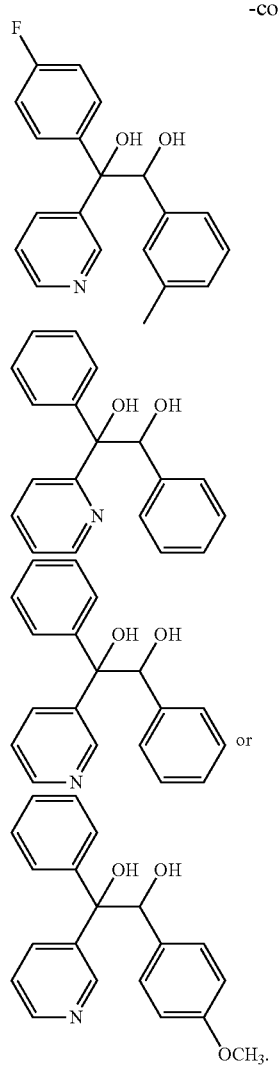

2. A compound of claim 1, or a pharmaceutically acceptable salt thereof, wherein B is a pyridyl ring, wherein the point of attachment to the pyridyl ring is a carbon atom, and wherein the pyridyl ring is unsubstituted, mono-substituted with $R^4$, disubstituted with groups independently selected from $R^4$, trisubstituted with groups independently selected from $R^4$, or tetrasubstituted with groups independently selected from $R^4$, and wherein the N atom is unsubstituted or substituted with oxo;

X is OH;

A is selected from the group consisting of
1) a phenyl ring, and
2) a pyridyl ring, wherein the point of attachment to the pyridyl ring is a carbon atom, wherein the phenyl ring and pyridyl ring are unsubstituted, mono-substituted with $R^4$, disubstituted with groups independently selected from $R^4$, trisubstituted with groups independently selected from $R^4$, or tetrasubstituted with groups independently selected from $R^4$, and wherein the N pyridyl ring atom is unsubstituted or substituted with oxo;

C is selected from the group consisting of

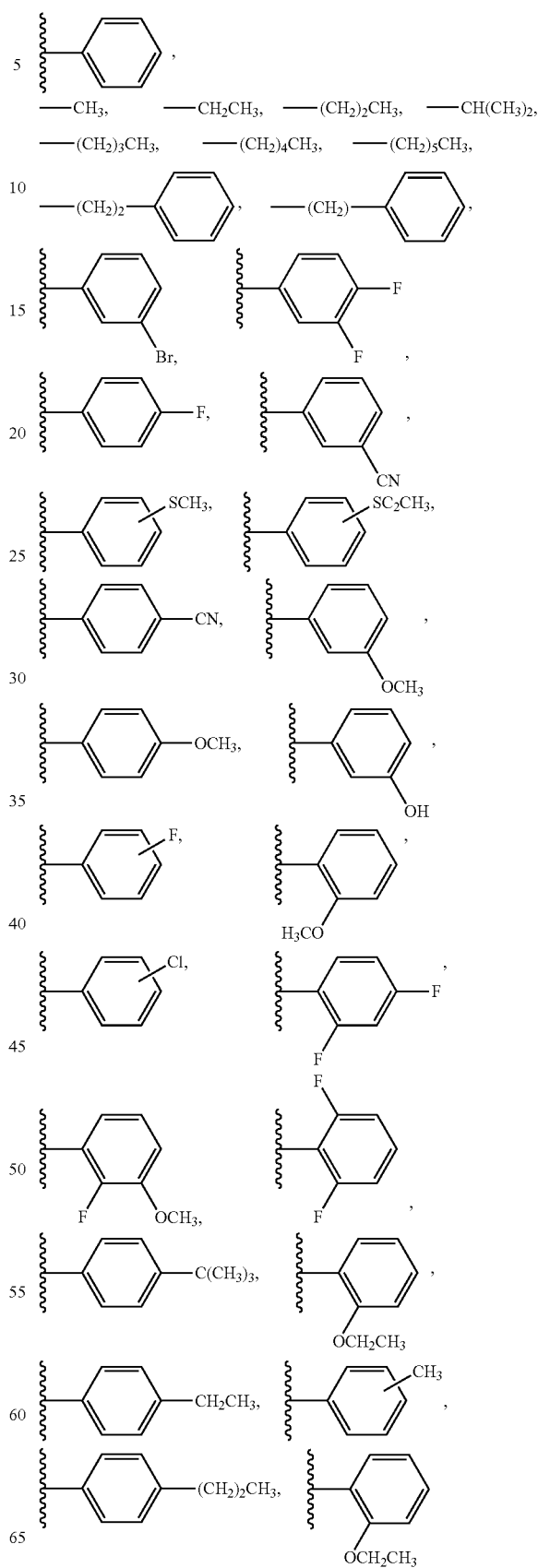

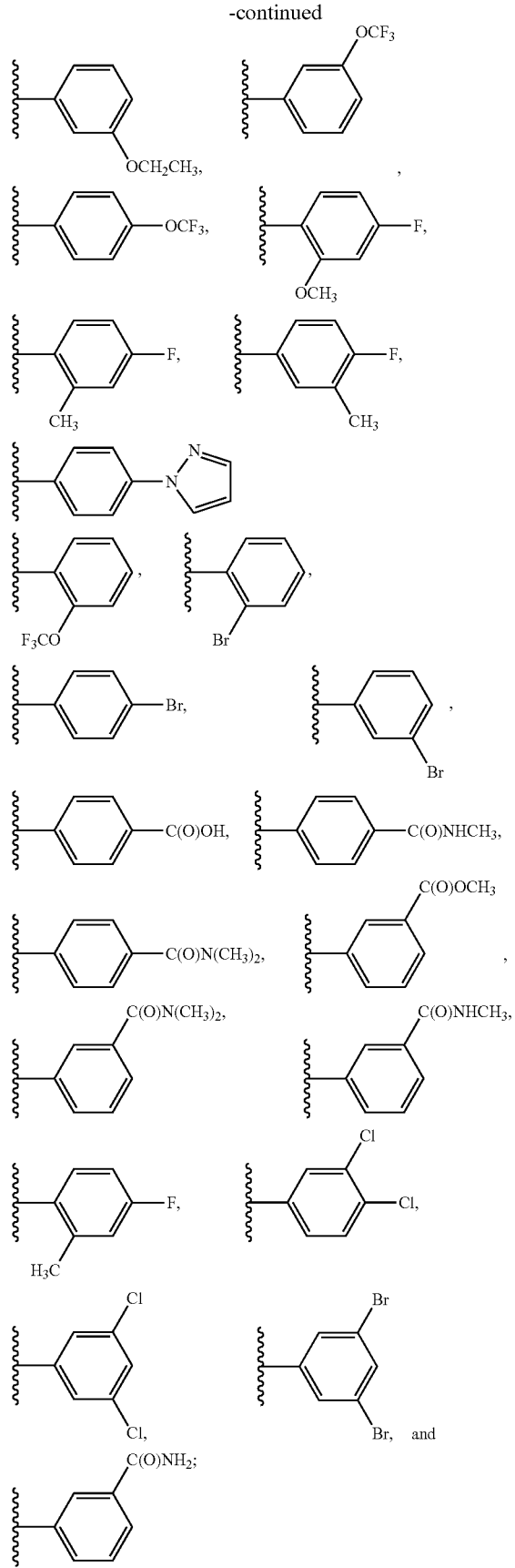
-continued
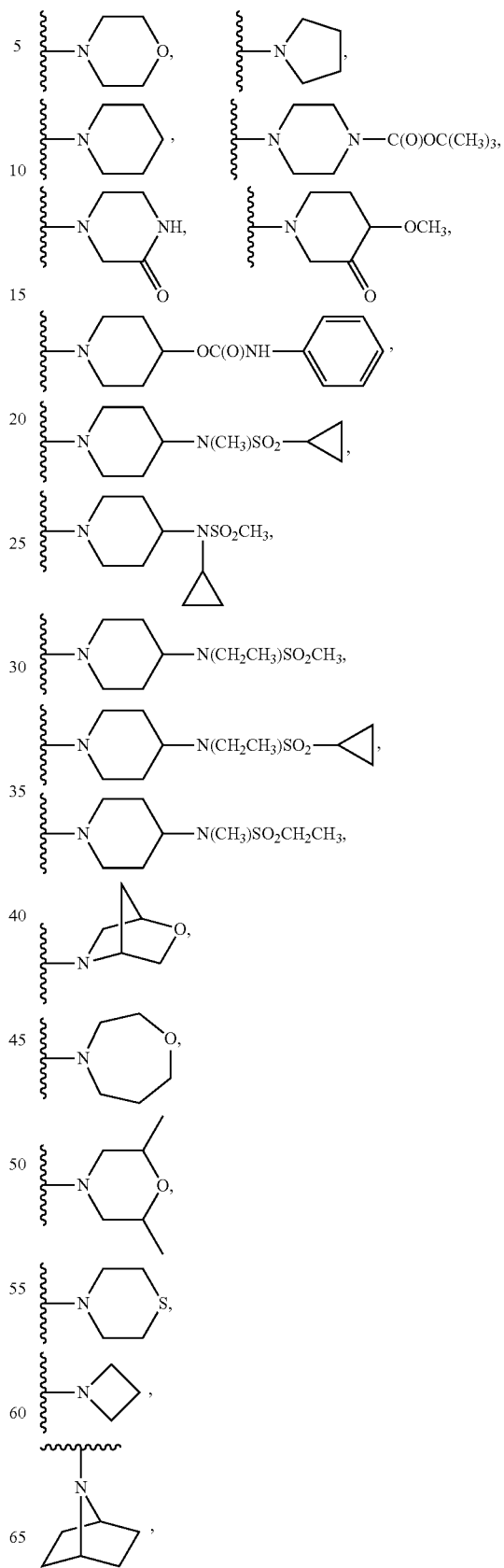
Y is selected from the group consisting of

-continued
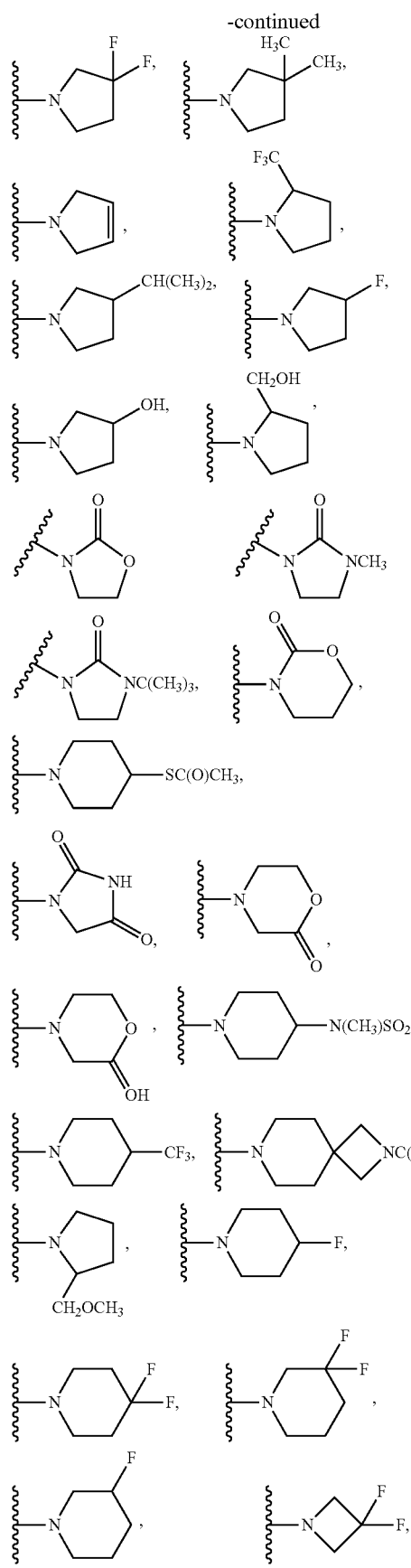
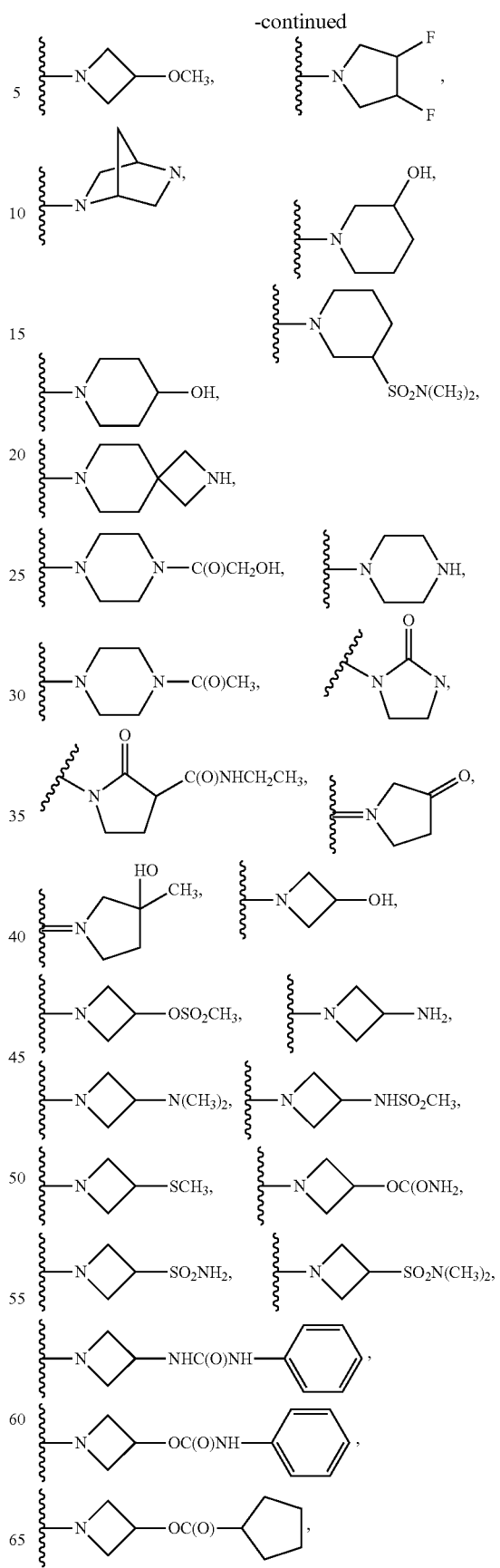

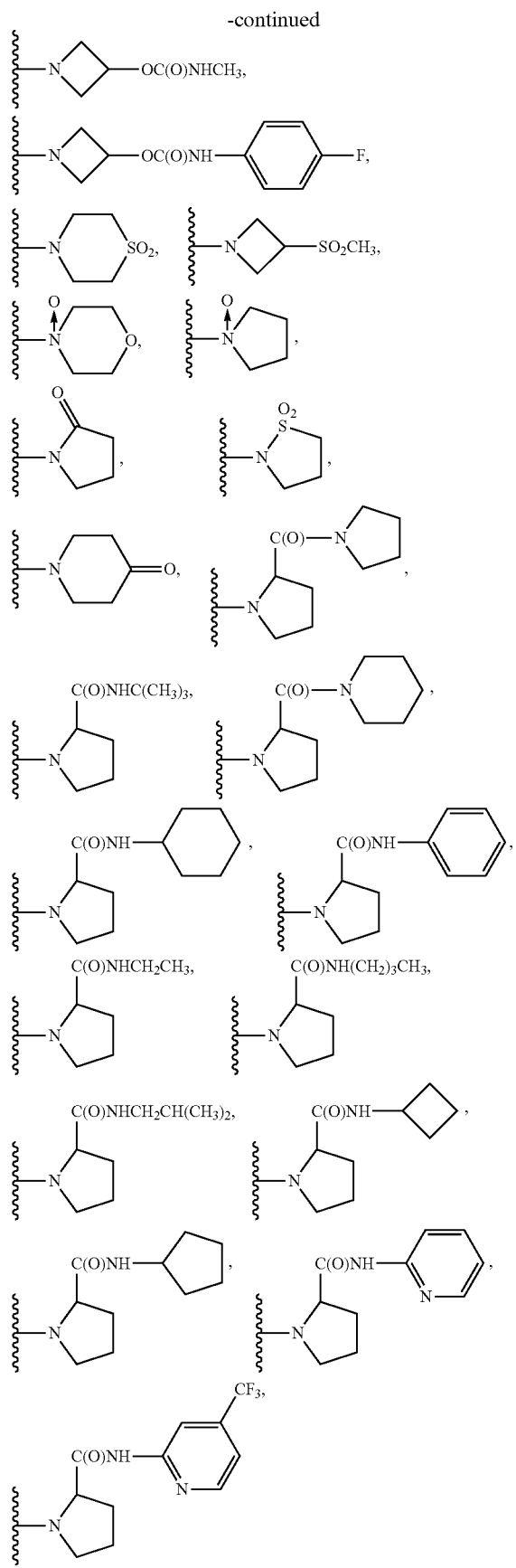
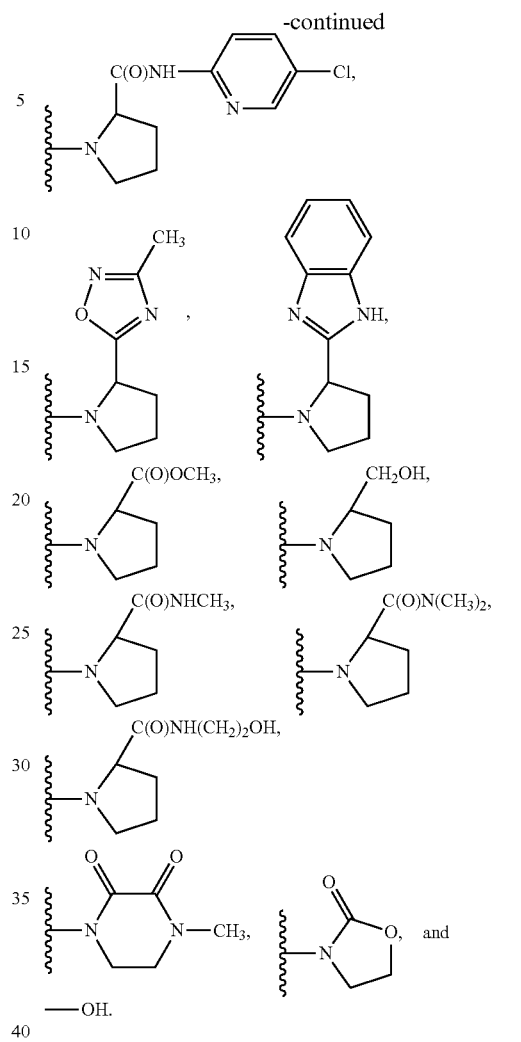

—OH.

3. A compound, or a pharmaceutically acceptable salt thereof, selected from the group consisting of
(±)-2-Morpholin-4-yl-2-phenyl-1,1-dipyridin-3-yl-ethanol,
(±)-3-methyl-2-morpholin-4-yl-1,1-dipyridin-3-ylbutan-1-ol,
(±)-2-[(2-methoxyethyl)(methyl)amino]-2-phenyl-1,1-dipyridin-3-ylethanol,
(±)-2-phenyl-2-piperidin-1-yl-1,1-dipyridin-3-ylethanol,
(±)-2-phenyl-1,1-dipyridin-3-yl-2-pyrrolidin-1-ylethanol,
(±)-tert-butyl 4-(2-hydroxy-1-phenyl-2,2-dipyridin-3-ylethyl)piperazine-1-carboxylate,
2-[(1S,4S)-2-oxa-5-azabicyclo[2.2.1]hept-5-yl]-2-phenyl-1,1-dipyridin-3-ylethanol,
(±)-2-(1,4-oxazepan-4-yl)-2-phenyl-1,1-dipyridin-3-ylethanol,
(±)-2-phenyl-1,1-dipyridin-3-yl-2-thiomorpholin-4-ylethanol,
(±)-2-(diethylamino)-2-phenyl-1,1-dipyridin-3-ylethanol,
(±)-2-(7-azabicyclo[2.2.1]hept-7-yl)-2-phenyl-1,1-dipyridin-3-ylethanol,
(±)-2-(3,3-difluoropyrrolidin-1-yl)-2-phenyl-1,1-dipyridin-3-ylethanol,
(±)-2-phenyl-1,1-dipyridin-3-yl-2-[2-(trifluoromethyl)pyrrolidin-1-yl]ethanol, (±)-2-(2-isopropylpyrrolidin-1-yl)-2-phenyl-1,1-dipyridin-3-ylethanol,
(2R)-2-cyclopropyl-1,1-dipyridin-3-yl-2-pyrrolidin-1-ylethanol,
(±)-2-[cyclobutyl(ethyl)amino]-2-phenyl-1,1-dipyridin-3-ylethanol,
(±)-2-[ethyl(2,2,2-trifluoroethyl)amino]-2-phenyl-1,1-dipyridin-3-ylethanol,
(±)-2-(3-fluoropyrrolidin-1-yl)-2-phenyl-1,1-dipyridin-3-ylethanol,
(±)-2-morpholin-4-yl-1,2-diphenyl-1-pyridin-2-yl-ethanol,
2-morpholin-4-yl-2-phenyl-1-pyridin-2-yl-1-pyridin-3-ylethanol,
(±)-2-phenyl-2-(phenylsulfonyl)-1,1-dipyridin-3-ylethanol,
(±)-2-(1,3-dimethyl-1H-1,2,4-triazol-5-yl)-1,1-dipyridin-3-yl-2-pyrrolidin-1-ylethanol,
(±)-1,2-diphenyl-2-(1H-pyrazol-1-yl)-1-pyridin-4-ylethanol,
(±)-3-(2-hydroxy-1-phenyl-2,2-dipyridin-3-ylethyl)-1,3-oxazolidin-2-one,
(±)-3-[2-hydroxy-1-(2-oxo-1,3-oxazolidin-3-yl)-2,2-dipyridin-3-ylethyl]benzonitrile,
(±)-1-[1-(4-fluorophenyl)-2-hydroxy-2,2-dipyridin-3-ylethyl]-3-methylimidazolidin-2-one,
(±)-1-tert-butyl-3-[1-(4-fluorophenyl)-2-hydroxy-2,2-dipyridin-3-ylethyl]imidazolidin-2-one,
(±)-3-(2-hydroxy-1-pyridin-2-yl-2,2-dipyridin-3-ylethyl)-1,3-oxazolidin-2-one,
(±)-2-(1H-pyrazol-1-yl)-2-pyridin-2-yl-1,1-dipyridin-3-ylethanol,
(±)-2-(1H-pyrazol-1-yl)-1,1,2-tripyridin-3-ylethanol,
(±)-1,1,2-tripyridin-3-yl-2-(1H-1,2,3-triazol-1-yl)ethanol,
(±)-4-[2-hydroxy-2,2-dipyridin-3-yl-1-(2H-1,2,3-triazol-2-yl)ethyl]benzonitrile,
(±)-3-[2-hydroxy-2,2-dipyridin-3-yl-1-(1H-1,2,3-triazol-1-yl)ethyl]benzonitrile,
(±)-(1-benzyl-1H-pyrazol-5-yl)(dipyridin-3-yl)methanol,
(±)-1-[1-(4-fluorophenyl)-2-hydroxy-2,2-dipyridin-3-ylethyl]pyridin-2(1H)-one,
(±)-1-[1-(4-fluorophenyl)-2-hydroxy-2,2-dipyridin-3-ylethyl]pyrazin-2(1H)-one,
(±)-2-[1-(4-fluorophenyl)-2-hydroxy-2,2-dipyridin-3-ylethyl]pyridazin-3(2H)-one,
(R)-1-(2-hydroxy-1-pyridin-2-yl-2,2-dipyridin-3-ylethyl)pyridin-2(1H)-one,
(S)-1-(2-hydroxy-1-pyridin-2-yl-2,2-dipyridin-3-ylethyl)pyridin-2(1H)-one,
(±)-3-(2-hydroxy-2,2-dipyridin-3-yl-1-pyrrolidin-1-ylethyl)benzonitrile,
(±)-2-(4-fluorophenyl)-1,1-dipyridin-3-yl-2-pyrrolidin-1-ylethanol,
(±)-2-(3-methoxyphenyl)-1,1-dipyridin-3-yl-2-pyrrolidin-1-ylethanol,
2-[(2r)-2-(methoxymethyl)pyrrolidin-1-yl]-2-phenyl-1,1-dipyridin-3-ylethanol,
(±)-2-(3-bromophenyl)-1,1-dipyridin-3-yl-2-pyrrolidin-1-ylethanol,
(±)-2-(3,3-difluoroazetidin-1-yl)-2-(4-fluorophenyl)-1,1-dipyridin-3-ylethanol,
(±)-2-(5-chloro-2-thienyl)-1,1-dipyridin-3-yl-2-pyrrolidin-1-ylethanol,
2-[(3R,4R)-3,4-difluoropyrrolidin-1-yl]-2-phenyl-1,1-dipyridin-3-ylethanol,
(±)-1-(2-hydroxy-1-phenyl-2,2-dipyridin-3-ylethyl)piperidin-3-ol,
2-(4-fluorophenyl)-2-[(2S)-2-(hydroxymethyl)pyrrolidin-1-yl]-1,1-dipyridin-3-ylethanol,
(±)-2-(cyclobutylamino)-2-(4-fluorophenyl)-1,1-dipyridin-3-ylethanol,
(±)-2-phenyl-1,1-dipyridin-3-yl-2-[(2,2,2-trifluoroethyl)amino]ethanol,
2-(benzyloxy)-N-[(1R)-2-hydroxy-1-phenyl-2,2-dipyridin-3-ylethyl]acetamide,
N-[(1R)-1-(4-fluorophenyl)-2-hydroxy-2,2-dipyridin-3-ylethyl]-3-pyridin-2-yl-1H-pyrazole-5-carboxamide,
N-[(1R)-1-(4-fluorophenyl)-2-hydroxy-2,2-dipyridin-3-ylethyl]-4-phenylbutanamide,
benzyl[(1R)-1-(4-fluorophenyl)-2-hydroxy-2,2-dipyridin-3-ylethyl]carbamate,
N-[(1R)-1-(4-fluorophenyl)-2-hydroxy-2,2-dipyridin-3-ylethyl]-1-phenyl-1H-pyrazole-4-carboxamide,
(±)-2-phenyl-1,1-dipyridin-3-yl-2-(1H-pyrrol-1-yl)ethanol,
(±)-3-(2-hydroxy-1-morpholin-4-yl-2,2-dipyridin-3-ylethyl)benzonitrile,
(±)-3,3'-(1-fluoro-2-phenyl-2-pyrrolidin-1-ylethane-1,1-diyl)dipyridine,
(±)-1-[1-(4-fluorophenyl)-2-hydroxy-2,2-dipyridin-3-ylethyl]azetidin-3-ol,
(±)-1-[1-(4-fluorophenyl)-2-hydroxy-2,2-dipyridin-3-ylethyl]azetidin-3-yl phenylcarbamate,
(±)-2-(3,3-difluoroazetidin-1-yl)-2-(4-fluorophenyl)-1-(1-oxidopyridin-3-yl)-1-pyridin-3-ylethanol,
(±)-4-[1-(6-methoxypyridin-2-yl)-2,2-dipyridin-3-ylethyl]morpholine,
(±)-N-[1-(4-fluorophenyl)-2-phenyl-2-pyridin-3-ylethyl]-2-methoxyacetamide,
(±)-4-[1-(4-fluorophenyl)-2-phenyl-2-pyridin-3-ylethyl]morpholine,
(±)-1-[1-(4-fluorophenyl)-2,2-dipyridin-3-ylethyl]pyrrolidin-2-one,
(±)-4-[1-(4-fluorophenyl)-2,2-dipyridin-3-ylethyl]morpholine,
(±)-[1-(4-fluorophenyl)-2,2-dipyridin-3-ylethyl](2,2,2-trifluoroethyl)amine,
(±)-4-[1-(3,4-dichlorophenyl)-2,2-dipyridin-3-ylethyl]morpholine,
(±)-4-(1-pyridin-2-yl-2,2-dipyridin-3-ylethyl)morpholine,
(±)-3,3'-[2-(4-fluorophenyl)-2-pyrrolidin-1-ylethane-1,1-diyl]dipyridine,
(±)-4-[1-(4-fluorophenyl)-2-pyridin-2-yl-2-pyridin-3-ylethyl]morpholine,
(±)-4-[1-(3-chlorophenyl)-2,2-dipyridin-3-ylethyl]morpholine,
(±)-4-[1-(3,5-dichlorophenyl)-2,2-dipyridin-3-ylethyl]morpholine,
(±)-[1-(4-fluorophenyl)-2,2-dipyridin-3-ylethyl](3,3,3-trifluoropropyl)amine,
(±)-[1-(3-chlorophenyl)-2,2-dipyridin-3-ylethyl](2,2,2-trifluoroethyl)amine,
(±)-[1-(3,5-dichlorophenyl)-2,2-dipyridin-3-ylethyl](2,2,2-trifluoroethyl)amine,
(±)-[1-(3,4-dichlorophenyl)-2,2-dipyridin-3-ylethyl](2,2,2-trifluoroethyl)amine,
(±)-3,3'-[2-(1,1-dioxidoisothiazolidin-2-yl)-2-(4-fluorophenyl)ethane-1,1-diyl]dipyridine,
(±)-4-[1-(6-methoxypyridin-2-yl)-2-phenyl-2-pyridin-2-ylethyl]morpholine,
(±)-4-[1-(6-bromopyridin-2-yl)-2,2-dipyridin-3-ylethyl]morpholine, (±)-6-(1-morpholin-4-yl-2,2-dipyridin-3-ylethyl)pyridin-2-amine,
(±)-N-methyl-6-(1-morpholin-4-yl-2,2-dipyridin-3-ylethyl)pyridin-2-amine,
(±)-methyl[6-(1-morpholin-4-yl-2,2-dipyridin-3-ylethyl)pyridin-2-yl]carbamate,
(±)-[1-(3-bromophenyl)-2,2-dipyridin-3-ylethyl]{[1-(phenylsulfonyl)-1H-pyrrol-2-yl]methyl}amine,
(±)-methyl[1-(3-cyanophenyl)-2,2-dipyridin-3-ylethyl]prolinate,
(±)-3-{1-[2-(hydroxymethyl)pyrrolidin-1-yl]-2,2-dipyridin-3-ylethyl}benzonitrile,
(±)-1-[1-(3-cyanophenyl)-2,2-dipyridin-3-ylethyl]-N,N-dimethylprolinamide,
(±)-1-[1-(3-bromophenyl)-2,2-dipyridin-3-yethyl]-4-methylpiperazine-2,3-dione,
(±)-3-[1-(6-bromopyridin-2-yl)-2,2-dipyridin-3-ylethyl]-1,3-oxazolidin-2-one,
(±)-3-[1-(2-oxo-1,3-oxazolidin-3-yl)-2,2-dipyridin-3-ylethyl]benzonitrile,
(±)-benzyl (1,2,2-tripyridin-3-ylethyl)carbamate,
(±)-n-[1-(3-cyanophenyl)-2,2-dipyridin-3-ylethyl]-2-phenylcyclopropanecarboxamide,
(±)-3-(1-{[(1-phenyl-1h-pyrazol-4-yl)methyl]amino}-2,2-dipyridin-3-ylethyl)benzonitrile,
(R)-3-(1-morpholin-4-yl-2,2-dipyridin-3-ylethyl)benzonitrile,
(S)-3-(1-morpholin-4-yl-2,2-dipyridin-3-ylethyl)benzonitrile,
(±)-3-[2-(4-fluorophenyl)-1-pyridin-3-yl-2-(2,2,2-trifluoroethoxy)ethyl]pyridine,
(±)-3-[2-(4-fluorophenyl)-2-methoxy-1-pyridin-3-ylethyl]pyridine,
(±)-3-[2-(cyclopentyloxy)-2-(4-fluorophenyl)-1-pyridin-3-ylethyl]pyridine,
(±)-1-[1-(6-chloropyridin-2-yl)-2,2-dipyridin-3-ylethyl]pyridin-2(1H)-one,
(±)-1-(1-pyridin-2-yl-2,2-dipyridin-3-ylethyl)pyridin-2(1H)-one,
(R)-1-(1-pyridin-2-yl-2,2-dipyridin-3-ylethyl)pyridin-2(1H)-one,
(S)-1-(1-pyridin-2-yl-2,2-dipyridin-3-ylethyl)pyridin-2(1H)-one,
(±)-2-[1-(1H-pyrazol-1-yl)-2,2-dipyridin-3-ylethyl]pyridine,
(±)-2-[2-(4-fluorophenyl)-1-(1H-pyrazol-1-yl)-2-pyridin-3-ylethyl]pyridine,
(±)-2-[2-(4-fluorophenyl)-1-(1H-pyrazol-1-yl)-2-pyridin-3-ylethyl]pyridine,
(±)-2-[1-(4-fluorophenyl)-2-(1H-imidazol-1-yl)-2-pyridin-3-ylethyl]pyridine,
(±)-1-(1,2,2-tripyridin-3-ylethyl)pyridin-2(1H)-one,
(±)-2-[2,2-dipyridin-3-yl-1-(1H-1,2,3-triazol-1-yl)ethyl]pyridine,
(±)-3-[2,2-dipyridin-3-yl-1-(1H-1,2,3-triazol-1-yl)ethyl]benzonitrile,
(±)-1-[1(2H)-yl)-2,2-dipyridin-3-ylethyl]pyridin-2(1H)-one,
(±)-1-phenyl-1,2-dipyridin-3-yl-2-(1H-1,2,3-triazol-1-yl)ethanol,
(±)-1-phenyl-1-pyridin-2-yl-2-pyridin-3-yl-2-(1H-1,2,3-triazol-1-yl)ethanol,
(±)-4-[2-hydroxy-2,2-dipyridin-3-yl-1-(1H-1,2,3-triazol-1-yl)ethyl]benzonitrile,
(±)-1-(2-hydroxy-2-phenyl-2-pyridin-2-yl-1-pyridin-3-ylethyl)pyridin-2(1H)-one,
(±)-1-(2-hydroxy-2-phenyl-1,2-dipyridin-3-ylethyl)pyridin-2(1H)-one,
(±)-1-(2-hydroxy-2-phenyl-2-pyridin-2-yl-1-pyridin-3-ylethyl)pyrazin-2(1H)-one,
(±)-2-(6-bromopyridin-3-yl)-1,1-dipyridin-3-yl-2-(1H-1,2,3-triazol-1-yl)ethanol,
(±)-3-[1-hydroxy-2-(2-oxopyridin-1(2H)-yl)-2-pyridin-2-yl-1-pyridin-3-ylethyl]benzonitrile,
(±)-3-(2-hydroxy-1-pyridin-2-yl-2,2-dipyridin-3-ylethyl)-1,3-oxazinan-2-one,
(±)-3-[2-(6-bromopyridin-3-yl)-1-hydroxy-1-pyridin-3-yl-2-(1H-1,2,3-triazol-1-yl)ethyl]benzonitrile,
(±)-3-[1-hydroxy-1,2-dipyridin-3-yl-2-(1H-1,2,3-triazol-1-yl)ethyl]benzonitrile,
(±)-3-[1-hydroxy-2-pyridin-2-yl-1-pyridin-3-yl-2-(1H-1,2,3-triazol-1-yl)ethyl]benzonitrile,
(±)-3-(2-hydroxy-1-phenyl-2,2-dipyridin-3-ylethyl)-1,3-oxazinan-2-one,
(±)-3-[1-hydroxy-2-(2-oxo-1,3-oxazinan-3-yl)-2-pyridin-2-yl-1-pyridin-3-ylethyl]benzonitrile,
(S)-{1-[1-(3-bromophenyl)-2,2-dipyridin-3-ylethyl]piperidin-4-yl}ethanethioate,
(±)-3-[1-(2,4-dioxoimidazolidin-1-yl)-2,2-dipyridin-3-ylethyl]benzonitrile,
(±)-3-[1-(2-oxomorpholin-4-yl)-2,2-dipyridin-3-ylethyl]benzonitrile,
(±)-3-[1-(2-hydroxymorpholin-4-yl)-2,2-dipyridin-3-ylethyl]benzonitrile,
(±)-1-[1-(3-cyanophenyl)-2,2-dipyridin-3-ylethyl]-N,N-bis(1-{1-[1-(3-cyanophenyl)-2,2-dipyridin-3-ylethyl]prolyl}pyrrolidin-2-yl)prolinamide,
(±)-3-(1-pyridin-2-yl-2,2-dipyridin-3-ylethyl)-1,3-oxazolidin-2-one,
(±)-tert-butyl 2-{[1-(3-cyanophenyl)-2,2-dipyridin-3-ylethyl]amino}ethylcarbamate,
(±)-3-[1-(2-oxo-1,3-oxazinan-3-yl)-2,2-dipyridin-3-ylethyl]benzonitrile,
(±)-N-(2-{[1-(3-bromophenyl)-2,2-dipyridin-3-ylethyl]amino}ethyl)methanesulfonamide,
(±)-3-(1-morpholin-4-yl-2,2-dipyridin-3-ylethyl)phenol,
(±)-3-[1-(6-bromopyridin-2-yl)-2,2-dipyridin-3-ylethyl]-1,3-oxazinan-2-one,
(±)-N-(2-{[1-(3-bromophenyl)-2,2-dipyridin-3-ylethyl]amino}ethyl)-n'-phenylurea,
(±)-N-(tert-butyl)-1-[1-(3-cyanophenyl)-2,2-dipyridin-3-ylethyl]prolinamide,
(±)-1-[(3-cyanophenyl)-2,2-dipyridin-3-ylethyl]-piperidinylprolinamide,
(±)-1-[1-(3-cyanophenyl)-2,2-dipyridin-3-ylethyl]-N-cyclohexylprolinamide,
(±)-1-[1-(3-cyanophenyl)-2,2-dipyridin-3-ylethyl]-N-phenylprolinamide,
(±)-methyl 1-[1-(6-bromopyridin-2-yl)-2,2-dipyridin-3-ylethyl]prolinate,
(±)-3-(1-{[(1-phenyl-1H-pyrazol-4-yl)methyl]amino}-2,2-dipyridin-3-ylethyl)benzonitrile,
(±)-methyl 1-[1-(4-fluorophenyl)-2,2-dipyridin-3-ylethyl]prolinate,
(±)-methyl 1-[1-(6-aminopyridin-2-yl)-2,2-dipyridin-3-ylethyl]prolinate,
(±)-N-{1-[1-(3-cyanophenyl)-2,2-dipyridin-3-ylethyl]piperidin-4-yl}-N-methylmethanesulfonamide,
(±)-3-[1-(2-oxopyrrolidin-1-yl)-2,2-dipyridin-3-ylethyl]benzonitrile,
(±)-1-[1-(3-cyanophenyl)-2,2-dipyridin-3-ylethyl]piperidin-4-yl phenylcarbamate, (±)-1-[1-(4-fluorophenyl)-2,2-dipyridin-3-ylethyl]-N-methylprolinamide,
(±)-N-ethyl-1-[1-(4-fluorophenyl)-2,2-dipyridin-3-ylethyl]prolinamide,
(±)-N-{1-[1-(3-cyanophenyl)-2,2-dipyridin-3-ylethyl]piperidin-4-yl}-N-methylcyclopropanesulfonamide,
(±)-3-[1-(1,1-dioxidoisothiazolidin-2-yl)-2,2-dipyridin-3-ylethyl]benzonitrile,
(±)-3-[1-(4,5-dihydro-1,3-thiazol-2-ylamino)-2,2-dipyridin-3-ylethyl]benzonitrile,
(±)-methyl 1-(1-pyridin-2-yl-2,2-dipyridin-3-ylethyl)prolinate,
(±)-N-butyl-1-[1-(3-cyanophenyl)-2,2-dipyridin-3-ylethyl]prolinamide,
(±)-1-[1-(3-cyanophenyl)-2,2-dipyridin-3-ylethyl]-N-isobutylprolinamide,
(±)-1-[1-(3-cyanophenyl)-2,2-dipyridin-3-ylethyl]-N-cyclobutylprolinamide,
(±)-1-[1-(3-cyanophenyl)-2,2-dipyridin-3-ylethyl]-N-cyclopentylprolinamide,
(±)-1-[1-(4-fluorophenyl)-2,2-dipyridin-3-ylethyl]-N-pyridin-2-ylprolinamide,
(±)-1-[1-(3-cyanophenyl)-2,2-dipyridin-3-ylethyl]-N-[4-(trifluoromethyl)pyridin-2-yl]prolinamide,
(±)-N-(5-chloropyridin-2-yl)-1-[1-(3-cyanophenyl)-2,2-dipyridin-3-ylethyl]prolinamide,
(±)-4-[1-(3-bromophenyl)-2,2-dipyridin-3-ylethyl]morpholin-2-one,
(±)-N-{1-[1-(3-cyanophenyl)-2,2-dipyridin-3-ylethyl]piperidin-4-yl}-N-cyclopropylmethanesulfonamide,
(±)-N-{1-[(3-cyanophenyl)-2,2-dipyridin-3-ylethyl]piperidin-4-yl}-N-ethylmethanesulfonamide,
(±)-N-{1-[1-(3-cyanophenyl)-2,2-dipyridin-3-ylethyl]piperidin-4-yl}-N-ethylcyclopropanesulfonamide,
(±)-N-{1-[1-(3-cyanophenyl)-2,2-dipyridin-3-ylethyl]piperidin-4-yl}-N-methylethanesulfonamide,
(±)-methyl 1-[1-(3-cyanophenyl)-2-pyrazin-2-yl-2-pyridin-3-ylethyl]prolinate,
(±)-2-{1-[1-(4-fluorophenyl)-2,2-dipyridin-3-ylethyl]pyrrolidin-2-yl}-1H-benzimidazole,
(±)-methyl 1-[1-(6-methoxypyridin-2-yl)-2,2-dipyridin-3-ylethyl]prolinate,
(±)-3-{1-[2-(1H-benzimidazol-2-yl)pyrrolidin-1-yl]-2,2-dipyridin-3-ylethyl}benzonitrile,
(±)-N-(tert-butyl)-1-[1-(6-methoxypyridin-2-yl)-2,2-dipyridin-3-ylethyl]prolinamide,
(±)-2-{1-[1-(6-methoxypyridin-2-yl)-2,2-dipyridin-3-ylethyl]pyrrolidin-2-yl}-1H-benzimidazole,
(±)-tert-butyl 3-{[1-(3-cyanophenyl)-2,2-dipyridin-3-ylethyl]amino}piperidine-1-carboxylate,
(±)-{1-[2-(6-aminopyridin-2-yl)-1,2-dipyridin-3-ylethyl]pyrrolidin-2-yl}methanol,
(±)-3-(1-{[(4-phenyl-1,3-thiazol-2-yl)methyl]amino}-2,2-dipyridin-3-ylethyl)benzonitrile,
(±)-3-(1-{[(2-phenyl-1,3-thiazol-5-yl)methyl]amino}-2,2-dipyridin-3-ylethyl)benzonitrile,
(±)-3-{2,2-dipyridin-3-yl-1-[(pyridin-2-ylmethyl)amino]ethyl}benzonitrile,
(±)-3-(1-{[3-(4-methoxyphenoxy)benzyl]amino}-2,2-dipyridin-3-ylethyl)benzonitrile,
(±)-3-{2,2-dipyridin-3-yl-1-[(quinolin-3-ylmethyl)amino]ethyl}benzonitrile,
(±)-3-(1-{[4-(methylthio)benzyl]amino}-2,2-dipyridin-3-ylethyl)benzonitrile,
(±)-3-{1-[(2,2-dimethylpent-4-en-1-yl)amino]-2,2-dipyridin-3-ylethyl}benzonitrile,
(±)-3-{1-[(4-propoxybenzyl)amino]-2,2-dipyridin-3-ylethyl}benzonitrile,
(±)-3-{1-[(biphenyl-4-ylmethyl)amino]-2,2-dipyridin-3-ylethyl}benzonitrile,
(±)-3-{1-[(1-benzothien-2-ylmethyl)amino]-2,2-dipyridin-3-ylethyl}benzonitrile,
(±)-3-(2,2-dipyridin-3-yl-1-{[3-(trifluoromethyl)benzyl]amino}ethyl)benzonitrile,
(±)-3-{-[(4-cyanobenzyl)amino]-2,2-dipyridin-3-ylethyl}benzonitrile,
(±)-3-{1-[2-(3-methyl-1,2,4-oxadiazol-5-yl)pyrrolidin-1-yl]-2,2-dipyridin-3-ylethyl}benzonitrile,
(±)-6-{1-[2-(3-methyl-1,2,4-oxadiazol-5-yl)pyrrolidin-1-yl]-2,2-dipyridin-3-ylethyl}pyridin-2-amine,
(±)-2-methoxy-6-{1-[2-(3-methyl-1,2,4-oxadiazol-5-yl)pyrrolidin-1-yl]-2,2-dipyridin-3-ylethyl}pyridine,
(±)-3-{2-(4-fluorophenyl)-2-[2-(3-methyl-1,2,4-oxadiazol-5-yl)pyrrolidin-1-yl]-1-pyridin-3-ylethyl}pyridine,
(±)-3-{1-[2-(3-methyl-1,2,4-oxadiazol-5-yl)pyrrolidin-1-yl]-2-pyrazin-2-yl-2-pyridin-3-ylethyl}benzonitrile,
(±)-3-{1-[2-(3-methyl-1,2,4-oxadiazol-5-yl)pyrrolidin-1-yl]-2-pyrazin-2-yl-2-pyridin-3-ylethyl}benzonitrile,
(±)-3-[1-(3-hydroxypiperidin-1-yl)-2,2-dipyridin-3-ylethyl]benzonitrile,
(±)-4-[2-(6-aminopyridin-2-yl)-2-(3-hydroxypiperidin-1-yl)-1-pyridin-3-ylethyl]benzonitrile,
(±)-4-{2,2-dipyridin-3-yl-1-[(2,2,2-trifluoroethyl)amino]ethyl}benzonitrile,
(±)-4-{1-[(2-fluoroethyl)amino]-2,2-dipyridin-3-ylethyl}benzonitrile,
(±)-4-{1-[(2,2-difluoroethyl)amino]-2,2-dipyridin-3-ylethyl}benzonitrile,
(±)-N-{1-[4-(methylthio)phenyl]-2,2-dipyridin-3-ylethyl}-N-(2,2,2-trifluoroethyl)amine,
(±)-N-{1-[4-(methylsulfonyl)phenyl]-2,2-dipyridin-3-ylethyl}-N-(2,2,2-trifluoroethyl)amine,
(±)-6-{2,2-dipyridin-3-yl-1-[(2,2,2-trifluoroethyl)amino]ethyl}pyridin-2-amine,
(±)-N-{1-[2-(methylthio)phenyl]-2,2-dipyridin-3-ylethyl}-N-(2,2,2-trifluoroethyl)amine,
(±)-N-{1-[2-(methylsulfonyl)phenyl]-2,2-dipyridin-3-ylethyl}-N-(2,2,2-trifluoroethyl)amine,
(±)-N-{1-[3-(methylthio)phenyl]-2,2-dipyridin-3-ylethyl}-N-(2,2,2-trifluoroethyl)amine,
(±)-N-{1-[3-(methylsulfonyl)phenyl]-2,2-dipyridin-3-ylethyl}-N-(2,2,2-trifluoroethyl)amine,
(±)-1-(2,3'-bipyridin-3-yl)-2,2-dipyridin-3-ylethanamine,
(±)-1-(2,3'-bipyridin-3-yl)-2,2-dipyridin-3-yl-N-(2,2,2-trifluoroethyl)ethanamine,
(±)-3-[1-(4-fluorophenyl)-2,2-dipyridin-3-ylethyl]-1,3-oxazolidin-2-one,
(±)-3-[1-(4-chlorophenyl)-2,2-dipyridin-3-ylethyl]-1,3-oxazolidin-2-one,
benzyl(±)-1-(4-chlorophenyl)-2,2-dipyridin-3-ylethylcarbamate,
(±)-4-[1-(2-oxo-1,3-oxazolidin-3-yl)-2,2-dipyridin-3-ylethyl]benzonitrile,
(±)-neopentyl 1-(4-chlorophenyl)-2,2-dipyridin-3-ylethylcarbamate,
(±)-N-{1-[2-(methylthio)pyrimidin-4-yl]-2,2-dipyridin-3-ylethyl}-n-(2,2,2-trifluoroethyl)amine,
(±)-4-{2-(2-fluoropyridin-3-yl)-2-pyridin-3-yl-1-[(2,2,2-trifluoroethyl)amino]ethyl}pyrimidin-2-amine,
(±)-6-{2-(4-fluorophenyl)-1-pyridin-3-yl-2-[(2,2,2-trifluoroethyl)amino]ethyl}pyridin-2-amine,
(±)-1-(2-morpholin-4-ylpyridin-3-yl)-2,2-dipyridin-3-ylethanol, (±)-1-{2-[methyl(pyridin-3-yl)amino]pyridin-3-yl}-2,2-dipyridin-3-ylethanol, (±)-3,3',3"-[2-(1H-tetrazol-1-yl)ethane-1,1,2-triyl]tripyridine, (±)-3-[2-pyridin-2-yl-1-pyridin-3-yl-2-(1H-1,2,3-triazol-1-yl)ethyl]benzonitrile, (±)-2-[2,2-dipyridin-3-yl-1-(4H-1,2,4-triazol-4-yl)ethyl]pyridine, (±)-4-{2-(4-chlorophenyl)-1-[2-(methylthio)pyrimidin-4-yl]-2-pyridin-3-ylethyl}morpholine, (±)-4-[2-(4-chlorophenyl)-1-morpholin-4-yl-2-pyridin-3-ylethyl]pyrimidin-2-amine, and (±)-6-[1-(3,3-difluoropyrrolidin-1-yl)-2,2-dipyridin-3-ylethyl]pyridin-2-amine.

4. A pharmaceutical formulation comprising a pharmaceutically acceptable carrier and the compound claim 1 or a pharmaceutically acceptable crystal form or hydrate thereof.

5. A pharmaceutical composition made by combining the compound of claim 1 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,879,839 B2 | Page 1 of 1 |
| APPLICATION NO. | : 11/658114 | |
| DATED | : February 1, 2011 | |
| INVENTOR(S) | : Dinsmore et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 903 days.

Signed and Sealed this
Thirty-first Day of May, 2011

David J. Kappos
*Director of the United States Patent and Trademark Office*